(12) United States Patent
Battagliarin et al.

(10) Patent No.: US 10,290,817 B2
(45) Date of Patent: *May 14, 2019

(54) LUMINESCENT DIAZA-MONOAZA-AND BENZIMIDAZOLE METAL CARBENE COMPLEXES FOR USE IN ELECTRONIC DEVICES SUCH AS OLEDS

(71) Applicant: UDC Ireland Limited, Dublin (IE)

(72) Inventors: Glauco Battagliarin, Mannheim (DE); Flavio Luiz Benedito, Ludwigshafen (DE); Stefan Metz, Mannheim (DE); Korinna Dormann, Bad Dürkheim (DE); Peter Murer, Oberwil (CH); Soichi Watanabe, Seoul (KR); Christian Lennartz, Schifferstadt (DE); Georg Beck, Böbingen (DE); Thomas Geßner, Heidelberg (DE)

(73) Assignee: UDC Ireland Limited, Dublin (IE)

( * ) Notice: Subject to any disclaimer, the term of this patent is extended or adjusted under 35 U.S.C. 154(b) by 446 days.

This patent is subject to a terminal disclaimer.

(21) Appl. No.: 14/908,740

(22) PCT Filed: Jul. 31, 2014

(86) PCT No.: PCT/EP2014/066510
§ 371 (c)(1),
(2) Date: Jan. 29, 2016

(87) PCT Pub. No.: WO2015/014944
PCT Pub. Date: Feb. 5, 2015

(65) Prior Publication Data
US 2016/0172606 A1    Jun. 16, 2016

(30) Foreign Application Priority Data

Jul. 31, 2013  (EP) ..................................... 13178675
Jul. 4, 2014  (EP) ..................................... 14175848

(51) Int. Cl.
*H01L 51/00* (2006.01)
*C07F 15/00* (2006.01)
(Continued)

(52) U.S. Cl.
CPC .......... *H01L 51/0085* (2013.01); *C07F 5/025* (2013.01); *C07F 15/0033* (2013.01);
(Continued)

(58) Field of Classification Search
CPC ............. H01L 51/0085; H01L 51/0072; H01L 51/5012; H01L 51/5016; H05B 33/14;
(Continued)

(56) References Cited

U.S. PATENT DOCUMENTS 8,258,297 B2  9/2012  Molt et al.
8,383,828 B2  2/2013  Molt et al.
(Continued)

FOREIGN PATENT DOCUMENTS

| JP | 2009057505 | 3/2009 |
| JP | 2012167028 | 9/2012 |

(Continued)

OTHER PUBLICATIONS

Baldo, M., et al., "Very high-efficiency green organic light-emitting devices based on electrophosphorescence", Applied Physics Letters, vol. 75, No. 1, pp. 4-6.
(Continued)

*Primary Examiner* — Ruiyun Zhang
(74) *Attorney, Agent, or Firm* — Riverside Law LLP

(57) ABSTRACT

A cyclometallated Ir complex comprising one, two or three ligands of formula (I) or (I') substituted at the $R_5$ and $R_7$ position; an organic electronic device comprising at least one inventive cyclometallated Ir complex; a light-emitting layer comprising at least one inventive cy-clometallated Ir complex; the use of the inventive cyclometallated Ir complex in an OLED; an apparatus selected from the group consisting of stationary visual display units, mobile visual display units, illumination units, units in items of clothing, units in handbags, units in accessories, units in furniture and units in wallpaper, comprising the organic electronic device; and a process for preparing a the inventive cyclometallated Ir complex.

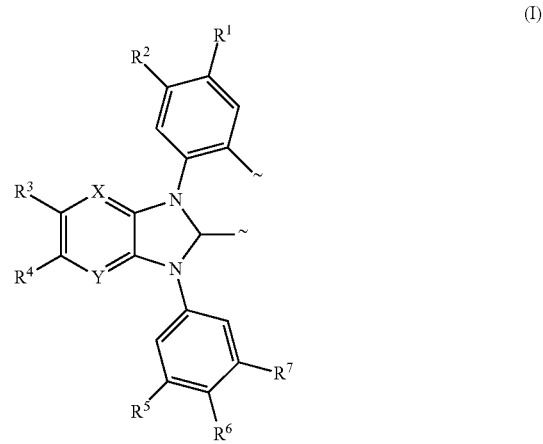

(I)

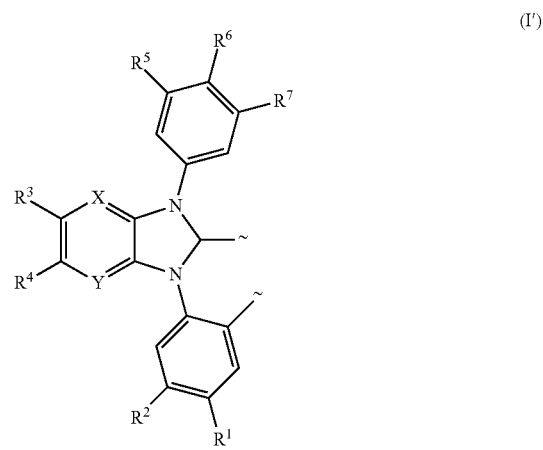

(I')

18 Claims, No Drawings

(51) Int. Cl.
*H05B 33/14* (2006.01)
*C09K 11/06* (2006.01)
*C07F 5/02* (2006.01)
*C09K 11/02* (2006.01)
*H01L 51/50* (2006.01)

(52) U.S. Cl.
CPC ........ *C07F 15/0086* (2013.01); *C09K 11/025* (2013.01); *C09K 11/06* (2013.01); *H05B 33/14* (2013.01); *C09K 2211/1007* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/0072* (2013.01); *H01L 51/0073* (2013.01); *H01L 51/5012* (2013.01); *H01L 51/5016* (2013.01); *H01L 51/5056* (2013.01); *H01L 51/5096* (2013.01); *Y02E 10/549* (2013.01); *Y02P 70/521* (2015.11)

(58) Field of Classification Search
CPC .................. C09K 11/025; C09K 11/06; C09K 2211/1007; C09K 2211/1044; C09K 2211/1059; C07F 5/025; C07F 15/0033; C07F 15/0086
USPC ................ 428/690, 917; 438/99; 548/103; 252/301.16; 313/506; 257/40
See application file for complete search history.

(56) References Cited

U.S. PATENT DOCUMENTS

| | | | |
|---|---|---|---|
| 8,728,632 | B2 | 5/2014 | Molt et al. |
| 2006/0127696 | A1 | 6/2006 | Stossel |
| 2006/0258043 | A1* | 11/2006 | Bold ................. C07F 15/0033 438/99 |
| 2009/0096367 | A1 | 4/2009 | Fuchs et al. |
| 2011/0057559 | A1 | 3/2011 | Xia et al. |
| 2011/0233528 | A1 | 9/2011 | Levermore et al. |
| 2012/0205645 | A1 | 8/2012 | Fuchs et al. |
| 2012/0305894 | A1 | 12/2012 | Kim et al. |
| 2013/0032766 | A1 | 2/2013 | Molt et al. |
| 2014/0027733 | A1 | 1/2014 | Zeng et al. |
| 2014/0309428 | A1 | 10/2014 | Egen et al. |
| 2016/0181549 | A1* | 6/2016 | Murer ................. C07F 15/0033 544/225 |

FOREIGN PATENT DOCUMENTS

| | | |
|---|---|---|
| JP | 2016530494 | 9/2016 |
| WO | WO-2005/113704 A2 | 12/2005 |
| WO | WO-2006/056418 A2 | 6/2006 |
| WO | WO-2006/121811 A1 | 11/2006 |
| WO | WO-2007/095118 A2 | 8/2007 |
| WO | WO-2007/115970 A1 | 10/2007 |
| WO | WO-2007/115981 A1 | 10/2007 |
| WO | WO-2008/156879 A1 | 12/2008 |
| WO | WO-2009/050281 A1 | 4/2009 |
| WO | WO-2009/050290 A1 | 4/2009 |
| WO | WO-2010/068876 A1 | 6/2010 |
| WO | WO-2011/051404 A1 | 5/2011 |
| WO | WO-2011/073149 A1 | 6/2011 |
| WO | WO-2011/106344 A1 | 9/2011 |
| WO | WO-2012/048266 A1 | 4/2012 |
| WO | WO-2012/121936 A2 | 9/2012 |
| WO | WO-2012/170461 A1 | 12/2012 |
| WO | WO-2012/170463 A1 | 12/2012 |
| WO | WO-2012/170571 A1 | 12/2012 |
| WO | WO-2012/172482 A1 | 12/2012 |
| WO | 2015014835 | 2/2015 |

OTHER PUBLICATIONS

Chianese, A., et al., "Flexible, Bowl-Shaped N-Heterocyclic Carbene Ligands: Substrate Specificity in Iridium-Catalyzed Ketone Hydrosilyation", Organometallics, vol. 28, No. 2, (2009), pp. 465-472.
International Search Report for PCT/EP2014/66510 dated Oct. 10, 2014.

* cited by examiner

LUMINESCENT DIAZA-MONOAZA-AND BENZIMIDAZOLE METAL CARBENE COMPLEXES FOR USE IN ELECTRONIC DEVICES SUCH AS OLEDS

CROSS-REFERENCE TO RELATED APPLICATIONS

This application is a national stage application (under 35 U.S.C. § 371) of PCT/EP2014/066510, filed Jul. 31, 2014, which claims benefit of European Application Nos. 13178675.8, filed Jul. 31, 2013, and 14175848.2, filed Jul. 4, 2014, all of which are incorporated herein by reference in their entirety.

The present invention relates to a cyclometallated Ir complex comprising one, two or three N,N diaryl substituted carbene ligands, bearing substituents in the 3 and 5 position of the non-cyclometallated aryl ring; an organic electronic device, preferably an organic light-emitting diode (OLED), comprising at least one cyclometallated Ir complex as described above, to a light-emitting layer comprising said cyclometallated Ir complex preferably as emitter material, preferably in combination with at least one host material, to the use of said cyclometallated Ir complex in an OLED and to an apparatus selected from the group consisting of stationary visual display units, mobile visual display units, illumination units, units in items of clothing, units in handbags, units in accessories, units in furniture and units in wallpaper comprising said organic electronic device, preferably said OLED, or said light-emitting layer. The present invention further relates to a process for the preparation of said cyclometallated Ir complex.

Organic electronics, i.e. organic electronic devices, are an important sector in the field of electronics. Organic electronics is a subfield of electronics which uses electronic circuits which comprise polymers or smaller organic compounds. Fields of use of organic electronics are the use of polymers or smaller organic compounds in organic electronic devices, for example in organic light-emitting diodes (OLED), light-emitting electrochemical cells (LEEC), organic photovoltaic cells (OPV) and organic field-effect transistors (OFET).

The use of suitable novel organic materials thus allows various new types of components based on organic electronics to be provided, such as displays, illumination, sensors, transistors, data stores or photovoltaic cells. This makes possible the development of new devices which are thin, light, flexible and producible at low cost.

The synthesis and provision of new materials for organic electronic devices is therefore an important research topic. Especially the synthesis and provision of dyes for use in organic electronic devices (useful for example as emitter materials in OLEDs and LEECs or as absorption dyes in OPVs) is important for providing organic electronic devices having good stabilities and long lifetimes as well as—in the case of OLEDs and LEECs—high quantum efficiencies.

A preferred field of use according to the present application is the use of relatively small organic compounds in organic light-emitting diodes (OLED). OLEDs exploit the propensity of materials to emit light when they are excited by electrical current. OLEDs are of particular interest as an alternative to cathode ray tubes and liquid-crystal displays for production of flat visual display units. Owing to the very compact design and the intrinsically low power consumption, devices comprising OLEDs are suitable especially for mobile applications, for example for applications in cell-phones, smartphones, digital cameras, mp3 players, tablet computers, laptops, etc. In addition, white OLEDs give great advantage over the illumination technologies known to date, especially a particularly high efficiency.

The basic principles of the way in which OLEDs work and suitable structures (layers) of OLEDs are specified, for example, in WO 2005/113704 and the literature cited therein.

The light-emitting materials (emitters) used may, as well as fluorescent materials (fluorescent emitters), be phosphorescent materials (phosphorescent emitters). The phosphorescent emitters are typically organometallic complexes which, in contrast to the fluorescence emitters which exhibit singlet emission, exhibit triplet emission (M. A. Baldow et al., Appl. Phys. Lett. 1999, 75, 4 to 6). For quantum-mechanical reasons, when the phosphorescent emitters are used, up to four times the quantum efficiency, energy efficiency and power efficiency is possible.

Of particular interest are organic light-emitting diodes with a good color purity, low operational voltage, high efficiency, high efficacy, high resistance to thermal stress and long operational lifetime.

In order to implement the aforementioned properties in practice, it is necessary to provide suitable emitter materials. The selection of suitable emitter materials has a significant influence on parameters including the color purity, efficiency, lifetime and operating voltages of the OLEDs.

One important class of compounds useful in organic electronic devices, especially in OLEDs, preferably as phosphorescent emitters are cyclometallated transition metal carbene complexes. Such complexes are described for example in WO 2006/056418 A2, WO 2005/113704, WO 2007/115970, WO 2007/115981, WO 2008/000727, WO2009/050281, WO2009/050290, WO2011/051404, US2011/057559 WO2011/073149, WO2012/121936A2, US2012/0305894A1, WO2012/170571, WO2012/170461, WO 2012/170463, WO2006/121811, WO2007/095118, WO2008/156879, WO2008/156879, WO2010/068876, US2011/0057559, WO2011/106344, US2011/0233528, WO2012/048266 and WO2012/172482.

According to the prior art mentioned above, transition metal complexes bearing carbene ligands are usually prepared according to one of the following three routes:

i) Deprotonation of (aza)benzimidazolium salts;
ii) Transmetallation of silver carbenes;
iii) Producing a carbene starting from the corresponding alkoxy derivative.

However, independently from the method used, in the case of asymmetric diaryl substituted carbene ligands, wherein both aryl residues are in general suitable for a cyclometallation with the central metal, it is not possible to influence the cyclometallation in order to achieve only one cyclometallation isomer of the carbene complex. The separation of the isomers is accompanied by a loss of material associated with low yields. Further, the separation of the isomers is desirable since the isomers may have different optical properties.

US 2012/0305894 A1 relates to a blue phosphorescent compound with high color purity and a high efficiency and an organic electroluminescent device using the same. The blue phosphorescent compound mentioned in the example according to US 2012/0305894 A1 is characterized by the following formula:

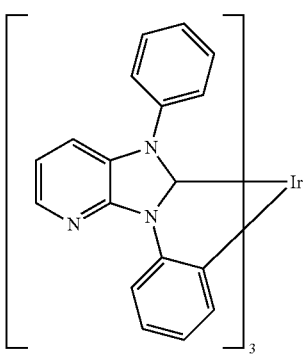

It is mentioned that the Ir complex shown above is obtained as a major isomer. However, it is not mentioned in US 2012/0305894 A1 how the formation of cyclometallation isomers may be avoided.

WO 2012/121936 A2 discloses organometallic compounds comprising an imidazole carbene ligand having an N-containing ring fused to the imidazole ring. In particular, the N-containing ring fused to the imidazole ring may contain one nitrogen atom or more than one nitrogen atom. These materials are—according to WO 2012/121936 A2—useful as blue phosphorescent emitters for OLEDs.

WO 2011/073149 A1 relates to metal-carbene complexes comprising a central atom selected from iridium and platinum, and diazabenzimidazol carbene-ligands, to organic light-emitting diodes comprising said complexes, to light-emitting layers comprising at least one such metal-carbene complex, to a device selected from the group comprising lighting elements, to stationary screens and mobile screens comprising such an OLED, and to the use of such a metal-carbene complex in OLEDs, for example as an emitter, matrix material, charge transport material, and/or charge or excitonic blocker.

WO 2012/172482 A1 relates to metal-carbene complexes comprising a central atom selected from iridium and platinum, and specific azabenzimidazolocarbene ligands, to OLEDs (Organic Light Emitting Diode, OLED) which comprise such complexes, to a device selected from the group consisting of illuminating elements, stationary visual display units and mobile visual display units comprising such an OLED, to the use of such a metal-carbene complex in OLEDs, for example as emitter, matrix material, charge transport material and/or charge or exciton blocker. The three documents, WO 2011/073149 A1, WO 2011/073149 A1 and WO 2012/172482 A1 disclose a number of carbene complexes comprising N-alkyl, N-aryl substituted carbene ligands In such carbene complexes only one cyclometallation isomer is present.

US 2014/0027733 A1 concerns compounds having a metal $M_1$ which may be Ir complexed to a ligand $L_3$ containing a substituted imidazole carbene group as light emitting material for OLEDs. However, all exemplified compounds mentioned in US 2014/0027733 A1 concern carbene complexes comprising N-alkyl, N-aryl substituted carbene ligands In such carbene complexes only one cyclometallation isomer is present.

It is an object of the present invention to provide metal-carbene complexes having diaryl substituted carbene ligands in form of only one or mainly one cyclometallation isomer. Said metal-carbene complexes having diaryl substituted carbene ligands are suitable for use in organic light-emitting diodes with a good color purity, low operational voltage, high efficiency, high efficacy, high resistance to thermal stress and reasonable operational lifetime. Since only one or mainly one cyclometallation isomer is present, the separation of the isomers which is usually accompanied by a loss of material associated with low yields is not necessary.

This object is achieved by a cyclometallated Ir complex comprising one, two or three ligands of formula (I) or (I')

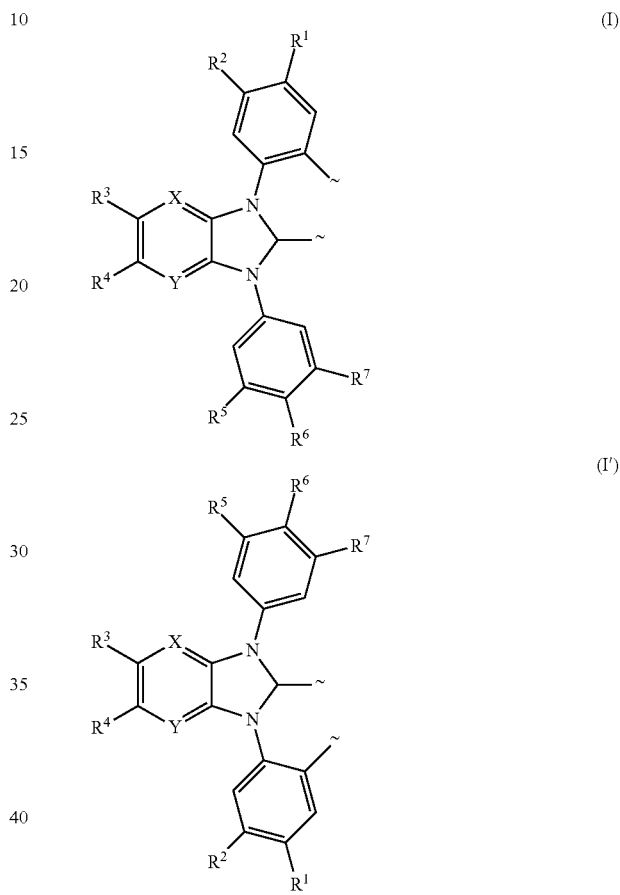

wherein
$R^1$, $R^2$, $R^3$, $R^4$ and $R^6$
are each independently hydrogen; deuterium; a linear or branched, substituted or unsubstituted alkyl radical having 1 to 20 carbon atoms, optionally interrupted by at least one heteroatom, selected from O, S and N; a substituted or unsubstituted cycloalkyl radical having a total of from 3 to 30 carbon atom; a substituted or unsubstituted heterocycle alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action; preferably, $R^1$, $R^2$, $R^3$, $R^4$ and $R^6$ are each independently hydrogen, deuterium, a linear or branched, substituted or unsubstituted alkyl radical, having 1 to 6 carbon atoms; an unsubstituted aryl radical, having from 6 to 18 carbon atoms, a monosubstituted aryl radical having from 6 to 18 carbon atoms, a disubstituted aryl radical having from 6 to 21 carbon atoms; an unsubstituted heteroaryl radical, having a total of from 5 to 18 carbon atoms and/or heteroatoms, a monosubstituted heteroaryl radical, having a total of from 5 to 18 carbon atoms and/or heteroatoms, a disubstituted heteroaryl radical, having a total of from 5 to 21 carbon atoms and/or heteroatoms; more preferably, the aryl radical or heteroaryl radical are selected from the group consisting of phenyl, pyridyl, pyrimidyl, pyrazinyl, carbazolyl, dibenzofuranyl, dibenzthiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, methoxy, phenyl or $CF_3$; a group with donor or acceptor action, selected from OPh; halogen radicals, preferably F or Cl, more preferably F; $CF_3$, CN; or $SiR^{10}R^{11}R^{12}$, preferably $SiMe_3$, $SiPh_3$, $SiEt_3$ or $SiPh_2tBu$;

$R^{10}$, $R^{11}$, $R^{12}$ are each independently a linear or branched alkyl radical, having from 1 to 6 carbon atoms, preferably methyl, ethyl, n-propyl, iso-propyl, n-butyl, tert-butyl, sec-butyl or iso-butyl; a substituted or unsubstituted aryl radical, having from 6 to 18 carbon atoms, preferably phenyl or tolyl; a substituted or unsubstituted heteroaryl radical, having a total of from 5 to 18 carbon atoms and/or heteroatoms; a substituted or unsubstituted cycloalkyl radical having a total of from 3 to 18 carbon atoms, preferably cyclopentyl or cyclohexyl;

or $R^1$ and $R^2$ or $R^3$ and $R^4$ may form, independently of each other, together with the carbon atoms to which they are bonded, a saturated or unsaturated or aromatic, optionally substituted ring, which is optionally interrupted by at least one heteroatom, selected from O, S and N, has a total of from 5 to 21 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 21 carbon atoms and/or heteroatoms;

$R^5$ and $R^7$ are each independently a linear or branched, substituted or unsubstituted alkyl radical having 1 to 20 carbon atoms, optionally interrupted by at least one heteroatom, selected from O, S and N; a substituted or unsubstituted aryl radical, having a total of from 6 to 30 carbon atoms; or a substituted or an unsubstituted heteroaryl radical, having a total of from 5 to 30 carbon atoms and/or heteroatoms, selected from O, S and N;

a cycloalkyl radical having a total of from 3 to 30 carbon atoms, optionally substituted by a linear or branched, substituted or unsubstituted alkyl radical, optionally interrupted by at least one heteroatom, selected from O, S and N, and/or at least one of the groups mentioned above concerning the linear or branched alkyl radical; or a heterocycle alkyl radical, interrupted by at least one heteroatom, selected from O, S and N, and having a total of from 3 to 30 carbon atoms and/or heteroatoms, optionally substituted by a linear or branched, substituted or unsubstituted alkyl radical, optionally interrupted by at least one heteroatom, selected from O, S and N, and/or at least one of the groups mentioned above concerning the linear or branched alkyl radical;

preferably, $R^5$ and $R^7$ are each independently a linear or branched, substituted or unsubstituted alkyl radical, having 1 to 6 carbon atoms; a substituted or unsubstituted cycloalkyl radical having a total of from 3 to 12 carbon atoms; an unsubstituted aryl radical, having from 6 to 18 carbon atoms, a monosubstituted aryl radical having from 6 to 18 carbon atoms, a disubstituted aryl radical having from 6 to 21 carbon atoms; an unsubstituted heteroaryl radical, having a total of from 5 to 18 carbon atoms and/or heteroatoms, a monosubstituted heteroaryl radical, having a total of from 5 to 18 carbon atoms and/or heteroatoms, a disubstituted heteroaryl radical, having a total of from 5 to 21 carbon atoms and/or heteroatoms; more preferably, the aryl radical or heteroaryl radical are selected from the group consisting of phenyl, pyridyl, pyrimidyl, pyrazinyl, carbazolyl, dibenzofuranyl, dibenzthiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, methoxy, phenyl or $CF_3$; a group with donor or acceptor action, selected from OPh; halogen radicals, preferably F or Cl, more preferably F; $CF_3$, CN; or $SiR^{10}R^{11}R^{12}$, preferably $SiMe_3$, $SiPh_3$, $SiEt_3$ or $SiPh_2tBu$;

or $R^5$ and $R^6$ or $R^6$ and $R^7$ may form, independently of each other, together with the carbon atoms to which they are bonded, a saturated or unsaturated or aromatic, optionally substituted ring, which is optionally interrupted by at least one heteroatom, selected from O, S and N, has a total of from 5 to 21 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 21 carbon atoms and/or heteroatoms;

X is $CR^8$ or N;

Y is $CR^9$ or N;

$R^8$ and $R^9$ are each independently hydrogen; deuterium; a linear or branched, substituted or unsubstituted alkyl radical having 1 to 20 carbon atoms, optionally interrupted by at least one heteroatom, selected from O, S and N; a substituted or unsubstituted cycloalkyl radical having a total of from 3 to 30 carbon atom; a substituted or unsubstituted heterocycle alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action; preferably, $R^8$ and $R^9$ are each independently hydrogen, deuterium, a linear or branched, substituted or unsubstituted alkyl radical, having 1 to 6 carbon atoms; an unsubstituted aryl radical, having from 6 to 21 carbon atoms, a monosubstituted aryl radical having from 6 to 21 carbon atoms, a disubstituted aryl radical having from 6 to 21 carbon atoms; an unsubstituted heteroaryl radical, having a total of from 5 to 21 carbon atoms and/or heteroatoms, a monosubstituted heteroaryl radical, having a total of from 5 to 21 carbon atoms and/or heteroatoms, a disubstituted heteroaryl radical, having a total of from 5 to 21 carbon atoms and/or heteroatoms; more preferably, the aryl radical or heteroaryl radical are selected from the group consisting of phenyl, pyridyl, pyrimidyl, pyrazinyl, carbazolyl, dibenzofuranyl, dibenztthiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, methoxy, phenyl, $CF_3$ or CN; a group with donor or acceptor action, selected from halogen radicals, preferably F or Cl, more preferably F; $CF_3$, CN; or $SiR^{10}R^{11}R^{12}$, preferably $SiMe_3$, $SiPh_3$, $SiEt_3$ or $SiPh_2tBu$;

~ is the bonding site to the metal.

The key of the present invention is the provision of Ir carbene complexes having asymmetric diaryl substituted carbene ligands bearing substituents at the 3 and 5 position of one of the aryl residues bond to one of the carbene nitrogen atoms. By substitution of the 3 and 5 position of the aryl residue, cyclometallation of said aryl residue with Ir is avoided respectively substantially reduced. Therefore, the specific cyclometallated Ir complexes comprising one, two or three ligands of formula (I) or (I') according to the present invention are present in form of only one or mainly one cyclometallation isomer.

Additionally, the emission lifetime/emission decay time) of said complexes is short, the color purity is very good and the quantum yields are high to very high. Devices comprising the complexes according to the present invention show high efficiency and luminous efficacy as well as low voltage.

The complexes are particularly suitable as emitter materials for OLEDs showing electroluminescence in the blue region (CIEy<0.40), more particularly in the deeper blue region (CIEy<0.30, preferably CIEy<0.25), of the electromagnetic spectrum, which enables, for example, the production of full-color displays and white OLEDs.

Chianese et al. Organometallics 2010, 29, 3019-3026 describes the synthesis and catalytic CH functionalization of Ir complexes of CCC-pincer N-heterocyclic carbene ligands. The Ir complexes have the following formulae:

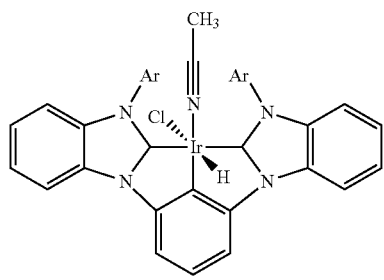

wherein Ar is

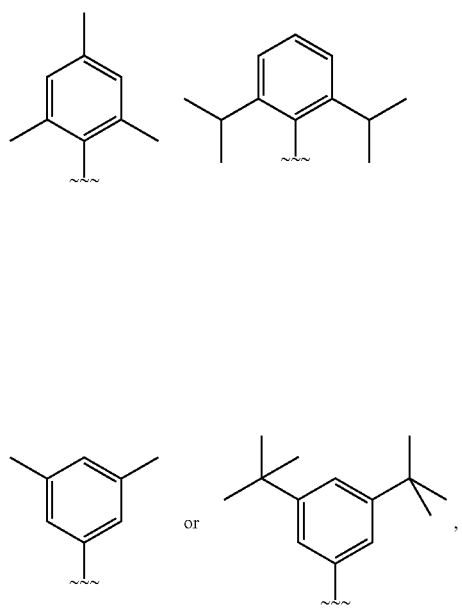

i.e. Ar may be substituted in the 3 and 5 position. However, the carbene ligands are clearly different from the carbene ligands of the specific cyclometallated Ir complexes comprising one, two or three ligands of formula (I) or (I') according to the present invention. The complexes according to Chianese et al. are used as catalysts for the CH borylation of arenes with $B_2pin_2$ and in the dehydrogenation of cyclooctane.

In the context of the present invention, cyclometallated Ir complex means that the aryl residue substituted to one of the carbene nitrogen atoms (i.e. nitrogen atoms of the of the carbene unit) undergoes intramolecular metallation with formation of an Ir-carbon a bond, as shown in the following for a cyclometallated Ir complex of formula (II):

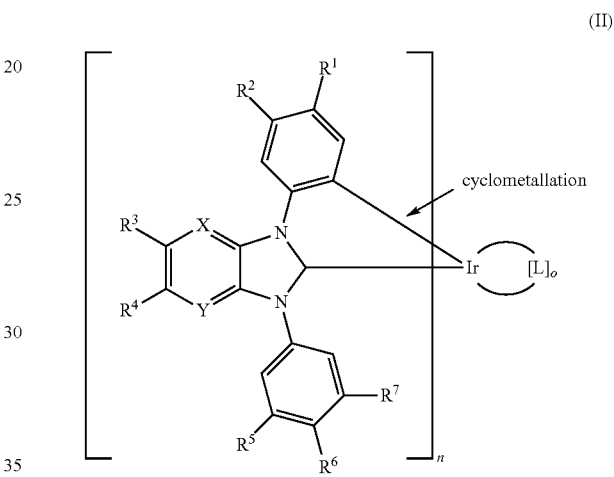

In the context of the present invention, cyclometallation isomer means that—in the case of an Ir complex of formula (II)—two cyclometallation isomers (isomer A and isomer B) per each of the n carbene ligands are possible in principle:

A

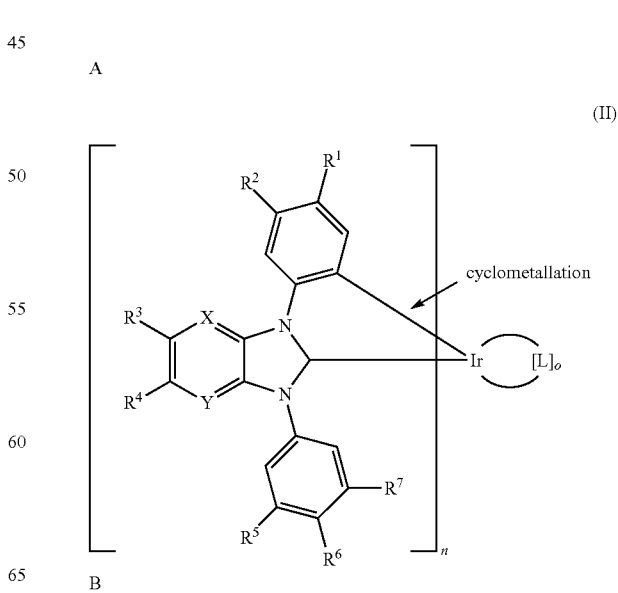

B

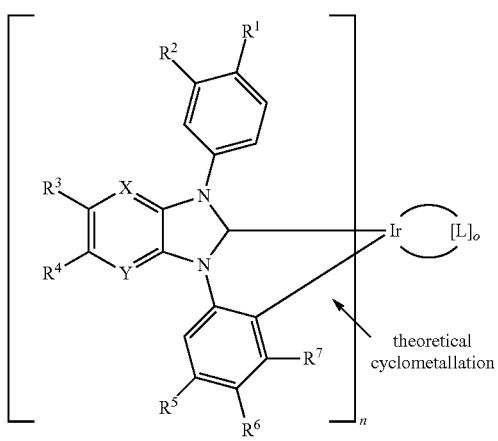

theoretical cyclometallation

However, since the Ir carbene complex according to the present invention comprises at least one carbene ligand bearing substituents at the 3 and 5 position of one of the aryl residues bound to one of the carbene nitrogen atoms ($R^5$ and $R^7$), the formation of the cyclometallation isomer B is avoided respectively substantially reduced.

The 3 and the 5 positions of one of the aryl residues bound to one of the carbene nitrogen atoms in the Ir carbene complex according to the present invention are—in the context of the present invention—the positions substituted with $R^5$ and $R^7$.

In the context of the present invention, the terms aryl radical, unit or group, heteroaryl radical, unit or group, alkyl radical, unit or group, cycloalkyl radical, unit or group, cycloheteroalkyl radical, unit or group, and groups with donor or acceptor action are each defined as follows—unless stated otherwise:

In the aryl radicals, heteroaryl radicals, alkyl radicals, cycloalkyl radicals, cycloheteroalkyl radicals and groups with donor or acceptor action mentioned below, one or more hydrogen atoms (if present) may be substituted by deuterium atoms.

Aryl radicals or substituted or unsubstituted aryl radicals having 6 to 30, preferably 6 to 18 carbon atoms ($C_6$-$C_{30}$-aryl radicals) refer in the present invention to radicals which are derived from monocyclic, bicyclic or tricyclic aromatics which do not comprise any ring heteroatoms. When the systems are not monocyclic systems, the term "aryl" for the second ring also includes the saturated form (perhydro form) or the partly unsaturated form (for example the dihydro form or tetrahydro form), provided that the particular forms are known and stable. This means that the term "aryl" in the present invention encompasses, for example, also bicyclic or tricyclic radicals in which either both or all three radicals are aromatic, and bicyclic or tricyclic radicals in which only one ring is aromatic, and also tricyclic radicals in which two rings are aromatic. Examples of aryl are: phenyl, naphthyl, indanyl, 1,2-dihydronaphthenyl, 1,4-dihydronaphthenyl, indenyl, anthracenyl, phenanthrenyl or 1,2,3,4-tetrahydronaphthyl. Particular preference is given to aryl radicals having a base structure of 6 to 13 carbon atoms, for example phenyl, naphthyl or fluorenyl, very particular preference is given to aryl radicals having a base structure of 6 carbon atoms.

The aryl radicals or $C_6$-$C_{30}$-aryl radicals may be unsubstituted or substituted by one or more further radicals.

Suitable further radicals are selected from the group consisting of $C_1$-$C_{20}$-alkyl, $C_6$-$C_{24}$-aryl and substituents with donor or acceptor action, suitable substituents with donor or acceptor action are specified below. Preferred are unsubstituted aryl radicals, having from 6 to 18 carbon atoms, a monosubstituted aryl radicals having from 6 to 18 carbon atoms or disubstituted aryl radicals having from 6 to 21 carbon atoms. Preferred substituents are $C_1$-$C_{20}$-alkyl groups, $C_1$-$C_{20}$-alkoxy groups, CN, $CF_3$, halogen radicals, $SiR^{10}R^{11}R^{12}$, wherein $R^{10}$, $R^{11}$ and $R^{12}$ are specified below or amino groups ($NR^{32}R^{33}$ where suitable $R^{32}$ and $R^{33}$ radicals are specified below), more preferred substituents are methyl, ethyl, n-propyl, iso-propyl, n-butyl, tert-butyl, sec-butyl, iso-butyl, cyclopentyl, cyclohexyl, methoxy, phenyl or $CF_3$; a group with donor or acceptor action, selected from OPh, halogen radicals, preferably F or Cl, more preferably F; $CF_3$; or $SiR^{10}R^{11}R^{12}$, preferably $SiMe_3$, $SiPh_3$, $SiEt_3$ or $SiPh_2tBu$.

Heteroaryl radicals or substituted or unsubstituted heteroaryl radicals having a total of 5 to 30, preferably 5 to 21 carbon atoms and/or heteroatoms are understood to mean monocyclic, bicyclic or tricyclic heteroaromatics, some of which can be derived from the aforementioned aryl, in which at least one carbon atom in the aryl base structure has been replaced by a heteroatom. Preferred heteroatoms are N, O and S. The base structure of the heteroaryl radicals is especially preferably selected from systems such as pyridine, pyrimidine and pyrazine and five-membered heteroaromatics such as thiophene, pyrrole, imidazole, thiazole, oxazole or furan. These base structures may optionally be fused to one or two six-membered aromatic radicals. Suitable fused heteroaromatics are carbazolyl, benzimidazolyl, benzofuranyl, benzothiazolyl, benzoxazolyl, dibenzofuranyl, dibenzothiophenyl, indolyl or benzimidazo[1,2-a]benzimidazolyl. Particularly preferred base structures are pyridyl, pyrimidyl, pyrazinyl, carbazolyl, dibenzofuranyl, dibenzothiophenyl, indolyl, benzofuranyl and benzothiophenyl.

The base structure may be substituted at one, more than one or all substitutable positions, suitable substituents being the same as those already specified under the definition of $C_6$-$C_{30}$-aryl. Preferred are unsubstituted heteroaryl radicals, having a total of from 5 to 18 carbon atoms and/or heteroatoms, monosubstituted heteroaryl radicals, having a total of from 5 to 18 carbon atoms and/or heteroatoms and disubstituted heteroaryl radicals, having a total of from 5 to 21 carbon atoms and/or heteroatoms.

An alkyl radical in the context of the present application is a linear or branched alkyl radical, optionally interrupted by at least one heteroatom, and having 1 to 20 carbon atoms. Preference is given to $C_1$- to $C_{10}$-alkyl radicals, particular preference to $C_1$- to $C_6$-alkyl radicals. In addition, the alkyl radicals may be unsubstituted or substituted by one or more substituents. Preferred substituents are selected from the group consisting of groups with donor or acceptor action, preferably $C_1$-$C_{20}$-alkoxy, halogen, more preferably F, $C_1$-$C_{20}$-haloalkyl, e.g. $CF_3$; deuterium; a substituted or unsubstituted cycloalkyl radical having a total of from 3 to 30 carbon atoms; a substituted or unsubstituted heterocycle alkyl radical, interrupted by at least one heteroatom, selected from O, S and N, and having a total of from 3 to 30 carbon atoms and/or heteroatoms; a substituted or unsubstituted aryl radical, having a total of from 6 to 30 carbon atoms; or a substituted or an unsubstituted heteroaryl radical, having a total of from 5 to 30 carbon atoms and/or heteroatoms, selected from O, S and N. Suitable aryl substituents are specified above and suitable alkoxy and halogen substituents are specified below. Examples of suitable alkyl groups are methyl, ethyl, propyl, butyl, pentyl, hexyl, heptyl and octyl, and also $C_1$-$C_{20}$-haloalkyl-, $C_6$-$C_{30}$-aryl-, $C_1$-$C_{20}$-alkoxy- and/or halogen-substituted, especially F-substituted, derivatives of the alkyl groups mentioned, for example $CF_3$ or $CF_2CF_3$. This comprises both the n-isomers of the radicals mentioned and branched isomers such as isopropyl, isobutyl, isopentyl, sec-butyl, tert-butyl, iso-butyl, neopentyl, 3,3-dimethylbutyl, 3-ethylhexyl, etc. Preferred alkyl groups are methyl, ethyl, n-propyl, isopropyl, n-butyl, sec-butyl, iso-butyl, tert-butyl, $CF_3$ and $CF_2CF_3$. Most preferred alkyl radicals are $CF_3$, methyl, ethyl, n-propyl, iso-propyl, n-butyl, tert-butyl, sec-butyl and iso-butyl.

A cycloalkyl radical is understood in the context of the present invention to mean a substituted or unsubstituted cycloalkyl radical having 3 to 30 carbon atoms. Preferred are cycloalkyl radicals having 3 to 18, more preferably 3 to 12 and most preferably 3 to 7 carbon atoms in the base structure (ring) to understand. Suitable substituents are the substituents mentioned for the alkyl groups. Examples of suitable cycloalkyl groups, which may be unsubstituted or substituted by the radicals mentioned above for the alkyl groups, are cyclopentyl, cyclohexyl, cycloheptyl, cyclooctyl, cyclononyl and cyclodecyl. They may also be polycyclic ring systems such as decalinyl, norbornyl, bornanyl or adamantyl.

A heterocycle alkyl radical or a substituted or unsubstituted heterocycle alkyl radical having 3 to 30 carbon atoms and/or heteroatoms is understood to mean heterocycle alkyl radicals having 3 to 18, preferably 5 to 10 and more preferably 5 to 8 ring atoms, where at least one carbon atom in the heterocycle alkyl base structure has been replaced by a heteroatom. Preferred heteroatoms are N, O and S. Suitable substituents are the substituents mentioned for the alkyl groups. Examples of suitable heterocycle alkyl groups, which may be unsubstituted or substituted by the radicals mentioned above for the alkyl groups, are radicals derived from the following heterocycles: pyrrolidine, thiolane, tetrahydrofuran, 1,2-oxathiolane, oxazolidine, piperidine, thiane, oxane, dioxane, 1,3-dithiane, morpholine, piperazine. They may also be polycyclic ring systems.

Suitable alkoxy radicals and alkylthio radicals derive correspondingly from the aforementioned alkyl radicals. Examples here include $OCH_3$, $OC_2H_5$, $OC_3H_7$, $OC_4H_9$ and $OC_8H_{17}$, and also $SCH_3$, $SC_2H_5$, $SC_3H_7$, $SC_4H_9$ and $SC_8H_{17}$. In this context, $C_3H_7$, $C_4H_9$ and $C_8H_{17}$ comprise both the n-isomers and branched isomers such as isopropyl, isobutyl, sec-butyl, tert-butyl and 2-ethylhexyl. Particularly preferred alkoxy or alkylthio groups are methoxy, ethoxy, n-octyloxy, 2-ethylhexyloxy and $SCH_3$.

Suitable halogen radicals or halogen substituents in the context of the present application are fluorine, chlorine, bromine and iodine, preferably fluorine, chlorine and bromine, more preferably fluorine and chlorine, most preferably fluorine.

In the context of the present application, groups with donor or acceptor action are understood to mean the following groups:
$C_1$-$C_{20}$-alkoxy, $C_6$-$C_{30}$-aryloxy, $C_1$-$C_{20}$-alkylthio, $C_6$-$C_{30}$-arylthio, $SiR^{10}R^{11}R^{12}$, halogen radicals, halogenated $C_1$-$C_{20}$-alkyl radicals, carbonyl (—CO($R^{32}$)), carbonylthio (—C=O(S$R^{32}$)), carbonyloxy (—C=O(O$R^{32}$)), oxycarbonyl (—OC=O($R^{32}$)), thiocarbonyl (—SC=O($R^{32}$)), amino (—N$R^{32}R^{33}$), OH, pseudohalogen radicals, amido (—C=O(N$R^{32}R^{33}$)), —N$R^{32}$C=O($R^{33}$), phosphonate (—P(O) (O$R^{32}$)$_2$), phosphate (—OP(O) (O$R^{32}$)$_2$), phosphine (—P$R^{32}R^{33}$), phosphine oxide (—P(O)$R^{32}_2$), sulfate (—OS(O)$_2$O$R^{32}$), sulfoxide (—S(O)$R^{32}$), sulfonate (—S(O)$_2$O$R^{32}$), sulfonyl (—S(O)$_2R^{32}$), sulfonamide (—S(O)$_2$N$R^{32}R^{33}$), $NO_2$, boronic esters (—OB(O$R^{32}$)$_2$), imino (—C=N$R^{32}R^{33}$)), borane radicals, stannate radicals, hydrazine radicals, hydrazone radicals, oxime radicals, nitroso groups, diazo groups, vinyl groups, sulfoximines, alanes, germanes, boroxines and borazines.

Preferred substituents with donor or acceptor action are selected from the group consisting of: $C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{10}R^{11}R^{12}$; halogen radicals, preferably F, Cl, Br, more preferably F or Cl, most preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diphenylamino; OH, pseudohalogen radicals, preferably CN, SCN or OCN, more preferably CN, —O(O)O$C_1$-$C_4$-alkyl, preferably —C(O)OMe, P(O)$R_2$, preferably P(O)$Ph_2$, and $SO_2R_2$, preferably $SO_2Ph$.

Very particularly preferred substituents with donor or acceptor action are selected from the group consisting of methoxy, phenyloxy, halogenated $C_1$-$C_4$-alkyl, preferably $CF_3$, $CH_2F$, $CHF_2$, $C_2F_5$, halogen, preferably F, CN, $SiR^{10}R^{11}R^{12}$, where suitable $R^{10}$, $R^{11}$ and $R^{12}$ radicals are specified below, diphenylamino, or —C(O)O$C_1$-$C_4$-alkyl. Even more preferred are OPh, halogen radicals, preferably F or Cl, more preferably F; $CF_3$, CN; or $SiR^{10}R^{11}R^{12}$, preferably $SiMe_3$, $SiPh_3$, $SiEt_3$ or $SiPh_2tBu$.

The aforementioned groups with donor or acceptor action are not intended to rule out the possibility that further radicals and groups among those specified above may also have donor or acceptor action. For example, the aforementioned heteroaryl radicals are likewise groups with donor or acceptor action, and the $C_1$-$C_{20}$-alkyl radicals are groups with donor action.

The $R^{32}$ and $R^{33}$ radicals mentioned are each independently:
Hydrogen, substituted or unsubstituted $C_1$-$C_{20}$-alkyl or substituted or unsubstituted $C_6$-$C_{30}$-aryl or substituted or unsubstituted heteroaryl having 5 to 30 ring atoms, suitable and preferred alkyl and aryl radicals having been specified above. More preferably, the $R^{32}$, $R^{33}$ and $R^{34}$ radicals are $C_1$-$C_6$-alkyl, e.g. methyl, ethyl, i-propyl or tert-butyl, or phenyl or pyridyl, most preferably methyl or phenyl.

The $R^{10}$, $R^{11}$ and $R^{12}$ radicals mentioned are each independently:
a linear or branched alkyl radical, having from 1 to 6 carbon atoms, preferably methyl, ethyl, n-propyl, iso-propyl, n-butyl, tert-butyl, sec-butyl or iso-butyl; a substituted or unsubstituted aryl radical, having from 6 to 18 carbon atoms, preferably phenyl or tolyl; a substituted or unsubstituted heteroaryl radical, having a total of from 5 to 18 carbon atoms and/or heteroatoms; a substituted or unsubstituted cycloalkyl radical having a total of from 3 to 18 carbon atoms, preferably cyclopentyl or cyclohexyl.

Cyclometallated Ir Complex Comprising One, Two or Three Ligands of Formula (I) or (I')

The metal in the cyclometallated Ir complex comprising one, two or three ligands of formula (I) or (I') is preferably Ir(III).

The radicals, groups and symbols in the bidentate ligands of formula (I) and/or (I') of the cyclometallated Ir complex preferably have—independently of each other—the following meanings:

$R^1$, $R^2$, $R^3$, $R^4$ and $R^6$ are each independently hydrogen; deuterium; a linear or branched, substituted or unsubstituted alkyl radical having 1 to 20 carbon atoms, optionally interrupted by at least one heteroatom, selected from O, S and N; a substituted or unsubstituted cycloalkyl radical having a total of from 3 to 30 carbon atom; a substituted or unsubstituted heterocycle alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action; preferably, $R^1$, $R^2$, $R^3$, $R^4$ and $R^6$ are each independently hydrogen, deuterium, a linear or branched, substituted or unsubstituted alkyl radical, having 1 to 6 carbon atoms; an unsubstituted aryl radical, having from 6 to 18 carbon atoms, a monosubstituted aryl radical having from 6 to 18 carbon atoms, a disubstituted aryl radical having from 6 to 21 carbon atoms; an unsubstituted heteroaryl radical, having a total of from 5 to 18 carbon atoms and/or heteroatoms, a monosubstituted heteroaryl radical, having a total of from 5 to 18 carbon atoms and/or heteroatoms, a disubstituted heteroaryl radical, having a total of from 5 to 21 carbon atoms and/or heteroatoms; more preferably, the aryl radical or heteroaryl radical are selected from the group consisting of phenyl, pyridyl, pyrimidyl, pyrazinyl, carbazolyl, dibenzofuranyl, dibenzothiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, methoxy, phenyl or $CF_3$; a group with donor or acceptor action, selected from OPh; halogen radicals, preferably F or Cl, more preferably F; $CF_3$, CN; or $SiR^{10}R^{11}R^{12}$, preferably $SiMe_3$, $SiPh_3$, $SiEt_3$ or $SiPh_2tBu$;

more preferably, $R^1$, $R^2$, $R^3$, $R^4$ and $R^6$ are each independently hydrogen; deuterium; methyl, ethyl, n-propyl, iso-propyl, n-butyl, tert-butyl, sec-butyl, iso-butyl, $OCH_3$, Otertbutyl, $OCF_3$, OPh, OTolyl, OXylyl, $CF_3$, —CN, phenyl, tolyl, xylyl, diisopropylphenyl, triisopropylphenyl, tert-butylphenyl, dimethoxyphenyl, dicyanophenyl, trifluoromethylphenyl, ditrifluoromethylphenyl, pyridyl, methylpyridyl, dimethylpyridyl, diisopropylpyridyl, tertbutylpyridyl, pyrimidyl, pyrazinyl, carbazolyl, dibenzofuranyl, diisopropyldibenzofuranyl, dibenzothiophenyl, diisopropyldibenzothiophenyl, fluorenyl, dimethylfluorenyl, indolyl, methylindolyl, benzofuranyl and benzothiophenyl;

or $R^1$ and $R^2$ or $R^3$ and $R^4$ may form, independently of each other, together with the carbon atoms to which they are bonded, a saturated or unsaturated or aromatic, optionally substituted ring, which is optionally interrupted by at least one heteroatom, selected from O, S and N, has a total of from 5 to 18 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 18 carbon atoms and/or heteroatoms.

$R^{10}$, $R^{11}$, $R^{12}$ are each independently a linear or branched alkyl radical, having from 1 to 6 carbon atoms, preferably methyl, ethyl, n-propyl, iso-propyl, n-butyl, tert-butyl, sec-butyl or iso-butyl; a substituted or unsubstituted aryl radical, having from 6 to 18 carbon atoms, preferably phenyl or tolyl; a substituted or unsubstituted heteroaryl radical, having a total of from 5 to 18 carbon atoms and/or heteroatoms; a substituted or unsubstituted cycloalkyl radical having a total of from 3 to 18 carbon atoms, preferably cyclopentyl or cyclohexyl.

$R^5$ and $R^7$ are each independently a linear or branched, substituted or unsubstituted alkyl radical having 1 to 20 carbon atoms, optionally interrupted by at least one heteroatom, selected from O, S and N; a substituted or unsubstituted aryl radical, having a total of from 6 to 30 carbon atoms; or a substituted or an unsubstituted heteroaryl radical, having a total of from 5 to 30 carbon atoms and/or heteroatoms, selected from O, S and N;

a cycloalkyl radical having a total of from 3 to 30 carbon atoms, optionally substituted by a linear or branched, substituted or unsubstituted alkyl radical, optionally interrupted by at least one heteroatom, selected from O, S and N, and/or at least one of the groups mentioned above concerning the linear or branched alkyl radical; or a heterocycle alkyl radical, interrupted by at least one heteroatom, selected from O, S and N, and having a total of from 3 to 30 carbon atoms and/or heteroatoms, optionally substituted by a linear or branched, substituted or unsubstituted alkyl radical, optionally interrupted by at least one heteroatom, selected from O, S and N, and/or at least one of the groups mentioned above concerning the linear or branched alkyl radical;

preferably, $R^5$ and $R^7$ are each independently a linear or branched, substituted or unsubstituted alkyl radical, having 1 to 6 carbon atoms; a substituted or unsubstituted cycloalkyl radical having a total of from 3 to 12 carbon atoms; an unsubstituted aryl radical, having from 6 to 18 carbon atoms, a monosubstituted aryl radical having from 6 to 18 carbon atoms, a disubstituted aryl radical having from 6 to 21 carbon atoms; an unsubstituted heteroaryl radical, having a total of from 5 to 18 carbon atoms and/or heteroatoms, a monosubstituted heteroaryl radical, having a total of from 5 to 18 carbon atoms and/or heteroatoms, a disubstituted heteroaryl radical, having a total of from 5 to 21 carbon atoms and/or heteroatoms; more preferably, the aryl radical or heteroaryl radical are selected from the group consisting of phenyl, pyridyl, pyrimidyl, pyrazinyl, carbazolyl, dibenzofuranyl, dibenzothiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, methoxy, phenyl or $CF_3$; a group with donor or acceptor action, selected from OPh; halogen radicals, preferably F or Cl, more preferably F; $CF_3$, CN; or $SiR^{10}R^{11}R^{12}$, preferably $SiMe_3$, $SiPh_3$, $SiEt_3$ or $SiPh_2tBu$;

more preferably, $R^5$ and $R^7$ are each independently a linear or branched, substituted or unsubstituted alkyl radical having 1 to 6 carbon atoms, preferably methyl, ethyl, n-propyl, iso-propyl, n-butyl, tert-butyl, sec-butyl, iso-butyl, $OCH_3$, $OCF_3$, $CF_3$, CN; an unsubstituted aryl radical, having from 6 to 18 carbon atoms, a monosubstituted aryl radical having from 6 to 18 carbon atoms, a disubstituted aryl radical having from 6 to 21 carbon atoms; an unsubstituted heteroaryl radical, having a total of from 5 to 18 carbon atoms and/or heteroatoms, a monosubstituted heteroaryl radical, having a total of from 5 to 18 carbon atoms and/or heteroatoms, a disubstituted heteroaryl radical, having a total of from 5 to 21 carbon atoms and/or heteroatoms; more preferably, the aryl radical or heteroaryl radical are selected from the group consisting of phenyl, tolyl, xylyl, diisopropylphenyl, pyridyl, methylpyridyl, carbazolyl, dibenzofuranyl, dibenzothiophenyl, fluorenyl, dimethylfluorenyl, indolyl, methylindolyl, benzofuranyl and benzothiophenyl;
or
$R^5$ and $R^6$ or $R^6$ and $R^7$ may form, independently of each other, together with the carbon atoms to which they are bonded, a saturated or unsaturated or aromatic, optionally substituted ring, which is optionally interrupted by at least one heteroatom, selected from O, S and N, has a total of from 5 to 21 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 21 carbon atoms and/or heteroatoms;
preferably, $R^5$ and $R^6$ or $R^6$ and $R^7$ may form, independently of each other, together with the carbon atoms to which they are bonded, a saturated or unsaturated or aromatic, optionally substituted ring, which is optionally interrupted by at least one heteroatom, selected from O, S and N, has a total of from 5 to 13 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 13 carbon atoms and/or heteroatoms.
X is $CR^8$ or N, preferably CH or N;
Y is $CR^9$ or N, preferably CH or N.
$R^8$ and $R^9$
are each independently hydrogen; deuterium; a linear or branched, substituted or unsubstituted alkyl radical having 1 to 20 carbon atoms, optionally interrupted by at least one heteroatom, selected from O, S and N; a substituted or unsubstituted cycloalkyl radical having a total of from 3 to 30 carbon atom; a substituted or unsubstituted heterocycle alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action;
preferably, $R^8$ and $R^9$ are each independently hydrogen, deuterium, a linear or branched, substituted or unsubstituted alkyl radical, having 1 to 6 carbon atoms; an unsubstituted aryl radical, having from 6 to 21 carbon atoms, a monosubstituted aryl radical having from 6 to 21 carbon atoms, a disubstituted aryl radical having from 6 to 21 carbon atoms; an unsubstituted heteroaryl radical, having a total of from 5 to 21 carbon atoms and/or heteroatoms, a monosubstituted heteroaryl radical, having a total of from 5 to 21 carbon atoms and/or heteroatoms, a disubstituted heteroaryl radical, having a total of from 5 to 21 carbon atoms and/or heteroatoms; more preferably, the aryl radical or heteroaryl radical are selected from the group consisting of phenyl, pyridyl, pyrimidyl, pyrazinyl, carbazolyl, dibenzofuranyl, dibenztthiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, methoxy, phenyl, $CF_3$ or CN; a group with donor or acceptor action, selected from halogen radicals, preferably F or Cl, more preferably F; $CF_3$, CN; or $SiR^{10}R^{11}R^{12}$, preferably $SiMe_3$, $SiPh_3$, $SiEt_3$ or $SiPh_2tBu$.
~ is the bonding site to the metal.
According to the invention, the carbene ligands of formulae (I) and (I')

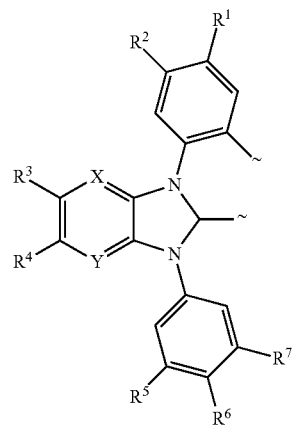

(I)

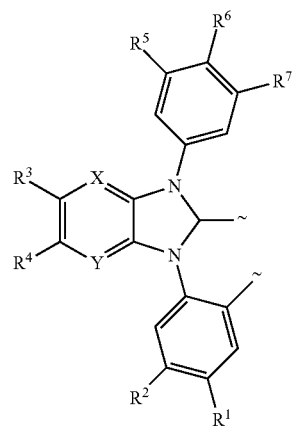

(I')

in the cyclometallated Ir complex are monoanionic bidentate ligands.

Examples for preferred carbene ligands of formulae (I) and (I') are:

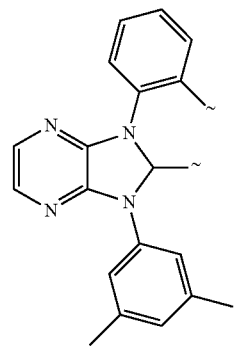

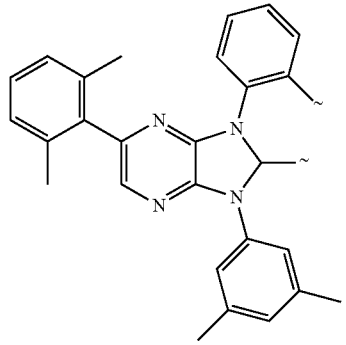
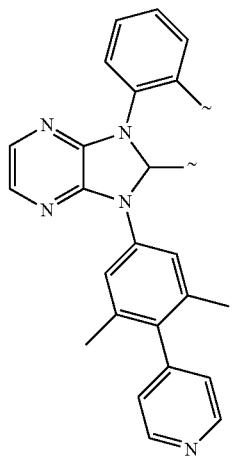
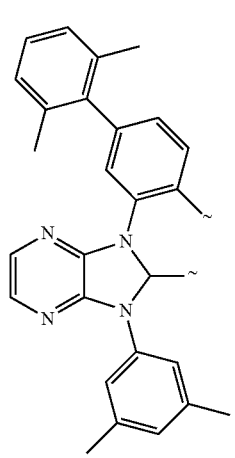
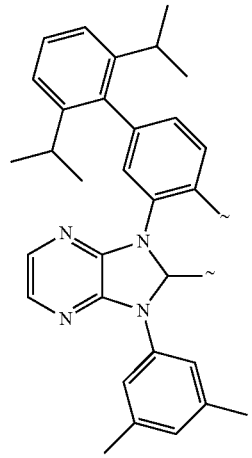
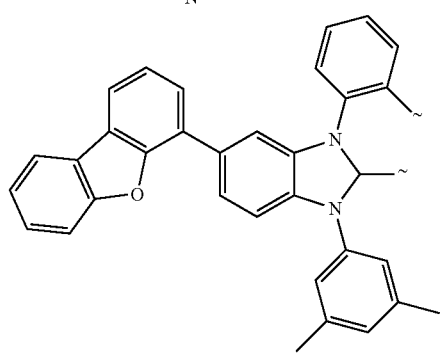
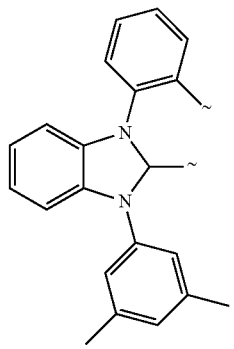
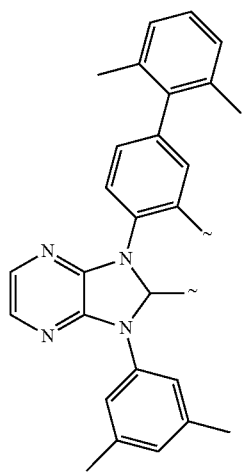
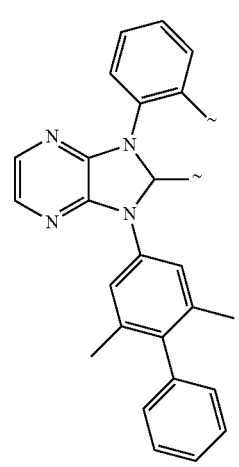
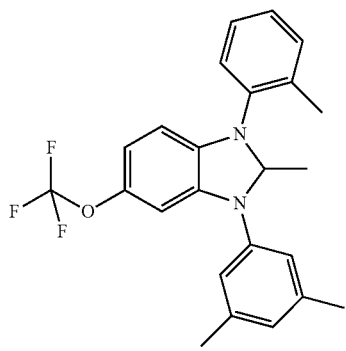
More preferably, the cyclometallated Ir complex comprising one, two or three ligands of formula (I) or (I') has one of the following formulae (II), (II') or (II''):

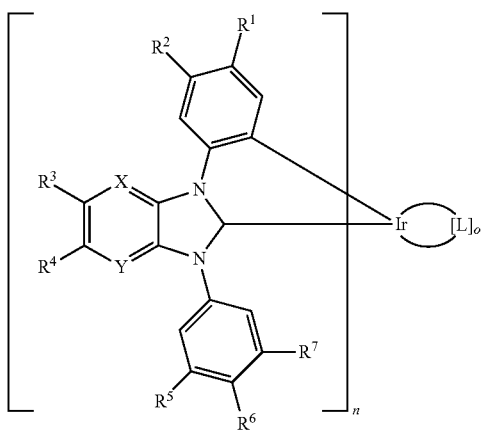

(II)

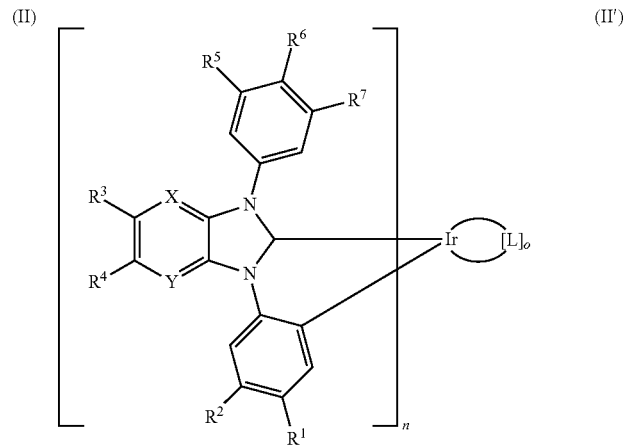

(II')

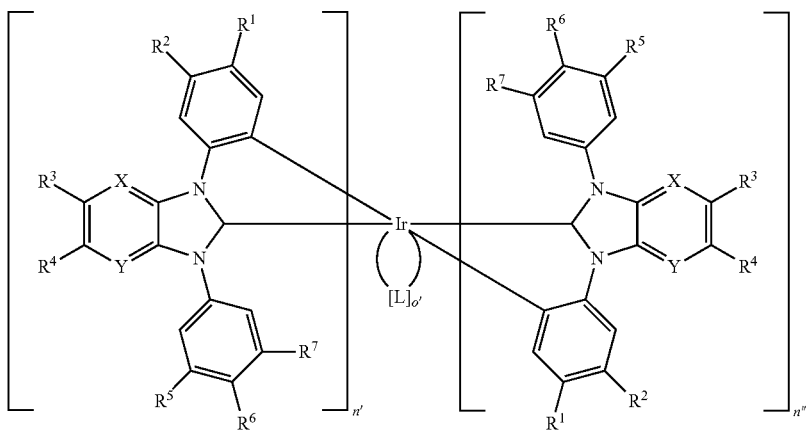

(II")

wherein $R^1$, $R^2$, $R^3$, $R^4$ and $R^6$ are each independently hydrogen; deuterium; a linear or branched, substituted or unsubstituted alkyl radical having 1 to 20 carbon atoms, optionally interrupted by at least one heteroatom, selected from O, S and N; a substituted or unsubstituted cycloalkyl radical having a total of from 3 to 30 carbon atom; a substituted or unsubstituted heterocycle alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action; preferably, $R^1$, $R^2$, $R^3$, $R^4$ and $R^6$ are each independently hydrogen, deuterium, a linear or branched, substituted or unsubstituted alkyl radical, having 1 to 6 carbon atoms; an unsubstituted aryl radical, having from 6 to 21 carbon atoms, a monosubstituted aryl radical having from 6 to 21 carbon atoms, a disubstituted aryl radical having from 6 to 21 carbon atoms; an unsubstituted heteroaryl radical, having a total of from 5 to 21 carbon atoms and/or heteroatoms, a monosubstituted heteroaryl radical, having a total of from 5 to 21 carbon atoms and/or heteroatoms, a disubstituted heteroaryl radical, having a total of from 5 to 21 carbon atoms and/or heteroatoms; more preferably, the aryl radical or heteroaryl radical are selected from the group consisting of phenyl, pyridyl, pyrimidyl, pyrazinyl, carbazolyl, dibenzofuranyl, dibenzothiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, methoxy, phenyl or $CF_3$; a group with donor or acceptor action, selected from OPh; halogen radicals, preferably F or Cl, more preferably F; $CF_3$, CN; or $SiR^{10}R^{11}R^{12}$, preferably $SiMe_3$, $SiPh_3$, $SiEt_3$ or $SiPh_2tBu$;

$R^{10}$, $R^{11}$, $R^{12}$ are each independently a linear or branched alkyl radical, having from 1 to 6 carbon atoms, preferably methyl, ethyl, n-propyl, iso-propyl, n-butyl, tert-butyl, sec-butyl or iso-butyl; a substituted or unsubstituted aryl radical, having from 6 to 18 carbon atoms, preferably phenyl or tolyl; a substituted or unsubstituted heteroaryl radical, having a total of from 5 to 18 carbon atoms and/or heteroatoms; a substituted or unsubstituted cycloalkyl radical having a total of from 3 to 18 carbon atoms, preferably cyclopentyl or cyclohexyl;

or $R^1$ and $R^2$ or $R^3$ and $R^4$ may form, independently of each other, together with the carbon atoms to which they are bonded, a saturated or unsaturated or aromatic, optionally substituted ring, which is optionally interrupted by at least one heteroatom, selected from O, S and N, has a total of from 5 to 21 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 21 carbon atoms and/or heteroatoms R⁵ and R⁷
are each independently a linear or branched, substituted or unsubstituted alkyl radical having 1 to 20 carbon atoms, optionally interrupted by at least one heteroatom, selected from O, S and N; a substituted or unsubstituted aryl radical, having a total of from 6 to 30 carbon atoms; or a substituted or an unsubstituted heteroaryl radical, having a total of from 5 to 30 carbon atoms and/or heteroatoms, selected from O, S and N;
a cycloalkyl radical having a total of from 3 to 30 carbon atoms, optionally substituted by a linear or branched, substituted or unsubstituted alkyl radical, optionally interrupted by at least one heteroatom, selected from O, S and N, and/or at least one of the groups mentioned above concerning the linear or branched alkyl radical; or
a heterocycle alkyl radical, interrupted by at least one heteroatom, selected from O, S and N, and having a total of from 3 to 30 carbon atoms and/or heteroatoms, optionally substituted by a linear or branched, substituted or unsubstituted alkyl radical, optionally interrupted by at least one heteroatom, selected from O, S and N, and/or at least one of the groups mentioned above concerning the linear or branched alkyl radical;
preferably, R⁵ and R⁷ are each independently a linear or branched, substituted or unsubstituted alkyl radical, having 1 to 6 carbon atoms; a substituted or unsubstituted cycloalkyl radical having a total of from 3 to 12 carbon atoms; an unsubstituted aryl radical, having from 6 to 18 carbon atoms, a monosubstituted aryl radical having from 6 to 18 carbon atoms, a disubstituted aryl radical having from 6 to 21 carbon atoms; an unsubstituted heteroaryl radical, having a total of from 5 to 18 carbon atoms and/or heteroatoms, a monosubstituted heteroaryl radical, having a total of from 5 to 18 carbon atoms and/or heteroatoms, a disubstituted heteroaryl radical, having a total of from 5 to 21 carbon atoms and/or heteroatoms; more preferably, the aryl radical or heteroaryl radical are selected from the group consisting of phenyl, pyridyl, pyrimidyl, pyrazinyl, carbazolyl, dibenzofuranyl, dibenztthiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, methoxy, phenyl or CF₃; a group with donor or acceptor action, selected from OPh; halogen radicals, preferably F or Cl, more preferably F; CF₃, CN; or SiR¹⁰R¹¹R¹², preferably SiMe₃, SiPh₃, SiEt₃ or SiPh₂tBu;
or
R⁵ and R⁶ or R⁶ and R⁷ may form, independently of each other, together with the carbon atoms to which they are bonded, a saturated or unsaturated or aromatic, optionally substituted ring, which is optionally interrupted by at least one heteroatom, selected from O, S and N, has a total of from 5 to 18 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 18 carbon atoms and/or heteroatoms;
X is CR⁸ or N;
Y is CR⁹ or N;
R⁸ and R⁹
are each independently hydrogen; deuterium; a linear or branched, substituted or unsubstituted alkyl radical having 1 to 20 carbon atoms, optionally interrupted by at least one heteroatom, selected from O, S and N; a substituted or unsubstituted cycloalkyl radical having a total of from 3 to 30 carbon atom; a substituted or unsubstituted heterocycle alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action;
preferably, R⁸ and R⁹ are each independently hydrogen, deuterium, a linear or branched, substituted or unsubstituted alkyl radical, having 1 to 6 carbon atoms; an unsubstituted aryl radical, having from 6 to 21 carbon atoms, a monosubstituted aryl radical having from 6 to 21 carbon atoms, a disubstituted aryl radical having from 6 to 21 carbon atoms; an unsubstituted heteroaryl radical, having a total of from 5 to 21 carbon atoms and/or heteroatoms, a monosubstituted heteroaryl radical, having a total of from 5 to 21 carbon atoms and/or heteroatoms, a disubstituted heteroaryl radical, having a total of from 5 to 21 carbon atoms and/or heteroatoms; more preferably, the aryl radical or heteroaryl radical are selected from the group consisting of phenyl, pyridyl, pyrimidyl, pyrazinyl, carbazolyl, dibenzofuranyl, dibenzothiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, methoxy, phenyl, CF₃ or CN; a group with donor or acceptor action, selected from halogen radicals, preferably F or Cl, more preferably F; CF₃, CN; or SiR¹⁰R¹¹R¹², preferably SiMe₃, SiPh₃, SiEt₃ or SiPh₂tBu;
n is 1, 2 or 3, preferably 3;
L is a monoanionic bidentate ligand,
o is 0, 1 or 2, where, when o=2, the L ligands may be the same or different, preferably 0;
n' is 1 or 2;
n" is 1 or 2;
wherein the sum of n'+n" is 2 or 3, preferably 3;
o' is 0 or 1, preferably 0;
wherein the sum of n+o in formulae (II) and (II') and the sum of n'+n"+o' in formula (II") is 3, with the proviso that n in formula (II) and (II') is at least 1 and n', as well as n" in formula (II") are at least 1.

The carbene ligands in the cyclometallated Ir complexes of formulae (II), (II') and (II") are monoanionic bidentate ligands.

The carbene ligands in the cyclometallated Ir complexes of formulae (II), (II') and (II") correspond to the carbene ligands of formulae (I) and (I') mentioned above.

Preferred definitions mentioned concerning the radicals and groups R¹, R², R³, R⁴, R⁶, R⁵, R⁷, X and Y in the carbene ligands of formulae (I) and (I') mentioned above are also preferred definitions concerning said radicals and groups in the cyclometallated Ir complexes of formulae (II), (II') and (II").

A bidentate ligand is understood to mean a ligand coordinated at two sites to the transition metal atom M.

Suitable monoanionic bidentate ligands L are preferably selected from the group of ligands (A), (B) and (C). Ligands (A), (B) and (C) are mentioned below:

Ligands of the formula (A):

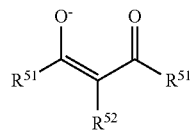

(A)

in which
R$^{51}$ is in each case independently a linear or branched alkyl radical having 1 to 6 carbons atoms, preferably methyl, ethyl, isopropyl or tert-butyl; a substituted or unsubstituted aryl radical having 6 to 18 carbon atoms, preferably an unsubstituted phenyl or 2,6-dialkylphenyl; a substituted or unsubstituted heteroaryl radical having a total of 5 to 18 carbon atoms and/or heteroatoms, R$^{52}$ is hydrogen; a linear or branched alkyl radical having 1 to 6 carbon atoms; a substituted or unsubstituted aryl radical having 6 to 18 carbon atoms; preferably hydrogen or 2,6-dimethylphenyl;

where the ligand of the formula (A) is preferably acetylacetonato.

Ligands of the formula (B):

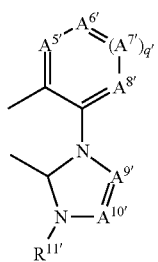

(B)

where
A$^{9'}$ is CR$^{12'}$ or N;
A$^{10'}$ is CR$^{13'}$ or N;
R$^{11'}$ is a linear or branched, substituted or unsubstituted alkyl radical having 1 to 20 carbon atoms, optionally interrupted by at least one heteroatom, selected from O, S and N; a substituted or unsubstituted cycloalkyl radical having 3 to 18 carbon atoms; a substituted or unsubstituted heterocycloalkyl radical interrupted by at least one heteroatom, selected from O, S and N, and having 3 to 18 carbon atoms and/or heteroatoms; a substituted or unsubstituted aryl radical having 6 to 30 carbon atoms, a substituted or unsubstituted heteroaryl radical interrupted by at least one heteroatom, selected from O, S and N and having a total of 5 to 30 carbon atoms and/or heteroatoms;

R$^{12'}$, R$^{13'}$ are each independently hydrogen; deuterium; a linear or branched, substituted or unsubstituted alkyl radical having 1 to 20 carbon atoms, optionally interrupted by at least one heteroatom, selected from O, S and N; a substituted or unsubstituted cycloalkyl radical having 3 to 18 carbon atoms; a substituted or unsubstituted heterocyclealkyl radical interrupted by at least one heteroatom, selected from O, S and N, and having 3 to 18 carbon atoms and/or heteroatoms; a substituted or unsubstituted aryl radical having 6 to 30 carbon atoms; a substituted or unsubstituted heteroaryl radical interrupted by at least one heteroatom, selected from O, S and N and having a total of 5 to 30 carbon atoms and/or heteroatoms; or a group with donor or acceptor action;

if A$^{9'}$ is CR$^{12'}$ and A$^{10'}$ is CR$^{13'}$, CR$^{12'}$ and CR$^{13'}$ together may form, a saturated or unsaturated or aromatic, optionally substituted ring, which is optionally interrupted by at least one heteroatom, selected from O, S and N, has a total of from 5 to 18 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 18 carbon atoms and/or heteroatoms;

A$^{5'}$ is CR$^{14'}$ or N; preferably CR$^{14'}$;
A$^{6'}$ is CR$^{15'}$ or N; preferably CR$^{15'}$;
A$^{7'}$ is CR$^{16'}$ or N; preferably CR$^{16'}$;
A$^{8'}$ is CR$^{17'}$ or N; preferably CR$^{17'}$;
R$^{14'}$, R$^{15'}$, R$^{16'}$, R$^{17'}$ are each independently hydrogen; deuterium; a linear or branched, substituted or unsubstituted alkyl radical having 1 to 20 carbon atoms, optionally interrupted by at least one heteroatom, selected from O, S and N; a substituted or unsubstituted cycloalkyl radical having 3 to 18 carbon atoms; a substituted or unsubstituted heterocyclealkyl radical interrupted by at least one heteroatom, selected from O, S and N, and having 3 to 18 carbon atoms and/or heteroatoms; a substituted or unsubstituted aryl radical having 6 to 30 carbon atoms; a substituted or unsubstituted heteroaryl radical interrupted by at least one heteroatom, selected from O, S and N and having a total of 5 to 30 carbon atoms and/or heteroatoms; or a group with donor or acceptor action;
or
R$^{14'}$ and R$^{15'}$, R$^{15'}$ and R$^{16'}$ or R$^{16'}$ and R$^{17'}$ may form, together with the carbon atoms to which they are bonded, a saturated or unsaturated or aromatic, optionally substituted ring, which is optionally interrupted by at least one heteroatom, selected from O, S and N, has a total of from 5 to 18 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 18 carbon atoms and/or heteroatoms;
or
if A$^{9'}$ is CR$^{12'}$, R$^{12'}$ and R$^{17'}$ together may form a saturated or unsaturated, linear or branched bridge optionally comprising heteroatoms, selected from O, S and N, to which is optionally fused a substituted or unsubstituted, five- to eight-membered ring comprising carbon atoms and/or heteroatoms, and which are optionally substituted with aromatic units, heteroaromatic units or groups with donor or acceptor action;
q' is 0 or 1.

More preferred ligands of formula (B) are:

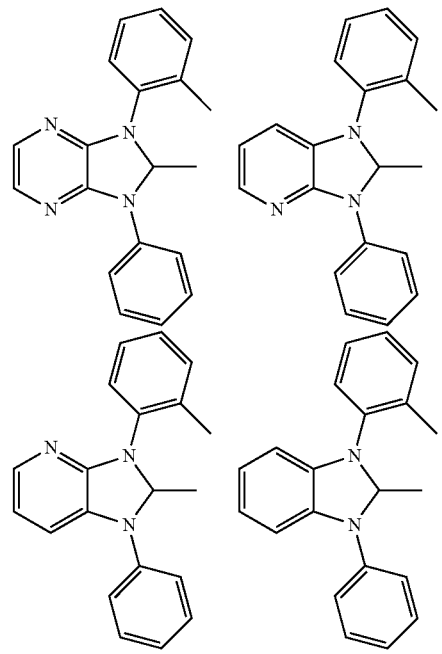

A most preferred ligand of formula (B) is:

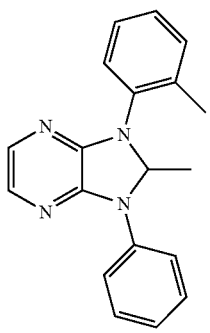 [SMILES: Cc1ccccc1N1c2nccnc2N(c2ccccc2)C1C]

Ligands of Formula (C):

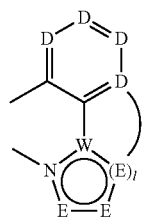
(C)

in which the symbols are each defined as follows:
D are each independently $CR^{34''''}$ or N;
W is C or N;
E are each independently $CR^{35''''}$, N, $NR^{36''''}$ or O;
l is 1 or 2;

$R^{34''''}$, $R^{35''''}$, $R^{36''''}$
  are each independently hydrogen; alkyl; aryl or heteroaryl;
  or
  in each case two $R^{34''''}$, $R^{35''''}$ or $R^{36''''}$ radicals together form a fused ring which may optionally comprise at least one heteroatom;
  or
  $R^{34''''}$, $R^{35''''}$, $R^{36''''}$ or $R^{37''''}$ is a radical having donor or acceptor action;
  where the dotted line means an optional bridge between one of the D groups and one of the E groups; where the bridge may be defined as follows:
  alkylene, arylene, heteroarylene, alkynylene, alkenylene, $NR^{38''''}$, O, S, $SiR^{41''''}R^{42''''}$, CO, CO—O, O—CO and $(CR^{43''''}R^{44''''})_v$, where one or more nonadjacent $(CR^{43''''}R^{44''''})$ groups may be replaced by $NR^{38''''}$, O, S, $SiR^{41''''}R^{42''''}$, CO, CO—O or O—CO, where
  v is from 2 to 10;
  and
  $R^{38''''}$, $R^{41''''}$, $R^{42''''}$, $R^{43''''}$, $R^{44''''}$
  are each H, alkyl, aryl or heteroaryl.

Preferred ligands L in the Ir complexes of formulae (II), (II') and (II'') are ligands (B). Therefore, in a preferred embodiment, the cyclometallated Ir complexes of formulae (II), (II') and (II''), exclusively have carbene ligands.

Preferably, o in the metal-carbene complexes of the formulae (II) and (II') is 0 and o' in the metal-carbene complexes of the formula (II'') is 0. In this case, n in formulae (II) and (II') is preferably 3 and n' and n'' in formula (II'') are 1 or 2, wherein the sum of n' and n'' is 3.

The n carbene ligands may each be the same or different in the cyclometallated Ir complexes of the general formulae (II), (II') and (II''). They are preferably the same.

Preferred cyclometallated Ir complexes of formulae (II), (II') and (II'') are:
Compounds of the Following Formulae

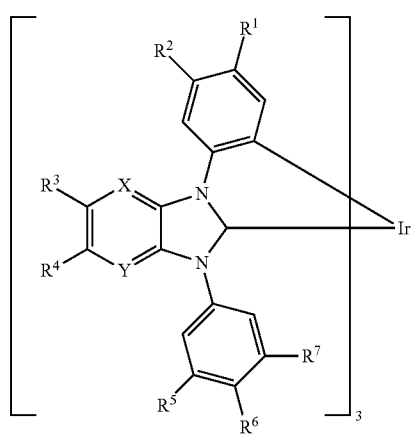 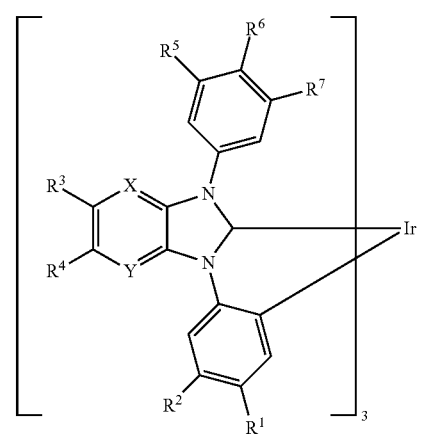

-continued

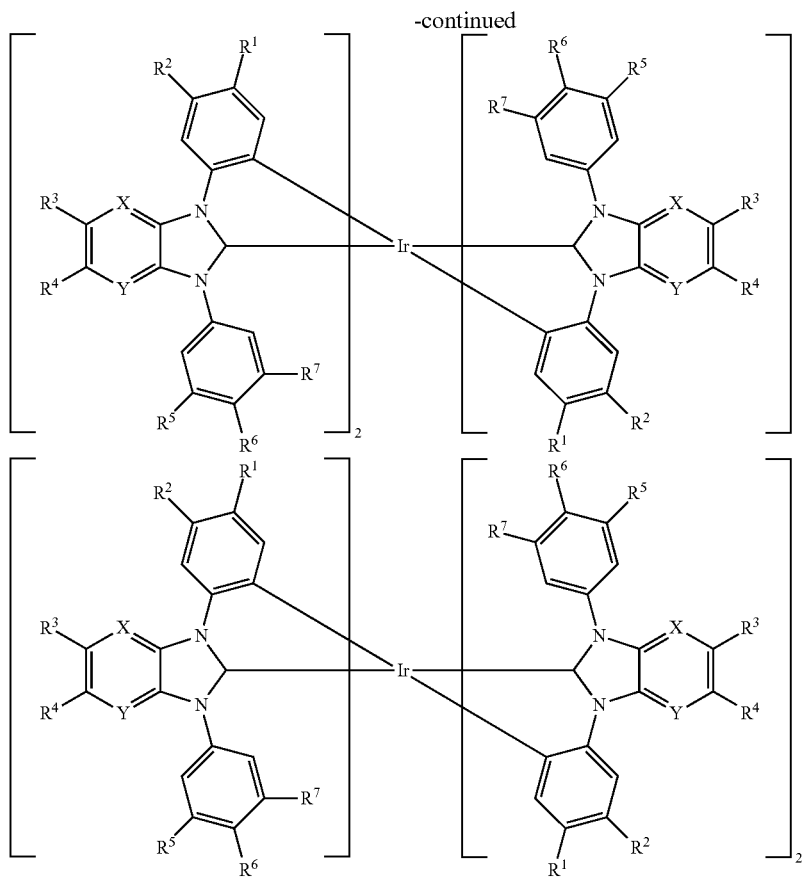

wherein the radicals and groups R¹, R², R³, R⁴, R⁶, R⁵, R⁷, X and Y have the following meanings:

| Cpd. | X | Y | R⁷ | R⁶ | R⁵ | R⁴ | R³ | R² | R¹ |
|---|---|---|---|---|---|---|---|---|---|
| A-1 | N | N | —CH₃ | H | —CH₃ | H | H | H | H |
| A-2 | N | N | —CH₂CH₃ | H | —CH₂CH₃ | H | H | H | H |
| A-3 | N | N | iso-propyl | H | iso-propyl | H | H | H | H |
| A-4 | N | N | iso-butyl | H | iso-butyl | H | H | H | H |
| A-5 | N | N | neopentyl | H | neopentyl | H | H | H | H |
| A-6 | N | N | cyclopentyl | H | cyclopentyl | H | H | H | H |
| A-7 | N | N | cyclohexyl | H | cyclohexyl | H | H | H | H |
| A-8 | N | N | tert-butyl | H | tert-butyl | H | H | H | H |
| A-9 | N | N | —CH₃ | 2-methoxyphenyl | | H | H | H | H |
| A-10 | N | N | —CH₃ | phenyl | —CH₃ | H | H | H | H |
| A-11 | N | N | —CH₃ | 4-pyridyl | —CH₃ | H | H | H | H |

-continued
| Cpd. | X | Y | R⁷ | R⁶ | R⁵ | R⁴ | R³ | R² | R¹ |
|---|---|---|---|---|---|---|---|---|---|
| A-12 | N | N | —CH₃ | H | —CH₃ | 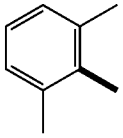 | H | H | H |
| A-13 | N | N | —CH₃ | H | —CH₃ | H | 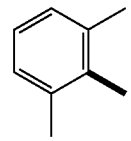 | H | H |
| A-14 | N | N | —CH₃ | H | —CH₃ | 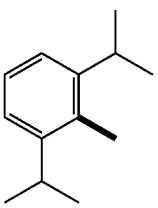 | H | H | H |
| A-15 | N | N | —CH₃ | H | —CH₃ | H | 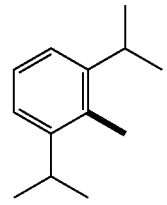 | H | H |
| A-16 | N | N | —CH₃ | H | —CH₃ | 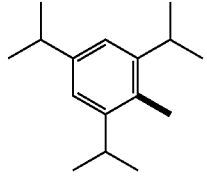 | H | H | H |
| A-17 | N | N | —CH₃ | H | —CH₃ | H | 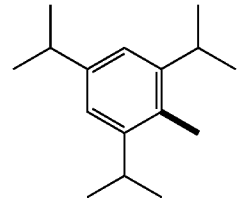 | H | H |
| A-18 | N | N | —CH₃ | H | —CH₃ | 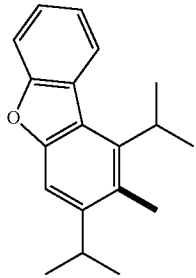 | H | H | H |

-continued

| Cpd. | X | Y | R⁷ | R⁶ | R⁵ | R⁴ | R³ | R² | R¹ |
|---|---|---|---|---|---|---|---|---|---|
| A-19 | N | N | —CH₃ | H | —CH₃ | H | (1-isopropyl-2-methyl-3-isopropyl dibenzofuranyl) | H | H |
| A-20 | N | N | —CH₃ | H | —CH₃ | (2-methyl-3-isopropyl-4-isopropyl dibenzofuranyl) | | H | H |
| A-21 | N | N | —CH₃ | H | —CH₃ | H | (2-isopropyl-3-methyl-4-isopropyl dibenzofuranyl) | H | H |
| A-22 | N | N | —CH₃ | H | —CH₃ | (1-isopropyl-2-isopropyl-4-methyl dibenzofuranyl) | | H | H |
| A-23 | N | N | —CH₃ | H | —CH₃ | H | (1-methyl-2-isopropyl-4-isopropyl dibenzofuranyl) | H | H |
| A-24 | N | N | —CH₂CH₃ | H | —CH₂CH₃ | (2,3-dimethylphenyl) | | H | H |
| A-25 | N | N | —CH₂CH₃ | H | —CH₂CH₃ | H | (2,3-dimethylphenyl) | H | H |

-continued

| Cpd. | X | Y | R⁷ | R⁶ | R⁵ | R⁴ | R³ | R² | R¹ |
|---|---|---|---|---|---|---|---|---|---|
| A-26 | N | N | —CH₂CH₃ | H | —CH₂CH₃ | 2,6-diisopropylphenyl | H | H | H |
| A-27 | N | N | —CH₂CH₃ | H | —CH₂CH₃ | H | 2,6-diisopropylphenyl | H | H |
| A-28 | N | N | —CH₂CH₃ | H | —CH₂CH₃ | 2,4,6-triisopropylphenyl | H | H | H |
| A-29 | N | N | —CH₂CH₃ | H | —CH₂CH₃ | H | 2,4,6-triisopropylphenyl | H | H |
| A-30 | N | N | —CH₂CH₃ | H | —CH₂CH₃ | (1,3-diisopropyldibenzofuran-2-yl) | H | H | H |
| A-31 | N | N | —CH₂CH₃ | H | —CH₂CH₃ | H | (1,3-diisopropyldibenzofuran-2-yl) | H | H |
| A-32 | N | N | —CH₂CH₃ | H | —CH₂CH₃ | (1,3-diisopropyldibenzofuran-2-yl) | H | H | H |

-continued

| Cpd. | X | Y | R⁷ | R⁶ | R⁵ | R⁴ | R³ | R² | R¹ |
|---|---|---|---|---|---|---|---|---|---|
| A-33 | N | N | —CH₂CH₃ | H | —CH₂CH₃ | H | (dibenzofuran with methyl and two isopropyl substituents) | H | H |
| A-34 | N | N | —CH₂CH₃ | H | —CH₂CH₃ | (dibenzofuran with methyl and two isopropyl substituents) | | H | H |
| A-35 | N | N | —CH₂CH₃ | H | —CH₂CH₃ | H | (dibenzofuran with methyl and two isopropyl substituents) | H | H |
| A-36 | N | N | iso-propyl | H | iso-propyl | (2,3-dimethylphenyl) | | H | H |
| A-37 | N | N | iso-propyl | H | iso-propyl | H | (2,3-dimethylphenyl) | H | H |
| A-38 | N | N | iso-propyl | H | iso-propyl | (2,6-diisopropylphenyl with methyl) | | H | H |
| A-39 | N | N | iso-propyl | H | iso-propyl | H | (2,6-diisopropylphenyl with methyl) | H | H |

-continued

| Cpd. | X | Y | R⁷ | R⁶ | R⁵ | R⁴ | R³ | R² | R¹ |
|---|---|---|---|---|---|---|---|---|---|
| A-40 | N | N | iso-propyl | H | iso-propyl | ![2,4,6-triisopropylphenyl] | H | H | H |
| A-41 | N | N | iso-propyl | H | iso-propyl | H | ![2,4,6-triisopropylphenyl] | H | H |
| A-42 | N | N | iso-propyl | H | iso-propyl | ![dibenzofuranyl with iPr, Me, iPr] | H | H | H |
| A-43 | N | N | iso-propyl | H | iso-propyl | H | ![dibenzofuranyl with iPr, Me, iPr] | H | H |
| A-44 | N | N | iso-propyl | H | iso-propyl | ![dibenzofuranyl with iPr, Me, iPr] | H | H | H |
| A-45 | N | N | iso-propyl | H | iso-propyl | H | ![dibenzofuranyl with iPr, Me, iPr] | H | H |

-continued
| Cpd. | X | Y | R⁷ | R⁶ | R⁵ | R⁴ | R³ | R² | R¹ |
|---|---|---|---|---|---|---|---|---|---|
| A-46 | N | N | iso-propyl | H | iso-propyl | 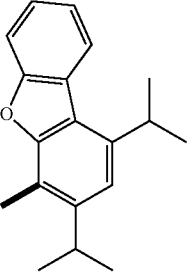 | H | H | H |
| A-47 | N | N | iso-propyl | H | iso-propyl | H | 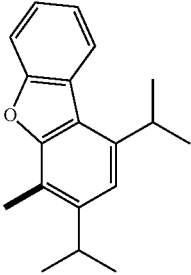 | H | H |
| A-48 | N | N | tert-butyl | H | tert-butyl | 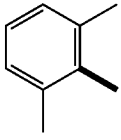 | H | H | H |
| A-49 | N | N | tert-butyl | H | tert-butyl | H | 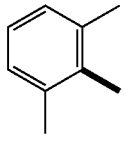 | H | H |
| A-50 | N | N | tert-butyl | H | tert-butyl | 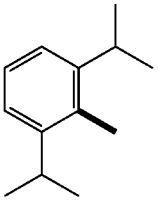 | H | H | H |
| A-51 | N | N | tert-butyl | H | tert-butyl | H | 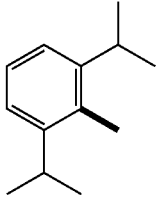 | H | H |
| A-52 | N | N | tert-butyl | H | tert-butyl | 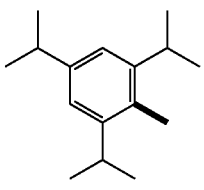 | H | H | H |

-continued

| Cpd. | X | Y | R⁷ | R⁶ | R⁵ | R⁴ | R³ | R² | R¹ |
|---|---|---|---|---|---|---|---|---|---|
| A-53 | N | N | tert-butyl | H | tert-butyl | H | ![2,4,6-triisopropylphenyl with methyl] | H | H |
| A-54 | N | N | tert-butyl | H | tert-butyl | ![dibenzofuran substituent] | H | H | H |
| A-55 | N | N | tert-butyl | H | tert-butyl | H | ![dibenzofuran substituent] | H | H |
| A-56 | N | N | tert-butyl | H | tert-butyl | ![dibenzofuran substituent] | H | H | H |
| A-57 | N | N | tert-butyl | H | tert-butyl | H | ![dibenzofuran substituent] | H | H |
| A-58 | N | N | tert-butyl | H | tert-butyl | ![dibenzofuran substituent] | H | H | H |

-continued

| Cpd. | X | Y | R⁷ | R⁶ | R⁵ | R⁴ | R³ | R² | R¹ |
|---|---|---|---|---|---|---|---|---|---|
| A-59 | N | N | tert-butyl | H | tert-butyl | H | *dibenzofuran with methyl and two isopropyl substituents* | H | H |
| A-60 | N | N | —CH₃ | H | —CH₃ | *2,3-dimethylphenyl* | H | H | H |
| A-61 | N | N | —CH₃ | H | —CH₃ | H | *2,3-dimethylphenyl* | H | H |
| A-62 | N | N | —CH₃ | H | —CH₃ | *2,6-diisopropyl-phenyl* (with methyl) | H | H | H |
| A-63 | N | N | —CH₃ | H | —CH₃ | H | *2,6-diisopropyl-phenyl* (with methyl) | H | H |
| A-64 | N | N | —CH₃ | H | —CH₃ | *2,4,6-triisopropylphenyl* (with methyl) | H | H | H |
| A-65 | N | N | —CH₃ | H | —CH₃ | H | *2,4,6-triisopropylphenyl* (with methyl) | H | H |

-continued

| Cpd. | X | Y | R⁷ | R⁶ | R⁵ | R⁴ | R³ | R² | R¹ |
|---|---|---|---|---|---|---|---|---|---|
| A-66 | N | N | —CH₃ | H | —CH₃ | (dibenzofuran with iPr, Me, iPr substituents) | H | H | H |
| A-67 | N | N | —CH₃ | H | —CH₃ | H | (dibenzofuran with iPr, Me, iPr substituents) | H | H |
| A-68 | N | N | —CH₃ | H | —CH₃ | (dibenzofuran with iPr, Me, iPr substituents) | H | H | H |
| A-69 | N | N | —CH₃ | H | —CH₃ | H | (dibenzofuran with iPr, Me, iPr substituents) | H | H |
| A-70 | N | N | —CH₃ | H | —CH₃ | (dibenzofuran with Me, iPr substituents) | H | H | H |
| A-71 | N | N | —CH₃ | H | —CH₃ | H | (dibenzofuran with Me, iPr substituents) | H | H |

-continued

| Cpd. | X | Y | R⁷ | R⁶ | R⁵ | R⁴ | R³ | R² | R¹ |
|---|---|---|---|---|---|---|---|---|---|
| A-72 | N | CH | —CH₃ | H | —CH₃ | H | H | H | H |
| A-73 | N | CH | —CH₂CH₃ | H | —CH₂CH₃ | H | H | H | H |
| A-74 | N | CH | iso-propyl | H | iso-propyl | H | H | H | H |
| A-75 | N | CH | iso-butyl | H | iso-butyl | H | H | H | H |
| A-76 | N | CH | neopentyl | H | neopentyl | H | H | H | H |
| A-77 | N | CH | cyclopentyl | H | cyclopentyl | H | H | H | H |
| A-78 | N | CH | cyclohexyl | H | cyclohexyl | H | H | H | H |
| A-79 | N | CH | tert-butyl | H | tert-butyl | H | H | H | H |
| A-80 | N | CH | —CH₃ | 2-methoxy-phenyl (ortho-methyl) | H | H | H | H |  |
| A-81 | N | CH | —CH₃ | phenyl | —CH₃ | H | H | H | H |
| A-82 | N | CH | —CH₃ | 4-pyridyl | —CH₃ | H | H | H | H |
| A-83 | N | CH | —CH₃ | H | —CH₃ | 2,3-dimethylphenyl | H | H | H |
| A-84 | N | CH | —CH₃ | H | —CH₃ | H | 2,3-dimethylphenyl | H | H |
| A-85 | N | CH | —CH₃ | H | —CH₃ | 2,6-di-iso-propylphenyl | H | H | H |
| A-86 | N | CH | —CH₃ | H | —CH₃ | H | 2,6-di-iso-propylphenyl | H | H |
| A-87 | N | CH | —CH₃ | H | —CH₃ | 2,4,6-tri-iso-propylphenyl | H | H | H |

-continued

| Cpd. | X | Y | R⁷ | R⁶ | R⁵ | R⁴ | R³ | R² | R¹ |
|---|---|---|---|---|---|---|---|---|---|
| A-88 | N | CH | —CH₃ | H | —CH₃ | H | 2,4,6-triisopropylphenyl | H | H |
| A-89 | N | CH | —CH₃ | H | —CH₃ | 1,3-diisopropyl-2-methyl-dibenzofuranyl | | H | H |
| A-90 | N | CH | —CH₃ | H | —CH₃ | H | 1,3-diisopropyl-2-methyl-dibenzofuranyl | H | H |
| A-91 | N | CH | —CH₃ | H | —CH₃ | 1,3-diisopropyl-2-methyl-dibenzofuranyl (isomer) | | H | H |
| A-92 | N | CH | —CH₃ | H | —CH₃ | H | 1,3-diisopropyl-2-methyl-dibenzofuranyl (isomer) | H | H |
| A-93 | N | CH | —CH₃ | H | —CH₃ | substituted dibenzofuranyl | | H | H |

-continued
| Cpd. | X | Y | R⁷ | R⁶ | R⁵ | R⁴ | R³ | R² | R¹ |
|---|---|---|---|---|---|---|---|---|---|
| A-94 | N | CH | —CH₃ | H | —CH₃ | H | 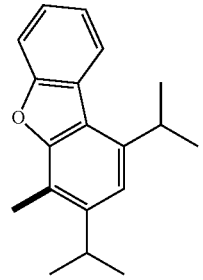 | H | H |
| A-95 | N | CH | —CH₂CH₃ | H | —CH₂CH₃ | 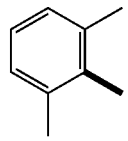 | | H | H |
| A-96 | N | CH | —CH₂CH₃ | H | —CH₂CH₃ | H | 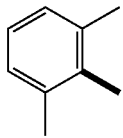 | H | H |
| A-97 | N | CH | —CH₂CH₃ | H | —CH₂CH₃ | 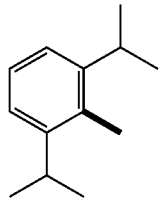 | H | H | H |
| A-98 | N | CH | —CH₂CH₃ | H | —CH₂CH₃ | H | 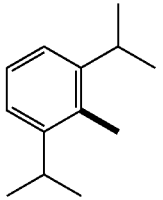 | H | H |
| A-99 | N | CH | —CH₂CH₃ | H | —CH₂CH₃ | 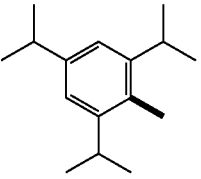 | H | H | H |
| A-272 | N | CH | —CH₂CH₃ | H | —CH₂CH₃ | H | 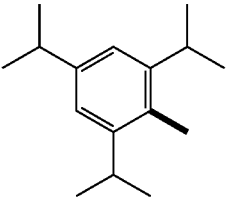 | H | H |

-continued

| Cpd. | X | Y | R⁷ | R⁶ | R⁵ | R⁴ | R³ | R² | R¹ |
|---|---|---|---|---|---|---|---|---|---|
| A-100 | N | CH | —CH₂CH₃ | H | —CH₂CH₃ | (dibenzofuran with iPr, Me, iPr substituents) | H | H | H |
| A-101 | N | CH | —CH₂CH₃ | H | —CH₂CH₃ | H | (dibenzofuran with iPr, Me, iPr substituents) | H | H |
| A-102 | N | CH | —CH₂CH₃ | H | —CH₂CH₃ | (dibenzofuran with iPr, Me, iPr substituents) | H | H | H |
| A-103 | N | CH | —CH₂CH₃ | H | —CH₂CH₃ | H | (dibenzofuran with iPr, Me, iPr substituents) | H | H |
| A-104 | N | CH | —CH₂CH₃ | H | —CH₂CH₃ | (dibenzofuran with Me, iPr substituents) | H | H | H |
| A-105 | N | CH | —CH₂CH₃ | H | —CH₂CH₃ | H | (dibenzofuran with Me, iPr substituents) | H | H |

-continued
| Cpd. | X | Y | R⁷ | R⁶ | R⁵ | R⁴ | R³ | R² | R¹ |
|---|---|---|---|---|---|---|---|---|---|
| A-106 | N | CH | iso-propyl | H | iso-propyl | 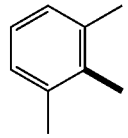 | H | H | H |
| A-107 | N | CH | iso-propyl | H | iso-propyl | H | 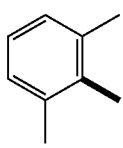 | H | H |
| A-108 | N | CH | iso-propyl | H | iso-propyl | 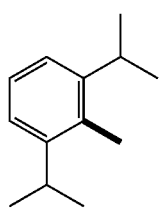 | H | H | H |
| A-109 | N | CH | iso-propyl | H | iso-propyl | H | 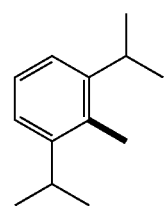 | H | H |
| A-110 | N | CH | iso-propyl | H | iso-propyl | 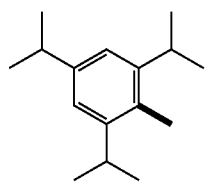 | H | H | H |
| A-111 | N | CH | iso-propyl | H | iso-propyl | H | 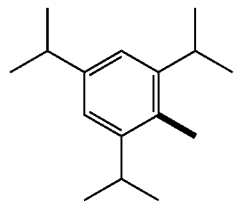 | H | H |
| A-112 | N | CH | iso-propyl | H | iso-propyl | 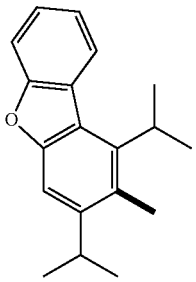 | H | H | H |

-continued
| Cpd. | X | Y | R⁷ | R⁶ | R⁵ | R⁴ | R³ | R² | R¹ |
|---|---|---|---|---|---|---|---|---|---|
| A-113 | N | CH | iso-propyl | H | iso-propyl | H | 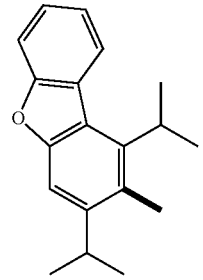 | H | H |
| A-114 | N | CH | iso-propyl | H | iso-propyl | 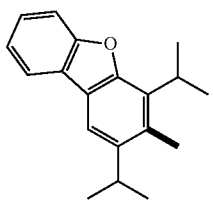 | | H | H |
| A-115 | N | CH | iso-propyl | H | iso-propyl | H | 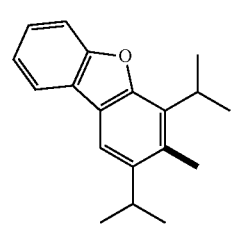 | H | H |
| A-116 | N | CH | iso-propyl | H | iso-propyl | 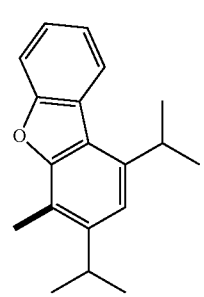 | | H | H |
| A-117 | N | CH | iso-propyl | H | iso-propyl | H | 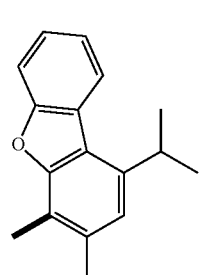 | H | H |
| A-118 | N | CH | tert-butyl | H | tert-butyl | 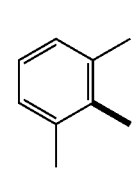 | H | H | H |
| A-119 | N | CH | tert-butyl | H | tert-butyl | H | 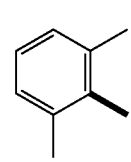 | H | H |

-continued

| Cpd. | X | Y | R⁷ | R⁶ | R⁵ | R⁴ | R³ | R² | R¹ |
|---|---|---|---|---|---|---|---|---|---|
| A-120 | N | CH | tert-butyl | H | tert-butyl | 2,6-diisopropylphenyl | H | H | H |
| A-121 | N | CH | tert-butyl | H | tert-butyl | H | 2,6-diisopropylphenyl | H | H |
| A-122 | N | CH | tert-butyl | H | tert-butyl | 2,4,6-triisopropylphenyl | H | H | H |
| A-123 | N | CH | tert-butyl | H | tert-butyl | H | 2,4,6-triisopropylphenyl | H | H |
| A-124 | N | CH | tert-butyl | H | tert-butyl | (1-isopropyl-3-isopropyl-dibenzofuran-2-yl) | H | H | H |
| A-125 | N | CH | tert-butyl | H | tert-butyl | H | (1-isopropyl-3-isopropyl-dibenzofuran-2-yl) | H | H |

-continued

| Cpd. | X | Y | R⁷ | R⁶ | R⁵ | R⁴ | R³ | R² | R¹ |
|---|---|---|---|---|---|---|---|---|---|
| A-126 | N | CH | tert-butyl | H | tert-butyl | 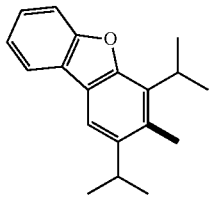 | H | H | H |
| A-127 | N | CH | tert-butyl | H | tert-butyl | H | 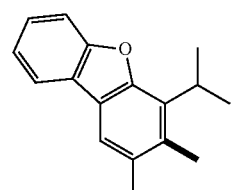 | H | H |
| A-128 | N | CH | tert-butyl | H | tert-butyl | 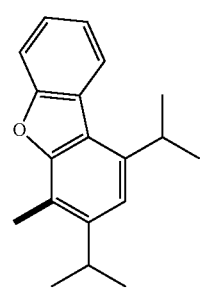 | H | H | H |
| A-129 | N | CH | tert-butyl | H | tert-butyl | H | 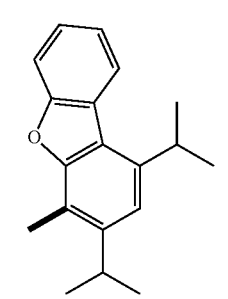 | H | H |
| A-130 | CH | N | —CH₃ | H | —CH₃ | H | H | H | H |
| A-131 | CH | N | —CH₂CH₃ | H | —CH₂CH₃ | H | H | H | H |
| A-132 | CH | N | iso-propyl | H | iso-propyl | H | H | H | H |
| A-133 | CH | N | iso-butyl | H | iso-butyl | H | H | H | H |
| A-134 | CH | N | neopentyl | H | neopentyl | H | H | H | H |
| A-135 | CH | N | 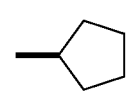 | H | 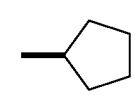 | H | H | H | H |
| A-136 | CH | N | 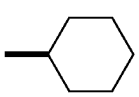 | H | 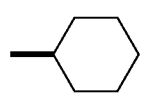 | H | H | H | H |
| A-137 | CH | N | tert-butyl | H | tert-butyl | H | H | H | H |
| A-138 | CH | N | —CH₃ | 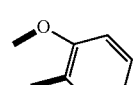 | H | H | H | H | |
| A-139 | CH | N | —CH₃ | 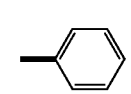 | —CH₃ | H | H | H | H |

-continued
| Cpd. | X | Y | R⁷ | R⁶ | R⁵ | R⁴ | R³ | R² | R¹ |
|---|---|---|---|---|---|---|---|---|---|
| A-140 | CH | N | —CH₃ | 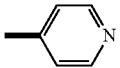 | —CH₃ | H | H | H | H |
| A-141 | CH | N | —CH₃ | H | —CH₃ | 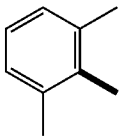 | H | H | H |
| A-142 | CH | N | —CH₃ | H | —CH₃ | H | 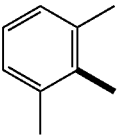 | H | H |
| A-143 | CH | N | —CH₃ | H | —CH₃ | 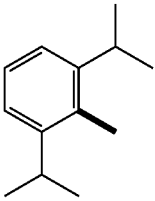 | H | H | H |
| A-144 | CH | N | —CH₃ | H | —CH₃ | H | 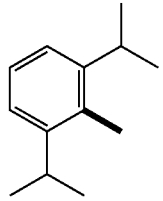 | H | H |
| A-145 | CH | N | —CH₃ | H | —CH₃ | 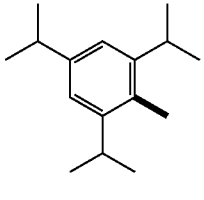 | H | H | H |
| A-146 | CH | N | —CH₃ | H | —CH₃ | H | 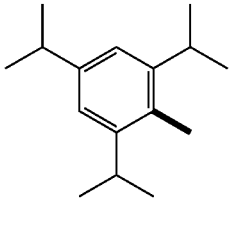 | H | H |
| A-147 | CH | N | —CH₃ | H | —CH₃ | 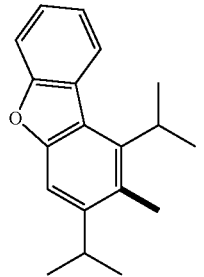 | H | H | H |

-continued

| Cpd. | X | Y | R⁷ | R⁶ | R⁵ | R⁴ | R³ | R² | R¹ |
|---|---|---|---|---|---|---|---|---|---|
| A-148 | CH | N | —CH₃ | H | —CH₃ | H | ![dibenzofuran with iPr, CH₃, iPr substituents] | H | H |
| A-149 | CH | N | —CH₃ | H | —CH₃ | ![dibenzofuran with iPr, CH₃, iPr substituents] | | H | H |
| A-150 | CH | N | —CH₃ | H | —CH₃ | H | ![dibenzofuran with iPr, CH₃, iPr substituents] | H | H |
| A-151 | CH | N | —CH₃ | H | —CH₃ | H | ![dibenzofuran with CH₃, iPr, iPr substituents] | H | H |
| A-152 | CH | N | —CH₃ | H | —CH₃ | H | ![dibenzofuran with CH₃, iPr, iPr substituents] | H | H |
| A-153 | CH | N | —CH₃ | H | —CH₃ | ![dimethylphenyl] | | H | H |
| A-154 | CH | N | —CH₃ | H | —CH₃ | H | ![dimethylphenyl] | H | H |

-continued

| Cpd. | X | Y | R⁷ | R⁶ | R⁵ | R⁴ | R³ | R² | R¹ |
|---|---|---|---|---|---|---|---|---|---|
| A-155 | CH | N | —CH₃ | H | —CH₃ | 2,6-diisopropylphenyl | H | H | H |
| A-156 | CH | N | —CH₃ | H | —CH₃ | H | 2,6-diisopropylphenyl | H | H |
| A-157 | CH | N | —CH₃ | H | —CH₃ | 2,4,6-triisopropylphenyl | H | H | H |
| A-158 | CH | N | —CH₃ | H | —CH₃ | H | 2,4,6-triisopropylphenyl | H | H |
| A-159 | CH | N | —CH₃ | H | —CH₃ | 1,3-diisopropyl-dibenzofuran-2-yl | H | H | H |
| A-160 | CH | N | —CH₃ | H | —CH₃ | H | 1,3-diisopropyl-dibenzofuran-2-yl | H | H |

-continued

| Cpd. | X | Y | R⁷ | R⁶ | R⁵ | R⁴ | R³ | R² | R¹ |
|---|---|---|---|---|---|---|---|---|---|
| A-161 | CH | N | —CH₃ | H | —CH₃ | (dibenzofuran with iPr, Me, iPr substituents) | H | H | H |
| A-162 | CH | N | —CH₃ | H | —CH₃ | H | (dibenzofuran with iPr, Me, iPr substituents) | H | H |
| A-163 | CH | N | —CH₃ | H | —CH₃ | (dibenzofuran with Me, iPr, iPr substituents) | H | H | H |
| A-164 | CH | N | —CH₃ | H | —CH₃ | H | (dibenzofuran with Me, iPr, iPr substituents) | H | H |
| A-165 | CH | N | —CH₂CH₃ | H | —CH₂CH₃ | (2,3-dimethylphenyl) | H | H | H |
| A-166 | CH | N | —CH₂CH₃ | H | —CH₂CH₃ | H | (2,3-dimethylphenyl) | H | H |
| A-167 | CH | N | —CH₂CH₃ | H | —CH₂CH₃ | (2,6-diisopropylphenyl with methyl) | H | H | H |

-continued

| Cpd. | X | Y | R⁷ | R⁶ | R⁵ | R⁴ | R³ | R² | R¹ |
|---|---|---|---|---|---|---|---|---|---|
| A-168 | CH | N | —CH₂CH₃ | H | —CH₂CH₃ | H | 2,6-diisopropylphenyl | H | H |
| A-169 | CH | N | —CH₂CH₃ | H | —CH₂CH₃ | 2,4,6-triisopropylphenyl | H | H | H |
| A-170 | CH | N | —CH₂CH₃ | H | —CH₂CH₃ | H | 2,4,6-triisopropylphenyl | H | H |
| A-171 | CH | N | —CH₂CH₃ | H | —CH₂CH₃ | 1,3-diisopropyldibenzofuran-2-yl | H | H | H |
| A-172 | CH | N | —CH₂CH₃ | H | —CH₂CH₃ | H | 1,3-diisopropyldibenzofuran-2-yl | H | H |
| A-173 | CH | N | —CH₂CH₃ | H | —CH₂CH₃ | 2,4-diisopropyldibenzofuran-3-yl | H | H | H |

-continued

| Cpd. | X | Y | R⁷ | R⁶ | R⁵ | R⁴ | R³ | R² | R¹ |
|---|---|---|---|---|---|---|---|---|---|
| A-174 | CH | N | —CH₂CH₃ | H | —CH₂CH₃ | H | dibenzofuran with isopropyl, methyl, isopropyl substituents | H | H |
| A-175 | CH | N | —CH₂CH₃ | H | —CH₂CH₃ | dibenzofuran with methyl, isopropyl, isopropyl substituents | H | H | H |
| A-176 | CH | N | —CH₂CH₃ | H | —CH₂CH₃ | H | dibenzofuran with isopropyl, isopropyl, methyl substituents | H | H |
| A-177 | CH | N | iso-propyl | H | iso-propyl | 2,3-dimethylphenyl | H | H | H |
| A-178 | CH | N | iso-propyl | H | iso-propyl | H | 2,3-dimethylphenyl | H | H |
| A-179 | CH | N | iso-propyl | H | iso-propyl | 2,6-diisopropylphenyl | H | H | H |
| A-180 | CH | N | iso-propyl | H | iso-propyl | H | 2,6-diisopropylphenyl | H | H |

-continued

| Cpd. | X | Y | R⁷ | R⁶ | R⁵ | R⁴ | R³ | R² | R¹ |
|---|---|---|---|---|---|---|---|---|---|
| A-181 | CH | N | iso-propyl | H | iso-propyl | (2,4,6-triisopropylphenyl) | H | H | H |
| A-182 | CH | N | iso-propyl | H | iso-propyl | H | (2,4,6-triisopropylphenyl) | H | H |
| A-183 | CH | N | iso-propyl | H | iso-propyl | (isopropyl-methyl-isopropyl-dibenzofuranyl) | H | H | H |
| A-184 | CH | N | iso-propyl | H | iso-propyl | H | (isopropyl-methyl-isopropyl-dibenzofuranyl) | H | H |
| A-185 | CH | N | iso-propyl | H | iso-propyl | (isopropyl-methyl-isopropyl-dibenzofuranyl) | H | H | H |
| A-186 | CH | N | iso-propyl | H | iso-propyl | H | (isopropyl-methyl-isopropyl-dibenzofuranyl) | H | H |

-continued

| Cpd. | X | Y | R⁷ | R⁶ | R⁵ | R⁴ | R³ | R² | R¹ |
|---|---|---|---|---|---|---|---|---|---|
| A-187 | CH | N | iso-propyl | H | iso-propyl | (dibenzofuran with methyl and two iso-propyl substituents) | H | H | H |
| A-188 | CH | N | iso-propyl | H | iso-propyl | H | (dibenzofuran with methyl and two iso-propyl substituents) | H | H |
| A-189 | CH | N | tert-butyl | H | tert-butyl | (2,3-dimethylphenyl) | H | H | H |
| A-190 | CH | N | tert-butyl | H | tert-butyl | H | (2,3-dimethylphenyl) | H | H |
| A-191 | CH | N | tert-butyl | H | tert-butyl | (2,6-diisopropyl-methylphenyl) | H | H | H |
| A-192 | CH | N | tert-butyl | H | tert-butyl | H | (2,6-diisopropylphenyl) | H | H |
| A-193 | CH | N | tert-butyl | H | tert-butyl | (2,4,6-triisopropyl-methylphenyl) | H | H | H |

-continued

| Cpd. | X | Y | R⁷ | R⁶ | R⁵ | R⁴ | R³ | R² | R¹ |
|---|---|---|---|---|---|---|---|---|---|
| A-194 | CH | N | tert-butyl | H | tert-butyl | H | (2,4,6-triisopropylphenyl) | H | H |
| A-195 | CH | N | tert-butyl | H | tert-butyl | (dibenzofuranyl with diisopropyl and methyl) | H | H | H |
| A-196 | CH | N | tert-butyl | H | tert-butyl | H | (dibenzofuranyl with diisopropyl and methyl) | H | H |
| A-197 | CH | N | tert-butyl | H | tert-butyl | (dibenzofuranyl with isopropyl and methyl) | H | H | H |
| A-198 | CH | N | tert-butyl | H | tert-butyl | H | (dibenzofuranyl with isopropyl and methyl) | H | H |
| A-199 | CH | N | tert-butyl | H | tert-butyl | (dibenzofuranyl with isopropyl and methyl) | H | H | H |

-continued
| Cpd. | X | Y | R7 | R6 | R5 | R4 | R3 | R2 | R1 |
|---|---|---|---|---|---|---|---|---|---|
| A-200 | CH | N | tert-butyl | H | tert-butyl | H | 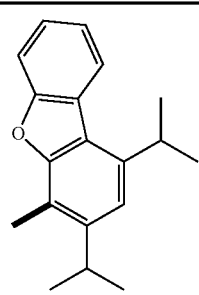 | H | H |
| A-201 | CH | CH | —CH3 | H | —CH3 | H | H | H | H |
| A-202 | CH | CH | —CH2CH3 | H | —CH2CH3 | H | H | H | H |
| A-203 | CH | CH | iso-propyl | H | iso-propyl | H | H | H | H |
| A-204 | CH | CH | iso-butyl | H | iso-butyl | H | H | H | H |
| A-205 | CH | CH | neopentyl | H | neopentyl | H | H | H | H |
| A-206 | CH | CH | 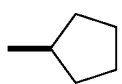 | H | 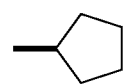 | H | H | H | H |
| A-207 | CH | CH | 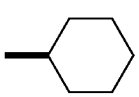 | H | 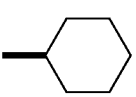 | H | H | H | H |
| A-208 | CH | CH | tert-butyl | H | tert-butyl | H | H | H | H |
| A-209 | CH | CH | —CH3 | 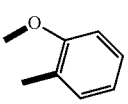 | H | H | H | H | |
| A-210 | CH | CH | —CH3 | 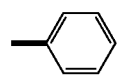 | —CH3 | H | H | H | H |
| A-211 | CH | CH | —CH3 | 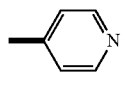 | —CH3 | H | H | H | H |
| A-212 | CH | CH | —CH3 | H | —CH3 | 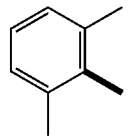 | H | H | H |
| A-213 | CH | CH | —CH3 | H | —CH3 | H | 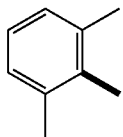 | H | H |
| A-214 | CH | CH | —CH3 | H | —CH3 | 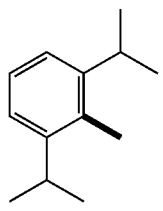 | H | H | H |

-continued

| Cpd. | X | Y | R⁷ | R⁶ | R⁵ | R⁴ | R³ | R² | R¹ |
|---|---|---|---|---|---|---|---|---|---|
| A-215 | CH | CH | —CH₃ | H | —CH₃ | H | (2,6-diisopropylphenyl with methyl) | H | H |
| A-216 | CH | CH | —CH₃ | H | —CH₃ | (2,4,6-triisopropylphenyl with methyl) | H | H | H |
| A-217 | CH | CH | —CH₃ | H | —CH₃ | H | (2,4,6-triisopropylphenyl with methyl) | H | H |
| A-218 | CH | CH | —CH₃ | H | —CH₃ | (dibenzofuranyl with diisopropyl and methyl) | H | H | H |
| A-219 | CH | CH | —CH₃ | H | —CH₃ | H | (dibenzofuranyl with diisopropyl and methyl) | H | H |
| A-220 | CH | CH | —CH₃ | H | —CH₃ | (dibenzofuranyl with diisopropyl and methyl) | H | H | H |
| A-221 | CH | CH | —CH₃ | H | —CH₃ | H | (dibenzofuranyl with diisopropyl and methyl) | H | H |

-continued

| Cpd. | X | Y | R⁷ | R⁶ | R⁵ | R⁴ | R³ | R² | R¹ |
|---|---|---|---|---|---|---|---|---|---|
| A-222 | CH | CH | —CH₃ | H | —CH₃ | (4-methyl-1,3-diisopropyldibenzofuranyl) | H | H | H |
| A-223 | CH | CH | —CH₃ | H | —CH₃ | H | (4-methyl-1,3-diisopropyldibenzofuranyl) | H | H |
| A-224 | CH | CH | —CH₃ | H | —CH₃ | (2,3-dimethylphenyl) | H | H | H |
| A-225 | CH | CH | —CH₃ | H | —CH₃ | H | (2,3-dimethylphenyl) | H | H |
| A-226 | CH | CH | —CH₃ | H | —CH₃ | (2,6-diisopropyl-3-methylphenyl) | H | H | H |
| A-227 | CH | CH | —CH₃ | H | —CH₃ | H | (2,6-diisopropyl-3-methylphenyl) | H | H |
| A-228 | CH | CH | —CH₃ | H | —CH₃ | (2,4,6-triisopropyl-3-methylphenyl) | H | H | H |

-continued

| Cpd. | X | Y | R⁷ | R⁶ | R⁵ | R⁴ | R³ | R² | R¹ |
|---|---|---|---|---|---|---|---|---|---|
| A-229 | CH | CH | —CH₃ | H | —CH₃ | H | 2,4,6-triisopropylphenyl with methyl | H | H |
| A-230 | CH | CH | —CH₃ | H | —CH₃ | dibenzofuranyl with diisopropyl and methyl | H | H | H |
| A-231 | CH | CH | —CH₃ | H | —CH₃ | H | dibenzofuranyl with diisopropyl and methyl | H | H |
| A-232 | CH | CH | —CH₃ | H | —CH₃ | dibenzofuranyl with diisopropyl and methyl | H | H | H |
| A-233 | CH | CH | —CH₃ | H | —CH₃ | H | dibenzofuranyl with diisopropyl and methyl | H | H |
| A-234 | CH | CH | —CH₃ | H | —CH₃ | dibenzofuranyl with diisopropyl and methyl | H | H | H |

-continued
| Cpd. | X | Y | R⁷ | R⁶ | R⁵ | R⁴ | R³ | R² | R¹ |
|---|---|---|---|---|---|---|---|---|---|
| A-235 | CH | CH | —CH₃ | H | —CH₃ | H | 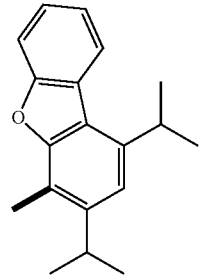 | H | H |
| A-236 | CH | CH | —CH₂CH₃ | H | —CH₂CH₃ | 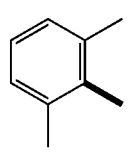 | | H | H |
| A-237 | CH | CH | —CH₂CH₃ | H | —CH₂CH₃ | H | 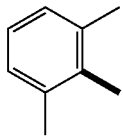 | H | H |
| A-238 | CH | CH | —CH₂CH₃ | H | —CH₂CH₃ | 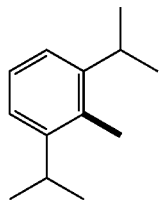 | H | H | H |
| A-239 | CH | CH | —CH₂CH₃ | H | —CH₂CH₃ | H | 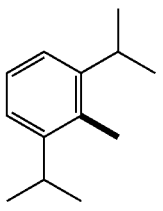 | H | H |
| A-240 | CH | CH | —CH₂CH₃ | H | —CH₂CH₃ | 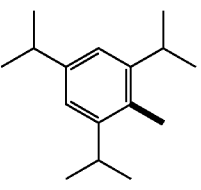 | H | H | H |
| A-241 | CH | CH | —CH₂CH₃ | H | —CH₂CH₃ | H | 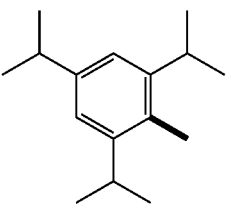 | H | H |

-continued

| Cpd. | X | Y | R⁷ | R⁶ | R⁵ | R⁴ | R³ | R² | R¹ |
|---|---|---|---|---|---|---|---|---|---|
| A-242 | CH | CH | —CH₂CH₃ | H | —CH₂CH₃ | (dibenzofuran with iPr, Me, iPr substituents) | H | H | H |
| A-243 | CH | CH | —CH₂CH₃ | H | —CH₂CH₃ | H | (dibenzofuran with iPr, Me, iPr substituents) | H | H |
| A-244 | CH | CH | —CH₂CH₃ | H | —CH₂CH₃ | (dibenzofuran with iPr, Me, iPr substituents) | H | H | H |
| A-245 | CH | CH | —CH₂CH₃ | H | —CH₂CH₃ | H | (dibenzofuran with iPr, Me, iPr substituents) | H | H |
| A-246 | CH | CH | —CH₂CH₃ | H | —CH₂CH₃ | (dibenzofuran with Me, iPr substituents) | H | H | H |
| A-247 | CH | CH | —CH₂CH₃ | H | —CH₂CH₃ | H | (dibenzofuran with Me, iPr substituents) | H | H |

-continued
| Cpd. | X | Y | R⁷ | R⁶ | R⁵ | R⁴ | R³ | R² | R¹ |
|---|---|---|---|---|---|---|---|---|---|
| A-248 | CH | CH | iso-propyl | H | iso-propyl | 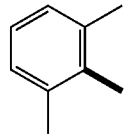 | H | H | H |
| A-249 | CH | CH | iso-propyl | H | iso-propyl | H | 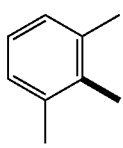 | H | H |
| A-250 | CH | CH | iso-propyl | H | iso-propyl | 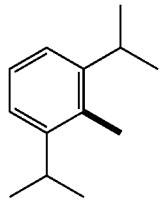 | H | H | H |
| A-251 | CH | CH | iso-propyl | H | iso-propyl | H | 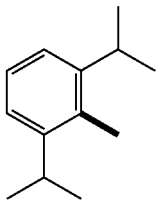 | H | H |
| A-252 | CH | CH | iso-propyl | H | iso-propyl | 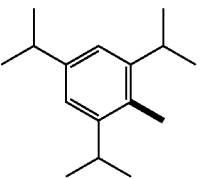 | H | H | H |
| A-253 | CH | CH | iso-propyl | H | iso-propyl | H | 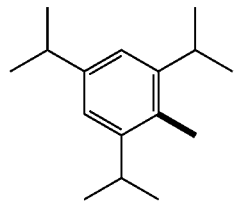 | H | H |
| A-254 | CH | CH | iso-propyl | H | iso-propyl | 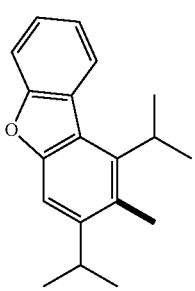 | H | H | H |

-continued

| Cpd. | X | Y | R⁷ | R⁶ | R⁵ | R⁴ | R³ | R² | R¹ |
|---|---|---|---|---|---|---|---|---|---|
| A-255 | CH | CH | iso-propyl | H | iso-propyl | H | (dibenzofuran with iso-propyl, methyl, iso-propyl substituents) | H | H |
| A-256 | CH | CH | iso-propyl | H | iso-propyl | (dibenzofuran with iso-propyl, methyl, iso-propyl substituents) | H | H | H |
| A-257 | CH | CH | iso-propyl | H | iso-propyl | H | (dibenzofuran with iso-propyl, methyl, iso-propyl substituents) | H | H |
| A-258 | CH | CH | iso-propyl | H | iso-propyl | (dibenzofuran with methyl, iso-propyl, iso-propyl substituents) | H | H | H |
| A-259 | CH | CH | iso-propyl | H | iso-propyl | H | (dibenzofuran with methyl, iso-propyl, iso-propyl substituents) | H | H |
| A-260 | CH | CH | tert-butyl | H | tert-butyl | (2,3-dimethylphenyl) | H | H | H |
| A-261 | CH | CH | tert-butyl | H | tert-butyl | H | (2,3-dimethylphenyl) | H | H |

-continued
| Cpd. | X | Y | R⁷ | R⁶ | R⁵ | R⁴ | R³ | R² | R¹ |
|---|---|---|---|---|---|---|---|---|---|
| A-262 | CH | CH | tert-butyl | H | tert-butyl | 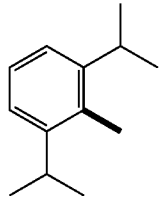 | H | H | H |
| A-263 | CH | CH | tert-butyl | H | tert-butyl | H | 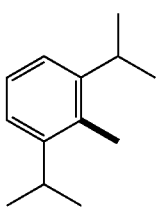 | H | H |
| A-264 | CH | CH | tert-butyl | H | tert-butyl | 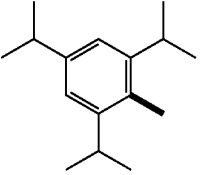 | H | H | H |
| A-265 | CH | CH | tert-butyl | H | tert-butyl | H | 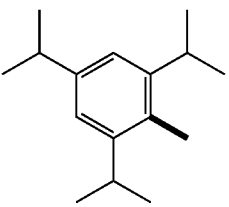 | H | H |
| A-266 | CH | CH | tert-butyl | H | tert-butyl | 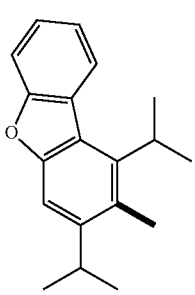 | H | H | H |
| A-267 | CH | CH | tert-butyl | H | tert-butyl | H | 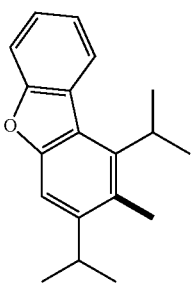 | H | H |

-continued
| Cpd. | X | Y | R⁷ | R⁶ | R⁵ | R⁴ | R³ | R² | R¹ |
|---|---|---|---|---|---|---|---|---|---|
| A-268 | CH | CH | tert-butyl | H | tert-butyl | 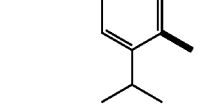 | H | H | H |
| A-269 | CH | CH | tert-butyl | H | tert-butyl | H |  | H | H |
| A-270 | CH | CH | tert-butyl | H | tert-butyl | 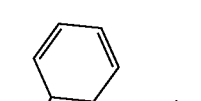 | H | H | H |
| A-271 | CH | CH | tert-butyl | H | tert-butyl | H | 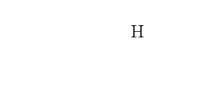 | H | H |

Further preferred cyclometallated Ir complexes of formulae (II), (II') and (II") are:
Compounds of the Following Formulae
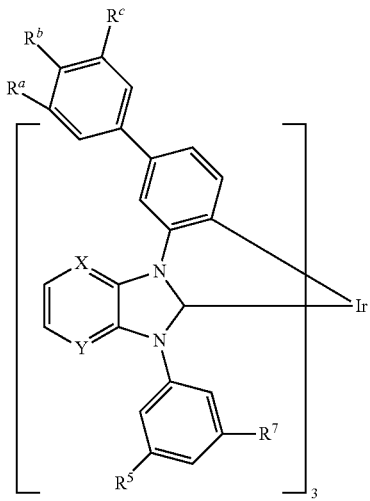
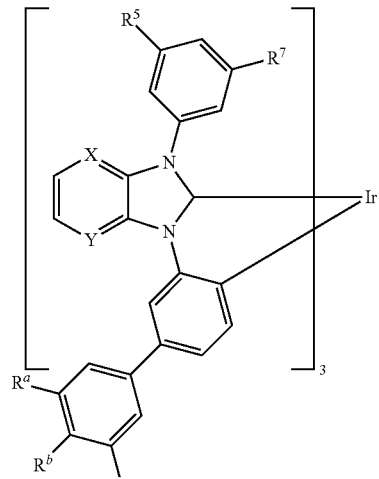
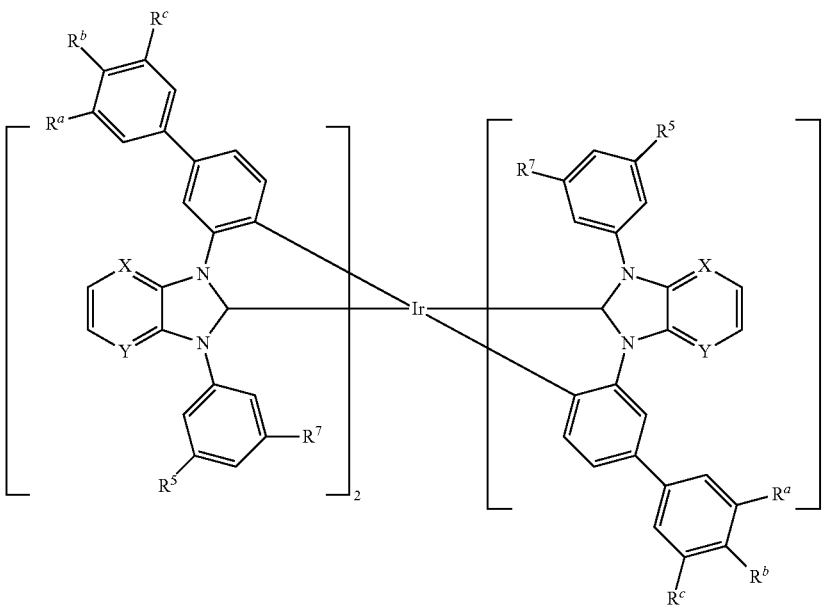

-continued

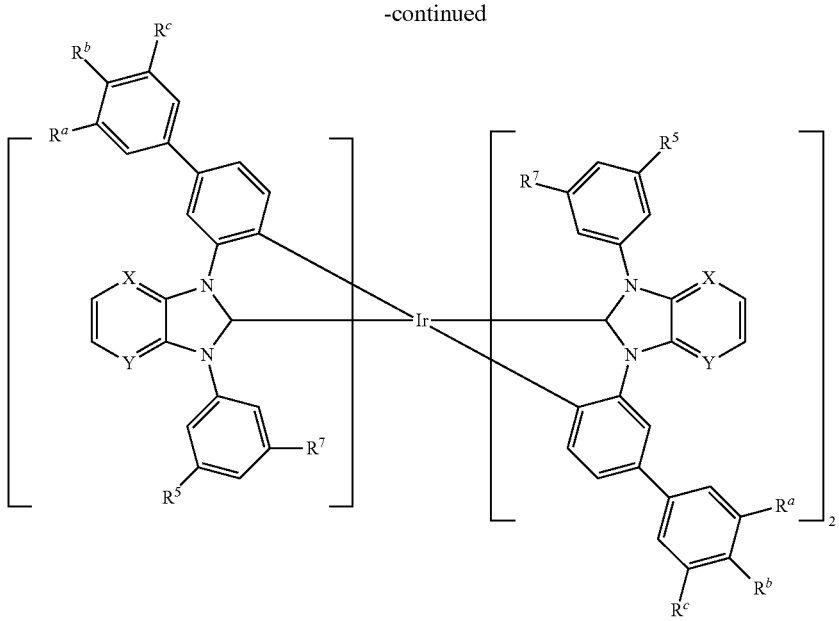

wherein the radicals and groups $R^a$, $R^b$, $R^c$, $R^5$, $R^7$, X and Y have the following meanings:

| Cpd. | X | Y | $R^a$ | $R^b$ | $R^c$ | $R^5 = R^7$ |
|---|---|---|---|---|---|---|
| E-1 | N | N | —CH₃ | H | —CH₃ | —CH₂CH₃ |
| E-2 | N | N | —CH₂CH₃ | H | —CH₂CH₃ | —CH₂CH₃ |
| E-3 | N | N | iso-propyl | H | iso-propyl | —CH₂CH₃ |
| E-4 | N | N | iso-butyl | H | iso-butyl | —CH₂CH₃ |
| E-5 | N | N | cyclopentyl | H | cyclopentyl | —CH₂CH₃ |
| E-6 | N | N | cyclohexyl | H | cyclohexyl | —CH₂CH₃ |
| E-7 | N | N | —CH₂CH₃ | H | —CH₃ | —CH₂CH₃ |
| E-8 | N | N | —CH₃ | H | —CH₂CH₃ | —CH₂CH₃ |
| E-9 | N | N | —CH₃ | —CH₃ | H | —CH₂CH₃ |
| E-10 | N | N | —CH₂CH₃ | —CH₂CH₃ | H | —CH₂CH₃ |
| E-11 | N | N | iso-butyl | iso-butyl | H | —CH₂CH₃ |
| E-12 | N | N | —CH₂CH₃ | —CH₃ | H | —CH₂CH₃ |
| E-13 | N | N | —CH₃ | —CH₂CH₃ | H | —CH₂CH₃ |
| E-14 | N | N | —CH₃ | H | —CH₃ | iso-propyl |
| E-15 | N | N | —CH₂CH₃ | H | —CH₂CH₃ | iso-propyl |
| E-16 | N | N | iso-propyl | H | iso-propyl | iso-propyl |
| E-17 | N | N | iso-butyl | H | iso-butyl | iso-propyl |
| E-18 | N | N | cyclopentyl | H | cyclopentyl | iso-propyl |
| E-19 | N | N | cyclohexyl | H | cyclohexyl | iso-propyl |
| E-20 | N | N | —CH₂CH₃ | H | —CH₃ | iso-propyl |
| E-21 | N | N | —CH₃ | H | —CH₂CH₃ | iso-propyl |
| E-22 | N | N | —CH₃ | —CH₃ | H | iso-propyl |
| E-23 | N | N | —CH₂CH₃ | —CH₂CH₃ | H | iso-propyl |
| E-24 | N | N | iso-butyl | iso-butyl | H | iso-propyl |
| E-25 | N | N | —CH₂CH₃ | —CH₃ | H | iso-propyl |
| E-26 | N | N | —CH₃ | —CH₂CH₃ | H | iso-propyl |

-continued

| Cpd. | X | Y | R$^a$ | R$^b$ | R$^c$ | R$^5$ = R$^7$ |
|---|---|---|---|---|---|---|
| E-27 | N | N | —CH$_3$ | H | —CH$_3$ | iso-butyl |
| E-28 | N | N | —CH$_2$CH$_3$ | H | —CH$_2$CH$_3$ | iso-butyl |
| E-29 | N | N | iso-propyl | H | iso-propyl | iso-butyl |
| E-30 | N | N | iso-butyl | H | iso-butyl | iso-butyl |
| E-31 | N | N | cyclopentyl | H | cyclopentyl | iso-butyl |
| E-32 | N | N | cyclohexyl | H | cyclohexyl | iso-butyl |
| E-33 | N | N | —CH$_2$CH$_3$ | H | —CH$_3$ | iso-butyl |
| E-34 | N | N | —CH$_3$ | H | —CH$_2$CH$_3$ | iso-butyl |
| E-35 | N | N | —CH$_3$ | —CH$_3$ | H | iso-butyl |
| E-36 | N | N | —CH$_2$CH$_3$ | —CH$_2$CH$_3$ | H | iso-butyl |
| E-37 | N | N | iso-butyl | iso-butyl | H | iso-butyl |
| E-38 | N | N | —CH$_2$CH$_3$ | —CH$_3$ | H | iso-butyl |
| E-39 | N | N | —CH$_3$ | —CH$_2$CH$_3$ | H | iso-butyl |
| E-40 | N | CH | —CH$_3$ | H | —CH$_3$ | —CH$_2$CH$_3$ |
| E-41 | N | CH | —CH$_2$CH$_3$ | H | —CH$_2$CH$_3$ | —CH$_2$CH$_3$ |
| E-42 | N | CH | iso-propyl | H | iso-propyl | —CH$_2$CH$_3$ |
| E-43 | N | CH | iso-butyl | H | iso-butyl | —CH$_2$CH$_3$ |
| E-44 | N | CH | cyclopentyl | H | cyclopentyl | —CH$_2$CH$_3$ |
| E-45 | N | CH | cyclohexyl | H | cyclohexyl | —CH$_2$CH$_3$ |
| E-46 | N | CH | —CH$_2$CH$_3$ | H | —CH$_3$ | —CH$_2$CH$_3$ |
| E-47 | N | CH | —CH$_3$ | H | —CH$_2$CH$_3$ | —CH$_2$CH$_3$ |
| E-48 | N | CH | —CH$_3$ | —CH$_3$ | H | —CH$_2$CH$_3$ |
| E-49 | N | CH | —CH$_2$CH$_3$ | —CH$_2$CH$_3$ | H | —CH$_2$CH$_3$ |
| E-50 | N | CH | iso-butyl | iso-butyl | H | —CH$_2$CH$_3$ |
| E-51 | N | CH | —CH$_2$CH$_3$ | —CH$_3$ | H | —CH$_2$CH$_3$ |
| E-52 | N | CH | —CH$_3$ | —CH$_2$CH$_3$ | H | —CH$_2$CH$_3$ |
| E-53 | N | CH | —CH$_3$ | H | —CH$_3$ | iso-propyl |
| E-54 | N | CH | —CH$_2$CH$_3$ | H | —CH$_2$CH$_3$ | iso-propyl |
| E-55 | N | CH | iso-propyl | H | iso-propyl | iso-propyl |
| E-56 | N | CH | iso-butyl | H | iso-butyl | iso-propyl |
| E-57 | N | CH | cyclopentyl | H | cyclopentyl | iso-propyl |
| E-58 | N | CH | cyclohexyl | H | cyclohexyl | iso-propyl |
| E-59 | N | CH | —CH$_2$CH$_3$ | H | —CH$_3$ | iso-propyl |
| E-60 | N | CH | —CH$_3$ | H | —CH$_2$CH$_3$ | iso-propyl |
| E-61 | N | CH | —CH$_3$ | —CH$_3$ | H | iso-propyl |
| E-62 | N | CH | —CH$_2$CH$_3$ | —CH$_2$CH$_3$ | H | iso-propyl |
| E-63 | N | CH | iso-butyl | iso-butyl | H | iso-propyl |
| E-64 | N | CH | —CH$_2$CH$_3$ | —CH$_3$ | H | iso-propyl |
| E-65 | N | CH | —CH$_3$ | —CH$_2$CH$_3$ | H | iso-propyl |
| E-66 | N | CH | —CH$_3$ | H | —CH$_3$ | iso-butyl |
| E-67 | N | CH | —CH$_2$CH$_3$ | H | —CH$_2$CH$_3$ | iso-butyl |
| E-68 | N | CH | iso-propyl | H | iso-propyl | iso-butyl |
| E-69 | N | CH | iso-butyl | H | iso-butyl | iso-butyl |
| E-70 | N | CH | cyclopentyl | H | cyclopentyl | iso-butyl |

| Cpd. | X | Y | $R^a$ | $R^b$ | $R^c$ | $R^5 = R^7$ |
|---|---|---|---|---|---|---|
| E-71 | N | CH | cyclohexyl | H | cyclohexyl | iso-butyl |
| E-72 | N | CH | —CH$_2$CH$_3$ | H | —CH$_3$ | iso-butyl |
| E-73 | N | CH | —CH$_3$ | H | —CH$_2$CH$_3$ | iso-butyl |
| E-74 | N | CH | —CH$_3$ | —CH$_3$ | H | iso-butyl |
| E-75 | N | CH | —CH$_2$CH$_3$ | —CH$_2$CH$_3$ | H | iso-butyl |
| E-76 | N | CH | iso-butyl | iso-butyl | H | iso-butyl |
| E-77 | N | CH | —CH$_2$CH$_3$ | —CH$_3$ | H | iso-butyl |
| E-78 | N | CH | —CH$_3$ | —CH$_2$CH$_3$ | H | iso-butyl |
| E-79 | CH | N | —CH$_3$ | H | —CH$_3$ | —CH$_2$CH$_3$ |
| E-80 | CH | N | —CH$_2$CH$_3$ | H | —CH$_2$CH$_3$ | —CH$_2$CH$_3$ |
| E-81 | CH | N | iso-propyl | H | iso-propyl | —CH$_2$CH$_3$ |
| E-82 | CH | N | iso-butyl | H | iso-butyl | —CH$_2$CH$_3$ |
| E-83 | CH | N | cyclopentyl | H | cyclopentyl | —CH$_2$CH$_3$ |
| E-84 | CH | N | cyclohexyl | H | cyclohexyl | —CH$_2$CH$_3$ |
| E-85 | CH | N | —CH$_2$CH$_3$ | H | —CH$_3$ | —CH$_2$CH$_3$ |
| E-86 | CH | N | —CH$_3$ | H | —CH$_2$CH$_3$ | —CH$_2$CH$_3$ |
| E-87 | CH | N | —CH$_3$ | —CH$_3$ | H | —CH$_2$CH$_3$ |
| E-88 | CH | N | —CH$_2$CH$_3$ | —CH$_2$CH$_3$ | H | —CH$_2$CH$_3$ |
| E-89 | CH | N | iso-butyl | iso-butyl | H | —CH$_2$CH$_3$ |
| E-90 | CH | N | —CH$_2$CH$_3$ | —CH$_3$ | H | —CH$_2$CH$_3$ |
| E-91 | CH | N | —CH$_3$ | —CH$_2$CH$_3$ | H | —CH$_2$CH$_3$ |
| E-92 | CH | N | —CH$_3$ | H | —CH$_3$ | iso-propyl |
| E-93 | CH | N | —CH$_2$CH$_3$ | H | —CH$_2$CH$_3$ | iso-propyl |
| E-94 | CH | N | iso-propyl | H | iso-propyl | iso-propyl |
| E-95 | CH | N | iso-butyl | H | iso-butyl | iso-propyl |
| E-96 | CH | N | cyclopentyl | H | cyclopentyl | iso-propyl |
| E-97 | CH | N | cyclohexyl | H | cyclohexyl | iso-propyl |
| E-98 | CH | N | —CH$_2$CH$_3$ | H | —CH$_3$ | iso-propyl |
| E-99 | CH | N | —CH$_3$ | H | —CH$_2$CH$_3$ | iso-propyl |
| E-100 | CH | N | —CH$_3$ | —CH$_3$ | H | iso-propyl |
| E-101 | CH | N | —CH$_2$CH$_3$ | —CH$_2$CH$_3$ | H | iso-propyl |
| E-102 | CH | N | iso-butyl | iso-butyl | H | iso-propyl |
| E-103 | CH | N | —CH$_2$CH$_3$ | —CH$_3$ | H | iso-propyl |
| E-104 | CH | N | —CH$_3$ | —CH$_2$CH$_3$ | H | iso-propyl |
| E-105 | CH | N | —CH$_3$ | H | —CH$_3$ | iso-butyl |
| E-106 | CH | N | —CH$_2$CH$_3$ | H | —CH$_2$CH$_3$ | iso-butyl |
| E-107 | CH | N | iso-propyl | H | iso-propyl | iso-butyl |
| E-108 | CH | N | iso-butyl | H | iso-butyl | iso-butyl |
| E-109 | CH | N | cyclopentyl | H | cyclopentyl | iso-butyl |
| E-110 | CH | N | cyclohexyl | H | cyclohexyl | iso-butyl |
| E-111 | CH | N | —CH$_2$CH$_3$ | H | —CH$_3$ | iso-butyl |
| E-112 | CH | N | —CH$_3$ | H | —CH$_2$CH$_3$ | iso-butyl |
| E-113 | CH | N | —CH$_3$ | —CH$_3$ | H | iso-butyl |
| E-114 | CH | N | —CH$_2$CH$_3$ | —CH$_2$CH$_3$ | H | iso-butyl |
| E-115 | CH | N | iso-butyl | iso-butyl | H | iso-butyl |
| E-116 | CH | N | —CH$_2$CH$_3$ | —CH$_3$ | H | iso-butyl |
| E-117 | CH | N | —CH$_3$ | —CH$_2$CH$_3$ | H | iso-butyl |
| E-118 | CH | CH | —CH$_3$ | H | —CH$_3$ | —CH$_2$CH$_3$ |

-continued

| Cpd. | X | Y | $R^a$ | $R^b$ | $R^c$ | $R^5 = R^7$ |
|---|---|---|---|---|---|---|
| E-119 | CH | CH | —CH$_2$CH$_3$ | H | —CH$_2$CH$_3$ | —CH$_2$CH$_3$ |
| E-120 | CH | CH | iso-propyl | H | iso-propyl | —CH$_2$CH$_3$ |
| E-121 | CH | CH | iso-butyl | H | iso-butyl | —CH$_2$CH$_3$ |
| E-122 | CH | CH | 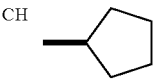 | H | 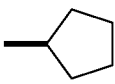 | —CH$_2$CH$_3$ |
| E-123 | CH | CH | 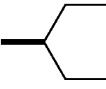 | H | 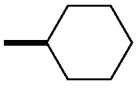 | —CH$_2$CH$_3$ |
| E-124 | CH | CH | —CH$_2$CH$_3$ | H | —CH$_3$ | —CH$_2$CH$_3$ |
| E-125 | CH | CH | —CH$_3$ | H | —CH$_2$CH$_3$ | —CH$_2$CH$_3$ |
| E-126 | CH | CH | —CH$_3$ | —CH$_3$ | H | —CH$_2$CH$_3$ |
| E-127 | CH | CH | —CH$_2$CH$_3$ | —CH$_2$CH$_3$ | H | —CH$_2$CH$_3$ |
| E-128 | CH | CH | iso-butyl | iso-butyl | H | —CH$_2$CH$_3$ |
| E-129 | CH | CH | —CH$_2$CH$_3$ | —CH$_3$ | H | —CH$_2$CH$_3$ |
| E-130 | CH | CH | —CH$_3$ | —CH$_2$CH$_3$ | H | —CH$_2$CH$_3$ |
| E-131 | CH | CH | —CH$_3$ | H | —CH$_3$ | iso-propyl |
| E-132 | CH | CH | —CH$_2$CH$_3$ | H | —CH$_2$CH$_3$ | iso-propyl |
| E-133 | CH | CH | iso-propyl | H | iso-propyl | iso-propyl |
| E-134 | CH | CH | iso-butyl | H | iso-butyl | iso-propyl |
| E-135 | CH | CH | 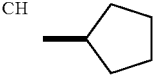 | H | 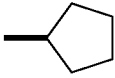 | iso-propyl |
| E-136 | CH | CH | 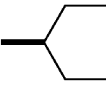 | H | 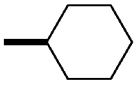 | iso-propyl |
| E-137 | CH | CH | —CH$_2$CH$_3$ | H | —CH$_3$ | iso-propyl |
| E-138 | CH | CH | —CH$_3$ | H | —CH$_2$CH$_3$ | iso-propyl |
| E-139 | CH | CH | —CH$_3$ | —CH$_3$ | H | iso-propyl |
| E-140 | CH | CH | —CH$_2$CH$_3$ | —CH$_2$CH$_3$ | H | iso-propyl |
| E-141 | CH | CH | iso-butyl | iso-butyl | H | iso-propyl |
| E-142 | CH | CH | —CH$_2$CH$_3$ | —CH$_3$ | H | iso-propyl |
| E-143 | CH | CH | —CH$_3$ | —CH$_2$CH$_3$ | H | iso-propyl |
| E-144 | CH | CH | —CH$_3$ | H | —CH$_3$ | iso-butyl |
| E-145 | CH | CH | —CH$_2$CH$_3$ | H | —CH$_2$CH$_3$ | iso-butyl |
| E-146 | CH | CH | iso-propyl | H | iso-propyl | iso-butyl |
| E-147 | CH | CH | iso-butyl | H | iso-butyl | iso-butyl |
| E-148 | CH | CH | 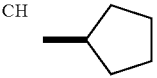 | H | 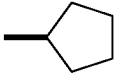 | iso-butyl |
| E-149 | CH | CH | 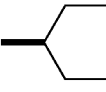 | H | 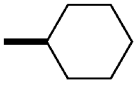 | iso-butyl |
| E-150 | CH | CH | —CH$_2$CH$_3$ | H | —CH$_3$ | iso-butyl |
| E-151 | CH | CH | —CH$_3$ | H | —CH$_2$CH$_3$ | iso-butyl |
| E-152 | CH | CH | —CH$_3$ | —CH$_3$ | H | iso-butyl |
| E-153 | CH | CH | —CH$_2$CH$_3$ | —CH$_2$CH$_3$ | H | iso-butyl |
| E-154 | CH | CH | iso-butyl | iso-butyl | H | iso-butyl |
| E-155 | CH | CH | —CH$_2$CH$_3$ | —CH$_3$ | H | iso-butyl |
| E-156 | CH | CH | —CH$_3$ | —CH$_2$CH$_3$ | H | iso-butyl |

Further preferred cyclometallated Ir complexes of formulae (II), (II') and (II'') are:

Compounds of the Following Formulae

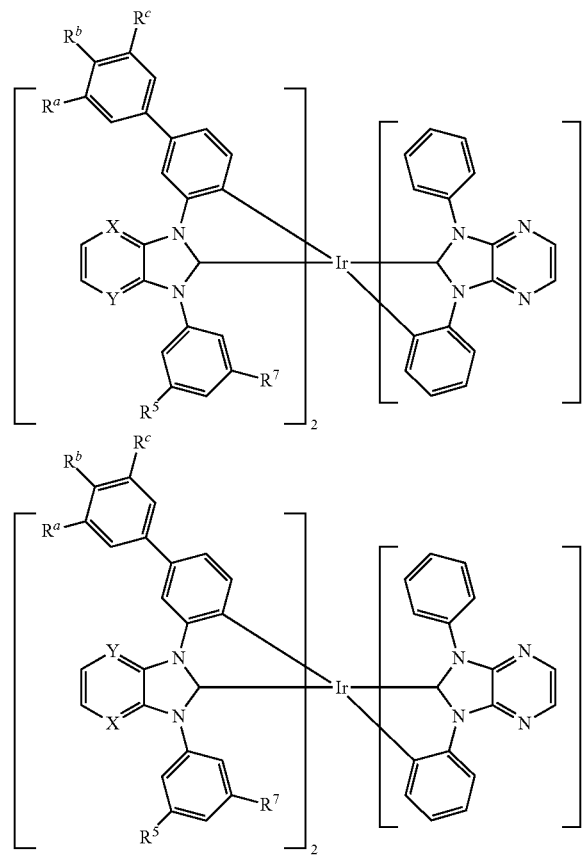

| Cpd. | X | Y | $R^a$ | $R^b$ | $R^c$ | $R^5 = R^7$ |
|---|---|---|---|---|---|---|
| F-1 | N | N | —CH₃ | H | —CH₃ | —CH₂CH₃ |
| F-2 | N | N | —CH₂CH₃ | H | —CH₂CH₃ | —CH₂CH₃ |
| F-3 | N | N | iso-propyl | H | iso-propyl | —CH₂CH₃ |
| F-4 | N | N | iso-butyl | H | iso-butyl | —CH₂CH₃ |
| F-5 | N | N | cyclopentyl | H | cyclopentyl | —CH₂CH₃ |
| F-6 | N | N | cyclohexyl | H | cyclohexyl | —CH₂CH₃ |
| F-7 | N | N | —CH₂CH₃ | H | —CH₃ | —CH₂CH₃ |
| F-8 | N | N | —CH₃ | H | —CH₂CH₃ | —CH₂CH₃ |
| F-9 | N | N | —CH₃ | —CH₃ | H | —CH₂CH₃ |
| F-10 | N | N | —CH₂CH₃ | —CH₂CH₃ | H | —CH₂CH₃ |
| F-11 | N | N | iso-butyl | iso-butyl | H | —CH₂CH₃ |
| F-12 | N | N | —CH₂CH₃ | —CH₃ | H | —CH₂CH₃ |
| F-13 | N | N | —CH₃ | —CH₂CH₃ | H | —CH₂CH₃ |
| F-14 | N | N | —CH₃ | H | —CH₃ | iso-propyl |
| F-15 | N | N | —CH₂CH₃ | H | —CH₂CH₃ | iso-propyl |
| F-16 | N | N | iso-propyl | H | iso-propyl | iso-propyl |
| F-17 | N | N | iso-butyl | H | iso-butyl | iso-propyl |
| F-18 | N | N | cyclopentyl | H | cyclopentyl | iso-propyl |
| F-19 | N | N | cyclohexyl | H | cyclohexyl | iso-propyl |
| F-20 | N | N | —CH₂CH₃ | H | —CH₃ | iso-propyl |
| F-21 | N | N | —CH₃ | H | —CH₂CH₃ | iso-propyl |
| F-22 | N | N | —CH₃ | —CH₃ | H | iso-propyl |
| F-23 | N | N | —CH₂CH₃ | —CH₂CH₃ | H | iso-propyl |
| F-24 | N | N | iso-butyl | iso-butyl | H | iso-propyl |
| F-25 | N | N | —CH₂CH₃ | —CH₃ | H | iso-propyl |
| F-26 | N | N | —CH₃ | —CH₂CH₃ | H | iso-propyl |
| F-27 | N | N | —CH₃ | H | —CH₃ | iso-butyl |
| F-28 | N | N | —CH₂CH₃ | H | —CH₂CH₃ | iso-butyl |
| F-29 | N | N | iso-propyl | H | iso-propyl | iso-butyl |
| F-30 | N | N | iso-butyl | H | iso-butyl | iso-butyl |
| F-31 | N | N | cyclopentyl | H | cyclopentyl | iso-butyl |
| F-32 | N | N | cyclohexyl | H | cyclohexyl | iso-butyl |
| F-33 | N | N | —CH₂CH₃ | H | —CH₃ | iso-butyl |
| F-34 | N | N | —CH₃ | H | —CH₂CH₃ | iso-butyl |
| F-35 | N | N | —CH₃ | —CH₃ | H | iso-butyl |
| F-36 | N | N | —CH₂CH₃ | —CH₂CH₃ | H | iso-butyl |
| F-37 | N | N | iso-butyl | iso-butyl | H | iso-butyl |
| F-38 | N | N | —CH₂CH₃ | —CH₃ | H | iso-butyl |
| F-39 | N | N | —CH₃ | —CH₂CH₃ | H | iso-butyl |
| F-40 | N | CH | —CH₃ | H | —CH₃ | —CH₂CH₃ |
| F-41 | N | CH | —CH₂CH₃ | H | —CH₂CH₃ | —CH₂CH₃ |
| F-42 | N | CH | iso-propyl | H | iso-propyl | —CH₂CH₃ |
| F-43 | N | CH | iso-butyl | H | iso-butyl | —CH₂CH₃ |
| F-44 | N | CH | cyclopentyl | H | cyclopentyl | —CH₂CH₃ |
| F-45 | N | CH | cyclohexyl | H | cyclohexyl | —CH₂CH₃ |
| F-46 | N | CH | —CH₂CH₃ | H | —CH₃ | —CH₂CH₃ |
| F-47 | N | CH | —CH₃ | H | —CH₂CH₃ | —CH₂CH₃ |
| F-48 | N | CH | —CH₃ | —CH₃ | H | —CH₂CH₃ |
| F-49 | N | CH | —CH₂CH₃ | —CH₂CH₃ | H | —CH₂CH₃ |
| F-50 | N | CH | iso-butyl | iso-butyl | H | —CH₂CH₃ |
| F-51 | N | CH | —CH₂CH₃ | —CH₃ | H | —CH₂CH₃ |
| F-52 | N | CH | —CH₃ | —CH₂CH₃ | H | —CH₂CH₃ |
| F-53 | N | CH | —CH₃ | H | —CH₃ | iso-propyl |
| F-54 | N | CH | —CH₂CH₃ | H | —CH₂CH₃ | iso-propyl |
| F-55 | N | CH | iso-propyl | H | iso-propyl | iso-propyl |
| F-56 | N | CH | iso-butyl | H | iso-butyl | iso-propyl |
| F-57 | N | CH | cyclopentyl | H | cyclopentyl | iso-propyl |
| F-58 | N | CH | cyclohexyl | H | cyclohexyl | iso-propyl |
| F-59 | N | CH | —CH₂CH₃ | H | —CH₃ | iso-propyl |
| F-60 | N | CH | —CH₃ | H | —CH₂CH₃ | iso-propyl |
| F-61 | N | CH | —CH₃ | —CH₃ | H | iso-propyl |
| F-62 | N | CH | —CH₂CH₃ | —CH₂CH₃ | H | iso-propyl |
| F-63 | N | CH | iso-butyl | iso-butyl | H | iso-propyl |
| F-64 | N | CH | —CH₂CH₃ | —CH₃ | H | iso-propyl |
| F-65 | N | CH | —CH₃ | —CH₂CH₃ | H | iso-propyl |
| F-66 | N | CH | —CH₃ | H | —CH₃ | iso-butyl |
| F-67 | N | CH | —CH₂CH₃ | H | —CH₂CH₃ | iso-butyl |
| F-68 | N | CH | iso-propyl | H | iso-propyl | iso-butyl |

-continued

| Cpd. | X | Y | Rᵃ | Rᵇ | Rᶜ | R⁵ = R⁷ |
|---|---|---|---|---|---|---|
| F-69 | N | CH | iso-butyl | H | iso-butyl | iso-butyl |
| F-70 | N | CH | cyclopentyl | H | cyclopentyl | iso-butyl |
| F-71 | N | CH | cyclohexyl | H | cyclohexyl | iso-butyl |
| F-72 | N | CH | —CH₂CH₃ | H | —CH₃ | iso-butyl |
| F-73 | N | CH | —CH₃ | H | —CH₂CH₃ | iso-butyl |
| F-74 | N | CH | —CH₃ | —CH₃ | H | iso-butyl |
| F-75 | N | CH | —CH₂CH₃ | —CH₂CH₃ | H | iso-butyl |
| F-76 | N | CH | iso-butyl | iso-butyl | H | iso-butyl |
| F-77 | N | CH | —CH₂CH₃ | —CH₃ | H | iso-butyl |
| F-78 | N | CH | —CH₃ | —CH₂CH₃ | H | iso-butyl |
| F-79 | CH | N | —CH₃ | H | —CH₃ | —CH₂CH₃ |
| F-80 | CH | N | —CH₂CH₃ | H | —CH₂CH₃ | —CH₂CH₃ |
| F-81 | CH | N | iso-propyl | H | iso-propyl | —CH₂CH₃ |
| F-82 | CH | N | iso-butyl | H | iso-butyl | —CH₂CH₃ |
| F-83 | CH | N | cyclopentyl | H | cyclopentyl | —CH₂CH₃ |
| F-84 | CH | N | cyclohexyl | H | cyclohexyl | —CH₂CH₃ |
| F-85 | CH | N | —CH₂CH₃ | H | —CH₃ | —CH₂CH₃ |
| F-86 | CH | N | —CH₃ | H | —CH₂CH₃ | —CH₂CH₃ |
| F-87 | CH | N | —CH₃ | —CH₃ | H | —CH₂CH₃ |
| F-88 | CH | N | —CH₂CH₃ | —CH₂CH₃ | H | —CH₂CH₃ |
| F-89 | CH | N | iso-butyl | iso-butyl | H | —CH₂CH₃ |
| F-90 | CH | N | —CH₂CH₃ | —CH₃ | H | —CH₂CH₃ |
| F-91 | CH | N | —CH₃ | —CH₂CH₃ | H | —CH₂CH₃ |
| F-92 | CH | N | —CH₃ | H | —CH₃ | iso-propyl |
| F-93 | CH | N | —CH₂CH₃ | H | —CH₂CH₃ | iso-propyl |
| F-94 | CH | N | iso-propyl | H | iso-propyl | iso-propyl |
| F-95 | CH | N | iso-butyl | H | iso-butyl | iso-propyl |
| F-96 | CH | N | cyclopentyl | H | cyclopentyl | iso-propyl |
| F-97 | CH | N | cyclohexyl | H | cyclohexyl | iso-propyl |
| F-98 | CH | N | —CH₂CH₃ | H | —CH₃ | iso-propyl |
| F-99 | CH | N | —CH₃ | H | —CH₂CH₃ | iso-propyl |
| F-100 | CH | N | —CH₃ | —CH₃ | H | iso-propyl |
| F-101 | CH | N | —CH₂CH₃ | —CH₂CH₃ | H | iso-propyl |
| F-102 | CH | N | iso-butyl | iso-butyl | H | iso-propyl |
| F-103 | CH | N | —CH₂CH₃ | —CH₃ | H | iso-propyl |
| F-104 | CH | N | —CH₃ | —CH₂CH₃ | H | iso-propyl |
| F-105 | CH | N | —CH₃ | H | —CH₃ | iso-butyl |
| F-106 | CH | N | —CH₂CH₃ | H | —CH₂CH₃ | iso-butyl |
| F-107 | CH | N | iso-propyl | H | iso-propyl | iso-butyl |
| F-108 | CH | N | iso-butyl | H | iso-butyl | iso-butyl |
| F-109 | CH | N | cyclopentyl | H | cyclopentyl | iso-butyl |
| F-110 | CH | N | cyclohexyl | H | cyclohexyl | iso-butyl |
| F-111 | CH | N | —CH₂CH₃ | H | —CH₃ | iso-butyl |
| F-112 | CH | N | —CH₃ | H | —CH₂CH₃ | iso-butyl |
| F-113 | CH | N | —CH₃ | —CH₃ | H | iso-butyl |
| F-114 | CH | N | —CH₂CH₃ | —CH₂CH₃ | H | iso-butyl |
| F-115 | CH | N | iso-butyl | iso-butyl | H | iso-butyl |
| F-116 | CH | N | —CH₂CH₃ | —CH₃ | H | iso-butyl |
| F-117 | CH | N | —CH₃ | —CH₂CH₃ | H | iso-butyl |
| F-118 | CH | CH | —CH₃ | H | —CH₃ | —CH₂CH₃ |
| F-119 | CH | CH | —CH₂CH₃ | H | —CH₂CH₃ | —CH₂CH₃ |
| F-120 | CH | CH | iso-propyl | H | iso-propyl | —CH₂CH₃ |
| F-121 | CH | CH | iso-butyl | H | iso-butyl | —CH₂CH₃ |
| F-122 | CH | CH | cyclopentyl | H | cyclopentyl | —CH₂CH₃ |
| F-123 | CH | CH | cyclohexyl | H | cyclohexyl | —CH₂CH₃ |
| F-124 | CH | CH | —CH₂CH₃ | H | —CH₃ | —CH₂CH₃ |
| F-125 | CH | CH | —CH₃ | H | —CH₂CH₃ | —CH₂CH₃ |
| F-126 | CH | CH | —CH₃ | —CH₃ | H | —CH₂CH₃ |
| F-127 | CH | CH | —CH₂CH₃ | —CH₂CH₃ | H | —CH₂CH₃ |
| F-128 | CH | CH | iso-butyl | iso-butyl | H | —CH₂CH₃ |
| F-129 | CH | CH | —CH₂CH₃ | —CH₃ | H | —CH₂CH₃ |
| F-130 | CH | CH | —CH₃ | —CH₂CH₃ | H | —CH₂CH₃ |
| F-131 | CH | CH | —CH₃ | H | —CH₃ | iso-propyl |
| F-132 | CH | CH | —CH₂CH₃ | H | —CH₂CH₃ | iso-propyl |
| F-133 | CH | CH | iso-propyl | H | iso-propyl | iso-propyl |
| F-134 | CH | CH | iso-butyl | H | iso-butyl | iso-propyl |
| F-135 | CH | CH | cyclopentyl | H | cyclopentyl | iso-propyl |
| F-136 | CH | CH | cyclohexyl | H | cyclohexyl | iso-propyl |
| F-137 | CH | CH | —CH₂CH₃ | H | —CH₃ | iso-propyl |
| F-138 | CH | CH | —CH₃ | H | —CH₂CH₃ | iso-propyl |
| F-139 | CH | CH | —CH₃ | —CH₃ | H | iso-propyl |
| F-140 | CH | CH | —CH₂CH₃ | —CH₂CH₃ | H | iso-propyl |
| F-141 | CH | CH | iso-butyl | iso-butyl | H | iso-propyl |
| F-142 | CH | CH | —CH₂CH₃ | —CH₃ | H | iso-propyl |
| F-143 | CH | CH | —CH₃ | —CH₂CH₃ | H | iso-propyl |
| F-144 | CH | CH | —CH₃ | H | —CH₃ | iso-butyl |
| F-145 | CH | CH | —CH₂CH₃ | H | —CH₂CH₃ | iso-butyl |
| F-146 | CH | CH | iso-propyl | H | iso-propyl | iso-butyl |
| F-147 | CH | CH | iso-butyl | H | iso-butyl | iso-butyl |
| F-148 | CH | CH | cyclopentyl | H | cyclopentyl | iso-butyl |
| F-149 | CH | CH | cyclohexyl | H | cyclohexyl | iso-butyl |
| F-150 | CH | CH | —CH₂CH₃ | H | —CH₃ | iso-butyl |
| F-151 | CH | CH | —CH₃ | H | —CH₂CH₃ | iso-butyl |
| F-152 | CH | CH | —CH₃ | —CH₃ | H | iso-butyl |
| F-153 | CH | CH | —CH₂CH₃ | —CH₂CH₃ | H | iso-butyl |
| F-154 | CH | CH | iso-butyl | iso-butyl | H | iso-butyl |
| F-155 | CH | CH | —CH₂CH₃ | —CH₃ | H | iso-butyl |
| F-156 | CH | CH | —CH₃ | —CH₂CH₃ | H | iso-butyl |

Particularly preferred inventive cyclometallated Ir complexes comprising three bidentate ligands of formula (I) and/or (I') are the following complexes:

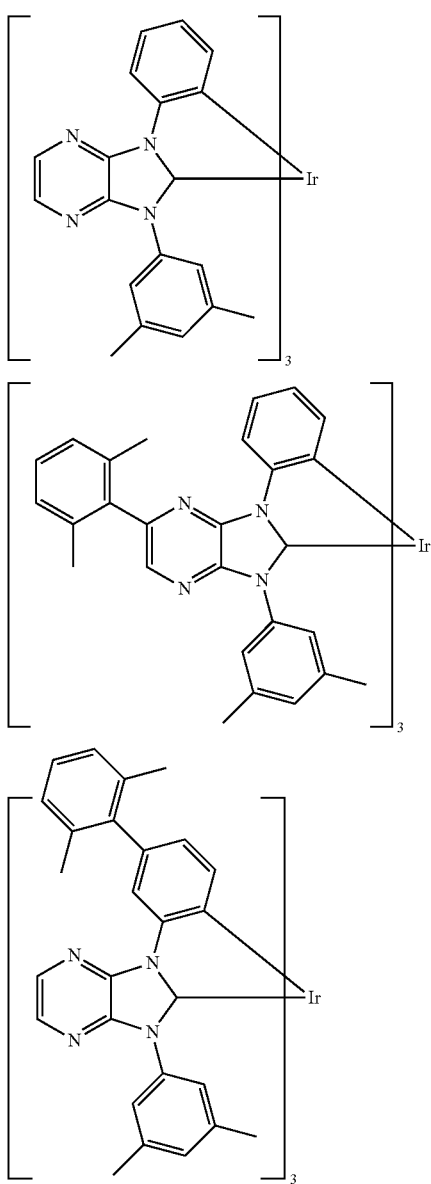
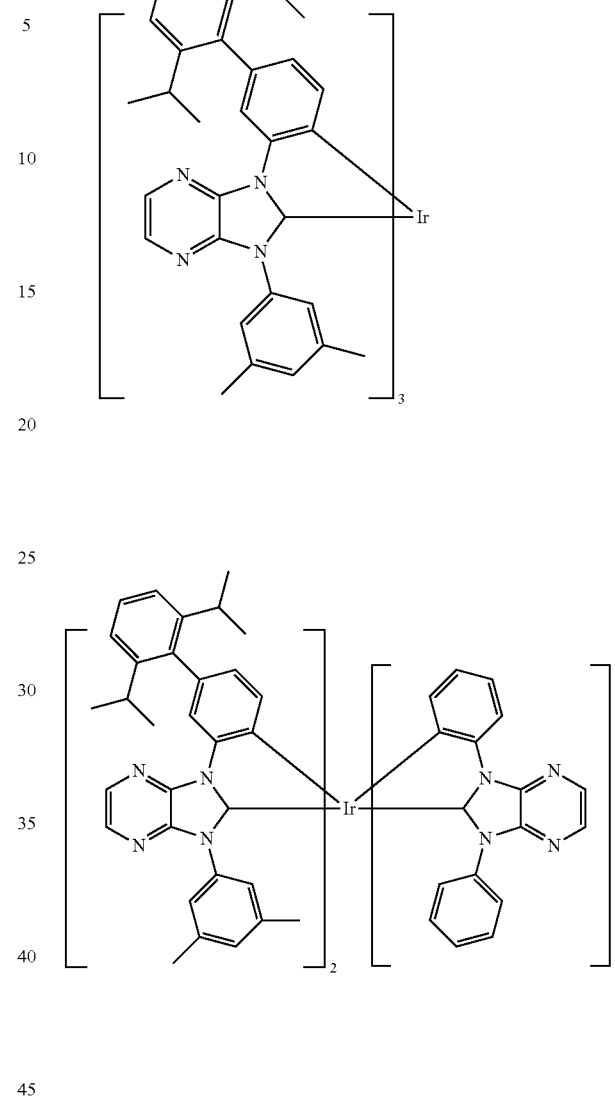
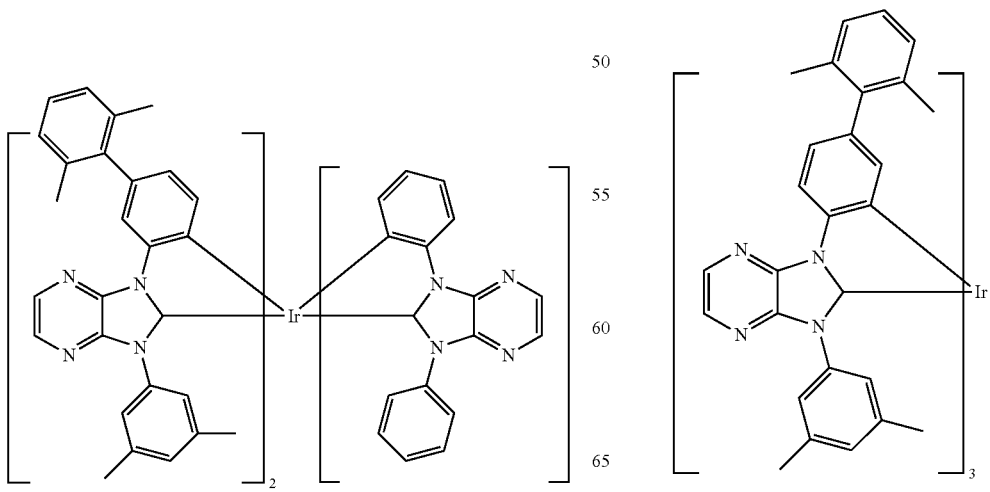

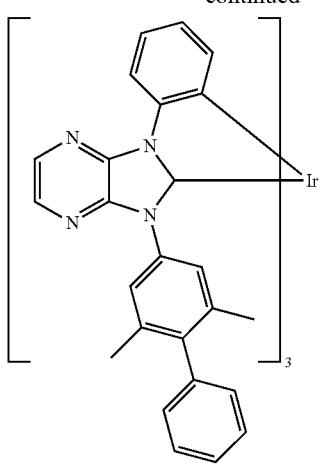

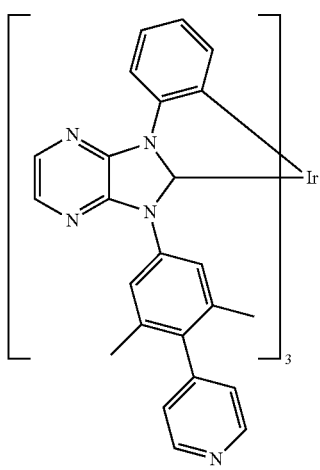

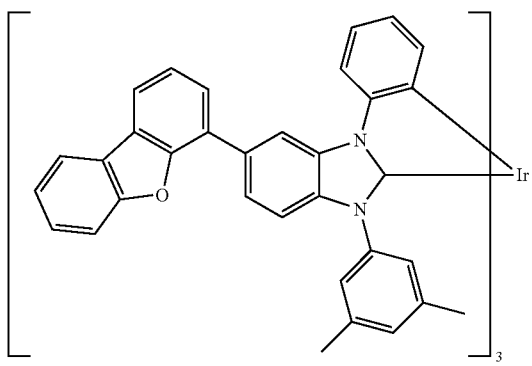

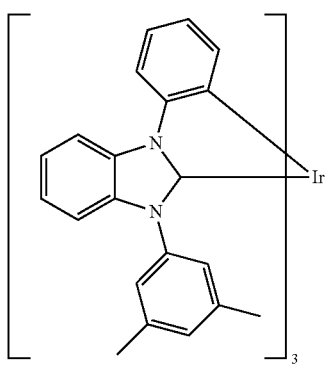

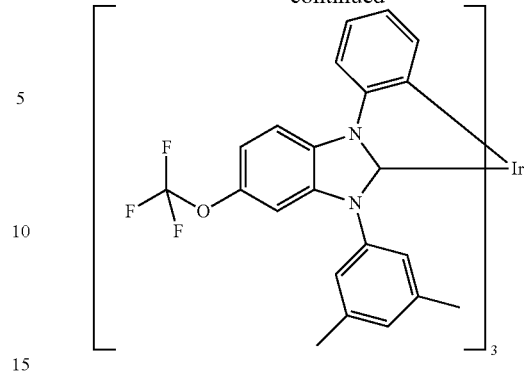

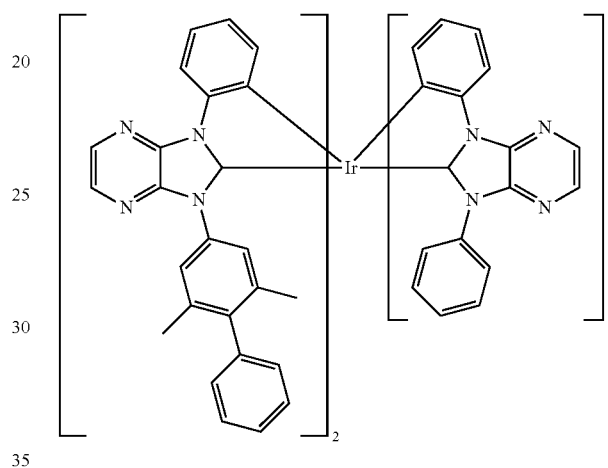

The present invention also relates to a process for preparing the inventive cyclometallated Ir complexes comprising one, two or three, preferably three, bidentate ligands of formula (I) and/or (I') by contacting suitable compounds comprising Ir with the appropriate ligands or ligand precursors.

In one embodiment of the process according to the invention, a suitable compound comprising iridium and appropriate carbene ligands, preferably in deprotonated form as the free carbene or in the form of a protected carbene, for example as the silver-carbene complex, are contacted.

The present invention therefore relates—in one embodiment—to a process according to the invention wherein the ligand precursor used is a corresponding Ag-carbene complex.

In a further preferred embodiment of the process according to the invention, the ligand precursors used are organic compounds which are reacted with suitable Ir comprising compounds. The carbene can be released from precursors of the carbene ligands by removing volatile substances, for example lower alcohols such as methanol or ethanol, for example at elevated temperature and/or under reduced pressure and/or using molecular sieves which bind the alcohol molecules eliminated. Corresponding processes are known to those skilled in the art.

The present invention also relates to the process according to the invention wherein the ligand precursor used is a compound of the general formula (IV)

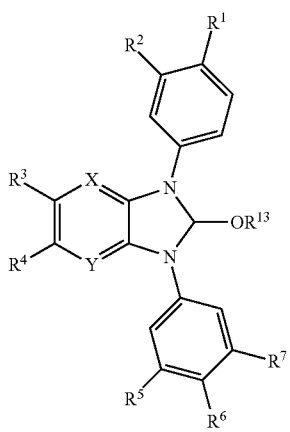

(IV)

wherein $R^1$, $R^2$, $R^3$, $R^4$, $R^6$, $R^5$, $R^7$, X and Y are each as already defined above for the compounds of the general formula (I), and $R^{13}$ is defined as follows:

$R^{13}$ is independently $SiR^{14}R^{15}R^{16}$, aryl, heteroaryl, alkyl, cycloalkyl or heterocyclealkyl, $R^{14}$, $R^{15}$, $R^{16}$ are each independently aryl, heteroaryl, alkyl, cycloalkyl or heterocyclealkyl.

The definitions of aryl, heteroaryl, alkyl, cycloalkyl and heterocyclealkyl have been specified above.

In a particularly preferred embodiment, $R^{13}$ is alkyl, especially $C_1$-$C_{20}$-alkyl, preferably $C_1$-$C_{10}$alkyl, more preferably $C_1$-$C_8$-alkyl, for example methyl, ethyl, propyl such as n-propyl, isopropyl, butyl such as n-butyl, isobutyl, tert-butyl, pentyl, hexyl, heptyl or octyl.

$R^{13}$ in the compound of the general formula (IV) is most preferably methyl or ethyl.

Compounds of the general formula (IV) are generally obtainable by processes known to those skilled in the art. Compounds of the general formula (IV) can be obtained for example by reacting compounds of the general formula (Va)

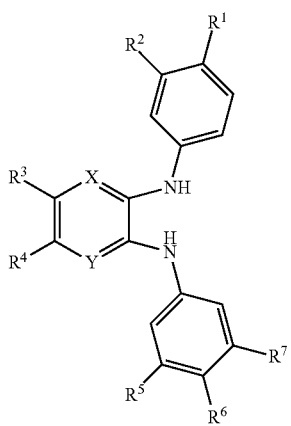

(Va)

or the corresponding Cl or $BF_4$ salt of formula (Vb)

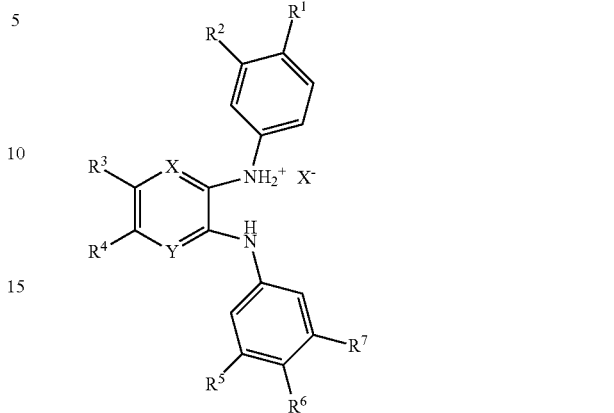

(Vb)

wherein $X^-$ is $Cl^-$ or $BF_4^-$,
with compounds of the general formula (VI)

$$HC(OR^{13})_3 \quad (VI),$$

or by reacting compounds of the general formula (V) in a first step with Vilsmeier reagent ((chloromethylene)dimethylammonium chloride) and a sodium salt selected from $NaBF_4$, NaCl, NaBr or NaI to obtain a compound of formula (Vc)

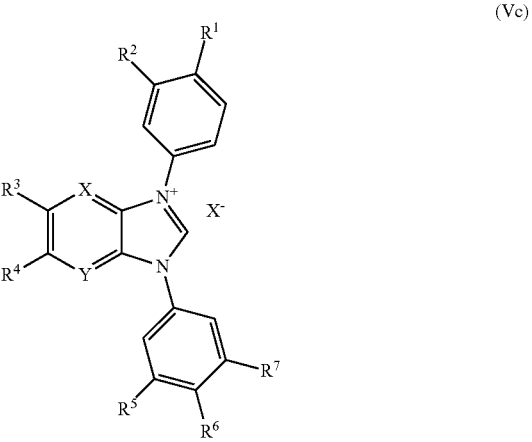

(Vc)

wherein $X^-$ is $BF_4^-$, $Cl^-$, Br or $I^-$ and
in a second step with $R^{13}OH$ or $M''OR^{13}$, wherein M" is an alkali metal salt, preferably Na,
and
where $R^1$, $R^2$, $R^3$, $R^4$, $R^6$, $R^5$, $R^7$, X, Y and $R^{13}$ are each as already defined above for the compounds of the general formula (IV) or for the cyclometallated Ir complexes comprising one, two or three bidentate ligands of formula (I) and/or (I').

This preparation of the compounds of the general formula (IV) can be effected in the presence or in the absence of a solvent. Suitable solvents are specified below. In one preferred embodiment, the compounds of the general formula (IV) are prepared in substance, or the compound of the general formula (VI) is added in an excess, such that it functions as a solvent.

Compounds of the general formulae (V) and (VI) are commercially available and/or obtainable by processes known to those skilled in the art; for example, compounds of the general formula (V) are obtainable by reacting the appropriate chlorides with the appropriate amines.

The compounds of the general formula (IV) are prepared generally at a temperature of 10 to 150° C., preferably 40 to 120° C., more preferably 60 to 110° C.

The reaction time is generally 2 to 48 hours, preferably 6 to 24 hours, more preferably 8 to 16 hours.

After the reaction has ended, the desired product can be isolated and purified by customary processes known to those skilled in the art, for example filtration, recrystallization, column chromatography, etc.

Appropriate compounds, especially complexes iridium, are known to those skilled in the art. Particularly suitable compounds comprising iridium comprise, for example, ligands such as halides, preferably chloride, 1,5-cyclooctadiene (COD), cyclooctene (COE), phosphines, cyanides, alkoxides, pseudohalides and/or alkyl.

Particularly preferred complexes comprising iridium are selected from the group consisting of $[Ir(COD)Cl]_2$, $[Ir(COE)_2Cl]_2$ $IrCl_3 \times H_2O$, $Ir(acac)_3$, $Ir(COD)_2BF_4$, $Ir(COD)_2BARF$ (BARF=tetrakis[3,5-bis(trifluoromethyl)phenyl]borate)) and mixtures thereof.

The carbene ligand precursors are deprotonated, preferably before the reaction, for example, by basic compounds known to those skilled in the art, for example basic metalates, basic metal acetates, acetylacetonates or alkoxides, or bases such as $KO^tBu$, $NaO^tBu$, $LiO^tBu$, $NaH$, silylamides, $Ag_2O$ and phosphazene bases. Particular preference is given to deprotonating with $Ag_2O$ to obtain the corresponding Ag-carbene, which is reacted with the compound comprising M to give the inventive complexes.

Particularly preferably, the carbene can be released from precursors of the carbene ligands by removing volatile substances, for example lower alcohols.

The process according to the invention for preparing the cyclometallated Ir complexes comprising one, two or three bidentate ligands of formula (I) and/or (I') according to the present invention using the compounds of the general formula (IV) has the advantage that the compounds of the general formula (IV) are stable intermediates which can be handled readily and can be isolated under standard laboratory conditions. In addition, the compounds of the general formula (IV) are soluble in customary organic solvents, such that the preparation of the inventive cyclometallated Ir complexes comprising one, two or three bidentate ligands of formula (I) and/or (I') in homogeneous solution is possible, such that a workup of the desired product, i.e. of the cyclometallated Ir complexes comprising one, two or three bidentate ligands of formula (I) and/or (I') is more readily possible, for example for isolation and/or purification.

The contacting is preferably effected in a solvent. Suitable solvents are known per se to those skilled in the art and are preferably selected from the group consisting of aromatic or aliphatic solvents, for example benzene, toluene, xylene or mesitylene, cyclic or acyclic ethers, for example dioxane or THF, alcohols, esters, amides, ketones, nitriles, halogenated compounds and mixtures thereof. Particularly preferred solvents are toluene, xylenes, mesitylene and dioxane.

The molar ratio of metal-noncarbene complex used to carbene ligand precursor used is generally 1:10 to 10:1, preferably 1:1 to 1:6, more preferably 1:2 to 1:5.

The contacting is generally effected at a temperature of 20 to 200° C., preferably 50 to 150° C., more preferably 60 to 150° C.

The reaction time depends on the desired carbene complex and is generally 0.02 to 50 hours, preferably 0.1 to 24 hours, more preferably 1 to 24 hours.

The cyclometallated Ir complexes comprising one, two or three bidentate ligands of formula (I) and/or (I') obtained after the reaction can optionally be purified by processes known to those skilled in the art, for example washing, crystallization or chromatography, and optionally isomerized (sine fac and mer isomers may be obtained) under conditions likewise known to those skilled in the art, for example with acid mediation, thermally or photochemically.

Suitable processes for preparing the cyclometallated Ir complexes comprising one, two or three, preferably three, bidentate ligands of formula (I) and/or (I'), especially suitable processes for preparing the inventive complexes of formulae (II), (II') and (II''), wherein at least one ligand L is present (o or o' are 1 or 2), are for example mentioned in WO 2011/073149 A1.

The particular advantage of the process according to the present invention is the formation of only one or mainly one cyclometallation isomer of the cyclometallated Ir complexes according to the present invention. This is due to the fact that asymmetric diaryl substituted carbene ligands bearing substituents at the 3 and 5 position of one of the aryl residues bond to one of the carbene nitrogen atoms are present in the cyclometallated Ir complexes and the corresponding compounds of formulae (IV), (Va), (Vb) or (Vc) are used in the preparation of the cyclometallated Ir complexes. By substitution of the 3 and 5 position of the aryl residue, cyclometallation of said aryl residue with Ir is avoided respectively substantially reduced. Therefore, the specific cyclometallated Ir complexes comprising one, two or three ligands of formula (I) or (I') according to the present invention are present in form of only one or mainly one cyclometallation isomer.

In the process of the present invention, the weight ratio of cyclometallation isomer (II) (cyclometallation occurring exclusively on the aryl residue bearing $R^1$ and $R^2$) to cyclometallation isomer (II') (cyclometallation occurring exclusively on the aryl residue bearing $R^5$, $R^6$ and $R^7$) is in general 100% to 60% by weight of isomer (II) to 0% to 40% by weight of isomer (II'), preferably 100% to 70% by weight of isomer (II) to 0% to 30% by weight of isomer (II'). Additionally, isomer (II'') may be present as a third isomer.

A process for preparing metal-carbene complexes of formula

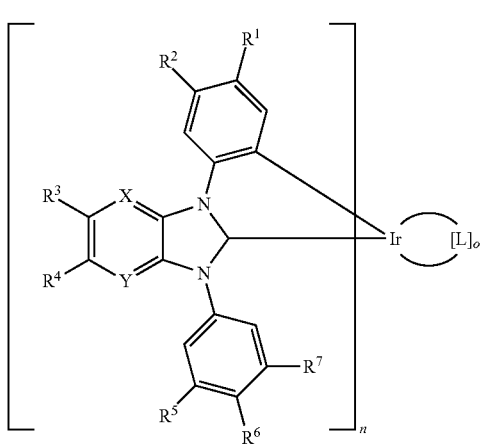 (II)

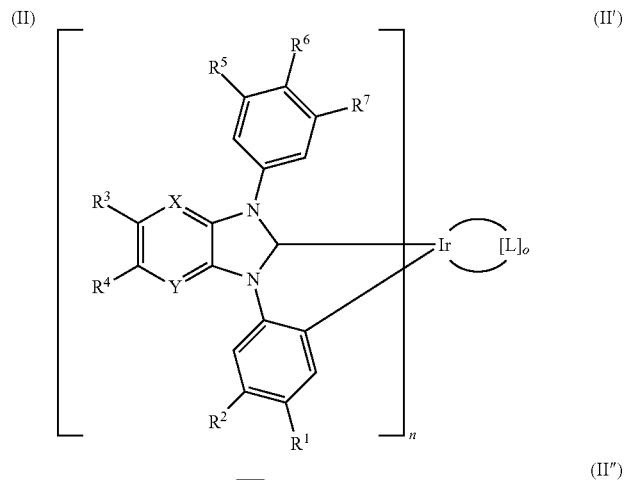 (II')

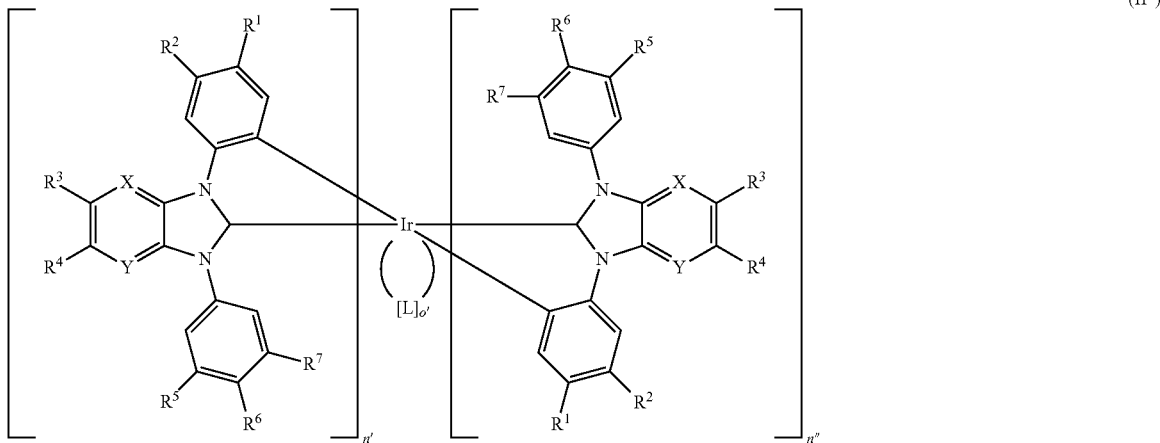 (II")

wherein one ore more of the residues $R^1$, $R^2$, $R^3$, $R^4$ and $R^6$ are substituted or unsubstituted aryl may comprise reacting a compound of formula (II), (II') or (II"), wherein the respective residue $R^1$, $R^2$, $R^3$, $R^4$ and/or $R^6$ in formula (II), (II') or (II") is replaced by $X^1$, with a substituted or unsubstituted aromatic compound corresponding to the respective substituted or unsubstituted aryl residue: (substituted or unsubstituted)aryl-Y, wherein
$X^1$ is Cl, Br, or I, especially Br;
Y is —B(OH)$_2$, —B(OY$^1$)$_2$,

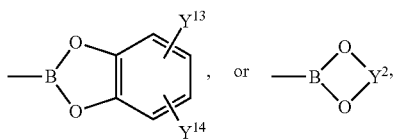

wherein $Y^1$ is a $C_1$-$C_{10}$alkyl group and $Y^2$ is independently in each occurrence a $C_2$-$C_{10}$alkylene group, such as —CY$^3$Y$^4$—CY$^5$Y$^6$—, or —CY$^7$Y$^8$—CY$^9$Y$^{10}$—CY$^{11}$Y$^{12}$—, wherein Y$^3$, Y$^4$, Y$^5$, Y$^6$, Y$^7$, Y$^8$, Y$^9$, Y$^9$, Y$^{10}$, Y$^{11}$ and Y$^{12}$ are independently of each other hydrogen, or a $C_1$-$C_{10}$alkyl group, especially —C(CH$_3$)$_2$C(CH$_3$)$_2$—, —CH$_2$C(CH$_3$)$_2$CH$_2$—, or —C(CH$_3$)$_2$CH$_2$C(CH$_3$)$_2$—, and Y$^{13}$ and Y$^{14}$ are independently of each other hydrogen, or a $C_1$-$C_{10}$alkyl group;
—SnR$^{307}$R$^{308}$R$^{309}$, wherein R$^{307}$, R$^{308}$ and R$^{309}$ are identical or different and are H or $C_1$-$C_6$alkyl, wherein two radicals optionally form a common ring and these radicals are optionally branched or unbranched;
ZnR$^{310}$R$^{311}$, wherein R$^{310}$ is halogen and R$^{311}$ is a $C_1$-$C_{10}$alkyl group, a $C_6$-$C_{12}$aryl group, or $C_1$-$C_{10}$alkenyl group; or
SiR$^{312}$R$^{313}$R$^{314}$, wherein R$^{312}$, R$^{313}$ and R$^{314}$ are identical or different and are halogen, or $C_1$-$C_6$alkyl; and
R', R$^1$, R$^2$, R$^3$, R$^{3'}$, R$^{3''}$, R$^4$, R$^{4'}$, R$^5$, R$^6$ and R$^7$ are as defined above.

Preferred reactions for the introduction of (substituted or unsubstituted)aryl substituents are in general metal catalyzed reactions and more specifically Suzuki, Ullmann, Negishi, Heck, Stille and Kumada coupling reactions (J. Hassan et al., Chemical Reviews 102 (2002) 5; L. Ackermann: "Modern Arylation Methods" (Ed.: L. Ackermann), Wiley-VCH, Weinheim, 2009).

Advantageously, the metal-carbene complexes of formula (II), (II') and (II"), wherein one ore more of the residues R$^1$, R$^2$, R$^5$, R$^6$ and R$^7$ are substituted or unsubstituted aryl can be synthesized by one of the following coupling reactions:
i) Negishi coupling reaction using a compound of formula: (substituted or unsubstituted)aryl-Y, wherein Y is ZnR$^{310}$R$^{311}$, wherein R$^{310}$ is halogen and R$^{311}$ is a $C_1$-$C_{10}$alkyl group, a $C_6$-$C_{12}$aryl group, or $C_1$-$C_{10}$alkenyl group. Reference is, for example, made to B. Vilas et al., Chem. Soc. Rev., 38 (2009) 1598-1607.
ii) Stille coupling reaction using a compound of formula: (substituted or unsubstituted)aryl-Y, wherein Y is —SnR$^{307}$R$^{308}$R$^{309}$, wherein R$^{307}$, R$^{308}$ and R$^{309}$ are identical or different and are H or $C_1$-$C_6$alkyl, wherein two radicals optionally form a common ring and these radicals are optionally branched or unbranched. Reference is, for example, made to J. K. Stille, Angew. Chem. 98 (1986) 504-519; P. Espinet et al., Angew. Chem. Int. Ed., 43 (2004) 4704-4734.

iii) Hiyama coupling reaction using a compound of formula: (substituted or unsubstituted)aryl-Y, wherein Y is $SiR^{312}R^{313}R^{314}$, wherein $R^{312}$, $R^{313}$ and $R^{314}$ are identical or different and are halogen, or $C_1$-$C_6$alkyl. Reference is, for example, made to T. Hiyama et al., Pure Appl. Chem. 66 (1994) 1471-1478 and T. Hiyama et al., Synlett (1991) 845-853; and iv) Suzuki coupling reaction using a compound of formula: (substituted or unsubstituted)aryl-Y, wherein Y is —B(OH)$_2$, —B(OY$^1$)$_2$,

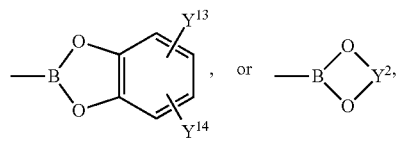

wherein $Y^1$ is a $C_1$-$C_{10}$alkyl group and $Y^2$ is independently in each occurrence a $C_2$-$C_{10}$alkylene group, such as —$CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, especially —$C(CH_3)_2C(CH_3)_2$—, —$CH_2C(CH_3)_2CH_2$—, or —$C(CH_3)_2CH_2C(CH_3)_2$—, and $Y^{13}$ and $Y^{14}$ are independently of each other hydrogen, or a $C_1$-$C_{10}$alkyl group. Reference is, for example, made to A. Suzuki et al., Chemical Reviews 95 (1995) 2457-2483, "Suzuki in Modern Arene Chemistry" (Ed.: D. Astruc), Wiley-VCH, Weinheim, 2002, pp. 53-106. More preferably Suzuki and Negishi coupling reactions are used. Suzuki type reactions are most preferred.

Preferably, the Suzuki reaction of a compound of formula (II), (II') or (II"), wherein the respective residue $R^1$, $R^2$, $R^5$, $R^6$ and/or $R^7$ in formula (II), (II') or (II") is replaced by $X^1$, with a substituted or unsubstituted aromatic compound corresponding to the respective substituted or unsubstituted aryl residue (i.e. (substituted or unsubstituted)aryl-Y) is carried out in presence of
a) a catalyst/ligand system comprising a palladium catalyst and an organic phosphine or phosphonium compound,
b) a base,
c) a solvent or a mixture of solvents.

The organic solvent is usually an aromatic hydrocarbon, a linear, branched, or cyclic ether, or a usual polar organic solvent, such as benzene, toluene, xylene, tetrahydrofurane, or dioxane, or mixtures thereof. If desired, water can be added to the organic reaction medium, in which case, depending on the organic solvent used, the reaction can be carried out in a single phase or in a two-phase mixture.

Usually, the amount of the solvent is chosen in the range of from 1 to 10 l per mol of boronic acid derivative.

Also preferred, the reaction is carried out under an inert atmosphere such as nitrogen, or argon.

Further, it is preferred to carry out the reaction in the presence of an aqueous base, such as an alkali metal hydroxide, metal phosphate, or carbonate such as NaOH, KOH, $K_3PO_4$, $Na_2CO_3$, $K_2CO_3$, or $Cs_2CO_3$.

Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein).

Usually, the molar ratio of the base to boronic acid or boronic ester derivative is chosen in the range of from 0.5:1 to 50:1, very especially in the range of 1:1 to 5:1.

Generally, the reaction temperature is chosen in the range of from 40 to 180° C., preferably under reflux conditions.

Generally, the reaction time is chosen in the range of from 0.5 to 80 hours, preferably from 2 hours to 60 hours.

In a preferred embodiment a usual catalyst for coupling reactions or for polycondensation reactions is used, preferably Pd-based, which is described in WO2007/101820. The palladium compound is added in a ratio of from 1:10000 to 1:50, preferably from 1:5000 to 1:200, based on the number of bonds to be closed. Preference is given, for example, to the use of palladium(II) salts such as $PdOAc_2$ or $Pd_2dba_3$ and to the addition of ligands selected from the group consisting of

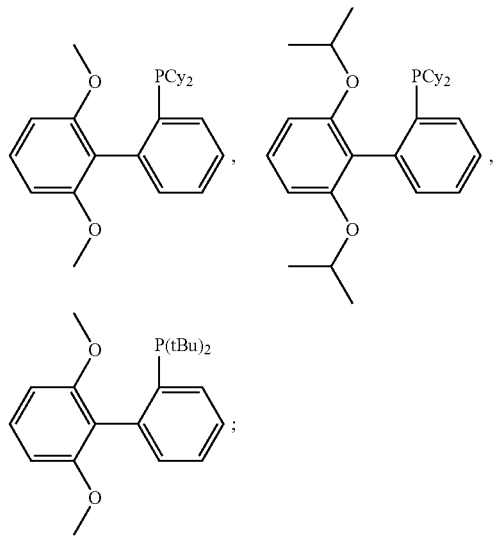

wherein

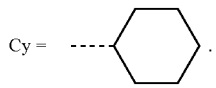

The ligand is added in a ratio of from 1:1 to 1:10, based on Pd. Also preferred, the catalyst is added as in solution or suspension. Preferably, an appropriate organic solvent such as the ones described above, preferably benzene, toluene, xylene, THF, dioxane, more preferably toluene, or mixtures thereof, is used. The amount of solvent usually is chosen in the range of from 1 to 10 l per mol of boronic acid derivative.

Other variations of reaction conditions are given by T. I. Wallow and B. M. Novak in J. Org. Chem. 59 (1994) 5034-5037; and M. Remmers, M. Schulze, G. Wegner in Macromol. Rapid Commun. 17 (1996) 239-252 and G. A. Molander and B. Canturk, Angew. Chem., 121 (2009) 9404-9425.

The following reaction systems are preferred:
i) aryl boronic acid, tris(dibenzylideneacetone) dipalladium (0), SPhos (Dicyclohexylphosphino-2',6'-dimethoxybiphenyl), tripotassium phosphate (solvent toluene/water mixture);

ii) aryl boronic acid, bis(tri-t-butylphosphin)palladium(0) (Pd[P(tBu)$_3$]$_2$), sodium hydroxide (solvent toluene/dioxane/water mixture); and iii) aryl boronic acid, palladium acetate (Pd(OAc)$_2$), SPhos (Dicyclohexylphosphino-2',6'-dimethoxybiphenyl), tripotassium phosphate (o-xylene mixture).

However, it is also possible to introduce the substituted or unsubstituted aryl residue $R^1$, $R^2$, $R^5$, $R^6$ and/or $R^7$ in the respective ligands of formula (I) or (I'), wherein the respective residue $R^1$, $R^2$, $R^5$, $R^6$ and/or $R^7$ in formula (II), (II') or (II") is replaced by $X^1$. The reaction conditions may be the same as mentioned above and are known to a person skilled in the art.

In a further embodiment, the present invention relates to an organic electronic device comprising at least one cyclometallated Ir complex according to the present invention.

Structures of the Organic Electronic Devices

Suitable structures of the organic electronic devices are known to those skilled in the art. Preferred organic electronic devices are selected from organic light-emitting diodes (OLED), light-emitting electrochemical cells (LEEC), organic photovoltaic cells (OPV) and organic field-effect transistors (OFET). More preferred organic electronic devices are OLEDs.

The organic light-emitting diode (OLED) is usually a light-emitting diode (LED) in which the emissive electroluminescent layer is a film of organic compound which emits light in response to an electric current. This layer of organic semiconductor is usually situated between two electrodes. Generally, at least one of these electrodes is transparent. The cyclometallated Ir complex comprising one, two or three, preferably three, bidentate ligands of formula (I) and/or (I') may be present in any desired layer, preferably in the emissive electroluminescent layer (light-emitting layer), of the OLED as emitter material.

The light-emitting electrochemical cell (LEEC) is usually a solid-state device that generates light from an electric current (electroluminescence). LEEC's are usually composed of two metal electrodes connected by (e.g. sandwiching) an organic semiconductor containing mobile ions. Aside from the mobile ions, their structure is very similar to that of an organic light-emitting diode (OLED). The cyclometallated Ir complex comprising one, two or three, preferably three, bidentate ligands of formula (I) and/or (I') may be present in any desired layer as emitter material.

The organic field-effect transistor (OFET) generally includes a semiconductor layer formed from an organic layer with hole transport capacity and/or electron transport capacity; a gate electrode formed from a conductive layer; and an insulation layer introduced between the semiconductor layer and the conductive layer. A source electrode and a drain electrode are mounted on this arrangement in order thus to produce the transistor element. In addition, further layers known to those skilled in the art may be present in the organic transistor. The cyclometallated Ir complex comprising one, two or three, preferably three, bidentate ligands of formula (I) and/or (I') may be present in any desired layer.

The organic photovoltaic cell (OPV) (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is usually formed from two sublayers, i.e. a layer with p-type semiconductor character or hole transport capacity, and a layer formed with n-type semiconductor character or electron transport capacity. In addition, it is possible for further layers known to those skilled in the art to be present in the organic solar cell. The cyclometallated Ir complex comprising one, two or three, preferably three, bidentate ligands of formula (I) and/or (I') may be present in any desired layer, of the OPV, preferably as absorption dye.

The organic electronic device is most preferably an OLED or OPV, wherein the cyclometallated Ir complex comprising one, two or three bidentate ligands of formula (I) and/or (I') is employed as emitter material in OLEDs or LEECs, preferably OLEDs, or absorption dye in OPVs. The organic electronic device is most preferably an OLED, wherein the metal-carbene complex comprising one, two or three bidentate ligands of formula (I) and/or (I') is employed as emitter material.

The present invention therefore preferably relates to an organic electronic device which is an OLED, wherein the OLED comprises (a) an anode, (b) a cathode, (c) a light-emitting layer between the anode and the cathode, (d) optionally a hole transport layer between the light-emitting layer and the anode, wherein the cyclometallated Ir complex comprising one, two or three bidentate ligands of formula (I) and/or (I') is present in the light-emitting layer and/or—if present—in the hole transport layer of the OLED.

The structure of the inventive OLED will be described in detail below.

Cyclometallated Ir Complex Comprising One, Two or Three, Preferably Three, Bidentate Ligands of Formula (I) and/or (I') as Emitter Material According to the present invention, the cyclometallated Ir complex comprising one, two or three, preferably three, bidentate ligands of formula (I) and/or (I') are employed in an organic electronic device, preferably in an OLED. More preferably, the cyclometallated Ir complex comprising one, two or three, preferably three, bidentate ligands of formula (I) and/or (I') are employed as emitter material, preferably as emitter material in the light-emitting layer of an OLED. Suitable OLEDs are known in the art and the preferred structures of suitable OLEDs are described above and—in more detail—below.

The cyclometallated Ir complex comprising one, two or three, preferably three, bidentate ligands of formula (I) and/or (I') have an emission maximum ($\lambda_{max}$) of from 400 to 500 nm. Preferably, the emitter has an emission maximum ($\lambda$), which of from 425 nm to 490 nm, more preferably of from 440 nm to 475 nm, preferably with a FWHM (full width at half maximum) of from 1 nm to 140 nm, more preferably of from 30 nm to 120 nm, most preferably of from 40 nm to 80 nm.

The cyclometallated Ir complex comprising one, two or three, preferably three, bidentate ligands of formula (I) and/or (I') are characterized by a high color purity, especially in the blue region of the electromagnetic spectrum. The preferred CIE-y values of said metal-carbene complexes according to the present invention are <035, more preferably <0.30, most preferably <0.25. (CIE 1931 XYZ color space, created by the International Commission on Illumination (CIE)). The CIE x and y values (coordinates) are extracted from the spectra according to CIE 1931 as known by a person skilled in the art.

The cyclometallated Ir complex comprising one, two or three, preferably three, bidentate ligands of formula (I) and/or (I') are preferably phosphorescence emitter showing emission of light by phosphorescence. However, this does not exclude that the phosphorescence emitter additionally shows emission of light by fluorescence.

The phosphorescence emitter show phosphorescence emission from triplet excited states, preferably at the operating temperatures of the OLED. Phosphorescence may be preceded by a transition from a triplet excited state to an intermediate non-triplet state from which the emissive decay occurs.

Further Emitter Materials

The cyclometallated Ir complex comprising one, two or three, preferably three, bidentate ligands of formula (I) and/or (I') may be employed alone as the only emitter material or in a mixture with one or more cyclometallated Ir complex comprising one, two or three, preferably three, bidentate ligands of formula (I) and/or (I') and/or one or more further emitter materials, preferably in the light-emitting layer of an OLED. Suitable further emitter materials are known by a person skilled in the art.

Suitable further emitter materials are for example:

Phosphorescence emitter compounds based on metal complexes, and especially the complexes of the metals Ru, Rh, Ir, Pd and Pt, in particular the complexes of Ir Suitable metal complexes for use in the inventive organic electronic device, preferably in the OLEDs, are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO 2010/086089, WO 2012/121936 A2, US 2011/0057559, WO 2011/106344, US 2011/0233528 and WO 2011/157339, WO2008156879, WO2010068876, US20110233528, WO2012048266, WO2013031662, WO2013031794.

Further suitable metal complexes are the commercially available metal complexes tris(2-phenylpyridine)iridium (III), iridium(III) tris(2-(4-tolyl)pyridinato-N,C$^{2'}$), bis(2-phenylpyridine)(acetylacetonato)iridium(III), iridium(III) tris(1-phenylisoquinoline), iridium(III) bis(2,2'-benzothienyl)(pyridinato-N,C$^{3'}$)(acetylacetonate), tris(2-phenylquinoline)iridium(III), iridium(III) bis(2-(4,6-difluorophenyl)pyridinato-N,C$^{2}$)picolinate, iridium(III) bis(1-phenylisoquinoline)(acetylacetonate), bis(2-phenylquinoline)(acetylacetonato)iridium(III), iridium(III) bis(dibenzo[f,h]quinoxaline)-(acetylacetonate), iridium(III) bis(2-methyldibenzo[f,h]quinoxaline)(acetylacetonate), bis[1-(9,9-dimethyl-9H-fluoren-2-yl)isoquinoline](acetylacetonato)iridium(III), bis(2-phenylbenzo-thiazolato)(acetylacetonato)iridium(III), bis(2-(9,9-dihexylfluorenyl)-1-pyridine)(acetyl-acetonato)iridium(III), bis(2-benzo[b]thiophen-2-ylpyridine)(acetylacetonato)iridium(III).

Preferred further phosphorescence emitters are carbene complexes. Carbene complexes which are suitable phosphorescent blue emitters are specified in the following publications: WO 2006/056418 A2, WO 2005/113704, WO 2007/115970, WO 2007/115981, WO 2008/000727, WO2009050281, WO2009050290, WO2011051404, US2011/057559 WO2011/073149, WO2012/121936A2, US2012/0305894A1, WO2012170571, WO2012170461, WO 2012170463, WO2006121811, WO2007095118, WO2008156879, WO2008156879, WO2010068876, US20110057559, WO2011106344, US20110233528, WO2012048266 and WO2012172482.

Preferably, the cyclometallated Ir complex comprising one, two or three, preferably three, bidentate ligands of formula (I) and/or (I') is employed alone—as the only emitter material, preferably in the light-emitting layer of an OLED.

In the case that more than one emitter material is used, for example in a white OLED, 0.01 to 20% by weight, preferably 0.1 to 10% by weight, more preferably 0.1 to 2% by weight of a red emitter are employed, 5 to 40% by weight, preferably 10 to 30% by weight, more preferably 15 to 25% by weight of the cyclometallated Ir complex according to the present invention as blue emitter are employed and 0.05 to 5% by weight, preferably 0.05 to 3% by weight, more preferably 0.1 to 1% by weight of a green emitter are employed. The residual amount to 100% in each emitter system is at least one host compound. Suitable host compounds for each emitter material are known to a person skilled in the art.

Host Material

The cyclometallated Ir complex comprising one, two or three, preferably three, bidentate ligands of formula (I) and/or (I') or the mixture of emitter materials mentioned above may be employed, preferably in the light-emitting layer of an OLED, without further additional components or with one or more further components in addition to the emitter material. For example, a fluorescent dye may be present in the light-emitting layer of an OLED in order to alter the emission color of the emitter material. In addition—in a preferred embodiment—one or more host (matrix) material can be used. This host material may be a polymer, for example poly(N-vinylcarbazole) or polysilane. The host material may, however, likewise be a small molecule, for example 4,4'-N,N'-dicarbazolebiphenyl (CDP=CBP) or tertiary aromatic amines, for example TCTA.

Suitable as host material are carbazole derivatives, for example 4,4'-bis(carbazol-9-yl)-2,2'-dimethylbiphenyl (CDBP), 4,4'-bis(carbazol-9-yl)biphenyl (CBP), 1,3-bis(N-carbazolyl)benzene (mCP), and the host materials specified in the following applications: WO2008/034758, WO2009/003919.

Further suitable host materials, which may be small molecules or (co)polymers of the small molecules mentioned, are specified in the following publications: WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913 H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co) polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446, WO06128800, WO2012014621, WO2012105310, WO2012/130709, European patent applications EP12175635.7 and EP12185230.5 and EP12191408.9 (in particular page 25 to 29 of EP12191408.9), WO2012048266, WO2012145173, WO2012162325, and EP2551932.

In a particularly preferred embodiment, one or more compounds of the general formula (IX) specified hereinafter are used as host material

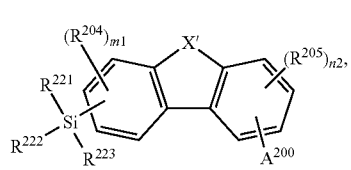

(IX)

wherein
X' is NR, S, O or PR;
R is aryl, heteroaryl, alkyl, cycloalkyl, or heterocyclealkyl;
$A^{200}$ is $-NR^{206}R^{207}$, $-P(O)R^{208}R^{209}$, $-PR^{210}R^{211}$, $-S(O)_2R^{212}$, $-S(O)R^{213}$, $-SR^{214}$, or $-OR^{215}$; $R^{221}$, $R^{222}$ and $R^{223}$ are independently of each other aryl, heteroaryl, alkyl, cycloalkyl, or heterocyclealkyl, wherein at least on of the groups $R^{221}$, $R^{222}$, or $R^{223}$ is aryl, or heteroaryl; $R^{204}$ and $R^{205}$ are independently of each other alkyl, cycloalkyl, heterocyclealkyl, aryl, heteroaryl, a group $A^{200}$, or a group having donor, or acceptor characteristics;
n2 and m1 are independently of each other 0, 1, 2, or 3;
$R^{206}$, $R^{207}$ form together with the nitrogen atom a cyclic residue having 3 to 10 ring atoms, which can be unsubstituted, or which can be substituted with one, or more substituents selected from alkyl, cycloalkyl, heterocyclealkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocyclealkyl, aryl, heteroaryl and a group having donor, or acceptor characteristics; and
$R^{208}$, $R^{209}$, $R^{210}$, $R^{211}$, $R^{212}$, $R^{213}$, $R^{214}$ and $R^{215}$ are independently of each other aryl, heteroaryl, alkyl, cycloalkyl, or heterocyclealkyl.

Compounds of formula (IX) and their preparation processes, such as, for example,

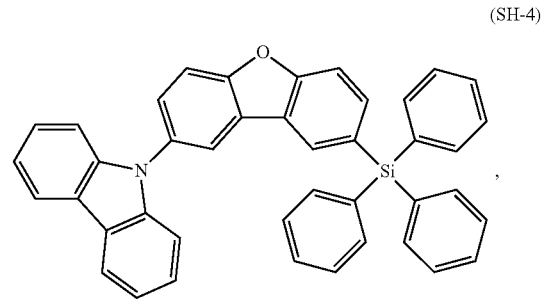

(SH-4)

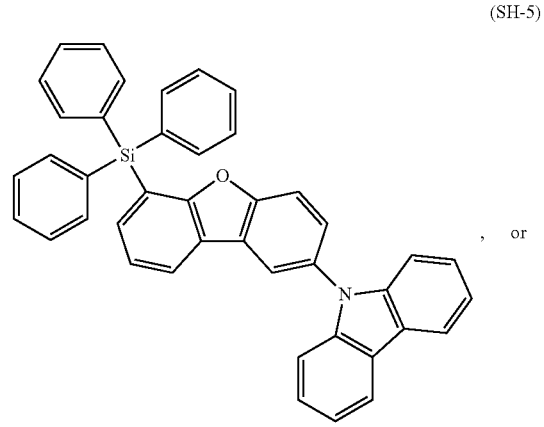

(SH-5), or

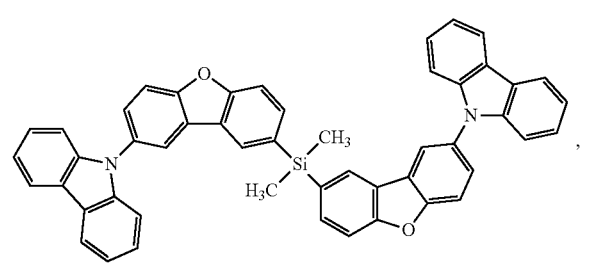

(SH-6)

are described in WO 2010/079051 A1 (in particular pages on 19 to 26 and in tables on pages 27 to 34, pages 35 to 37 and pages 42 to 43).

Additional host materials on basis of dibenzofurane are, for example, described in US 2009066226, EP1 885 818 B1, EP 1 970 976, EP 1 998 388 and EP 2 034 538. Examples of particularly preferred host materials are shown below:

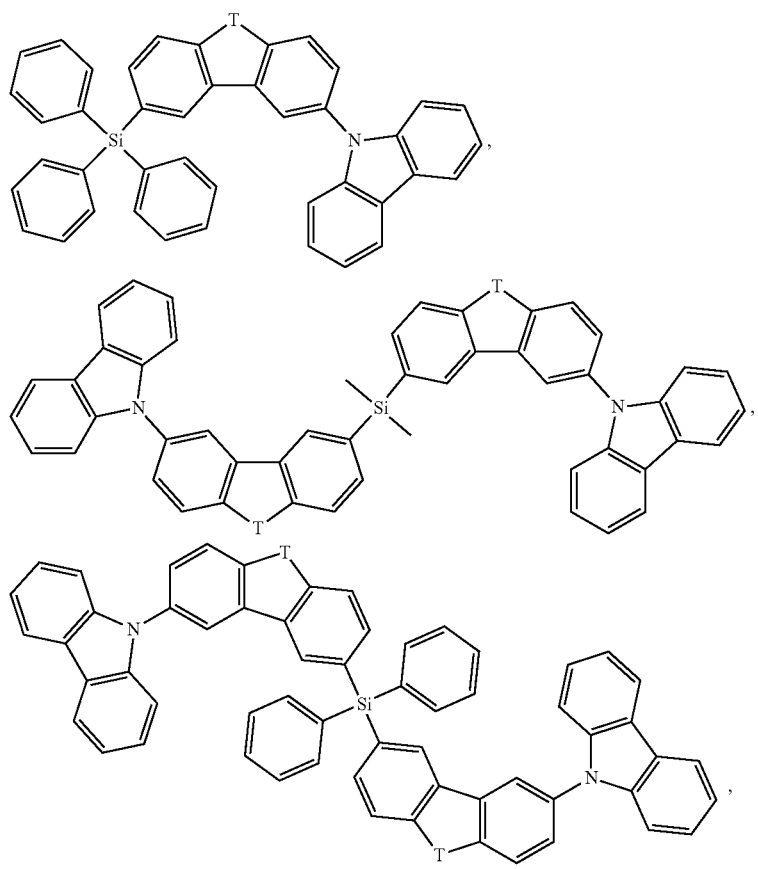
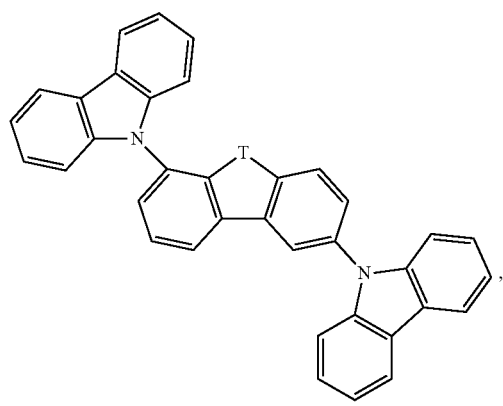
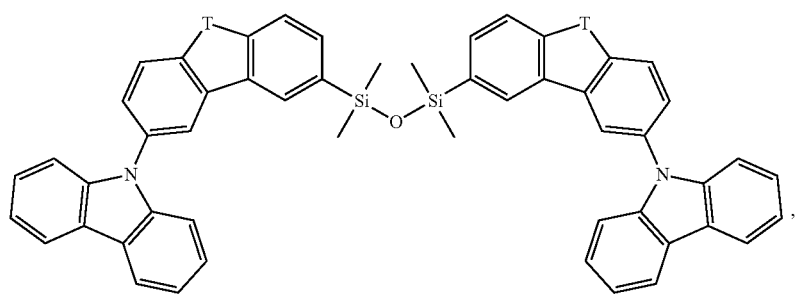

-continued
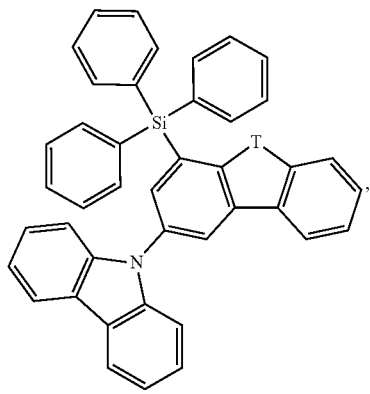
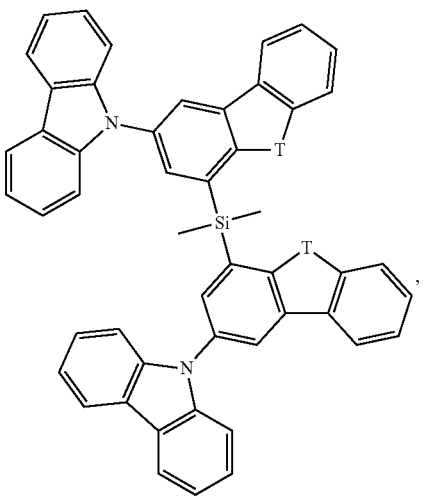
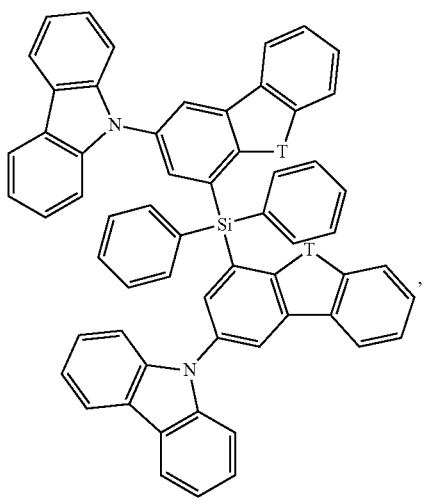
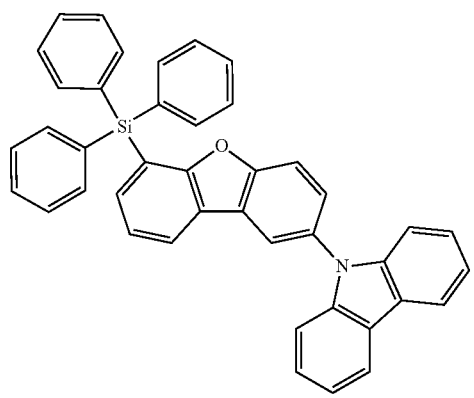
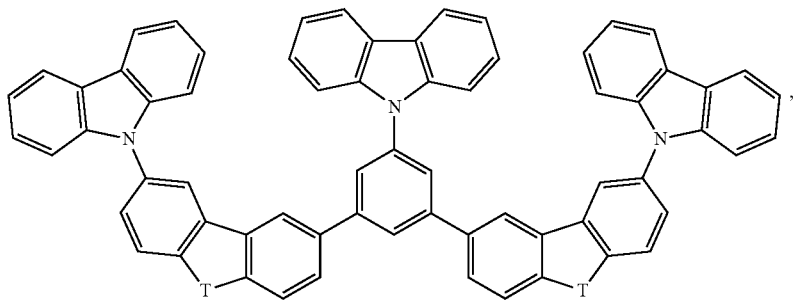
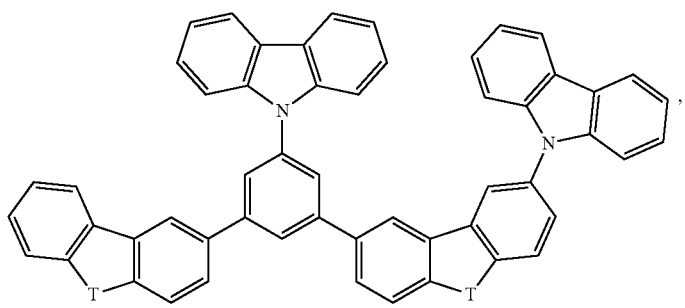

-continued
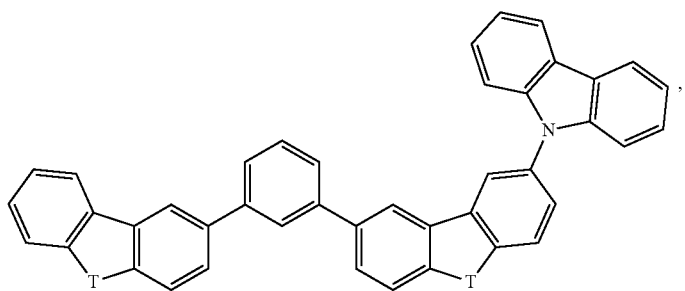
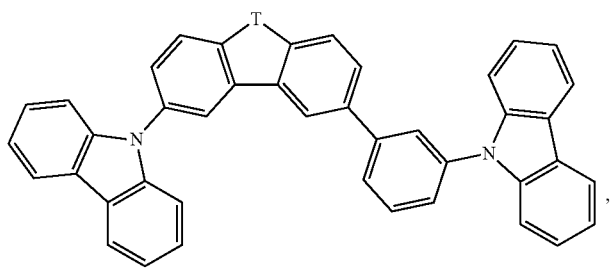
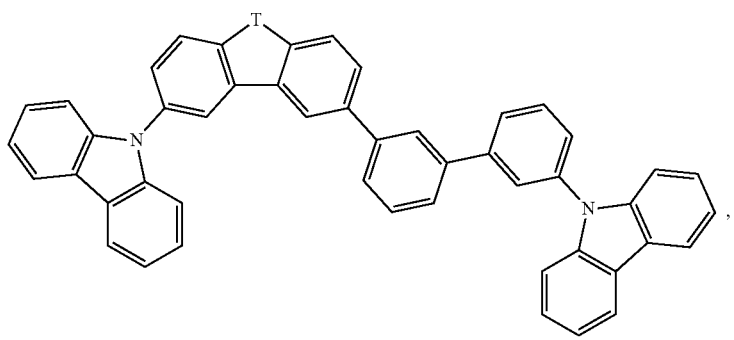
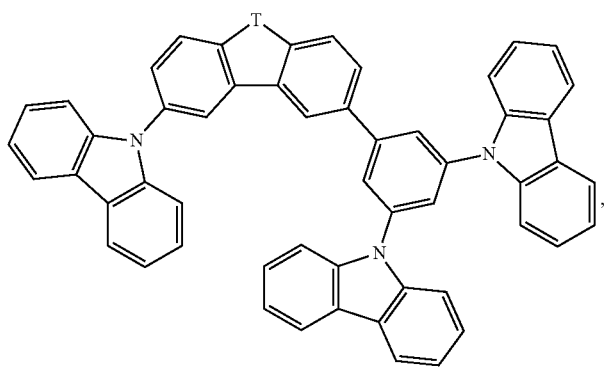
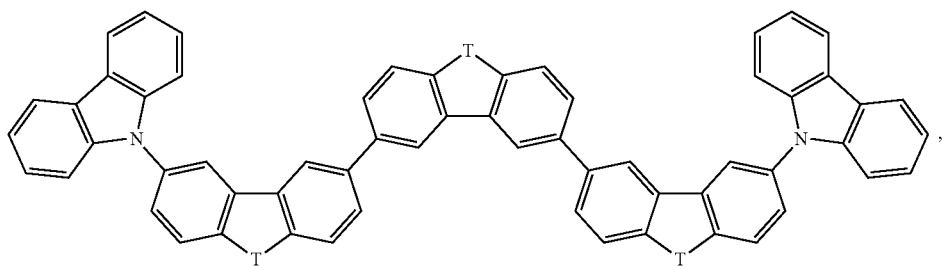

-continued
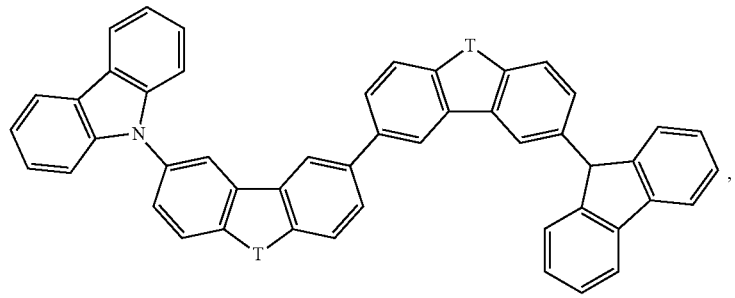
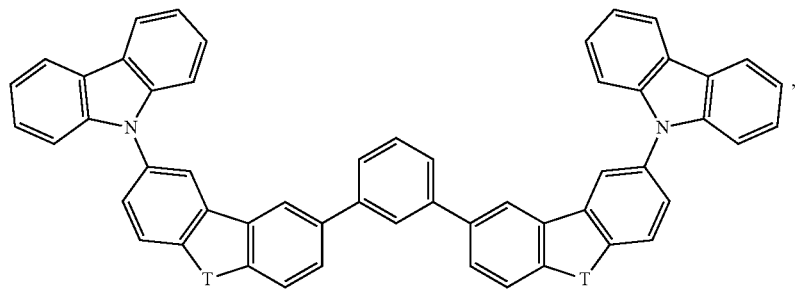
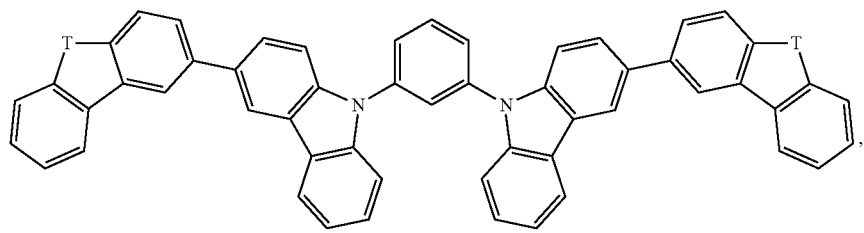
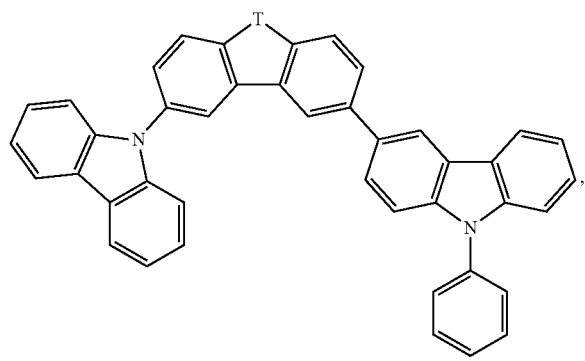
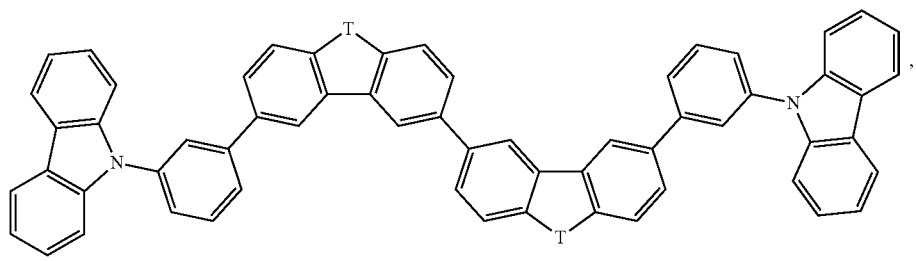

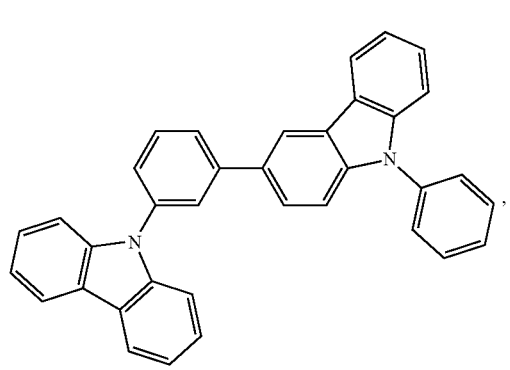
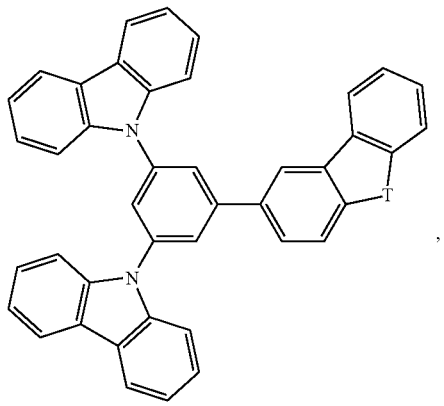
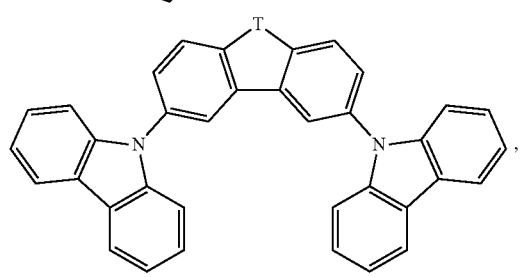
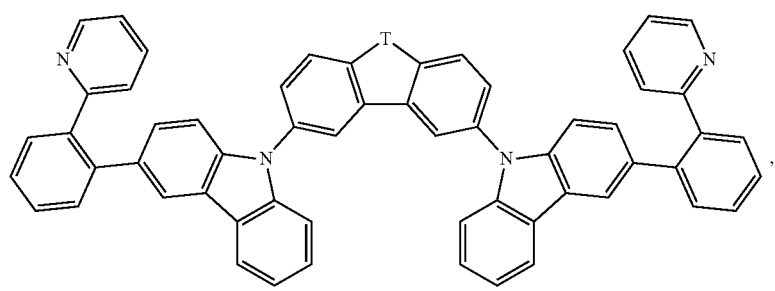
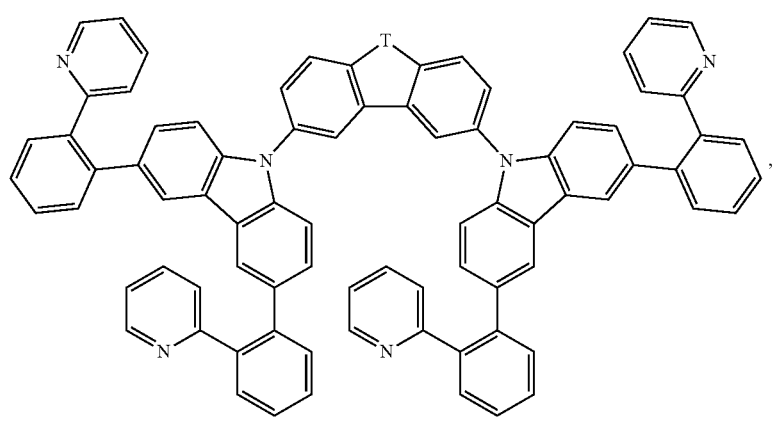
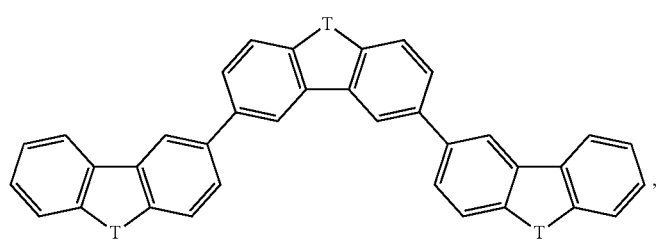

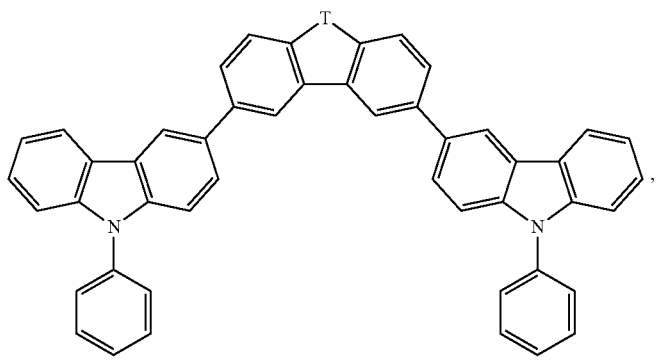
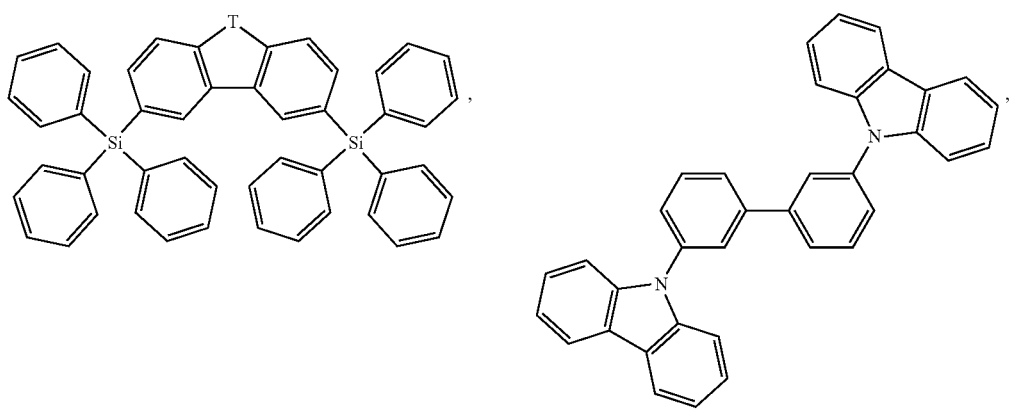
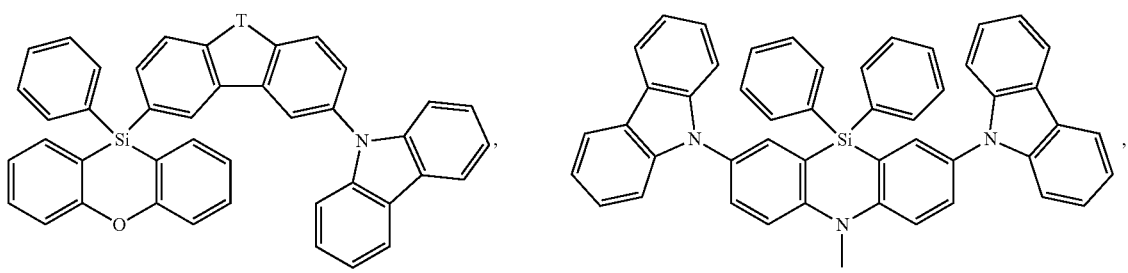
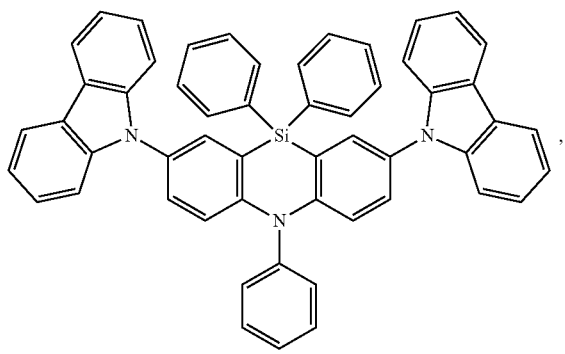

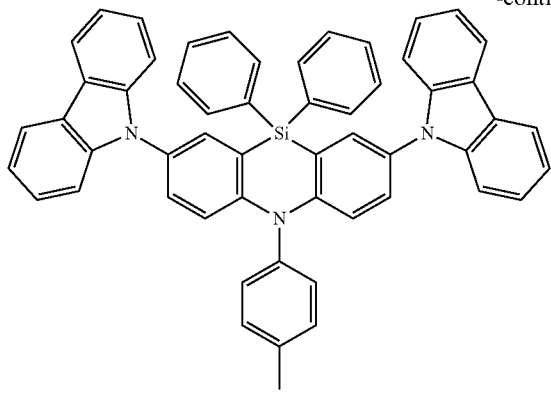
and
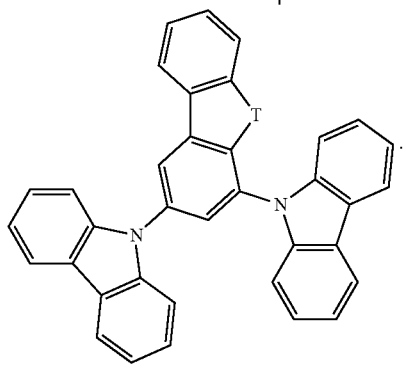
In the above-mentioned compounds T is O, or S, preferably O. If T occurs more than one time in a molecule, all groups T have the same meaning.
The more preferred host compounds are shown below:
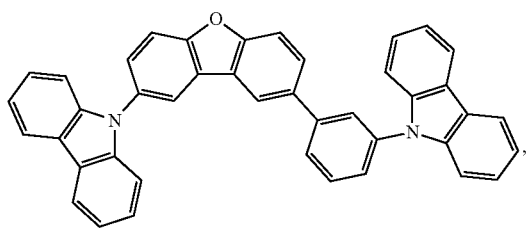
(SH-1)
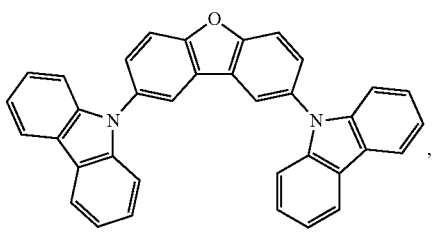
(SH-2)
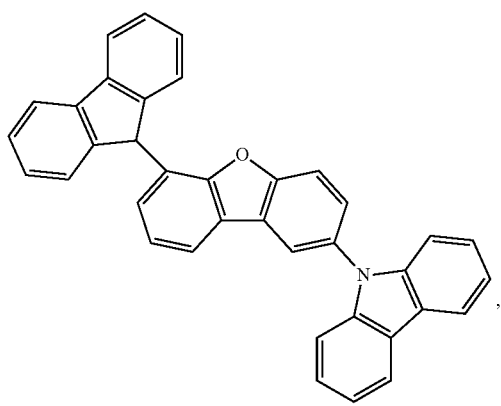
(SH-3), (SH-4), (SH-5), (SH-6)
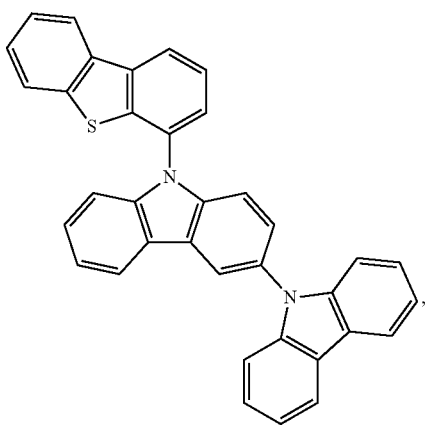
(SH-7a)

-continued
(SH-7b)
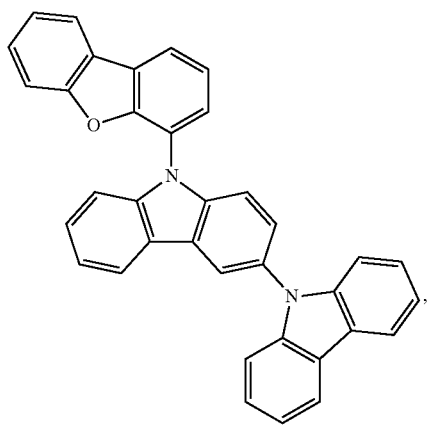
(SH-8)
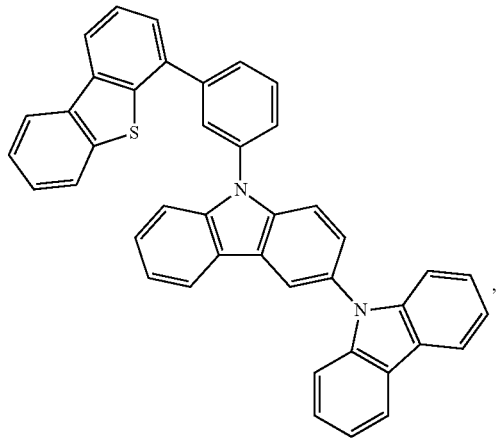
(SH-9)
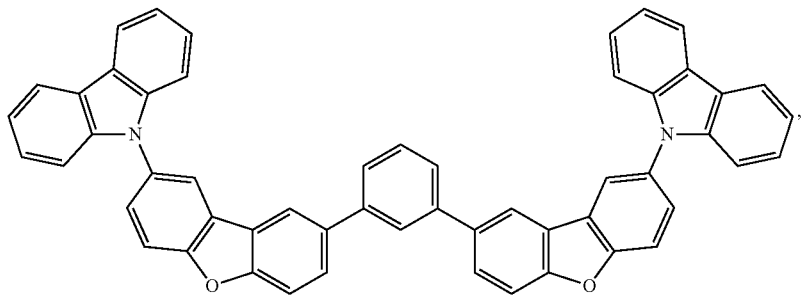
(SH-10)
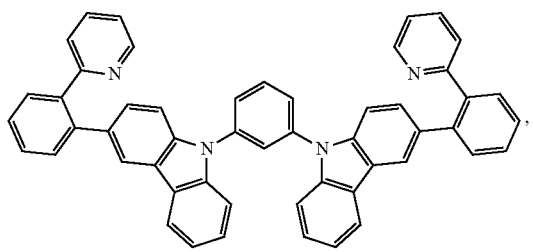
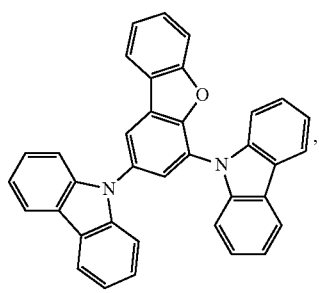
(SH-11)
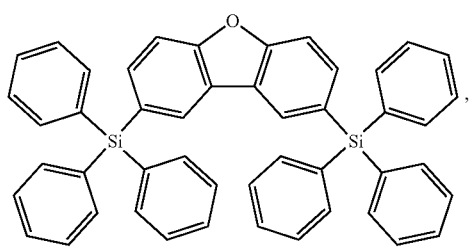 and
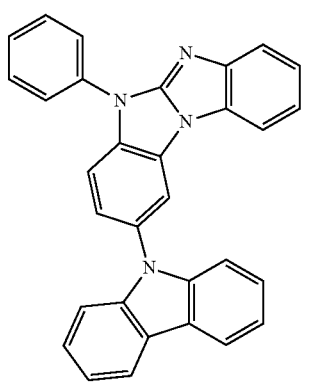

-continued
(SH-12)
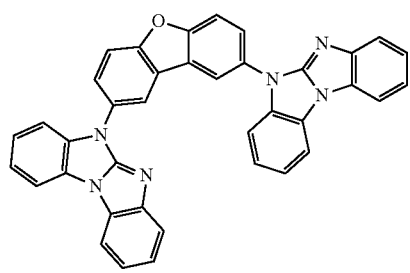
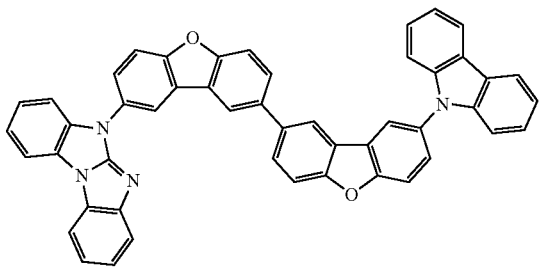
(published in WO2012/130709)
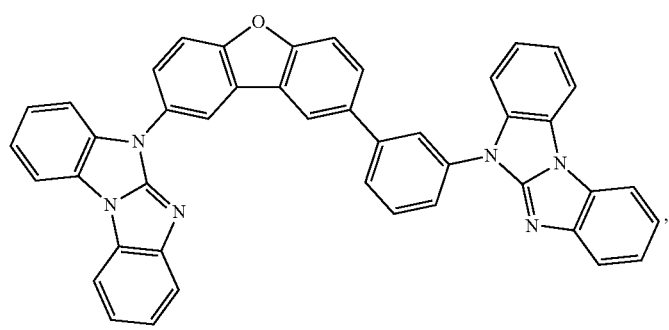
(published in WO2012/130709)
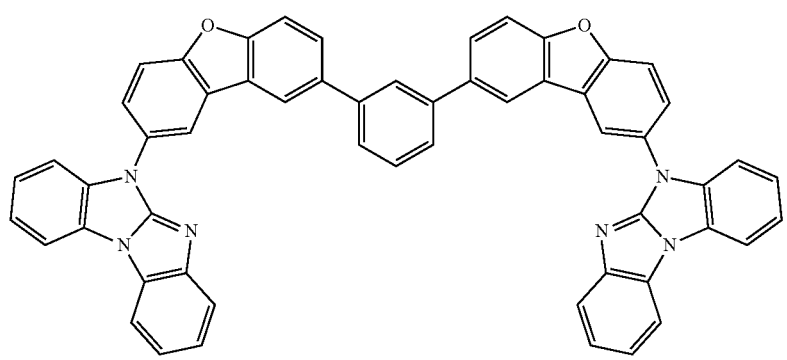
(published in WO2012/130709)
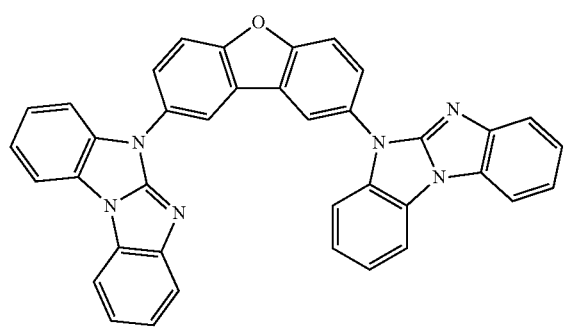
(published in WO2012/130709
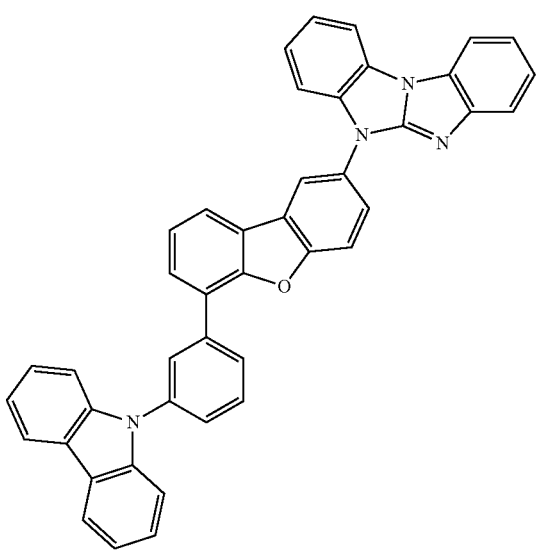
(published in WO2012/130709

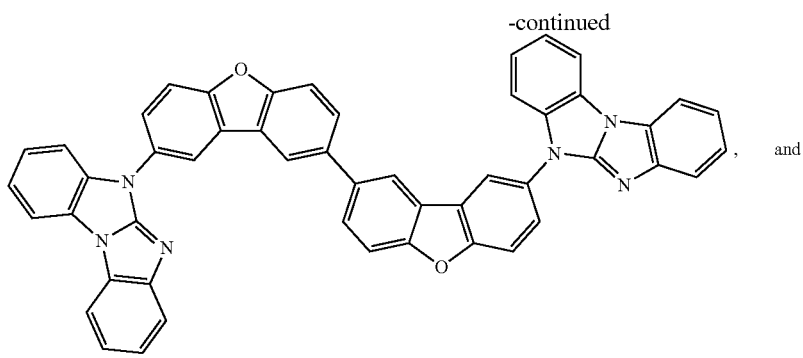
(published in WO2012/130709)
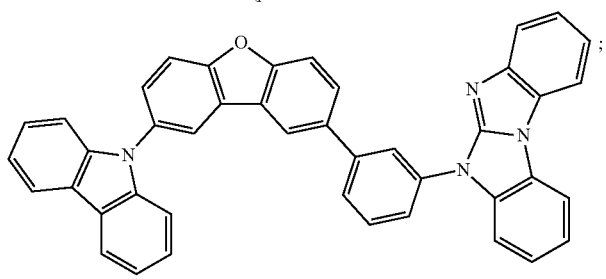
(published in WO2012/130709)
as well as the host materials published in WO2012048266, WO2012145173, WO2012162325, and EP2551932.
The most preferred host compounds are shown below:
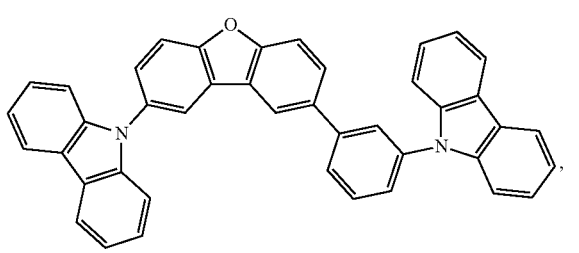
(SH-1; published in WO 2009/008100, example 4)
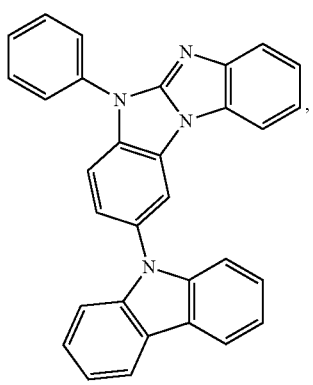
(SH-11; disclosed in EP1217635.7 and US61/669677)
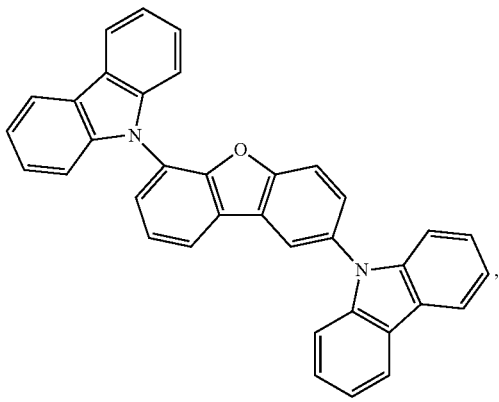
(published in WO 2011/004639, compound I-1, synthesis described in [0163])
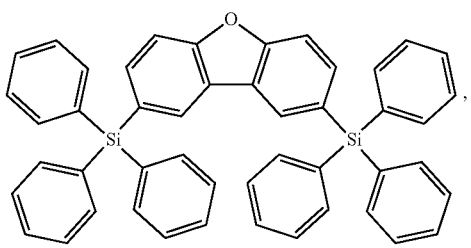
(published in WO2009/003898, compound 4g)

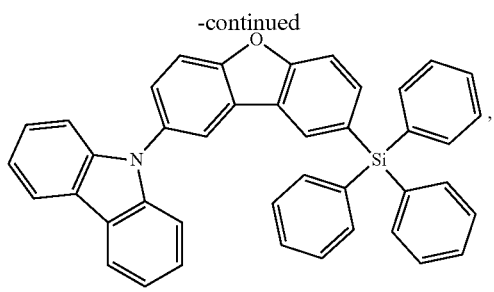

(SH-4, published in WO 2010/079051, compound 14)

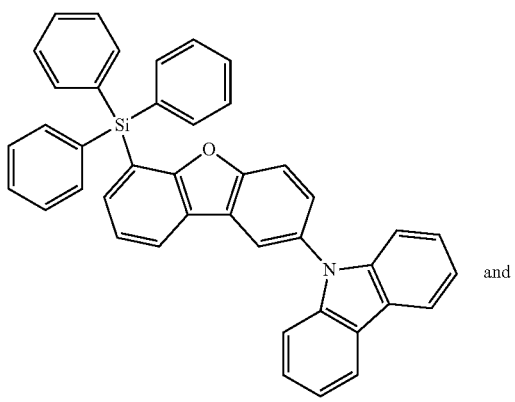

(SH-5, published in WO 2010/079051, structure on page 22, X = O)

and

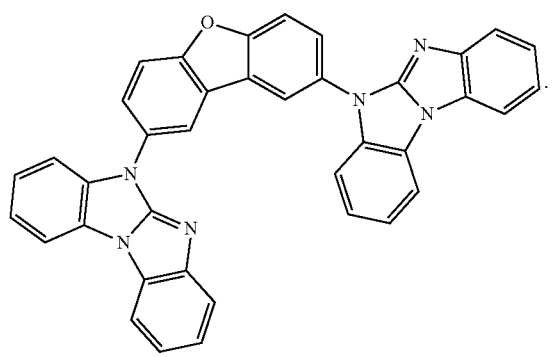

(SH-12; published in WO 2012/130709)

The present invention therefore also concerns the organic electronic device, preferably the OLED, according to the present invention, wherein the at least one cyclometallated Ir complex comprising one, two or three, preferably three bidentate ligands of formula (I) and/or (I') is employed in combination with at least one host material. Suitable and preferred host materials are mentioned above. More preferably, the at least one host material comprises at least one dibenzofuranyl unit and/or at least one benzimidazo[1,2-a]benzimidazolyl unit and/or at least one carbazolyl and/or at least one dibenzothiofuranyl unit. Suitable host materials and preferred host materials comprising at least one dibenzofuranyl unit and/or at least one benzimidazo[1,2-a]benz- imidazolyl unit and/or at least one carbazolyl and/or at least one dibenzothiofuranyl unit are mentioned above. The at least one cyclometallated Ir complex comprising one, two or three, preferably three, bidentate ligands of formula (I) and/or (I') which is employed in combination with at least one host material is preferably employed in the light-emitting layer of an OLED.

Preferably, the light-emitting layer comprises at least one emitter material, which is a cyclometallated Ir complex comprising one, two or three, preferably three, bidentate ligands of formula (I) and/or (I') according to the present invention, and at least one host material. Suitable and preferred emitter materials as well as suitable and preferred host materials are mentioned above.

Most preferably, the organic electronic device, preferably the OLED, comprises a light-emitting layer comprising at least one cyclometallated Ir complex comprising one, two or three, preferably three, bidentate ligands of formula (I) and/or (I') as emitter material in an amount of 5 to 40% by weight, preferably 5 to 30% by weight, more preferably 5 to 20 by weight, and at least one host material, preferably at least one host material comprising at least one dibenzofuranyl unit and/or at least one benzimidazo[1,2-a]benzimidazolyl unit and/or at least one carbazolyl and/or at least one dibenzothiofuranyl unit, more preferably at least one host material selected from the preferred and most preferred host materials comprising at least one dibenzofuranyl unit and/or at least one benzimidazo[1,2-a]benzimidazolyl unit and/or at least one carbazolyl and/or at least one dibenzothiofuranyl unit mentioned above, in an amount of 60 to 95% by weight, preferably 70 to 95% by weight, more preferably 80 to 95% by weight, where the amount of the at least one emitter material and the at least one host material adds up to a total of 100% by weight.

The light-emitting layer may comprise a second host compound. The second host compound can be one compound or it can be a mixture of two or more compounds. The carbene complexes Ir(DPBIC)$_3$ or Ir(DPABIC)$_3$ which are described below may be added as co-host.

Mixed matrix materials with two hosts selected from those hosts mentioned above, or one host from those hosts mentioned above and one Ir complex as described below, comprise preferably 5% by weight to 15% by weight of an Ir complex and 60% by weight to 90% by weight of a further host selected from the hosts as mentioned above.

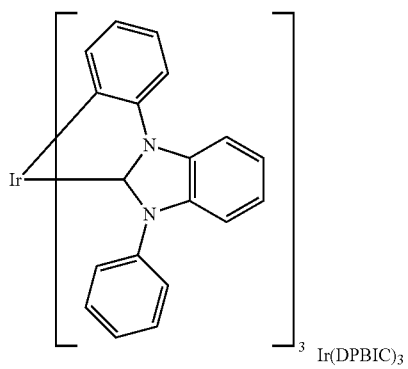

Ir(DPBIC)$_3$ (as described in WO 2005/019373A2)

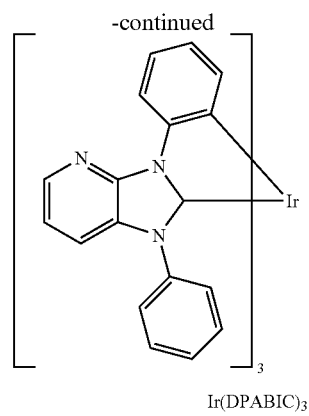

Ir(DPABIC)₃

(as described as complex fac-Em1 in WO2012/172182 (synthesis: example 1)).

The layer thickness of the light-emitting layer in the inventive OLED is preferably from 1 to 100 nm, more preferably 5 to 60 nm. Preferred OLED structures are mentioned above and—in more detail—below.

Device Structure—OLED Structure

Suitable structures of the organic electronic devices are known to those skilled in the art. Preferred organic electronic devices are selected from organic light-emitting diodes (OLED), light-emitting electrochemical cells (LEEC), organic photovoltaic cells (OPV) and organic field-effect transistors (OFET). More preferred organic electronic devices are OLEDs.

The device structures of said OLEDs, LEECs, OPVs and OFETs have been described above in general terms. In the following, the device structures of preferred OLEDs (which are preferred electronic devices according to the present invention) are described.

As mentioned above, the present invention preferably relates to an organic electronic device which is an OLED, wherein the OLED comprises (a) an anode,
(b) a cathode,
(c) a light-emitting layer between the anode and the cathode,
(d) optionally a hole transport layer between the light-emitting layer and the anode, wherein the cyclometallated Ir complex comprising one, two or three, preferably three, bidentate ligands of formula (I) and/or (I') is present in the light-emitting layer and/or—if present—in the hole transport layer of the OLED.

Preferred cyclometallated Ir complex comprising one, two or three, preferably three, bidentate ligands of formula (I) and/or (I') are mentioned before.

The layer sequence in the inventive OLED is preferably as follows:
1. anode (a)
2. hole-transport layer (d)
3. electron/exciton blocking layer (e)
4. light-emitting layer (c)
5. cathode (b)

Layer sequences different from the aforementioned construction are also possible, and are known to those skilled in the art. For example, it is possible that the OLED does not have all of the layers mentioned; for example, an OLED with the layers (a) (anode), (c) (light-emitting layer) and (b) (cathode) and layer (d) (hole-transport layer) or layer (e) (electron/exciton blocking layer) are likewise suitable.

The OLEDs may additionally have a blocking layer for holes/excitons (f) adjacent to the cathode side of the light-emitting layer (c) and/or an electron transport layer (g) adjacent to the cathode side of the blocking layer for holes/excitons (f), if present, respectively adjacent to the cathode side of the light-emitting layer (c), if the blocking layer for holes/excitons (f) is not present.

The present invention therefore more preferably relates to an inventive OLED having the following layer sequence:
1. anode (a)
2. hole-transport layer (d)
3. electron/exciton blocking layer (e)
4. light-emitting layer (c)
5. blocking layer for holes/excitons (f)
6. electron transport layer (g)
7. cathode (b)

In a further embodiment, the inventive OLED, in addition to layers (a), (b), (c), (d), (e), (f) and (g), comprises at least one of the further layers mentioned below:

A hole injection layer (h) between the anode (a) and the hole-transport layer (d);

an electron injection layer (i) between the electron-transport layer (g) and the cathode (b).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer.

Furthermore, the individual layers of the OLED among those specified above may in turn be formed from two or more layers. For example, the hole transport layer may be formed from a layer into which holes are injected from the electrode, and a layer which transports the holes away from the hole-injecting layer into the light-emitting layer. The electron transport layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used as emitter substances in accordance with the invention.

In order to obtain particularly efficient OLEDs, for example, the HOMO (highest occupied molecular orbital) of the hole-transport layer should be matched to the work function of the anode, and the LUMO (lowest unoccupied molecular orbital) of the electron conductor layer should be matched to the work function of the cathode, provided that the aforementioned layers are present in the inventive OLEDs.

Hole-Transport Material (d) and/or the Electron/Exciton Blocker Material (e)

The hole-transport material and/or the electron/exciton blocker material in the OLED of the present invention may be an Ir metal-carbene complex comprising one, two or three, preferably three, bidentate ligands of formula (III) and/or (III')

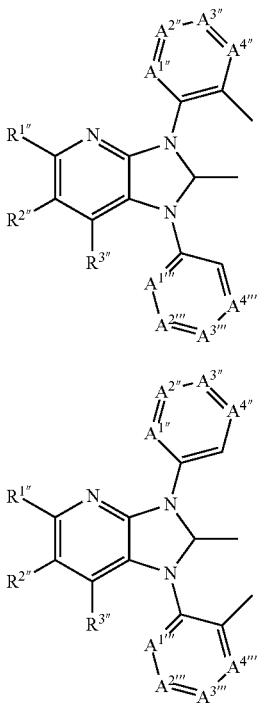

(III)

(III')

wherein
$R^{1'''}$, $R^{2'''}$ and $R^{3'''}$
are each independently hydrogen, deuterium, a linear or branched alkyl radical, optionally interrupted by at least one heteroatom, optionally bearing at least one functional group and having a total of from 1 to 20 carbon atoms and/or heteroatoms, a substituted or unsubstituted cycloalkyl radical, optionally bearing at least one functional group and having from 3 to 20 carbon atoms, a substituted or unsubstituted heterocycle alkyl radical, interrupted by at least one heteroatom, optionally bearing at least one functional group and having a total of from 3 to 20 carbon atoms and/or heteroatoms, a substituted or unsubstituted aryl radical, optionally bearing at least one functional group and having 6 to 30 carbon atoms, a substituted or unsubstituted heteroaryl radical, interrupted by at least one heteroatom, optionally bearing at least one functional group and having a total of from 5 to 18 carbon atoms and/or heteroatoms, a group with donor or acceptor action, preferably, $R^{1'''}$, $R^{2'''}$ and $R^{3'''}$ are each independently hydrogen, a linear or branched alkyl radical, having from 1 to 6 carbon atoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from the group consisting of halogen radicals, preferably F or Cl, more preferably F; $CF_3$, $SiPh_3$ and $SiMe_3$;
or
$R^{1'''}$ and $R^{2'''}$ or $R^{2'''}$ and $R^{3'''}$ form, independently of each other, together with a carbon atom to which they are bonded an optionally substituted saturated or unsaturated or aromatic ring, optionally interrupted by at least one heteroatom and having a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms;

$A^{1''}$ is $CR^{4''}$ or N, preferably $CR^{4''}$;
$A^{2''}$ is $CR^{5''}$ or N, preferably $CR^{5''}$;
$A^{3''}$ is $CR^{6''}$ or N, preferably $CR^{6''}$;
$A^{4''}$ is $CR^{7''}$ or N, preferably $CR^{7''}$;
$A^{1'''}$ is $CR^{4'''}$ or N, preferably $CR^{4'''}$;
$A^{2'''}$ is $CR^{5'''}$ or N, preferably $CR^{5'''}$;
$A^{3'''}$ is $CR^{6'''}$ or N, preferably $CR^{6'''}$;
$A^{4'''}$ is $CR^{7'''}$ or N, preferably $CR^{7'''}$;
$R^{4''}$, $R^{5''}$, $R^{6''}$, $R^{7''}$, $R^{4'''}$, $R^{5'''}$, $R^{6'''}$ and $R^{7'''}$
are each independently hydrogen, deuterium, a linear or branched alkyl radical, optionally interrupted by at least one heteroatom, optionally bearing at least one functional group and having a total of from 1 to 20 carbon atoms and/or heteroatoms, a substituted or unsubstituted cycloalkyl radical, optionally bearing at least one functional group and having from 3 to 20 carbon atoms, a substituted or unsubstituted heterocycle alkyl radical, interrupted by at least one heteroatom, optionally bearing at least one functional group and having a total of from 3 to 20 carbon atoms and/or heteroatoms, a substituted or unsubstituted aryl radical, optionally bearing at least one functional group and having from 6 to 30 carbon atoms, a substituted or unsubstituted heteroaryl radical, interrupted by at least one heteroatom, optionally bearing at least one functional group and having a total of from 5 to 18 carbon atoms and/or heteroatoms, a group with donor or acceptor action, preferably, $R^{4''}$, $R^{5''}$, $R^{6''}$, $R^{7''}$, $R^{4'''}$, $R^{5'''}$, $R^{6'''}$ and $R^{7'''}$ are each independently hydrogen, a linear or branched alkyl radical, optionally bearing at least one functional group, optionally interrupted by at least one heteroatom and having a total of from 1 to 20 carbon and/or heteroatoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from halogen radicals, preferably F or Cl, more preferably F; $CF_3$, CN, $SiPh_3$ and $SiMe_3$;
or
$R^{4''}$ and $R^{5''}$, $R^{5''}$ and $R^{6''}$ or $R^{6''}$ and $R^{7''}$ or $R^{4'''}$ and $R^{5'''}$, $R^{5'''}$ and $R^{6'''}$ or $R^{6'''}$ and $R^{7'''}$ form, independently of each other, together with the carbon atoms to which they are bonded, a saturated or unsaturated or aromatic, optionally substituted ring, which is optionally interrupted by at least one heteroatom, has a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms.

Preferred Ir metal-carbene complexes suitable as hole-transport materials and/or the electron/exciton blocker materials in the OLED of the present invention are described in detail in the EP application No. 13162776.2.

In the case that the OLED comprises a material different from the materials mentioned before in the hole-transport layer or in the electron/exciton blocking layer, suitable materials are mentioned below.

Hole-Transport Layer (d)

Further suitable hole-transport materials for layer (d) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole-transport material. Customarily used hole-transporting molecules are selected from the group consisting of

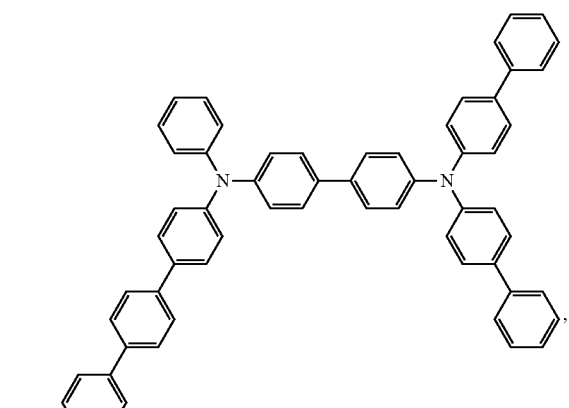

(4-phenyl-N-(4-phenylphenyl)-N-[4-[4-(N-[4-(4-phenylphenyl)phenyl]anilino)phenyl]phenyl]aniline)

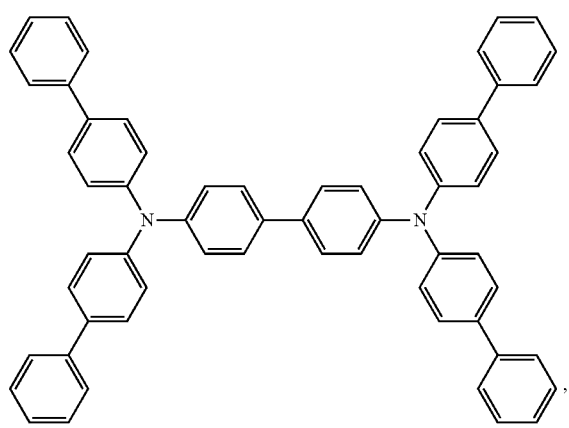

(4-phenyl-N-(4-phenylphenyl)-N-[4-[4-(4-phenyl-N-(4-phenylphenyl)anilino)phenyl]phenyl]aniline)

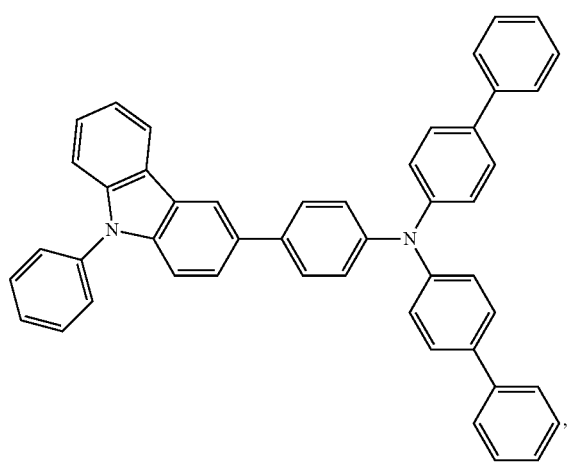

(4-phenyl-N-[4-(9-phenylcarbazol-3-yl)phenyl]-N-(4-phenylphenyl)aniline)

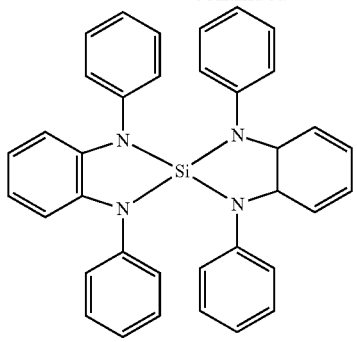

1,1′,3,3′-tetraphenylspiro[1,3,2-benzodiazasilole-2,2′-3a,7a-dihydro-1,3,2-benzodiazasilole]

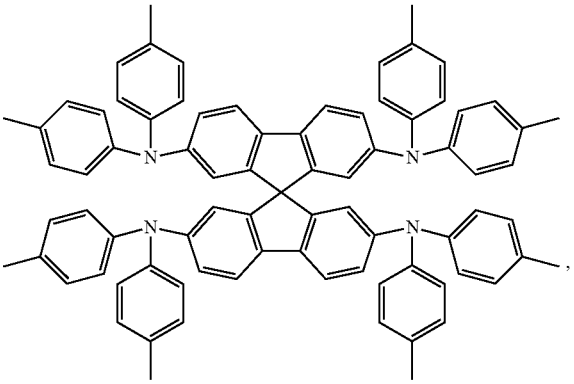

(N2,N2,N2′,N2′,N7,N7,N7′,N7′-octakis(p-tolyl)-9,9′-spirobi[fluorene]-2,2′,7,7′-tetramine)

4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)2-methylphenyl](4-methylphenyl)methane (MPMP), 1-phenyl-3-[p-(diethylamino)styryl]5-[p-(diethylamino)phenyl]pyrazoline (PPR or DEASP), 1,2-trans-bis(9H-carbazol9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino9,9-spirobifluorene (spiro-TTB), N,N'-bis(naphthalen-1-yl)-N,N'-bis(phenyl)9,9-spirobifluorene (spiro-NPB) and 9,9-bis(4-(N,N-bis-biphenyl-4-yl-amino)phenyl-9Hfluorene, benzidine compounds such as N,N'-bis(naphthalen-1-yl)-N,N'-bis(phenyl)benzidine and porphyrin compounds such as copper phthalocyanines. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

The hole-transport materials mentioned above are commercially available and/or prepared by processes known by a person skilled in the art.

In a preferred embodiment it is possible to use specific metal carbene complexes as hole-transport materials. Suitable carbene complexes are, for example, carbene complexes as described in WO2005/019373A2, WO2006/056418 A2, WO2005/113704, WO2007/115970, WO2007/115981 and WO2008/000727. One example of a suitable carbene complex is Ir(DPBIC)₃ with the formula:

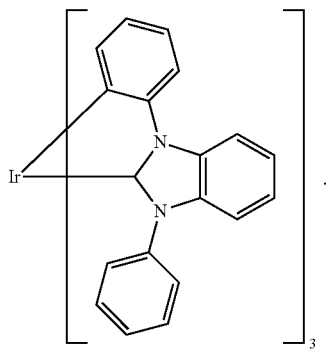

The preparation of Ir(DPBIC)₃ is for example mentioned in WO 2005/019373 A2. Another example of a suitable carbene complex is Ir(DPABIC)₃

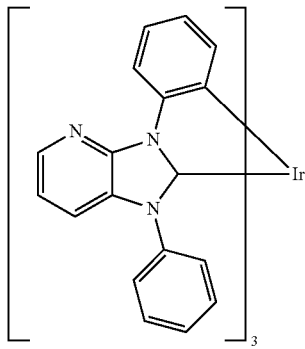

The preparation of Ir(DPABIC)₃ is for example mentioned in WO2012/172182 (as complex fac-Em1; synthesis: example 1)).

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide as doping material, for example $MoO_2$, $MoO_3$, WON, $ReO_3$ and/or $V_2O_5$, preferably $MoO_3$ and/or $ReO_3$, more preferably $MoO_3$ or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium) tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquino-dimethane, 2,5-difluoro-7,7,8,8-tetracyanoquinodimethane, dicyanomethylene-1,3,4,5,7,8-hexafluoro-6H-naphthalen-2-ylidene)malononitrile ($F_6$-TNAP), Mo(tfd)₃ (from Kahn et al., J. Am. Chem. Soc. 2009, 131 (35), 12530-12531), compounds as described in EP1988587 and in EP2180029 and quinone compounds as mentioned in EP 09153776.1.

Preferably, the hole-transport layer comprises 50 to 90% by weight, of the hole-transport material and 10 to 50% by weight of the doping material, wherein the sum of the amount of the hole-transport material and the doping material is 100% by weight.

Electron/Exciton Blocking Layer (e)

Blocking layers may also be used to block excitons from diffusing out of the emissive layer.

Further suitable metal complexes for use as electron/exciton blocker material are, for example, carbene complexes as described in WO 2005/019373 A2, WO 2006/056418 A2, WO 2005/113704, WO 2007/115970, WO 2007/115981 and WO 2008/000727. Explicit reference is made here to the disclosure of the WO applications cited, and these disclosures shall be considered to be incorporated into the content of the present application. One example of a suitable carbene complex is Ir(DPBIC)₃ with the formula:

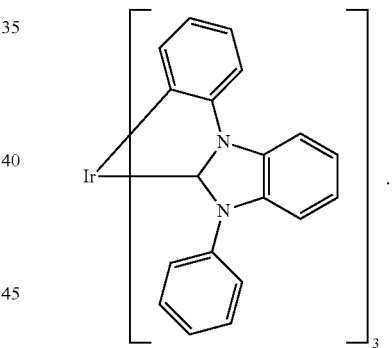

Another example of a suitable carbene complex is Ir(DPABIC)₃

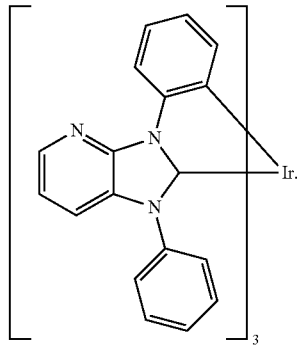

Anode (a)

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (a) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

The anode materials mentioned above are commercially available and/or prepared by processes known by a person skilled in the art.

Cathode (b)

The cathode (b) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used.

The cathode materials mentioned above are commercially available and/or prepared by processes known by a person skilled in the art.

Further Layers in the Inventive OLED

Blocking Layer for Holes/Excitons (f)

Among the materials mentioned below as electron transport materials, some may fulfil several functions. For example, some of the electron transport materials are simultaneously hole-blocking materials when they have a low-lying HOMO or exciton-blocking materials when they have a sufficiently high triplet energy. These can be used, for example, in the blocking layer for holes/excitons (f). However, it is likewise possible that the function as a hole/exciton blocker is also adopted by the layer (g), such that the layer (f) can be dispensed with.

Electron Transport Layer (g)

Electron transport layer may include a material capable of transporting electrons. Electron transport layer may be intrinsic (undoped), or doped. Doping may be used to enhance conductivity. Suitable electron-transporting materials for layer (g) of the inventive OLEDs comprise metals chelated with oxinoid compounds, such as tris(8-hydroxyquinolato)aluminum ($Alq_3$), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

The electron-transport materials mentioned above are commercially available and/or prepared by processes known by a person skilled in the art.

It is likewise possible to use mixtures of at least two materials in the electron-transporting layer, in which case at least one material is electron-conducting. Preferably, in such mixed electron-transporting layers, at least one phenanthroline compound is used, preferably BCP, or at least one pyridine compound according to the formula (VIII) below, preferably a compound of the formula (VIIIa) below. More preferably, in mixed electron-transporting layers, in addition to at least one phenanthroline compound, alkaline earth metal or alkali metal hydroxyquinolate complexes, for example Liq (8-hydroxyquinolatolithium), are used. Suitable alkaline earth metal or alkali metal hydroxyquinolate complexes are specified below (formula VII). Reference is made to WO2011/157779.

The electron transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transporting layer. n-Doping is achieved by the addition of reducing materials. These mixtures may, for example, be mixtures of the above-mentioned electron transport materials with alkali/alkaline earth metals or alkali/alkaline earth metal salts, for example Li, Cs, Ca, Sr, $Cs_2CO_3$, with alkali metal complexes, for example 8-hydroxyquinolatolithium (Liq), and with Y, Ce, Sm, Gd, Tb, Er, Tm, Yb, $Li_3N$, $Rb_2CO_3$, dipotassium phthalate, $W(hpp)_4$ from EP 1786050, or with compounds as described in EP1 837 926 B1.

In a preferred embodiment, the electron transport layer comprises at least one compound of the general formula (VII)

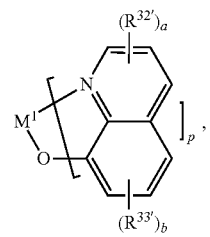

in which
$R^{32'}$ and $R^{33'}$ are each independently F, $C_1$-$C_8$-alkyl, or $C_6$-$C_{14}$-aryl, which is optionally substituted by one or more $C_1$-$C_8$-alkyl groups, or two R$^{32'}$ and/or R$^{33'}$ substituents together form a fused benzene ring which is optionally substituted by one or more C$_1$-C$_8$-alkyl groups;
a and b are each independently 0, 1, 2 or 3,
M$^1$ is an alkaline metal atom or alkaline earth metal atom, p is 1 when M$^1$ is an alkali metal atom, p is 2 when M$^1$ is an alkali metal atom.

A very particularly preferred compound of the formula (VII) is

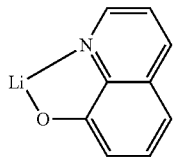

(Liq), which may be present as a single species, or in other forms such as Li$_g$Q$_g$ in which g is an integer, for example Li$_6$Q$_6$. Q is an 8-hydroxyquinolate ligand or an 8-hydroxyquinolate derivative.

In a further preferred embodiment, the electron-transporting layer comprises at least one compound of the formula (VIII),

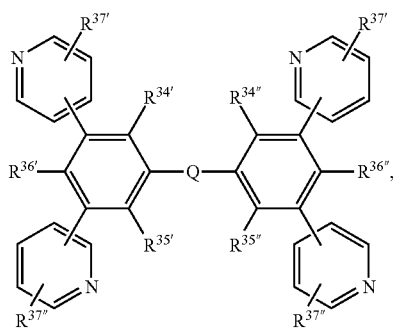

in which
R$^{34'}$, R$^{35'}$, R$^{36'}$, R$^{37'}$, R$^{34''}$, R$^{35''}$, R$^{36''}$ and R$^{37''}$ are each independently hydrogen, C$_1$-C$_{18}$-alkyl, C$_1$-C$_{18}$-alkyl which is substituted by E and/or interrupted by D, C$_6$-C$_{24}$-aryl, C$_6$-C$_{24}$-aryl which is substituted by G, C$_2$-C$_{20}$-heteroaryl or C$_2$-C$_{20}$-heteroaryl which is substituted by G,
Q is an arylene or heteroarylene group, each of which is optionally substituted by G;
D is —CO—; —COO—; —S—; —SO—; —SO$_2$—; —O—; —NR$^{40'}$—; —SiR$^{45'}$R$^{46'}$—; —POR$^{47'}$—; —CR$^{38'}$═CR$^{39'}$—; or —C≡C—;
E is —OR$^{44'}$; —SR$^{44'}$; —NR$^{40'}$R$^{41'}$; —COOR$^{43'}$; —COOR$^{42'}$; —CONR$^{40'}$R$^{41'}$; —CN; or F;
G is E, C$_1$-C$_{18}$-alkyl, C$_1$-C$_{18}$-alkyl which is interrupted by D, C$_1$-C$_{18}$-perfluoroalkyl, C$_1$-C$_{18}$-alkoxy, or C$_1$-C$_{18}$-alkoxy which is substituted by E and/or interrupted by D,
in which
R$^{38'}$ and R$^{39'}$ are each independently H, C$_6$-C$_{18}$-aryl; C$_6$-C$_{18}$-aryl which is substituted by C$_1$-C$_{18}$-alkyl or C$_1$-C$_{18}$-alkoxy; C$_1$-C$_{18}$-alkyl; or C$_1$-C$_{18}$-alkyl which is interrupted by —O—;
R$^{40'}$ and R$^{41'}$ are each independently C$_6$-C$_{18}$-aryl; C$_6$-C$_{18}$-aryl which is substituted by C$_1$-C$_{18}$-alkyl or C$_1$-C$_{18}$-alkoxy; C$_1$-C$_{18}$-alkyl; or C$_1$-C$_{18}$-alkyl which is interrupted by —O—; or R$^{40'}$ and R$^{41'}$ together form a 6-membered ring;
R$^{42'}$ and R$^{43'}$ are each independently C$_6$-C$_{18}$-aryl; C$_6$-C$_{18}$-aryl which is substituted by C$_1$-C$_{18}$-alkyl or C$_1$-C$_{18}$-alkoxy; C$_1$-C$_{18}$-alkyl; or C$_1$-C$_{18}$-alkyl which is interrupted by —O—,
R$^{44'}$ is C$_6$-C$_{18}$-aryl; C$_6$-C$_{18}$-aryl which is substituted by C$_1$-C$_{18}$-alkyl or C$_1$-C$_{18}$-alkoxy; C$_1$-C$_{18}$-alkyl; or C$_1$-C$_{18}$-alkyl which is interrupted by —O—,
R$^{45'}$ and R$^{46'}$ are each independently C$_1$-C$_{18}$-alkyl, C$_6$-C$_{18}$-aryl or C$_6$-C$_{18}$-aryl which is substituted by C$_1$-C$_{18}$-alkyl,
R$^{47'}$ is C$_1$-C$_{18}$-alkyl, C$_6$-C$_{18}$-aryl or C$_6$-C$_{18}$-aryl which is substituted by C$_1$-C$_{18}$-alkyl.

Preferred compounds of the formula (VIII) are compounds of the formula (VIIIa)

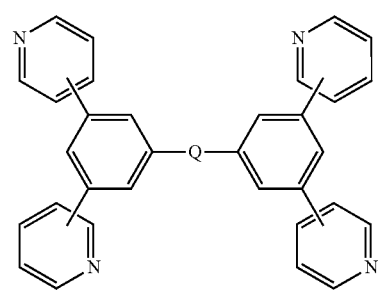

in which Q is:

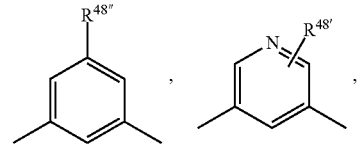

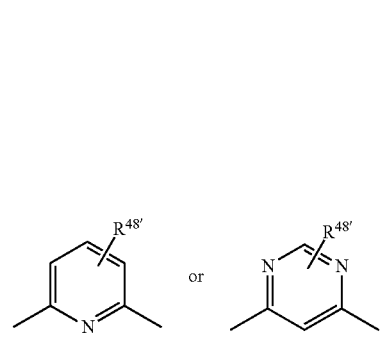

R$^{48'}$ is H or C$_1$-C$_{18}$-alkyl and R$^{48''}$ is H, C$_1$-C$_{18}$-alkyl or

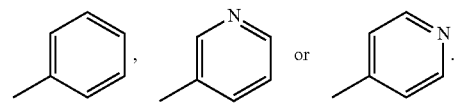

Particular preference is given to a compound of the formula

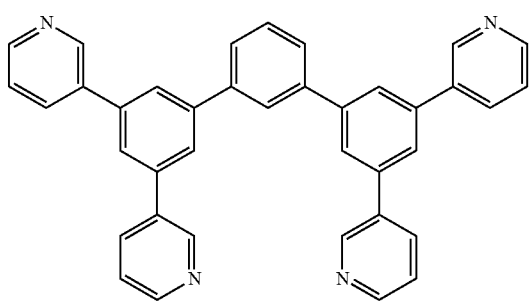

(ETM-1)

In a further, very particularly preferred embodiment, the electron transport layer comprises a compound of the formula

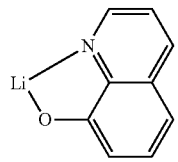

(Liq) and a compound ETM-1.

In a preferred embodiment, the electron transport layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008-127326, or the compounds can be prepared analogously to the processes disclosed in the aforementioned documents.

It is likewise possible to use mixtures of alkali metal hydroxyquinolate complexes, preferably Liq, and dibenzofuran compounds in the electron transport layer. Reference is made to WO2011/157790. Dibenzofuran compounds A-1 to A-36 and B-1 to B-22 described in WO 2011/157790 are preferred, wherein dibenzofuran compound

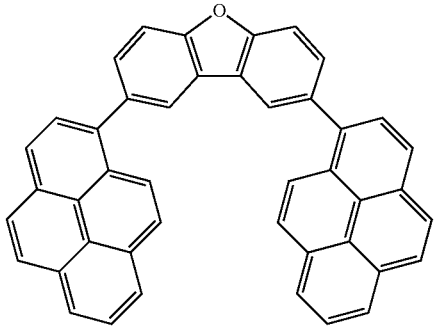 [SMILES: c1cc2ccc3ccc(-c4ccc5oc6ccc(-c7ccc8ccc9cccc%10ccc7c8c9%10)cc6c5c4)c4ccc(c1)c2c34]

(A-10; =ETM-2 is most preferred.

In a preferred embodiment, the electron transport layer comprises Liq in an amount of 99 to 1% by weight, preferably 75 to 25% by weight, more preferably about 50% by weight, where the amount of Liq and the amount of the dibenzofuran compound(s), especially ETM-2, adds up to a total of 100% by weight.

In a preferred embodiment, the electron transport layer comprises at least one phenanthroline derivative and/or pyridine derivative.

In a further preferred embodiment, the electron transport layer comprises at least one phenanthroline derivative and/or pyridine derivative and at least one alkali metal hydroxyquinolate complex.

In a further preferred embodiment, the electron transport layer comprises at least one of the dibenzofuran compounds A-1 to A-36 and B-1 to B-22 described in WO2011/157790, especially ETM-2.

In a further preferred embodiment, the electron transport layer comprises a compound described in WO 2012/111462, WO 2012/147397 and US 2012/0261654, such as, for example, a compound of formula

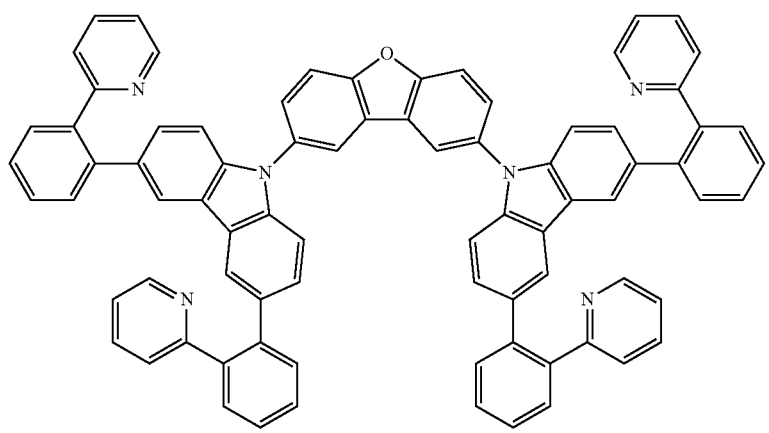

(ETM-4)

WO 2012/115034, such as for example, such as, for example, a compound of formula

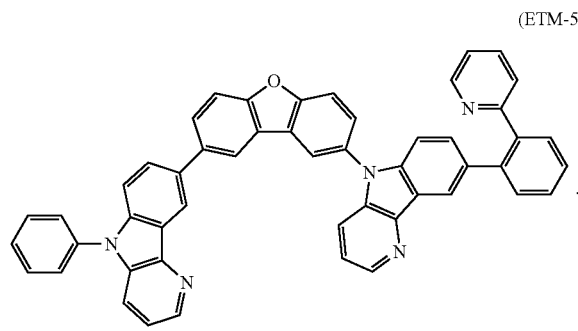

(ETM-5)

Hole Injection Layer (h)

Generally, injection layers are comprised of a material that may improve the injection of charge carriers from one layer, such as an electrode or a charge generating layer, into an adjacent organic layer. Injection layers may also perform a charge transport function. The hole injection layer may be any layer that improves the injection of holes from anode into an adjacent organic layer. A hole injection layer may comprise a solution deposited material, such as a spin-coated polymer, or it may be a vapor deposited small molecule material, such as, for example, CuPc or MTDATA. Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics, e.g. Plxecore AJ20-1000), and copolymers such as poly(3,4-ethylenedioxythiophene)/poly(4-styrenesulfonate) also called PEDOT/PSS.

The hole injection materials mentioned above are commercially available and/or prepared by processes known by a person skilled in the art.

Electron Injection Layer (i)

The electron injection layer may be any layer that improves the injection of electrons into an adjacent organic layer. Lithium-comprising organometallic compounds such as 8-hydroxyquinolatolithium (Liq), CsF, NaF, KF, $Cs_2CO_3$ or LiF may be applied between the electron transport layer (g) and the cathode (b) as an electron injection layer (i) in order to reduce the operating voltage.

The electron injection materials mentioned above are commercially available and/or prepared by processes known by a person skilled in the art.

In general, the different layers in the inventive OLED, if present, have the following thicknesses:
anode (a): 50 to 500 nm, preferably 100 to 200 nm;
a hole injection layer (h): 5 to 100 nm, preferably 20 to 80 nm,
hole-transport layer (d): 5 to 100 nm, preferably 10 to 80 nm,
electron/exciton blocking layer (e): 1 to 50 nm, preferably 5 to 10 nm,
light-emitting layer (c): 1 to 100 nm, preferably 5 to 60 nm,
a hole/exciton blocking layer (f): 1 to 50 nm, preferably 5 to 10 nm,
electron-transport layer (g): 5 to 100 nm, preferably 20 to 80 nm,
electron injection layer (i): 1 to 50 nm, preferably 2 to 10 nm,
cathode (b): 20 to 1000 nm, preferably 30 to 500 nm.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive organic electronic device, preferably OLED, can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the organic electronic device, preferably OLED, can be applied from solutions or dispersions in suitable solvents, employing coating techniques known to those skilled in the art.

The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to those skilled in the art. It is possible that the electron-conducting layer and/or the hole-conducting layer has/have greater thicknesses than the layer thicknesses specified when they are electrically doped.

In a further embodiment the present invention relates to the use of a cyclometallated Ir complex comprising one, two or three bidentate ligands of formula (I) and/or (I') according to the present invention in an OLED, preferably as emitter material. Suitable and preferred cyclometallated Ir complex comprising one, two or three bidentate ligands of formula (I) and/or (I') and suitable and preferred OLEDs are mentioned above. The emitter material is present in the light-emitting layer of the OLED.

Use of at least one cyclometallated Ir complex comprising one, two or three, preferably three, bidentate ligands of formula (I) and/or (I') according to the present invention in an OLED, preferably as emitter material makes it possible to obtain OLEDs with high color purity and high efficiency and/or high luminous efficacy and/or with high stability and long lifetimes.

The organic electronic devices, preferably OLEDs, can be used in all apparatus in which electroluminescence is useful. Suitable devices are preferably selected from the group consisting of stationary visual display units, such as visual display units of computers, televisions, visual display units in printers, kitchen appliances, advertising panels, information panels and illuminations; mobile visual display units such as visual display units in smartphones, cellphones, tablet computers, laptops, digital cameras, MP3-players, vehicles, keyboards and destination displays on buses and trains; illumination units; units in items of clothing; units in handbags, units in accessories, units in furniture and units in wallpaper.

The present invention therefore further relates to apparatus selected from the group consisting of stationary visual display units, such as visual display units of computers, televisions, visual display units in printers, kitchen appliances, advertising panels, information panels and illuminations; mobile visual display units such as visual display units in smartphones, cellphones, tablet computers, laptops, digital cameras, MP3-players, vehicles, keyboards and destination displays on buses and trains; illumination units; units in items of clothing; units in handbags, units in accessories, units in furniture and units in wallpaper, comprising at least one organic electronic device, preferably at least one OLED, according to the present invention or comprising at least one hole transport layer or at least one electron/exciton blocking layer according to the present invention or comprising at least one cyclometallated Ir complex comprising one, two or three, preferably three, bidentate ligands of formula (I) and/or (I') according to the present invention.

In a further embodiment, the cyclometallated Ir complex comprising one, two or three, preferably three, bidentate ligands of formula (I) and/or (I') can be used in white OLEDs.

The OLEDs may further comprise at least one second light-emitting layer. The overall emission of the OLEDs may be composed of the emission of the at least two light-emitting layers and may also comprise white light, as described for example in EP13160198.1.

In addition, the cyclometallated Ir complex comprising one, two or three, preferably three, bidentate ligands of formula (I) and/or (I') can be used in OLEDs with inverse structure. The structure of inverse OLEDs and the materials typically used therein are known to those skilled in the art.

It is also possible to stack two OLEDs or to stack three or more OLEDs ("stacked device concept"). These devices usually use a transparent charge generating interlayer such as indium tin oxide (ITO), $V_2O_5$, or an organic p-n junction.

The stacked OLED (SOLED) usually includes at least two individual sub-elements.

Each sub-element comprises at least three layers: an electron transport layer, an emitter layer and a hole-transport layer. Additional layers may be added to a sub-element. Each SOLED sub-element may include for example a hole injection layer, a hole transport layer, an electron/exciton blocking layer, an emitter layer, a hole/exciton blocking layer, an electron transport layer, an electron injection layer. Each SOLED sub-element may have the same layer structure or different layer structure from the other sub-elements.

Suitable SOLED structures are known by a person skilled in the art.

Not only the organic electronic devices as mentioned above are a subject of the present invention but also all cyclometallated Ir complexes comprising one, two or three bidentate ligands of formula (I) and/or (I') as described in the present application.

In a further embodiment, the present invention relates to a cyclometallated Ir complex comprising one, two or three bidentate ligands of formula (I) and/or (I') as described in the present application, and to a process for preparing the inventive metal-carbene complex, by contacting suitable compounds comprising Ir with appropriate ligands or ligand precursors. A suitable process is described above.

The present invention further relates to the use of the inventive cyclometallated Ir complex comprising one, two or three bidentate ligands of formula (I) and/or (I') as described in the present application in organic electronic devices, preferably in OLEDs, more preferably as emitter materials in OLEDs. Suitable organic electronic devices and suitable OLEDs are described above.

The following examples are included for illustrative purposes only and do not limit the scope of the claims.

EXAMPLES

The examples which follow, more particularly the methods, materials, conditions, process parameters, apparatus and the like detailed in the examples, are intended to support the present invention, but not to restrict the scope of the present invention.

All experiments are carried out in protective gas atmosphere.

The percentages and ratios mentioned in the examples below—unless stated otherwise—are % by weight and weight ratios.

I Synthesis Examples

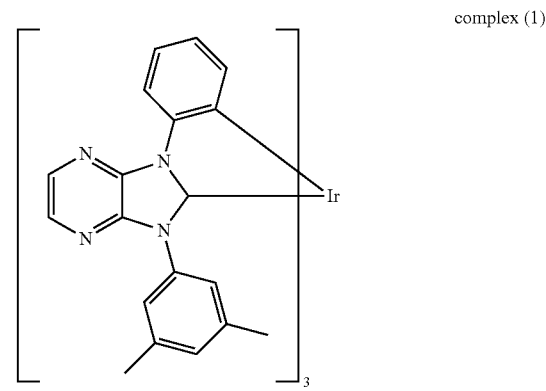

complex (1)

1. Synthesis of Complex (1)

a) Synthesis of N3-(3,5-dimethylphenyl)-N2-phenyl-pyrazine-2,3-diamine

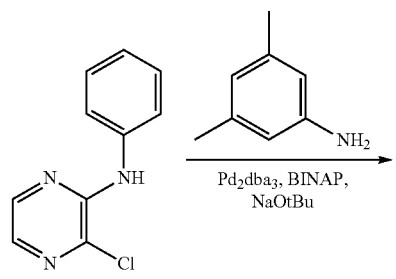

173
-continued

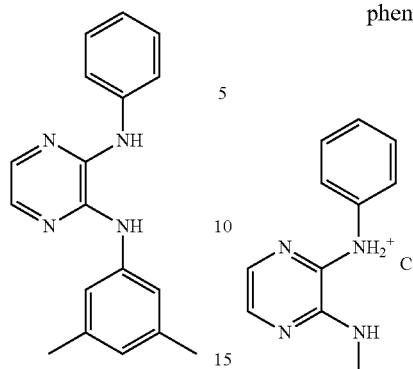

Compound 3-chloro-N-phenyl-pyrazin-2-amine (8.00 g, 38.2 mmol) is dissolved in 540 mL of dry toluene under argon atmosphere. The mixture is degassed under vacuum. Then 0.35 g (0.38 mmol) tris(dibenzylidenaceton)dipalladium(0), 0.739 g (1.15 mmol) 2,2'-bis(diphenylphosphino)-1,1'-binaphthyl, 7.72 g (80.0 mmol) sodium tert-butylate and 5.68 g (45.9 mmol) 3,5-dimethylaniline are added. The suspension is refluxed for 24 h. After cooling to room temperature, the solvent is removed and the residue dissolved in methylene chloride. The organic phase is then washed with water and dried over sodium sulfate. After removing the solvent the material is purified by column chromatography (silica, cyclohexane/ethyl acetate) to give the title product (yield: 7.90 g (71%)).

$^1$H-NMR (400 MHz, CD$_2$Cl$_2$): δ=7.90 (s, 2H), 7.47 (d, 4H), 7.19 (m, 1H), 7.06 (s, 2H), 6.85 (s, 1H), 6.44 (s, 1H), 6.33 (s, 1H), 2.43 (s, 6H).

b) Synthesis of [3-(3,5-dimethylanilino)pyrazin-2-yl]-phenyl-ammonium chloride

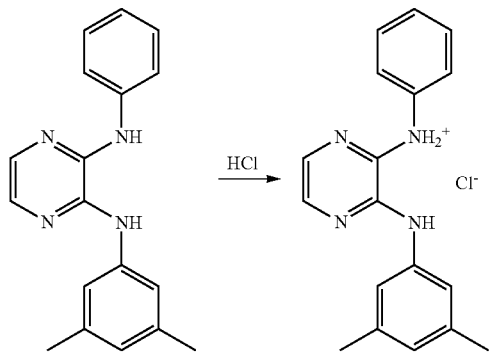 [SMILES: Cc1cc(C)cc(Nc2nccnc2Nc2ccccc2)c1 ; Cl ; Cc1cc(C)cc(Nc2nccnc2[NH2+]c2ccccc2)c1 ; [Cl-]]

N3-(3,5-dimethylphenyl)-N2-phenyl-pyrazine-2,3-diamine (0.58 g, 2.00 mmol) is dissolved in 45 mL of HCl (32%). After stirring the solution at room temperature overnight, 750 mL of water are added and the precipitate is filtered, washed with water and petroleum ether and then dried in vacuum, to give the desired product (0.380 g).

$^1$H-NMR (400 MHz, CD$_2$Cl$_2$): δ=7.66 (d, 2H), 7.40 (d, 2H), 7.32 (t, 2H), 7.06 (t, 1H), 6.98 (s, 2H), 6.74 (s, 1H), 2.33 (s, 6H).

c) Synthesis of 3-(3,5-dimethylphenyl)-2-ethoxy-1-phenyl-2H-imidazo[4,5-b]pyrazine

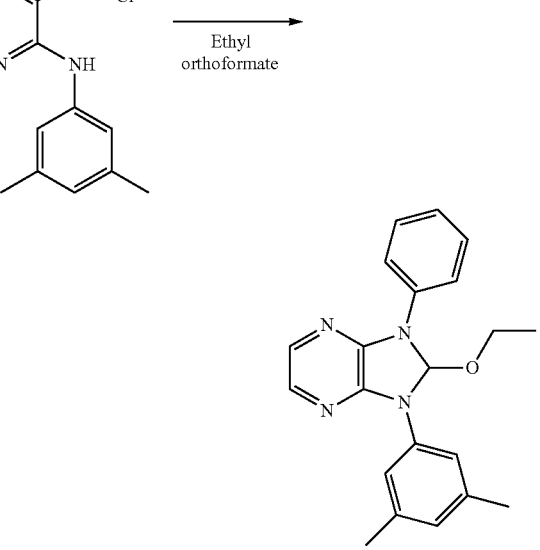

[3-(3,5-Dimethylanilino)pyrazin-2-yl]-phenyl-ammonium chloride (2.74 g, 8.41 mmol) is suspended in 110 ml of ethyl orthoformate. The reaction mixture is stirred under argon and heated to 70° C. After cooling to room temperature, the solvent is evaporated. The desired product is isolated after crystallization from ethanol in 87% yield (2.55 g).

$^1$H-NMR (400 MHz, CD$_2$Cl$_2$): δ=8.05 (d, 2H), 7.64 (s, 2H), 7.50 (q, 2H), 7.44 (t, 2H), 7.24 (s, 1H), 7.17 (t, 1H), 6.85 (s, 1H), 3.34-3.25 (m, 2H), 2.37 (s, 6h), 1.04 (t, 3H).

d) Synthesis of Complex (1)

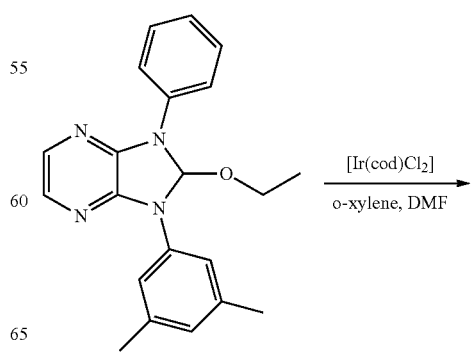

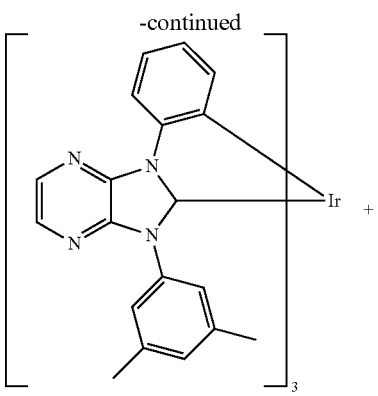

complex (1)

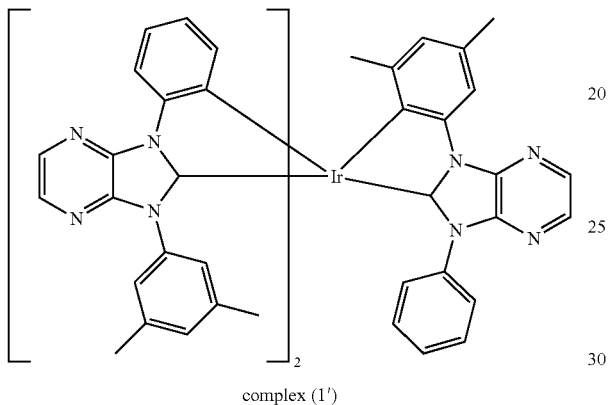

complex (1')

3-(3,5-dimethylphenyl)-2-ethoxy-1-phenyl-2H-imidazo[4,5-b]pyrazine (2.22 g, 6.40 mmol) is dissolved in 300 mL o-xylene. Molecular sieves (3 Å and 5 Å, 5 g each) are added, together with 7.5 mL of anhydrous DMF. After degassing the mixture, di-μ-chloro-bis[(cycloocta-1,5-dien)iridium(1)] (0.54 g, 0.78 mmol) is added and the reaction heated to 110° C. for 23 hours. After filtering the solution, the solid is washed with warm o-xylene. The solvent is then evaporated and the solid residue suspended in a mixture of 640 mL of 2-butanone and 80 mL of HCl (1M) and heated to 70° C. for 26 hours. After cooling the reaction to room temperature, the solid is dissolved in dichloromethane and extracted with water. The organic phase is then dried and complex (1) and complex (1') are isolated after chromatographic purification (silica, cyclohexane/ethyl acetate).

Complex (1): 15% yield (0.26 g) $^1$H-NMR (400 MHz, CD$_2$Cl$_2$): δ=8.68 (d, 3H), 8.24 (s, 3H), 8.02 (s, 3H), 7.13 (t, 3H), 6.90-6.75 (m, 6H), 6.62 (d, 3H), 6.45 (s, 3H), 5.81 (s, 3H), 2.34 (s, 9H), 1.80 (s, 9H).

Photoluminescence (2% in a PMMA film): $\lambda_{max}$=476 nm, CIE: (0.16; 0.28); QY=94%. Complex (1'): 7% yield (0.12 g)

$^1$H-NMR (400 MHz, CD$_2$Cl$_2$): δ=8.76 (d, 1H), 8.53 (br. s, 2H), 8.31 (br. s., 1H), 8.25 (br. s., 1H), 8.18 (br. s., 1H), 8.05-7.98 (m, 3H), 7.54 (br. s., 1H), 7.35 (br. s., 1H), 7.24 (t, 1H), 7.20-7.10 (m, 3H), 7.05-7.00 (m, 1H), 6.89-6.76 (m, 4H), 6.67-6.60 (m, 3H), 6.56 (1H), 6.45 (br. s, 1H), 6.36 (s, 1H), 6.35-6.27 (m, 2H), 5.87 (br. s, 1H), 5.60 (br. s, 1H), 2.37 (s, 3H), 2.18 (br. s, 6H), 2.06 (br. s, 3H), 1.90 (br. s, 3H).

Photoluminescence (2% in a PMMA film): $\lambda_{max}$=489 nm, CIE: (0.20; 0.39); QY=72%.

e) Isomerization of Complex (1')

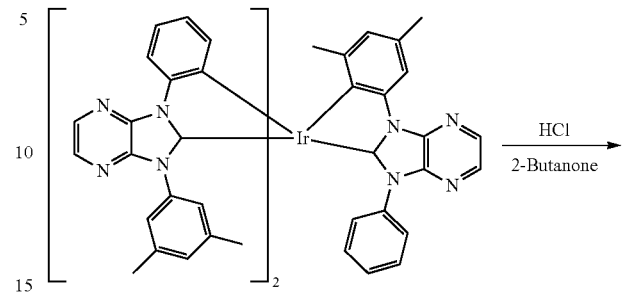

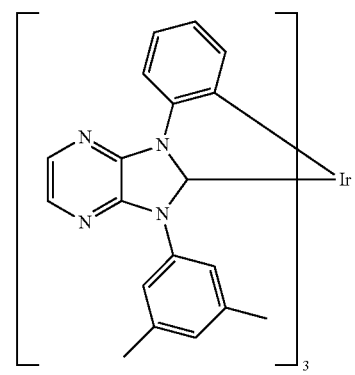

Complex (1') (1.37 g, 1.25 mmol) is suspended in a mixture of 350 mL of 2-butanone and 35 mL of HCl (1M) and heated to 70° C. for 20 hours. After cooling the reaction to room temperature, the solid is dissolved in dichloromethane and extracted with water. The organic phase is then dried. Complex (1) is isolated in quantitative yield.

complex (2)

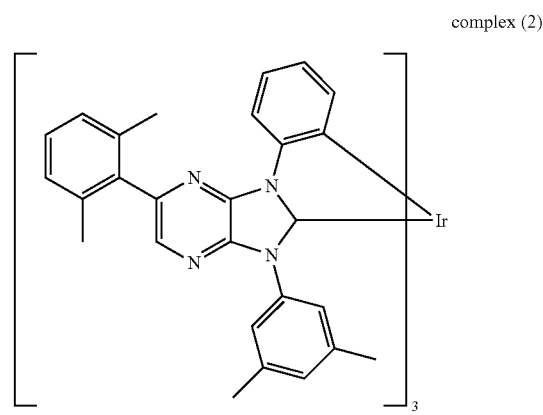

2. Synthesis of Complex (2)

a) Synthesis of 5-(2,6-dimethylphenyl)pyrazin-2-amine

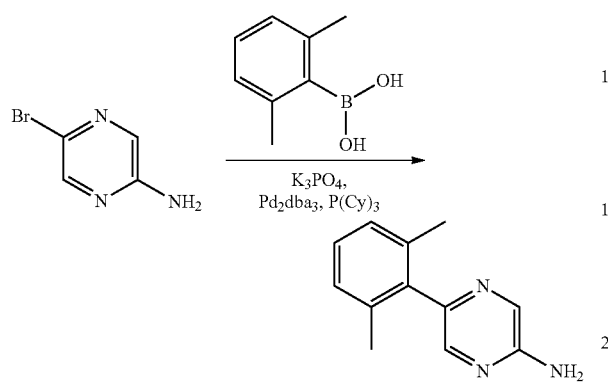

2-amino-5-bromopyrazine (6.96 g, 40.0 mmol) is dissolved in 1 L of dry toluene. 2,6-dimethylphenyl boronic acid (11.1 g, 72.0 mmol) and potassium phosphate (44.2 g, 208 mmol) are then added under argon atmosphere. After degassing the solution, tris(dibenzylidenacetone)dipalladium(0) (0.95 g, 1.04 mmol) and tricyclohexylphosphine (1.2 g, 4.4 mmol) are added and the reaction is heated to reflux for 72 h. After cooling to room temperature, the precipitate is removed by filtration, washed with toluene and the organic phases collected. After evaporation of the solvent, the material is dissolved with 1 L of dichloromethane. After addition of 200 mL of water, the volume is reduced by evaporation and the phases separated. The organic fraction is then extracted with water and dried over anhydrous sodium sulfate, before removing the solvent. The desired product is finally obtained after column chromatography (silica, cyclohexane/ethyl acetate) as a brown oil in 90% yields (7.16 g).

$^1$H-NMR (400 MHz, CD$_2$Cl$_2$): δ=8.08 (s, 1H), 7.89 (s, 1H), 7.18 (t, 1H), 7.10 (d, 2H), 4.66 (s, 2H), 2.06 (s, 6H).

b) Synthesis of 3-bromo-5-(2,6-dimethylphenyl)pyrazin-2-amine

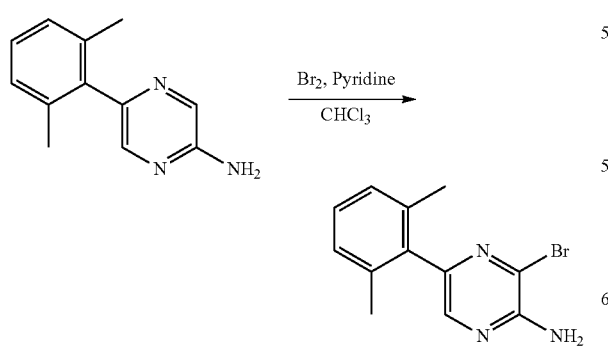

5-(2,6-Dimethylphenyl)pyrazin-2-amine (5.13 g, 25.8 mmol) is dissolved in 126 mL of chloroform. After adding 2.59 g (32.7 mmol) of pyridine, the flask is degassed with argon and cooled to 0° C. A solution of 1.68 mL (32.7 mmol) of bromine in 37 mL of chloroform is added dropwise. The reaction is then diluted with 37 mL of chloroform and stirred for 2 hours at 0° C. and then overnight at room temperature. The reaction is then quenched with a saturated solution of sodium metabisulfite in water. The two phases are then separated and the organic layer washed with water and dried over anhydrous sodium sulfate. After removing the solvent the desired product is isolated as a brown oil in 98% yield (6.87 g).

$^1$H-NMR (400 MHz, CD$_2$Cl$_2$): δ=7.88 (s, 1H), 7.19 (t, 1H), 7.10 (d, 2H), 5.12 (s, 2H), 2.09 (s, 6H).

c) Synthesis of 5-(2,6-dimethylphenyl)-N3-phenyl-pyrazine-2,3-diamine

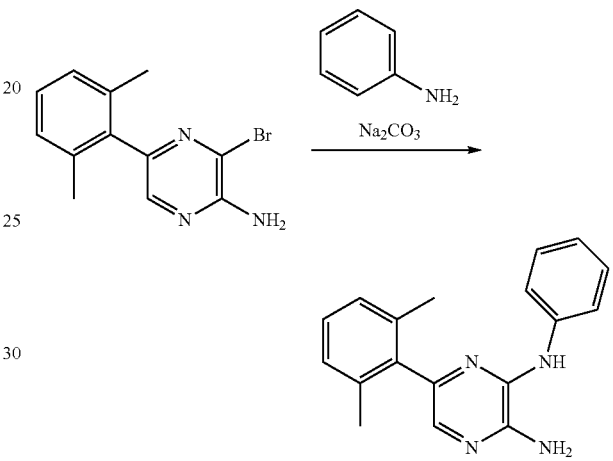

3-Bromo-5-(2,6-dimethylphenyl)pyrazin-2-amine (6.87 g, 23.6 mmol) and sodium carbonate (2.50 g, 23.6 mmol) are suspended in aniline (17.6 g, 119 mmol) and heated for 115 h at 180° C. under argon. After cooling to room temperature, the solvent is evaporated. Warm water is added to the brown residue and the precipitate is then filtered. The solid is then solved in dichloromethane and dried over anhydrous sodium sulfate. After removal of the solvent, the remaining material is dissolved in ethanol and reprecipitated from water. After filtration, the solid is washed with water and the reprecipitation process repeated. The desired product is isolated in 81% yield (5.57 g).

$^1$H-NMR (400 MHz, CD$_2$Cl$_2$): δ=7.52 (s, 1H), 7.41 (d, 2H), 7.28 (t, 2H), 7.17 (t, 1H), 7.09 (d, 2H), 6.98 (t, 1H), 6.30 (s, 1H), 4.43 (s, 2H), 2.12 (s, 6H).

d) Synthesis of 5-(2,6-dimethylphenyl)-N2-(3,5-dimethylphenyl)-N3-phenyl-pyrazine-2,3-diamine

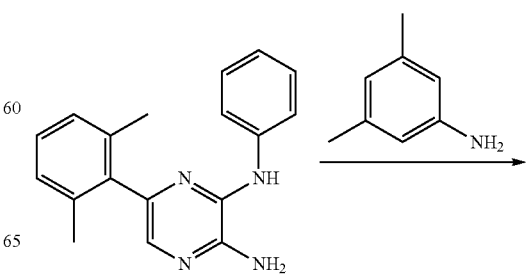

-continued

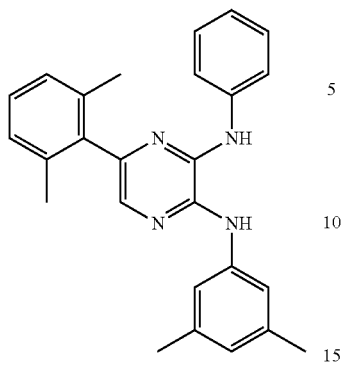

5-(2,6-dimethylphenyl)-N3-phenyl-pyrazine-2,3-diamine (0.200 g, 0.688 mmol), 3,5-dimethylaniline (15 mL) and para-toluensulfonic acid (0.786 g, 4.132 mmol) are added to a 20 mL microwave vial. The mixture is degassed with nitrogen and the vial sealed. The reaction is then heated in a microwave oven for 9 h at 160° C. The reaction is repeated for a total of seven times. All seven reaction mixtures are then collected together for a combined workup. The liquid portion of the reaction is evaporated under vacuum and the remaining solid is dissolved in dichloromethane and extracted with water. After drying over anhydrous sodium sulfate the solvent is removed and the material purified via column chromatography (silica, cyclohexane/ethyl acetate) to give 0.664 g of the desired product in 35% yield.

$^1$H-NMR (400 MHz, CD$_2$Cl$_2$): δ=7.69 (s, 1H), 7.33 (d, 2H), 7.28 (t, 2H), 7.19 (t, 1H), 7.11 (d, 2H), 7.00 (t, 1H), 6.97 (s, 2H), 6.71 (s, 1H), 6.39 (s, 1H), 6.21 (s, 1H), 2.30 (s, 6H), 2.16 (s, 6H).

e) Synthesis of [3-(3, 5-dimethylanilino)-6-(2, 6-dimethylphenyl)pyrazin-2-yl]-phenyl-ammonium chloride

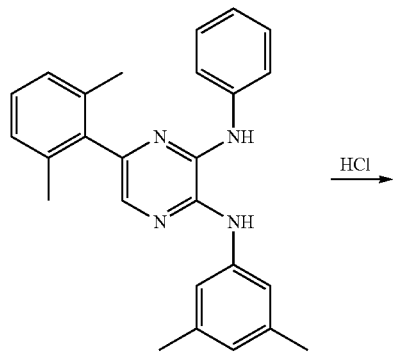

-continued

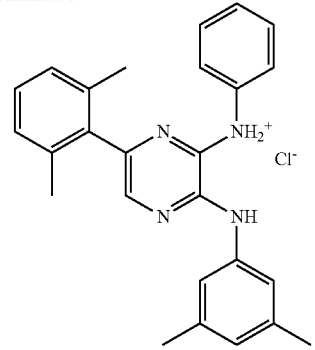

5-(2,6-Dimethylphenyl)-N2-(3,5-dimethylphenyl)-N3-phenyl-pyrazine-2,3-diamine (0.80 g, 2.03 mmol) is dissolved in 10 mL of hydrochloric acid (32%) and stirred overnight at room temperature. The suspension is diluted with 60 mL of water and the precipitate filtered. After washing with water and petroleum ether, the desired product is isolated as a yellow solid after drying under vacuum at 50° C. overnight in 83% yield (0.72 g).

$^1$H-NMR (400 MHz, CD$_2$Cl$_2$): δ=10.20 (s, 1H), 9.42 (s, 2H), 7.67 (d, 2H), 7.27 (t, 2H), 7.23-7.19 (m, 2H), 7.12-7.04 (m, 5H), 6.80 (s, 1H), 2.27 (s, 6H), 2.15 (s, 6H).

f) Synthesis of 5-(2,6-dimethylphenyl)-1-(3,5-dimethylphenyl)-2-ethoxy-3-phenyl-2H-imidazo[4,5-b]pyrazine

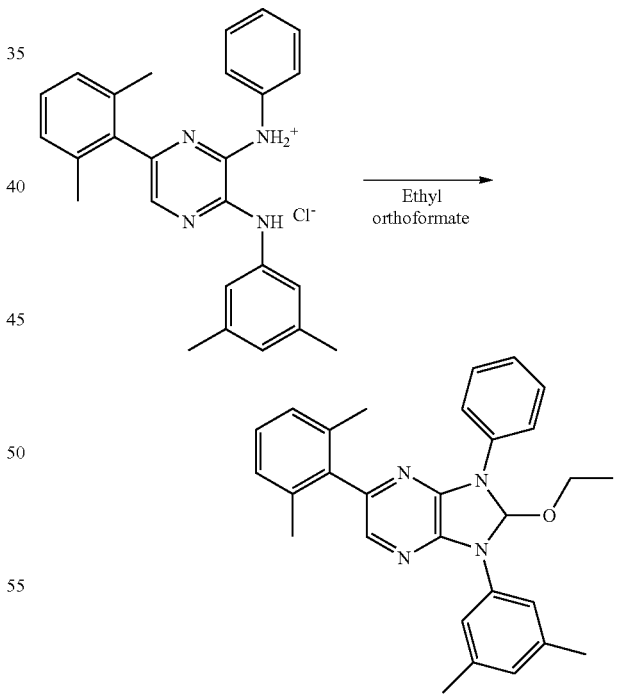

[3-(3,5-Dimethylanilino)-6-(2,6-dimethylphenyl)pyrazin-2-yl]-phenyl-ammonium chloride (0.179 g, 0.417 mmol) is suspended in 27 mL of ethyl orthoformate. The reaction is stirred for 4 h at room temperature and then heated at 40° C. for 1 h. After cooling to room temperature, the solvent is removed under vacuum to give the desired product in quantitative yield.

¹H-NMR (400 MHz, CD₂Cl₂): δ=8.05 (d, 2H), 7.71 (s, 2H), 7.45 (s, 1H), 7.41 (t, 2H), 7.32 (s, 1H), 7.20 (t, 1H), 7.16-7.12 (m, 3H), 6.86 (s, 1H), 3.40-3.34 (m, 2H), 2.39 (s, 6H), 2.19 (s, 6H), 1.08 (t, 3H).

g) Synthesis of Complex (2)

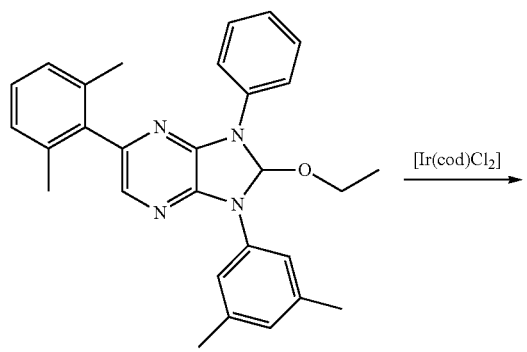

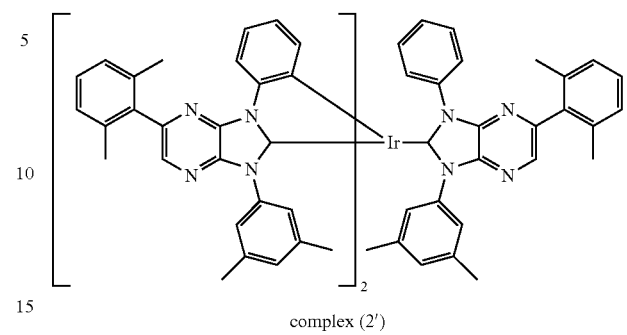

complex (2')

5-(2,6-Dimethylphenyl)-1-(3,5-dimethylphenyl)-2-ethoxy-3-phenyl-2H-imidazo[4,5-b]pyrazine (0.936 g, 2.076 mmol) is dissolved in 300 mL of o-xylene under argon. Molecular sieves (5 Å and 3 Å, 5 g each) and then chloro(1,5-cyclooctadiene) iridium(I)-dimer (0.174 g, 0.26 mmol) are added to the solution. After degassing the solution with argon flux for 5 minutes, the reaction is heated up to 140° C. overnight. The warm reaction mixture is filtered and the residue is washed with warm o-xylene. The filtrate is evaporated under vacuum and the obtained residue is purified via column chromatography (silica, cyclohexane/ethyl acetate) to give 625 mg of a mixture of complex (2) and complex (2') in a ratio of 3:1.

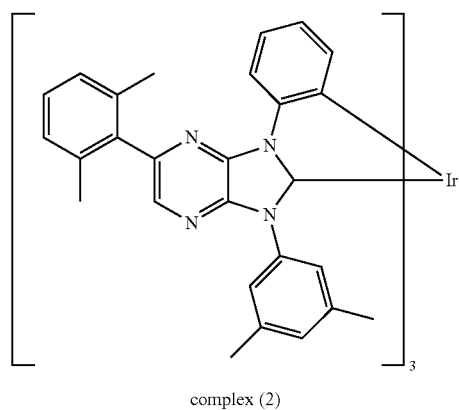

complex (2)

+

Synthesis of 3-(3,5-dimethylphenyl)-2-ethoxy-1-phenyl-5-(trifluoromethoxy)-2H-benzimidazole

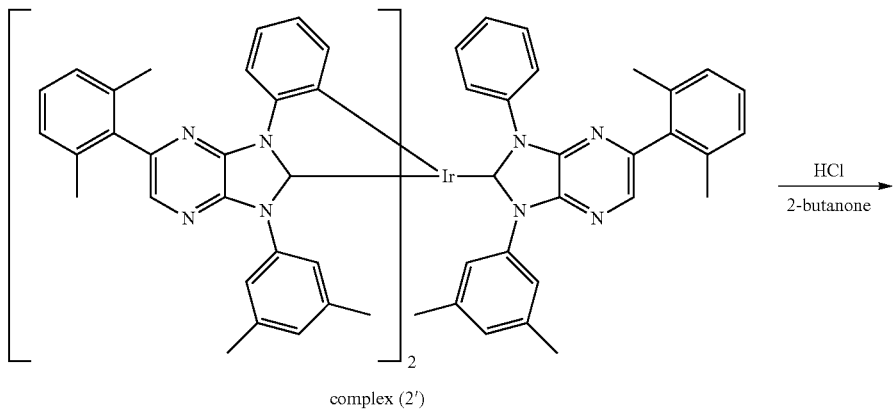

complex (2')

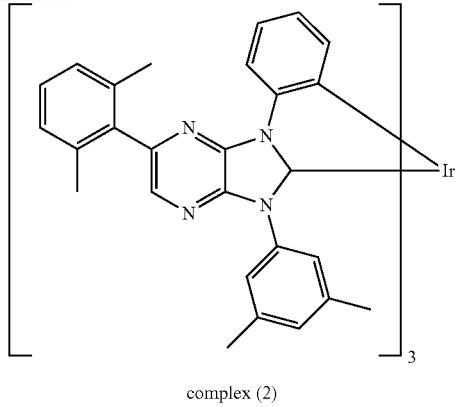

complex (2)

Complex 2' (625 mg, 0.44 mmol) is dissolved in 75 mL of 2-butanone under argon atmosphere. 75 mL of 1 M hydrochloric acid are added. The reaction mixture is stirred at reflux (70° C.) overnight. After cooling to room temperature the solvent is removed and the residue is solved in dichloromethane. The organic layer is washed three times with water, then dried over anhydrous sodium sulfate and evaporated under vacuum. The residue is purified first via column chromatography (silica, cyclohexane/ethyl acetate) to give 120 mg of the desired product. All fractions with product are collected and purified twice via column chromatography (reversed phase, acetonitrile/dichloromethane) to give 44 mg and 23 mg of the desired product. The three product batches are mixed together to give 187 mg of the desired product in 19.2% yield.

$^1$H-NMR (400 MHz, CD$_2$Cl$_2$): δ=8.66 (d, 3H), 8.00 (s, 3H), 7.30 (t, 3H), 7.22 (d, 6H), 7.08 (t, 3H), 6.87 (s, 3H), 6.75 (t, 3H), 6.65 (br. s, 3H), 6.58 (d, 3H), 5.98 (br. s, 3H) 2.43 (br. s, 9H), 2.25 (br. s, 18H) 1.83 (br. s, 9H).

Photoluminescence (2% in a PMMA film): $\lambda_{max}$=478 nm, CIE: (0.16; 0.30); QY=96%.

3. Synthesis of Complex (3)

a) Synthesis of 5-bromo-2-nitro-N-phenyl-aniline

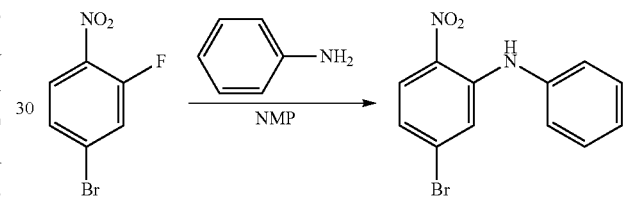

4-Bromo-2-fluoro-nitrobenzene (5.6 g, 20.9 mmol) and aniline (2.5 g, 72.2 mmol) are added to 50 mL of anhydrous NMP. The reaction is heated to 110° C. overnight. After cooling to room temperature and removing the solvent, the compound is purified via column chromatography (silica, cyclohexane/ethyl acetate 9:1) and obtained as an orange solid in 92% yield (5.7 g).

$^1$H-NMR (400 MHz, CD$_2$Cl$_2$): δ=9.48 (s, 1H), 8.06 (d, 1H), 7.46 (t, 2H), 7.30 (t, 4H), 6.89 (d, 1H).

b) Synthesis of 5-dibenzofuran-4-yl-2-nitro-N-phenyl-aniline

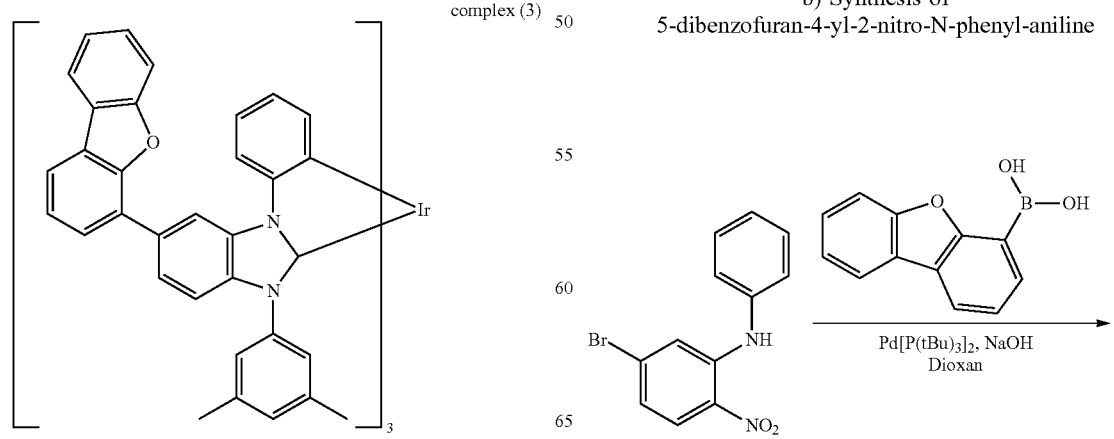

complex (3)

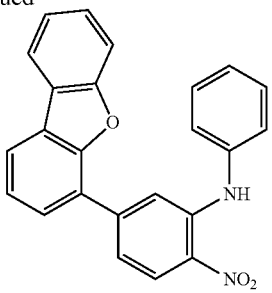

A 50% solution of sodium hydroxide (3.36 g, 42.0 mmol) and 280 ml of dioxane are mixed together and argon is bubbled through the solution for one hour. 4-Bromo-2-fluoro-nitrobenzene (4.10 g, 14.0 mmol) is added to the mixture. After stirring for 15 minutes under argon flux, bis(tri-t-butylphosphine)palladium(0) (0.25 g, 0.49 mmol) and dibenzofurane-4-boronic acid (5.94 g, 28.0 mmol) are added. After cooling to room temperature, the precipitate is removed by filtration and washed with dioxane, the organic phases collected and the solvent removed to obtain a dark solid. After adding dichloromethane and extracting the solution with water, the organic phases are dried over anhydrous sodium sulfate and the solvent removed. The desired product is obtained after column chromatography (silica, dichloromethane/cyclohexane 1/1) as a yellow solid in 99.8% yields (5.32 g).

$^1$H-NMR (400 MHz, $CD_2Cl_2$): δ=9.62 (s, 1H), 8.33 (d, 1H), 8.00 (d, 2H), 7.96 (s, 1H), 7.63-7.36 (m, 9H), 7.31 (d, 1H), 7.27-7.23 (m, 1H).

c) Synthesis of 4-dibenzofuran-4-yl-N2-phenyl-benzene-1,2-diamine

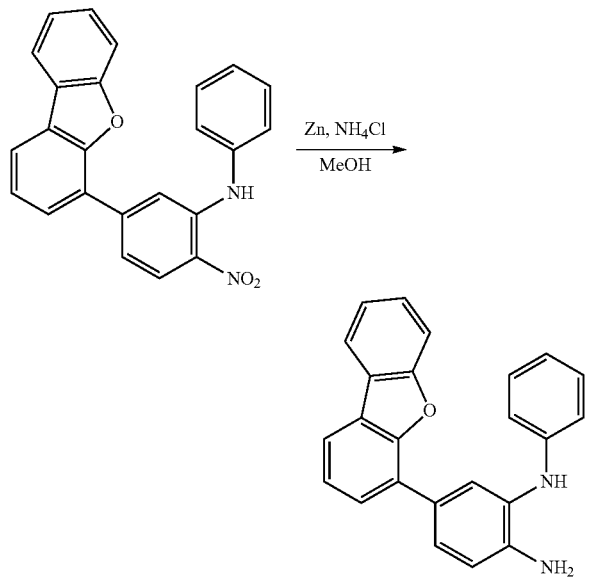

5-Dibenzofuran-4-yl-2-nitro-N-phenyl-aniline (0.96 g, 2.5 mmol) is dissolved in 50 ml of THF. Methanol (20 ml) is added to the solution and the mixture is sonicated under argon atmosphere. 10 ml of a saturated solution of ammonium chloride are added dropwise to the reaction and the system is then cooled to 10° C. Successively zinc powder (0.79 g, 12.0 mmol) is added portionwise and the reaction is stirred for about 6 hours at 10° C. and then at room temperature over weekend. The reaction mixture is then filtered over celite and washed with dichloromethane. The organic phase is extracted with water and dried over anhydrous sodium sulfate. The desired product is finally isolated as a beige solid in quantitative yield (0.880 g).

$^1$H-NMR (400 MHz, $CD_2Cl_2$): δ=7.99 (d, 1H), 7.88 (d, 1H), 7.76 (s, 1H), 7.00 (d, 2H), 7.55 (d, 1H), 7.47 (t, 1H), 7.40-7.34 (m, 2H), 7.23 (t, 2H), 6.97 (d, 1H), 6.87 (d, 2H), 6.83 (t, 1H), 5.40 (br. s, 1H), 3.98 (br. s, 2H).

d) Synthesis of 4-dibenzofuran-4-yl-N1-(3,5-dimethylphenyl)-N2-phenyl-benzene-1,2-diamine

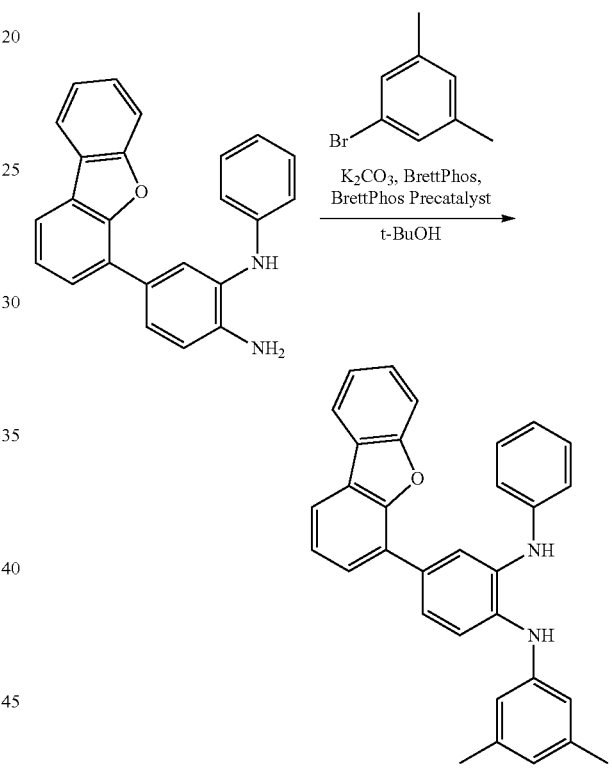

4-Dibenzofuran-4-yl-N2-phenyl-benzene-1,2-diamine (0.86 g, 2.5 mmol), 5-bromo-xylene (0.45 g, 2.45 mmol), potassium carbonate (0.47 g, 3.43 mmol), BrettPhos (2-(dicyclohexylphosphino)3,6-dimethoxy-2',4',6'-triisopropyl-1,1'-biphenyl, 0.065 g, 0.12 mmol), BrettPhos precatalyst (chloro[2-(dicyclohexylphosphino)-3,6-dimethoxy-2',4',6'-triisopropyl-1,1'-biphenyl][2-(2-aminoethyl)phenyl] palladium(II), 0.096 g, 0.12 mmol) and tert-butanol (80 ml) are mixed in a flask under argon atmosphere. The system is heated to 40° C. and stirred under argon flux for 30 minutes. Afterwards the reaction is heated at 80° C. overnight. Additional 5-bromo-xylene (0.093 g, 0.49 mmol) is given to the reaction, which is then heated for other four hours. After cooling to room temperature, dichloromethane is poured into the solution and the mixture extracted with water (3×100 ml), the organic phases are collected and dried over anhydrous magnesium sulfate. After removing the salt and evaporating the solvent, the material is purified via column chromatography (silica, cyclohexane/ethyl acetate). The target compound is isolated as a beige solid in 81% yield (0.96 g).

¹H-NMR (400 MHz, CD₂Cl₂): δ=8.00 (d, 1H), 7.95-7-87 (m, 2H), 7.62-7.55 (m, 3H), 7.51-7.35 (m, 4H), 7.27 (t, 2H), 7.05 (d, 2H), 6.89 (t, 1H), 6.68 (s, 2H), 6.60 (s, 1H), 5.80 (s, 1H), 5.74 (s, 1H), 2.26 (s, 6H).

e) Synthesis of 5-dibenzofuran-4-yl-1-(3,5-dimethylphenyl)-3-phenyl-benzimidazol-3-ium chloride

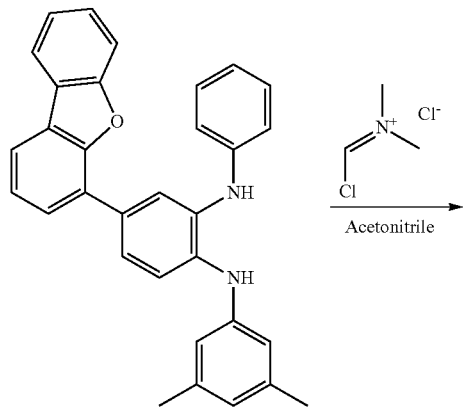

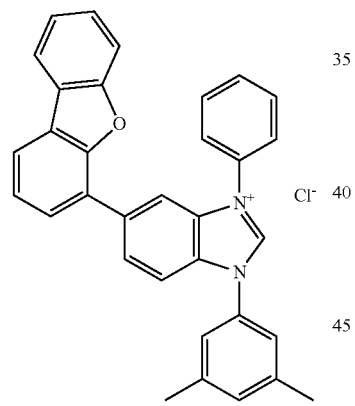

4-dibenzofuran-4-yl-N1-(3,5-dimethylphenyl)-N2-phenyl-benzene-1,2-diamine (0.82 g, 1.8 mmol) is dissolved in 80 ml of anhydrous acetonitrile. The solution is degassed and cooled down to 0° C. under argon atmosphere. (Chloromethylene)-dimethylammonium-chloride (0.69 g, 5.4 mmol) is then added to the solution. The reaction is stirred at 0° C. and left warming to room temperature overnight. After cooling to 5° C., the precipitate is filtered and washed with acetonitrile to give the desired product. Additional amounts of the target compound are isolated after evaporation of half of the amount of solvent and filtration to achieve a final yield of 97% (0.88 g).

¹H-NMR (400 MHz, CD₂Cl₂): δ=10.67 (s, 1H), 8.37-8.32 (m, 2H), 8.25 (t, 2H), 8.18 (d, 1H), 8.07 (d, 2H), 7.88-7.82 (m, 3H), 7.77 (t, 1H), 7.70 (d, 1H), 7.66 (s, 2H), 7.57 (t, 2H), 7.47 (t, 1H), 7.42 (s, 1H), 2.49 (s, 6H, overlapping with the solvent peak).

f) Synthesis of 5-dibenzofuran-4-yl-1-(3,5-dimethylphenyl)-2-methoxy-3-phenyl-2H-benzimidazole

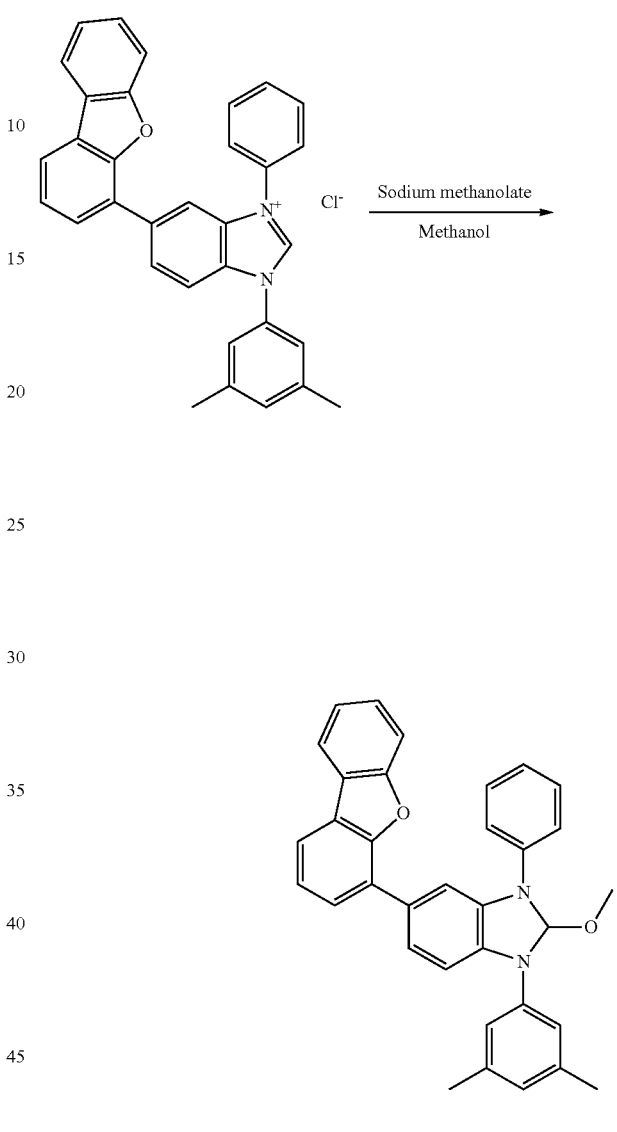

5-Dibenzofuran-4-yl-1-(3,5-dimethylphenyl)-3-phenyl-benzimidazol-3-ium chloride (0.88 g, 1.74 mmol) is dissolved in 50 ml of methanol and the solution is cooled to 0° C. Sodium methanolate (0.47 g, 2.61 mmol in a 30% methanol solution) is added dropwise to the reaction mixture, which is then left stirring overnight at room temperature. After diluting the reaction mixture with 25 ml of methanol, sodium methanolate (0.16 g, 0.87 mmol dissolved in a 30% methanol solution) is again added dropwise. After stirring over weekend at room temperature, the suspension is cooled down to 0° C., filtered and the solid washed with cold methanol. The desired product is isolated as a white solid in 85% yield (0.73 g).

¹H-NMR (400 MHz, DMSO-d₆): δ=8.01 (d, 1H), 7.91 (d, 1H), 7.74 (s, 1H), 7.67 (d, 2H), 7.62 (d, 2H), 7.49 (t, 1H), 7.45-7.36 (m, 5H), 7.27 (d, 1H), 7.23 (s, 2H), 7.14 (t, 1H), 6.81 (d, 2H), 3.19 (s, 3H), 2.36 (s, 6H).

g) Synthesis of Complex (3)

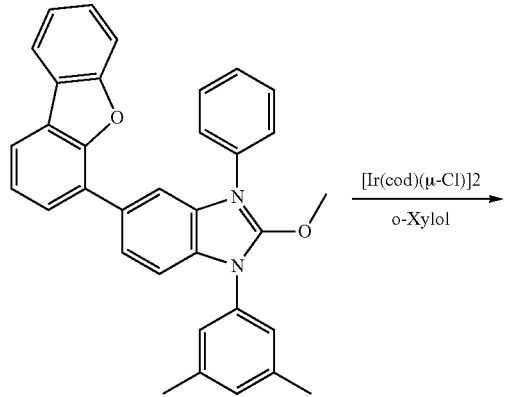

[Ir(cod)(μ-Cl)]2
o-Xylol

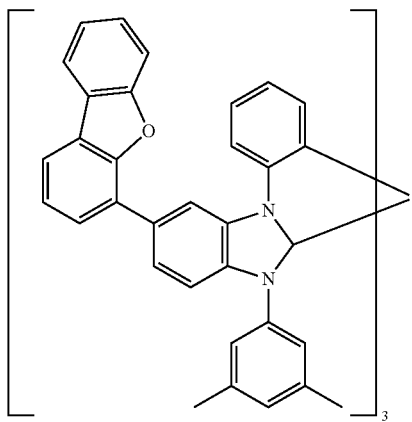

complex (3)
+

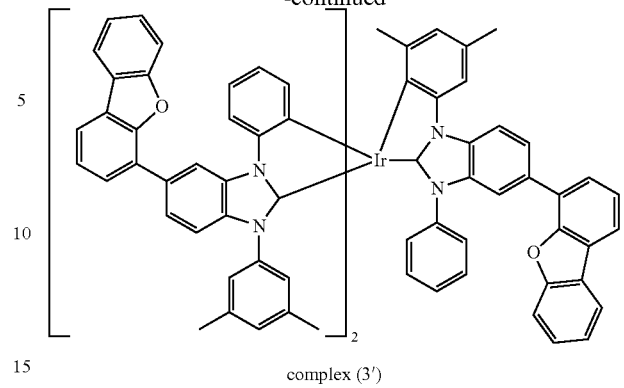

complex (3')

5-Dibenzofuran-4-yl-1-(3,5-dimethylphenyl)-2-methoxy-3-phenyl-2H-benzimidazole (0.71 g, 1.43 mmol) is dissolved in 60 ml of anhydrous xylene. Molecular sieves (5 Å and 3 Å, 0.46 g each) and then chloro(1,5cyclooctadien) iridium(I)-dimer (0.16 g, 0.24 mmol) are added to the solution. After flushing the solution with argon for 5 minutes, the reaction is heated at 140° C. overnight. After cooling to room temperature, the solid residues are removed by filtration and washed with ethyl acetate. The solvent is removed and the material purified by column chromatography (silica, cyclohexane/dichloromethane). Complex (3') is isolated from the reaction in 7% yield (0.55 g), while complex (3) is obtained as a white solid in 36% yield (0.27 g). Complex (3) $^1$H-NMR (400 MHz, CD$_2$Cl$_2$): δ=8.68 (s, 3H), 8.07 (d, 6H), 8.02 (d, 3H), 7.71 (d, 3H), 7.65 (d, 3H), 7.55-7.49 (q, 9H), 7.42 (t, 3H), 7.13-7.09 (m, 3H), 6.72 (m, 6H), 6.60 (d, 9H), 5.95 (s, 3H), 2.46 (s, 9H), 1.83 (s, 9H).

Photoluminescence (2% in a PMMA film): λ$_{max}$=468 nm, CIE: (0.18; 0.34); QY=42%.

h) Isomerization of Complex (3')

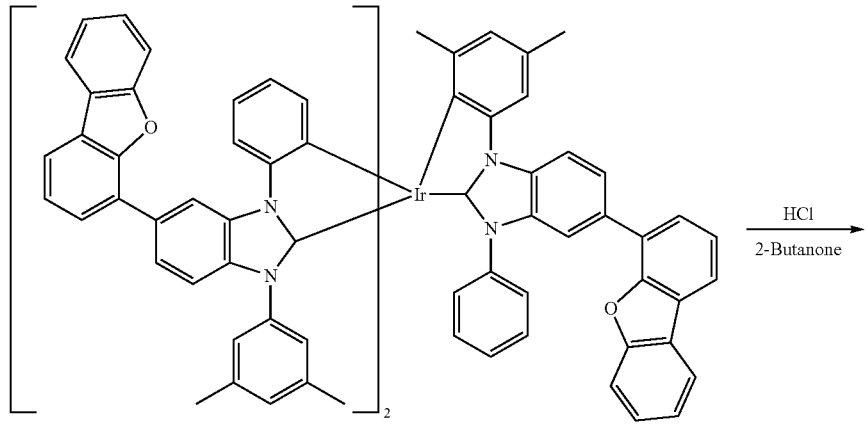

HCl
2-Butanone

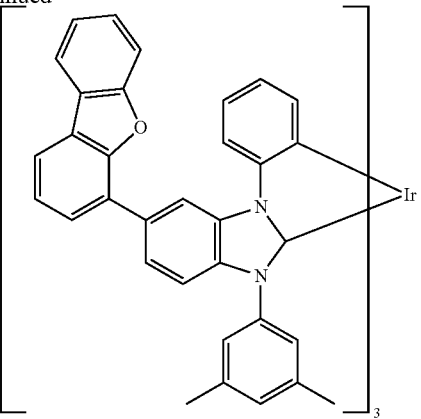

Complex (3') (0.055 g, 0.03 mmol) is dissolved in 5 ml 2-butanone. Hydrochloric acid (1 ml of 1 M solution) is added. After heating the reaction at 70° C. for 4 hours, the reaction is cooled to room temperature and the solvent removed. After dissolving the solid in dichloromethane, the solution is extracted with water and then dried over anhydrous magnesium sulfate. After filtering the solid, the solvent is removed. Complex (3) is obtained after column chromatography (silica, cyclohexane/dichloromethane first 7:3, then 6:4) in 36% yield (0.02 g).

complex (4)

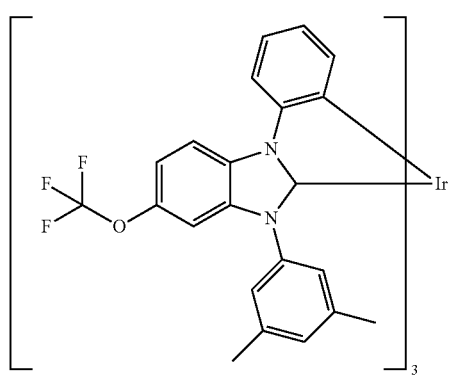

4. Synthesis of Complex (4)

a) Synthesis of 2-nitro-N-phenyl-4-(trifluoromethoxy)aniline

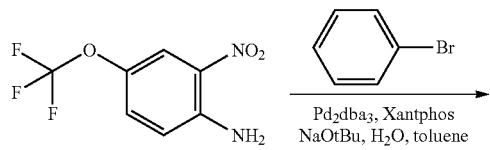

-continued

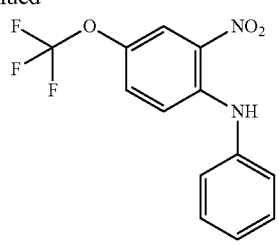

18.32 g (80.0 mmol) of 2-nitro-4-(trifluoromethoxy)aniline, and 15.1 g (95.7 mmol) of bromobenzene, in 320 ml of toluene and 4.3 g of water, are heated at 80° C. under nitrogen during 15 minutes. 8.72 g (90.7 mmol) of sodium tert-butylate are added and the yellow-red suspension stirred at 80° C. for 40 minutes. 0.73 g (0.8 mmol) of tris(dibenzylideneacetone)dipalladium(0), and 1.43 g of 4,5-bis(diphenylphosphino)-9,9-dimethylxanthene are added and the resulting suspension heated at 100° C. during 19 hours, cooled down to room temperature and filtered. The yellow-red solution is concentrated under vacuum and the resulting dark yellow oil further purified by chromatography (silica gel, cyclohexane/dichloromethane 3:1) giving the title product as yellow solid (yield: 18.8 g (79%)).

$^1$H-NMR (400 MHz, CD$_2$Cl$_2$): δ=7.29-7.36 (m, 5H), 7.46-7.54 (m, 2H), 8.13 (d, 1H), 9.50 (br. s, 1H).

b) Synthesis of N1-phenyl-4-(trifluoromethoxy)benzene-1,2-diamine

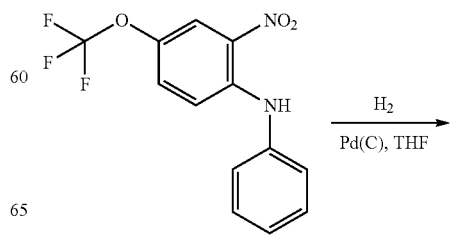

-continued

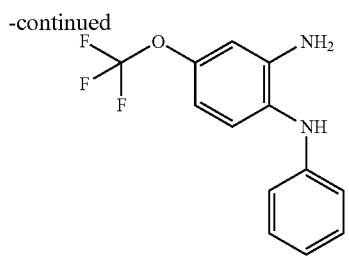

28.1 g (94.2 mmol) of 2-nitro-N-phenyl-4-(trifluoromethoxy)aniline and 2.8 g of 5 wt %-palladium on carbon in 150 mol tetrahydrofurane are reacted under 5 bar hydrogen pressure at 50° C. during 23 hours. The reaction mixture is filtered through a layer of Hyflo® filter aid and rinsed with additional tetrahydrofurane, followed by concentration under vacuum. The resulting red oil is further purified by chromatography over silica gel using heptane as eluent first, followed by a mixture of cycylohexane/toluene 1:1, giving the title product as off-white solid (yield: 18.0 g (74%)).

$^1$H-NMR (400 MHz, CD$_2$Cl$_2$): δ=4.03 (br. s, 2H), 5.22 (br. s, 1H), 6.60-6.65 (m, 1H), 6.69-6.73 (m, 1H), 6.74-6.79 (m, 2H), 6.83-6.90 (m, 1H), 7.14 (d, 1H), 7.21-7.28 (m, 2H).

c) Synthesis of N2-(3,5-dimethylphenyl)-N1-phenyl-4-(trifluoromethoxy)benzene-1,2-diamine

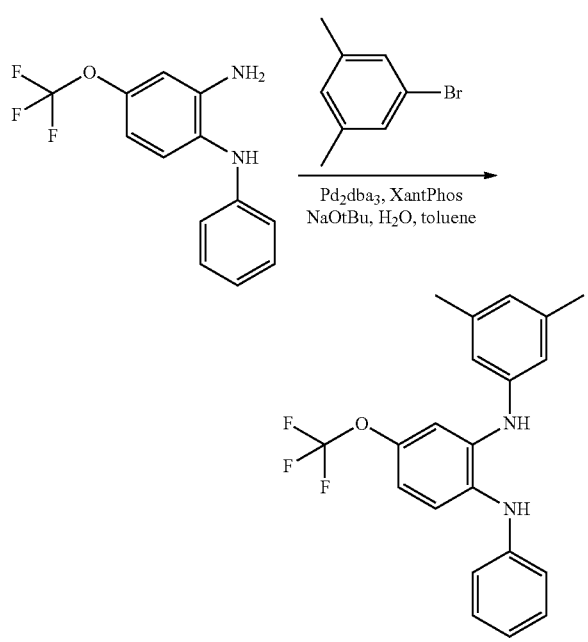

18.0 g (65.9 mmol) of N1-phenyl-4-(trifluoromethoxy) benzene-1,2-diamine, and 13.7 g (72.5 mmol) 3,5-dimethylbromobenzene, in 300 ml toluene and 1.78 g of water, are heated at 78° C. under nitrogen during 15 minutes. 7.83 g (79.1 mmol) of sodium tert-butylate are added and the suspension further heated during 20 minutes. 1.81 g (1.98 mmol) of tris(dibenzylideneacetone)dipalladium(0), and 98 mg (0.23 mmol) of 2-dicyclohexylphosphino-2',6'-dimethoxybiphenyl are added and the resulting suspension heated under reflux during 18 hours, cooled down to room temperature and filtered. The solution is dried over sodium sulfate and concentrated under vacuum. The blue-green oil is further purified by chromatography (silica gel, cyclohexane/toluene 3:2) giving the title product as viscous oil (yield: 20.4 g (83%)).

$^1$H-NMR (400 MHz, d$_6$-DMSO): δ=2.19 (s, 6H), 6.52 (br. s, 1H), 6.66 (br. s, 2H), 6.76-6.83 (m, 2H), 6.92-6.97 (m, 2H), 7.07-7.10 (m, 1H), 7.17-7.27 (m, 3H), 7.32 (s, 1H), 7.38 (s, 1H).

d) Synthesis of [2-anilino-5-(trifluoromethoxy)phenyl]-(3,5-dimethylphenyl)ammonium chloride

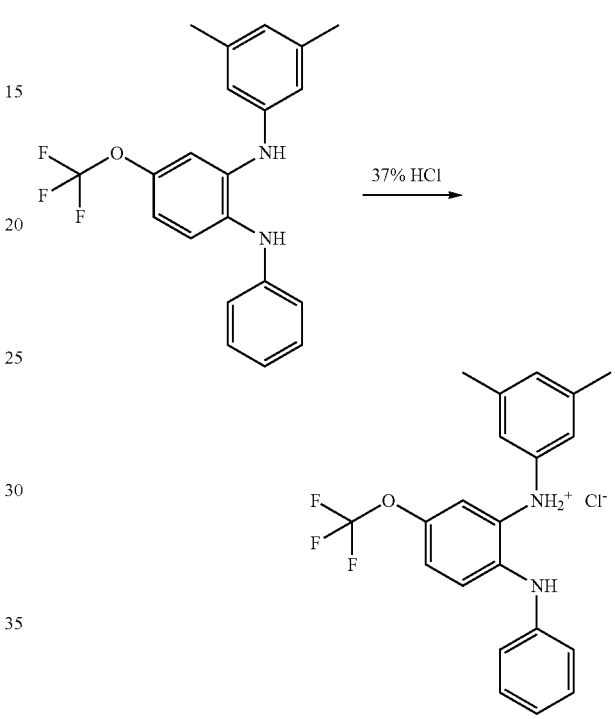

A green suspension of 20.3 g (52.7 mmol) of N2-(3,5-dimethylphenyl)-N1-phenyl-4-(trifluoromethoxy)benzene-1,2-diamine and 700 ml of 37% hydrochloric acid is stirred at room temperature during 21 hours. The resulting viscous oil is separated from the liquid phase by decantation, washed with 37% hydrochloric acid, and extensively dried on a filter funnel under vacuum. The title product is directly used in the next step.

e) Synthesis of 3-(3,5-dimethylphenyl)-1-phenyl-5-(trifluoromethoxy)benzimidazol-3-ium chloride

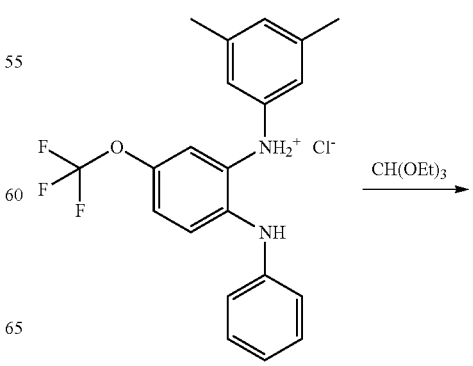

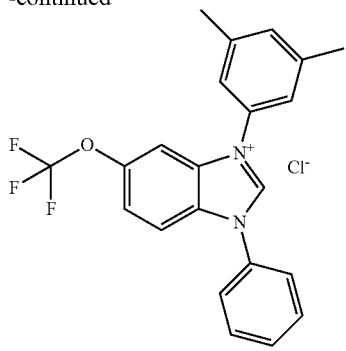

The crude product of the former reaction step and 200 ml of triethyl orthoformate are heated up under argon at 100° C. during 18 hours under continuous separation of the formed ethanol. The resulting red-brown suspension is filtered and washed with 40 ml of triethyl orthoformate and 200 ml of heptane and the solid dried under vacuum, giving a first fraction of the title product. The filtrate is further diluted with heptane under strong stirring until precipitation of the title product occurred. The remaining solution is concentrated by removal of a big part of heptane until a viscous oil separated. The solution is concentrated to a 15 ml volume and further diluted with 250 ml of heptane leading to precipitation of a third crop of the title product. The three crops of solid material are combined and dried under vacuum giving the title product as white solid (yield: 14.2 g (69%)).

$^1$H-NMR (400 MHz, $d_6$-DMSO): δ=2.46 (s, 6H), 7.40 (s, 1H), 7.54 (s, 2H), 7.74-7.85 (m, 4H), 7.92-7.97 (m, 2H), 8.05-8.13 (m, 2H), 10.66 (s, 1H).

f) Synthesis of 3-(3,5-dimethylphenyl)-2-ethoxy-1-phenyl-5-(trifluoromethoxy)-2H-benzimidazole

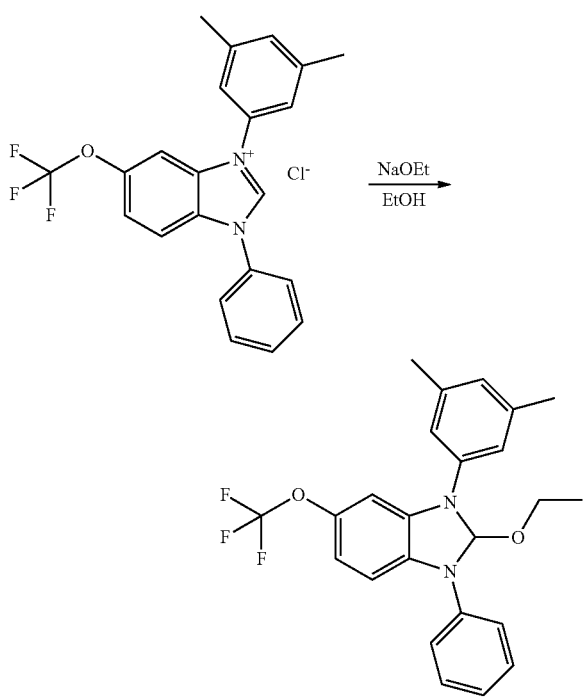

7.50 g (17.9 mmol) of 3-(3,5-dimethylphenyl)-1-phenyl-5-(trifluoromethoxy)benzimidazol-3-ium chloride is suspended in 200 ml of heptane under nitrogen. 5.8 g (17.9 mmol) of a 21 wt % sodium ethoxide solution in 18 ml of heptane are added dropwise during 30 minutes and the resulting suspension further stirred at room temperature during 2.5 hours. The resulting light brown suspension is filtered and the solution concentrated under vacuum giving the title product as dark yellow oil (yield: 7.67 g (quantitative)).

g) Synthesis of Complex (4)

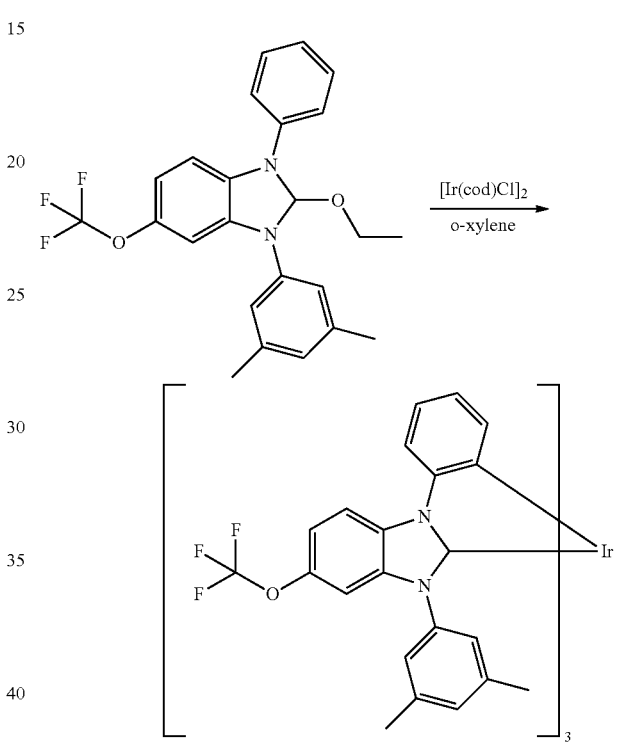

6.7 g (15.6 mmol) of 3-(3,5-dimethylphenyl)-2-ethoxy-1-phenyl-5-(trifluoromethoxy)-2H-benzimidazole and 1.16 g (1.73 mmol) of chloro(1,5-cyclooctadiene)iridium(I) dimer are suspended under nitrogen in 430 ml of o-xylene. The suspension is three times evacuated and backfilled with nitrogen, followed by heating at 122° C. during 18 hours. The resulting almost clear brown solution is filtered at 95° C. and the brown solution concentrated under vacuum at 65° C. The light brown residue is stirred together with 120 ml ethanol and 150 ml of cyclohexane until a clear brown solution resulted. 180 ml of tert-butanol are added and the solution concentrated under vacuum until most of cyclohexane and ethanol are removed and until precipitation of a solid started. The suspension is stirred during 16 hours followed by filtration and rinsing the resulting solid with tert-butanol until a clear washing is observed. The solid is dried under vacuum giving 3.08 g of crude product. APCI-LC-MS measurement of the isolated solid showed three signals [M+1]$^+$ with m/z 1337.3, corresponding to three cyclometallation isomers of the title iridium complex, with a ratio of the three isomers of ca. 7:3:1, based on area percent values determined in the HPLC measurement. The isolated solid is stirred in 85 ml cyclohexane and heated under reflux during one hour. The resulting light suspension is cooled down to 70° C. and filtered. The remaining solid is dried under vacuum and mixed with 150 ml of cyclohexane and 7.5 ml of tert-butanol followed by heating under reflux during 45 minutes. The suspension is cooled down to 80° C., 7 ml of chloroform are added in portions, and the resulting light suspension heated under reflux during one hour. Chloroform is distilled off under vacuum and stirring is continued at room temperature during three days. The suspension is filtered and the solid rinsed with a small amount of cyclohexane and further dried under vacuum giving the title product as a single isomer (=homoleptic complex according to NMR characterization), as a white solid (yield: 1.31 g (28%)).

APCI-LC-MS (positive, m/z): exact mass of $C_{66}H_{48}F_9IrN_6O_3$=1336.33. found 1337.3 $[M+1]^+$.

$^1$H-NMR (400 MHz, $d_6$-DMSO): δ=1.67 (s, 9H), 2.33 (s, 9H), 5.60 (s, 3H), 6.35 (d, 3H), 6.47-6.54 (m, 6H), 6.62 (t, 3H), 7.02-7.10 (t, 3H), 7.02-7.10 (t, 3H), 7.11-7.20 (m, 3H), 7.23-7.32 (m, 3H), 8.01 (d, 3H), 8.40 (d, 3H).

Photoluminescence (2% in a PMMA film): $\lambda_{max}$=412 nm, CIE: (0.17; 0.05); QY=44%.

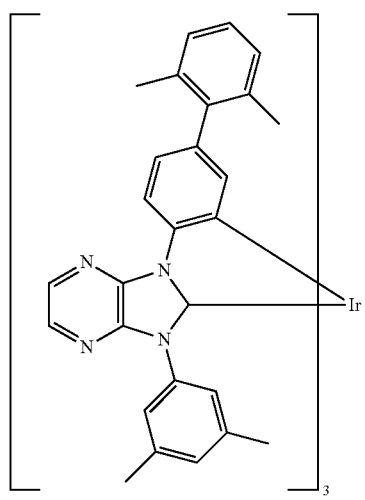

complex (5)

5. Synthesis of Complex (5)

a) Synthesis of 1,3-dimethyl-2-(4-nitrophenyl)benzene

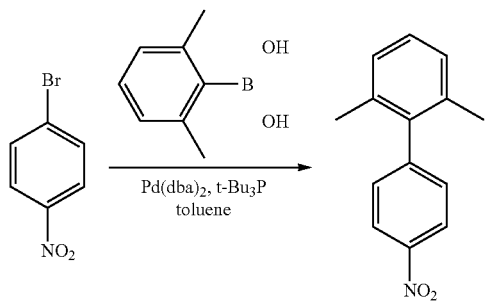

39.2 g (0.19 mol) of 4-bromo-nitrobenzene together with 37.8 g (0.25 mol) of 2,6-dimethylphenylboronic acid, 103 g (0.49 mol) of potassium phosphate tribasic monohydrate, 1.19 g (2.9 mmol) of 2-dicyclohexylphosphino-2',6'-dimethoxybiphenyl, and 0.22 g (1.0 mmol) of palladium(II) acetate are suspended in 200 ml of toluene at room temperature under argon. The suspension is three times evacuated and backfilled with argon, followed by heating under reflux for two hours. 4 ml of water are added and the light yellow suspension further heated under reflux for 30 minutes. 50 ml of toluene and 10 ml of water are added and heating continued under reflux for 15 hours. The reaction mixture is cooled down to room temperature and treated with 160 ml of water and 3.1 g of sodium cyanide, followed by heating under reflux for 30 minutes. The reaction mixture is cooled down to room temperature and the organic phase separated. The aqueous phase is washed with toluene and the combined organic phases further extracted with water and brine, followed by drying over sodium sulfate, and concentration under vacuum. The residual oil is diluted with 100 ml methanol and the resulting suspension stirred at ice-bath temperature during one hour. The suspension is filtered and the solid rinsed with a small amount of cold toluene and methanol giving the title product as light yellow solid (yield: 33.7 g (76.5%)).

$^1$H-NMR (400 MHz, $CD_2Cl_2$): δ=2.05 (s, 6H), 7.14-7.20 (m, 2H), 7.21-7.27 (m, 1H), 7.37-7.43 (m, 2H), 8.30-8.37 (m, 2H).

b) Synthesis of 4-(2, 6-dimethylphenyl)aniline

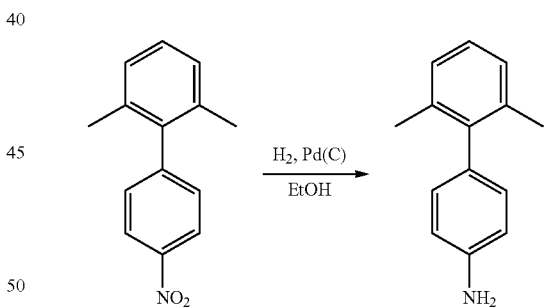

62.3 g (0.27 mol) of 1,3-dimethyl-2-(4-nitrophenyl)benzene and 3.0 g of 5 wt %-palladium on carbon in 300 ml of ethanol are reacted under 3 bar hydrogen pressure at 35° C. during 20 hours. The reaction mixture is filtered through a layer of Hyflo® filter aid and rinsed with additional ethanol, followed by concentration under vacuum. The yellow oil is further purified by chromatography (silica gel, heptane/ethyl acetate), followed by additional purification by distillation (0.15 mbar, 120° C.), giving the title product as a white solid (yield: 37.7 g (70%)).

$^1$H-NMR (400 MHz, $CD_2Cl_2$): δ=2.08 (s, 6H), 3.77 (br. s, 2H), 6.76-6.81 (m, 2H), 6.92-6.97 (m, 2H), 7.08-7.17 (m, 3H).

c) Synthesis of 3-chloro-N-[4-(2,6-dimethylphenyl)phenyl]pyrazin-2-amine

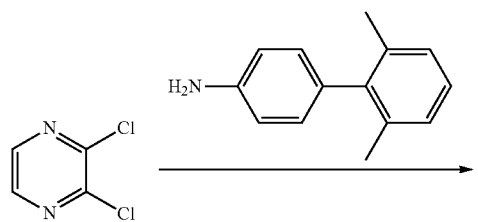

10.0 g (67.1 mmol) of 2,3-dichloropyrazine, 13.2 g (67.0 mmol) of 4-(2,6-dimethylphenyl)aniline, and 7.10 g (67.0 mmol) of sodium carbonate are suspended in 42 ml of 1-methyl-pyrrolidone and heated at 151° C. during 25 hours. The dark brown suspension is treated with 10.9 g (33.6 mmol) of cesium carbonate and heating continued for 20 hours. The reaction mixture is cooled down to room temperature and poured into 400 ml of water leading to the separation of a viscous oil. The supernatant solution is separated and the viscous oil dissolved in dichloromethane and filtered over a layer of silica gel, then dried over sodium sulfate and concentrated under vacuum. The crude product is further purified two times by chromatography (toluene/ethyl acetate 95:5). The resulting orange oil is diluted with 4 ml of dichloromethane and 50 ml of heptane and partly concentrated under vacuum. Further cooling and stirring of the solution leads to precipitation of a solid which is filtered off, giving the title product as a slightly orange solid (yield: 5.76 g (28%)).

$^1$H-NMR (300 MHz, CD$_2$Cl$_2$): δ=2.09 (s, 6H), 7.11-7.22 (m, 5H), 7.28 (br. s, 1H), 7.73-7.82 (m, 3H), 8.12 (d, 1H).

d) Synthesis of N3-(3,5-dimethylphenyl)-N2-[4-(2,6-dimethylphenyl)phenyl]pyrazine-2,3-diamine

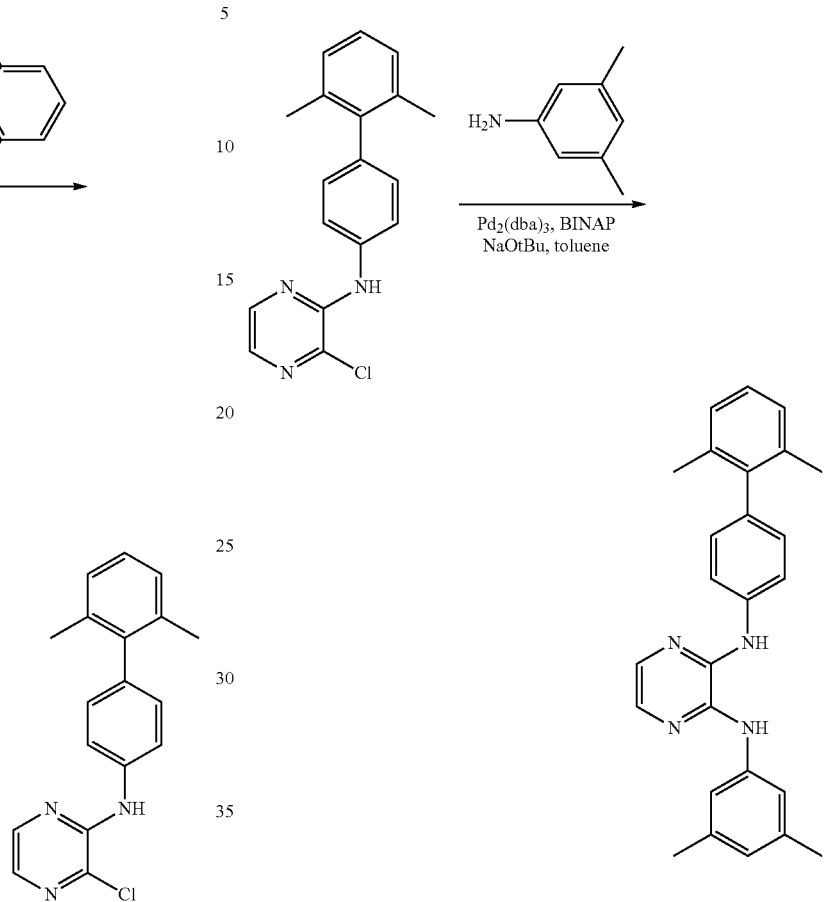

4.00 g (12.9 mmol) of 3-chloro-N-[4-(2,6-dimethylphenyl)phenyl]pyrazin-2-amine, and 1.72 g (14.2 mmol) of 3,5-dimethylaniline, and 118 mg (0.13 mmol) of tris(dibenzylideneacetone)dipalladium(0), and 241 mg (0.39 mmol) of 2,2'-bis(diphenylphosphino)-1,1'-binaphthalene, and 1.24 g (12.9 mmol) of sodium tert-butoxide are suspended in 30 ml of oxylene at room temperature under argon. The orange suspension is three times evacuated and backfilled with argon, followed by heating under reflux for 19 hours. The reaction mixture is cooled down to room temperature and 100 ml of hexane are added followed by filtration. The solid residue is further washed with hexane and taken up in 100 ml of water followed by filtration and washing with plenty of water. The solid is taken up in 300 ml of 5%-ammonia solution, stirred during 30 minutes, followed by filtration and washing with 100 ml of water. The brown solid is dissolved in 150 ml ethyl acetate and filtered through a 4 cm layer of silica gel followed by rinsing the silica gel layer with ethyl acetate. The combined ethyl acetate fractions are concentrated under vacuum and the resulting brown viscous oil dissolved in dichloromethane followed by filtration through a 4 cm layer of silica gel and additional rinsing of the silica gel layer with dichloromethane. The combined eluents are concentrated under vacuum. The orange viscous oil is dissolved in 5 ml of dichloromethane and treated with 100 ml of heptane giving a yellow suspension which is further stirred and filtered. The resulting solid is dried under vacuum giving the title product as light yellow solid (yield: 1.88 g (37%)).

¹H-NMR (400 MHz, CD$_2$Cl$_2$): δ=2.10 (s, 6H), 2.33 (s, 6H), 6.22 (br. s, 1H), 6.42 (br. s, 1H), 6.75 (s, 1H), 6.96 (s, 2H), 7.10-7.20 (m, 5H), 7.42-7.48 (m, 2H), 7.80-7.84 (m, 2H).

e) Synthesis of [3-(3,5-dimethylanilino)pyrazin-2-yl]-[4-(2,6-dimethylphenyl)phenyl]-ammonium chloride

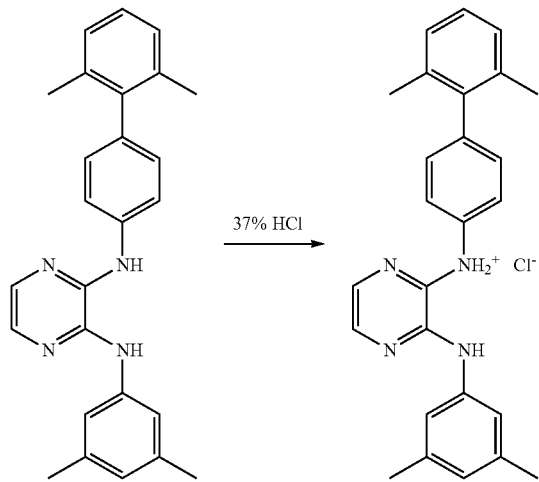 [SMILES: Cc1cc(C)cc(Nc2nccnc2Nc2ccc(-c3c(C)cccc3C)cc2)c1 ; Cc1cc(C)cc(Nc2nccnc2[NH2+]c2ccc(-c3c(C)cccc3C)cc2)c1 ; [Cl-]]

A suspension of 6.13 g (15.5 mmol) of N3-(3,5-dimethylphenyl)-N2-[4-(2,6-dimethylphenyl)phenyl]pyrazine-2,3-diamine and 50 ml of 37% hydrochloric acid is stirred at room temperature during 17 hours. The resulting yellow suspension is filtered and the solid washed with water and heptane, and dried after washing on the filter funnel under vacuum, giving the title product as a yellow solid (yield: 5.48 g (82%)).

¹H-NMR (400 MHz, d$_6$-DMSO): δ=2.03 (s, 6H), 2.29 (s, 6H), 6.73 (s, 1H), 7.07-7.20 (m, 5H), 7.34 (s, 2H), 7.51-7.61 (m, 2H), 7.82 (d, 2H), 9.32 (br. s, 2H).

f) Synthesis of 3-(3,5-dimethylphenyl)-1-[4-(2,6-dimethylphenyl)phenyl]-2-ethoxy-2H-imidazo[4,5-b]pyrazine

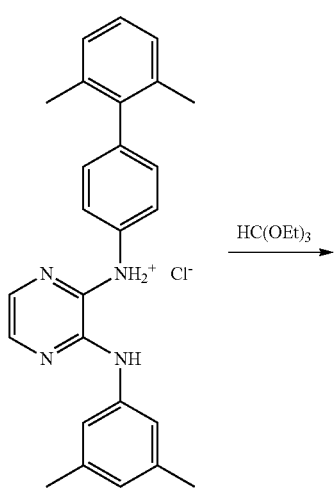

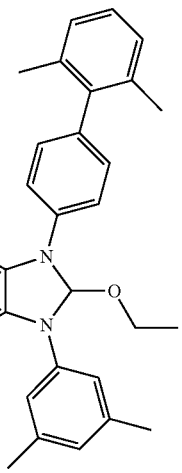

A greenish suspension of 2.0 g (4.6 mmol) of [3-(3,5-dimethylanilino)pyrazin-2-yl]-[4-(2,6-dimethylphenyl)phenyl]ammonium chloride and 18 g (0.12 mol) of triethyl orthoformate is heated up under argon at 100° C. during 20 hours. The resulting orange solution is filtered and the small amount of solid residue rinsed with 10 ml of triethyl orthoformate. The filtrate is concentrated under vacuum, and the resulting solid further dried under vacuum, giving the title product as orange-brown solid (yield 1.82 g (87%)).

¹H-NMR (400 MHz, d$_6$-DMSO): δ=0.94 (t, 3H), 2.03 (s, 6H), 2.34 (s, 6H), 3.19-3.30 (m, 2H), 6.86 (s, 1H), 7.11-7.21 (m, 3H), 7.26 (d, 2H), 7.53 (dd, 2H), 7.70 (s, 2H), 7.80 (s, 1H), 8.13 (d, 2H).

g) Synthesis of Complex (5)

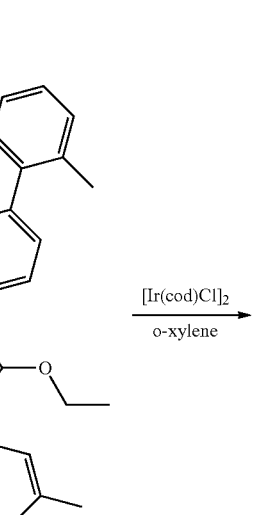

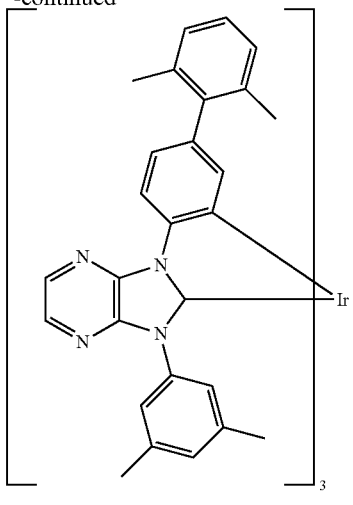

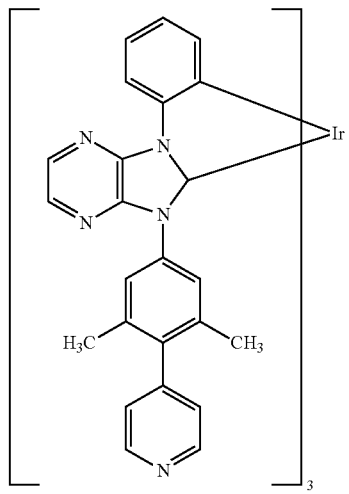

complex (6)

1.0 g (2.2 mmol) of 3-(3,5-dimethylphenyl)-1-[4-(2,6-dimethylphenyl)phenyl]-2-ethoxy-2H-imidazo[4,5-b]pyrazine and 0.19 g (0.74 mmol) of chloro(1,5-cyclooctadiene)iridium(I) dimer are suspended under argon in 25 ml of o-xylene. The suspension is five times evacuated and back-filled with argon, followed by heating at 137° C. during 16 hours. The brown solution is cooled down to room temperature and purified by chromatography (toluene/methanol). The product fractions are collected and concentrated under vacuum. The solid (230 mg) is further dissolved in dichloromethane and precipitation done by the addition of methanol. Stirring is continued for 30 minutes and the resulting solid filtered off and washed with methanol. The yellow solid is dissolved in 30 ml of acetonitrile under reflux, treated with 4 ml 1N aqueous HCl solution, and further heated under reflux for 18 hours. The solution is cooled down to room temperature leading to precipitation of a solid which is further dried under vacuum, giving the title product as a single isomer (=homoleptic complex according to NMR characterization), as a light yellow solid (yield: 200 mg (26%)).

APCI-LC-MS (positive, m/z): exact mass of $C_{81}H_{69}IrN_{12}$=1402.72. found 1403.6 [M+1]$^+$.

$^1$H-NMR (400 MHz, CD$_2$Cl$_2$): δ=1.61 (s, 9H), 1.72 (s, 9H), 1.96 (br. s, 9H), 2.36 (br. s, 9H), 5.99 (br. s, 3H), 6.51 (d, 6H), 6.83 (dd, 3H), 6.87-7.06 (m, 12H), 8.10 (d, 3H), 8.29 (d, 3H), 8.68 (d, 3H).

Photoluminescence (2% in a PMMA film): λ$_{max}$=476 nm, CIE: (0.16; 0.28); QY=86%.

6. Synthesis of Complex (6)

a) Synthesis of 3,5-dimethyl-4-(4-pyridylaniline)

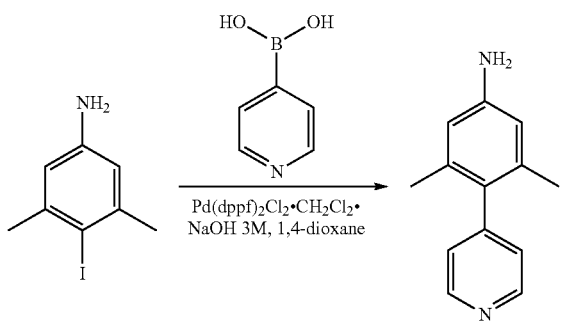

5.0 g of 3,5-dimethly-4-iodaniline (20.2 mmol) together with 3.32 g 4-pyridyl-boronsäure (26.3 mmol), 0.08 g [1,1"-Bis(diphenylphosphino)ferrocene] dichloropalladium(II) mono dichloromethane (1.01 mmol), and 20 ml NaOH 3M are suspended in 300 ml dioxane and heated at 90° C. under argon for 16° C. The reaction mixture is cooled down to room temperature and filtered under celite. The filtrate is concentrated under vacuum and treated with 160 ml of water and 160 ml of dichloromethane. The aqueous phase was washed three times with small portions of dichloromethane. The organic phase is separated, washed with NaCl solution, dried under MgSO$_4$ and concentrated under vacuum. The material is purified via chromatography with a mixture of dichloromethane ethyl acetate 20-100% gradient, giving the title product as off-white solid (yield: 3.3 g (82%)).

$^1$H-NMR (400 MHz, CD$_2$Cl$_2$): δ=1.94 (s, 6H), 3.6 (s, 2H), 6.44 (s, 2H), 7.08 (d, 2H), 8.59 (d, 2H)

b) Synthesis of N3-[3,5-dimethyl-4-(4-pyridyl)phenyl]-N2-phenyl-pyrazine-2,3-diamine

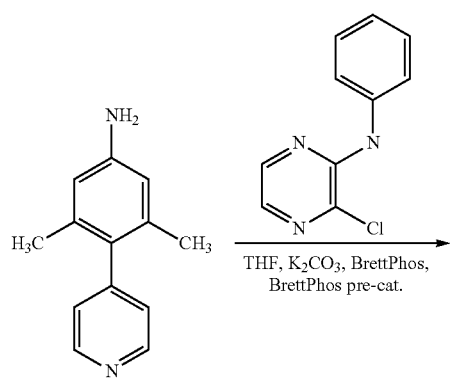

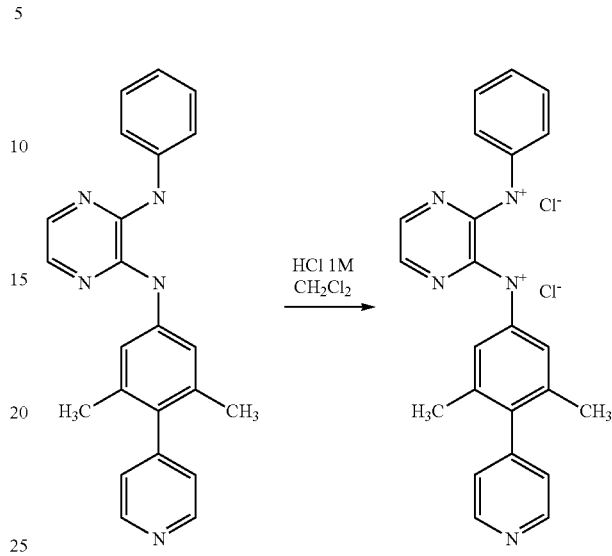

c) Synthesis of [3, 5-dimethyl-4-(4-pyridyl)phenyl]-[3-(phenylammonio)pyrazin-2-yl]ammonium dichloride 4.22 g N3-[3,5-dimethyl-4-(4-pyridyl)phenyl]-N2-phenyl-pyrazine-2,3-diamine (11.5 mmol) are dissolved in 100 ml dichloromethane and 50 ml etheric HCl 1M solution in diethyl ether is added dropwise at room temperature. The reaction mixture is stirred for 1 hour and the salt formation is controlled by thin layer chromatography using a dichloromethane/methanol (19:1) solution. The resulting yellow solid is filtered, washed with diethyl ether, and used directly in the next reaction. (yield: 4.69 g (93%)).

d) Synthesis of 3-[3,5-dimethyl-4-(4-pyridyl)phenyl]-2-ethoxy-1-phenyl-2H-imidazo[4,5-b]pyrazine

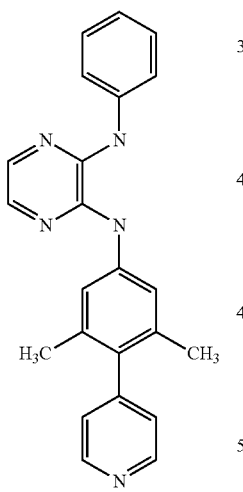

3.2 g 3,5-dimethyl-4-(4-pyridylaniline) (16.1 mmol) and 3.31 g 3-chloro-N-phenyl-pyrazin-2-amine (16.1 mmol), 6.68 g K₂CO₃ (48.3 mmol), 432 mg BrettPhos (0.81 mmol), and 643 mg BrettPhos pre-catalyst (0.81 mmol) are suspended in 300 ml dried tetrahydrofurane under argon at room temperature, followed by heating under reflux for 48 hours. The reaction mixture is cooled down to room temperature, filtered under celite and the filtratate concentrated under vacuum. The material is purified by chromatography using a mixture of dichloromethane methanol 1-10% gradient.

$^1$H-NMR (400 MHz, CD$_2$Cl$_2$): δ=2.00 (s, 6H), 6.56 (s, 1H), 6.64 (s, 1H), 7.04 (m, 1H), 7.10-7.18 (m, 4H), 7.29-7.40 (m, 4H), 7.74 (d, 2H), 8.64 (d, 2H).

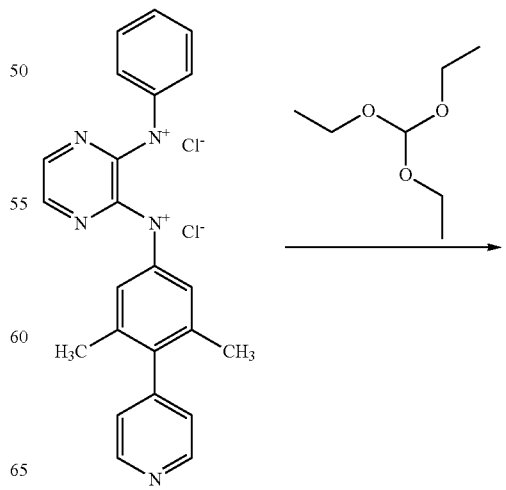

207
-continued

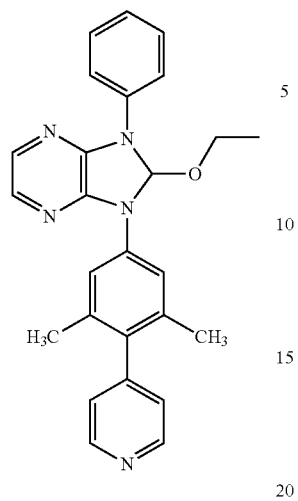

0.5 g [3,5-dimethyl-4-(4-pyridyl)phenyl]-[3-(phenylammonio)pyrazin-2-yl]ammonium dichloride (1.14 mmol) is suspended in 15 ml triethyl orthoformate (91.1 mmol) followed by heating under reflux for 15 minutes. The reaction mixture is coiled down to room temperature and the triethyl orthoformate removed under vacuum. The resulting solid is recrystallized from ethanol giving the title product as yellow needles (yield: 389 mg (83%)).

H-NMR (400 MHz, $CD_2Cl_2$): δ=1.08 (t, 3H), 2.09 (s, 6H), 3.34 (d, 2H), 7.14 (q, 2H), 7.17-7.22 (t, 1H), 7.30 (s, 1H), 7.45 (t, 2H), 7.53 (s, 2H), 7.81 (s, 2H), 8.06 (d, 2H), 8.65 (q, 2H)

e) Synthesis of Complex (6)

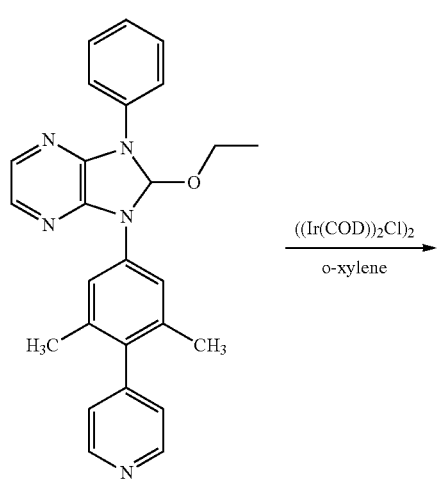

208
-continued

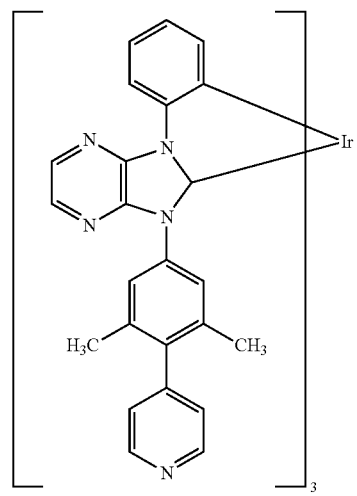

1.6 g of product 3-[3,5-dimethyl-4-(4-pyridyl)phenyl]-2-ethoxy-1-phenyl-2H-imidazo[4,5-b]pyrazine (2.74 mmol) and 672 mg of chloro(1,5-cyclooctadiene)iridium(I) dimer are suspended in o-xylene under argon and stirred overnight at 144° C. resulting an orange solution. The solvent is removed under vacuum and recrystallized with ethyl acetate. The resulting solid is filtered and washed with ethyl acetate giving a light yellow solid (the title product as a single isomer). (yield: 63 mg (2%)).

H-NMR (400 MHz, $CD_2Cl_2$): δ=1.30 (s, 9H), 2.12 (s, 9H), 6.11 (m, 3H), 6.36 (m, 3H), 6.59 (m, 6H), 6.81 (m, 3H), 7.00 (m, 3H), 7.17 (m, 3H), 8.14 (d, 3H), 8.25 (d, 3H), 8.60 (d, 6H), 8.82 (d, 3H).

Photoluminescence (2% in a PMMA film): $\lambda_{max}$=478 nm, CIE: (0.16; 0.29); QY=91%.

complex (7)

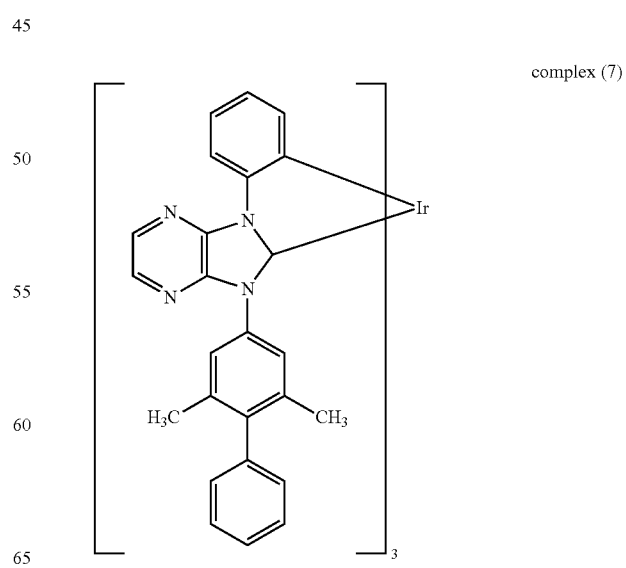

7. Synthesis of Complex (7)

a) Synthesis of 3,5-dimethyl-4-phenyl-aniline

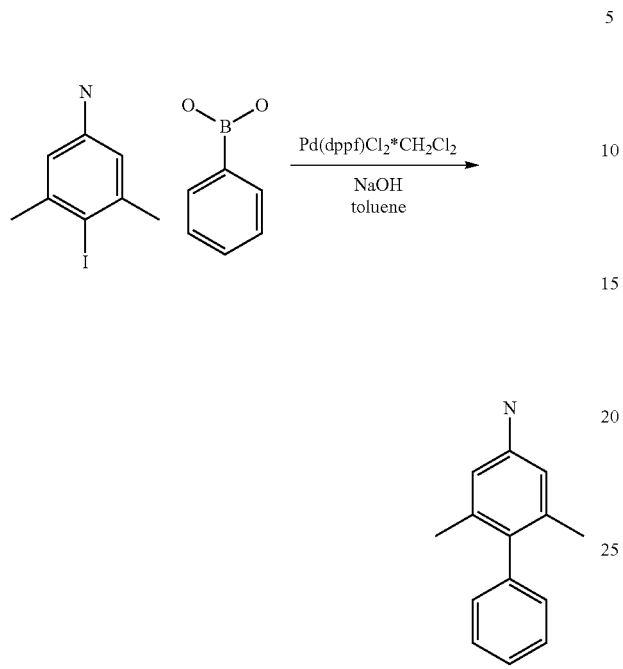

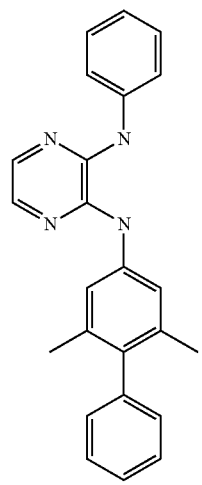

10.0 g of 4-iodo-3,5-dimethyl-phenylamine (70.5 mmol) is dissolved under argon in 500 ml toluene followed by the addition of 6.42 g phenylboronic acid (52.6 mmol) and 1.65 g Pd(dppf)Cl$_2$*CH$_2$Cl$_2$ (2.0 mmol). 40.5 mL of 3N NaOH (121.4 mmol) is added dropwise, the resulting brown solution is heated to 90° C. for 16 hours.

The suspension is filtered under Celite, the remaining filtrate concentrated under vacuum giving a brown residue which is taken up in dichloromethane. The organic phase is washed twice with water and finally once with brine, dried with magnesium sulfate and concentrated under vacuum. The resulting solid is purified by chromatography with a mixture of dichloromethane and ethyl acetate 1-5% gradient to give a yellow oil (yield: 7.22 g (90.4%))

H-NMR (400 MHz; CD$_2$Cl$_2$): δ=1.92 (s, 6H), 3.60 (s, 2H), 6.43 (s, 2H), 7.09-7.13 (d, 2H), 7.26-7.32 (m, 1H), 7.35-7.41 (m, 2H)

b) Synthesis of N3-(3,5-dimethyl-4-phenyl-phenyl)-N2-phenyl-pyrazine-2,3-diamine

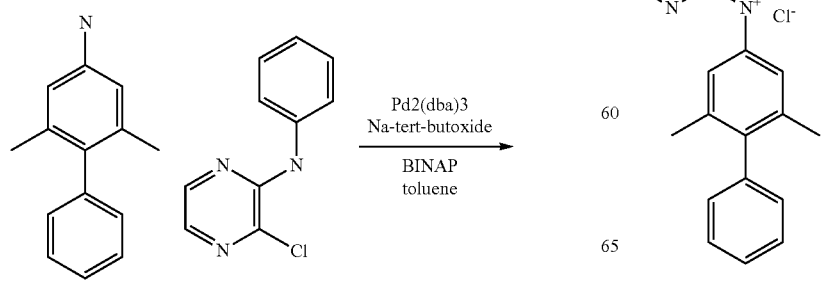

2.60 g of 3,5-dimethyl-4-phenyl-aniline (13.2 mmol) is dissolved under argon in 300 ml of anhydrous toluene, followed by the addition of 2.98 g 3-chloro-N-phenyl-pyrazin-2-amine (14.5 mmol), 1.77 g sodium tert-butoxide (18.45 mmol), 0.12 g Pd$_2$(dba)$_3$ (0.13 mmol) and 0.16 g BINAP (rac.) (0.26 mmol) to give a reddish brown suspension which is refluxed for 16 hours. The resulting orange suspension is filtered over Celite, the remaining filtrate is concentrated under vacuum. The residue is taken up in dichloromethane and washed twice with water and finally once with brine, dried with magnesium sulfate and concentrated under vacuum. The resulting solid is purified by chromatography with a mixture of cyclohexane and ethyl acetate 1-25% gradient to give an orange solid which is recrystallized from cyclohexane giving the title product as an off-white solid (yield: 1.02 g (21%))

H-NMR (400 MHz; CD$_2$Cl$_2$): δ=2.00 (s, 6H), 6.20 (s, 1H), 6.32 (s, 1H), 7.02-7.08 (m, 3H), 7.13-7.18 (d, 2H), 7.30-7.37 (m, 5H), 7.39-7.46 (t, 2H), 7.73-7.79 (m, 2H).

c) Synthesis of Complex (7) (One Pot-Reaction)

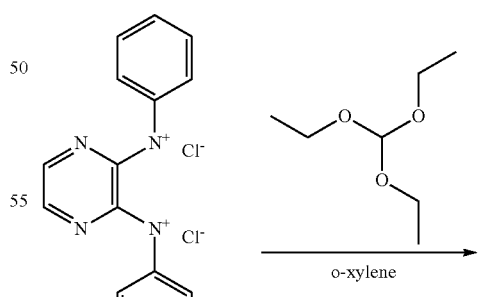

-continued

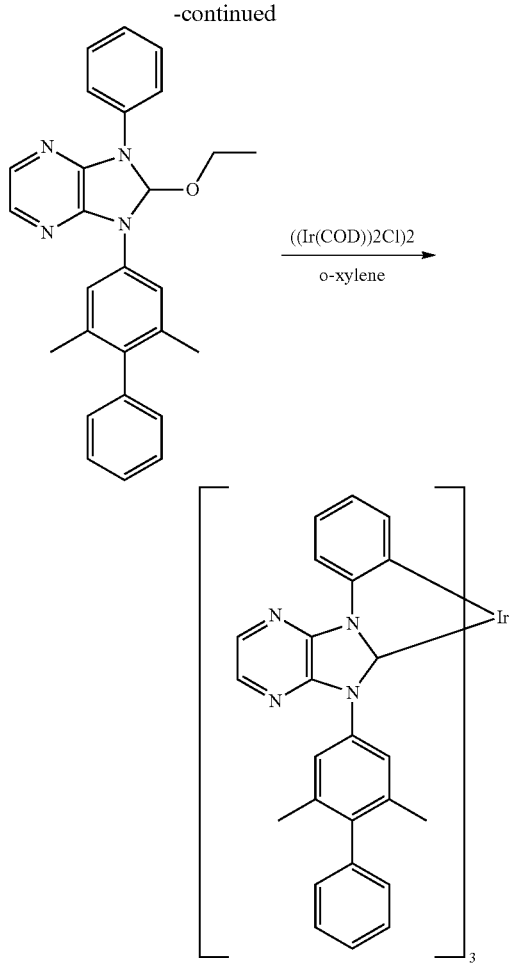

8. Synthesis of Heteroleptic Complex 8

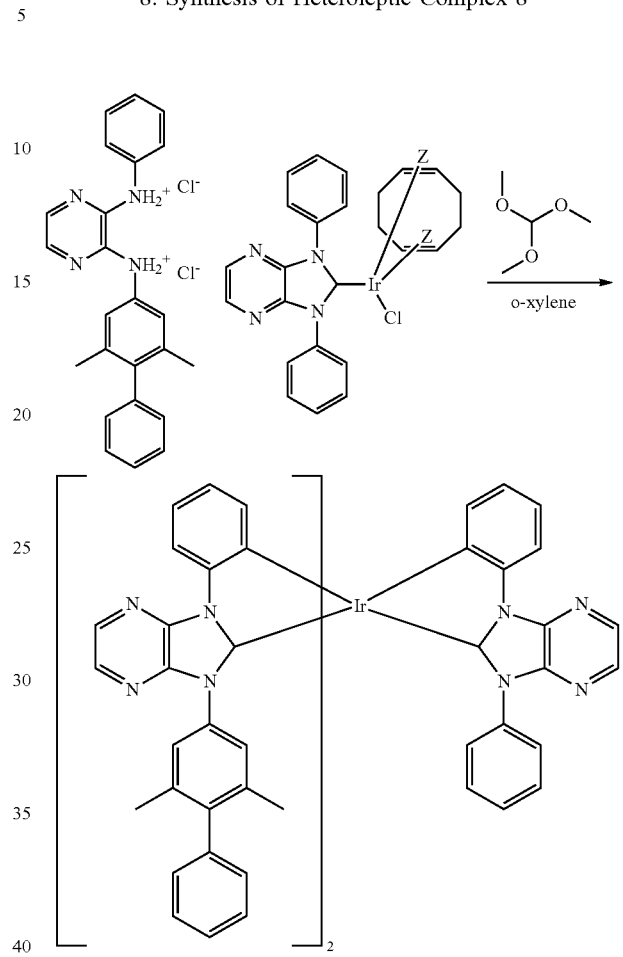

Step 1: Synthesis of 3-(3,5-dimethyl-4-phenyl-phenyl)-2-ethoxy-1-phenyl-2H-imidazo[4,5-b]pyrazine 500 mg of N3-(3,5-dimethyl-4-phenyl-phenyl)-N2-phenyl-pyrazine-2,3-diamine (1.14 mmol) as hydrochloride (formed by stirring the free base in DCM/1N hydrochloride solution in diethyl ether; yield: 100%) is suspended under argon and exclusion of light in 50 mL of o-xylene. 0.3 ml of triethyl orthoformate (1.71 mmol) is added dropwise and the resulting suspension is heated to 100° C. for 1 hour to clear up to a yellowish brown solution.

Step 2: Synthesis of Complex (7)

74 mg of [(Ir(cod))$_2$Cl]$_2$ (0.11 mmol) is added to the reaction solution and heated to reflux for 64 hours. The dark brown solution is evaporated, the residue is purified by chromatography with a mixture of cyclohexane and ethyl acetate 1-10% gradient to give a yellow solid, which is slurried in a mixture of acetonitrile/acetone 1/1 to give the final title compound as a bright yellow solid (the title product as a single isomer) (yield: 54 mg (18.6%))

H-NMR (400 MHz; CD$_2$Cl$_2$): δ=1.28 (s, 9H), 2.12 (s, 9H), 6.09 (s, 3H), 6.39-6.41 (d, 3H), 6.57-6.61 (t, 6H), 6.78-6.82 (t, 3H), 7.01-7.03 (d, 3H), 7.15-7.19 (t, 3H), 7.29-7.39 (m, 9H), 8.12-8.13 (d, 3H), 8.22-8.23 (d, 3H), 8.81-8.83 (d, 3H).

Photoluminescence (2% in a PMMA film): $\lambda_{max}$=479 nm, CIE: (0.16; 0.28); QY=96%.

150 mg (3,5-dimethyl-4-phenyl-phenyl)-[3-(phenylammonio)pyrazin-2-yl]ammonium dichloride (0.34 mmol) is suspended under argon in o-xylene, 0.1 ml triethyl orthoformate (0.51 mmol) is added dropwise. The mixture is stirred for 1 h at 100° C. to form the intermediate ethoxy-compound. 103 mg Mono-DABIC is added, the resulting brown solution is refluxed for 2 days. The solvent is removed under vacuum, the crude product purified by chromatography with a mixture of cyclohexane and ethyl acetate 5-25% gradient. Recrystallization from ethyl acetate giving the title product as light yellow solid (yield: 60 mg (29%))

H-NMR (400 MHz; CD$_2$Cl$_2$): δ=2.02-2.10 (s, 6H); 2.10-2.16 (s, 6H); 6.03-6.09 (d, 3H); 6.30-6.42 (m, 4H); 6.52-6.65 (m, 5H); 6.74-6.82 (m, 3H); 6.90-6.94 (t, 1H); 6.96-7.01 (m, 2H); 7.10-7.19 (m, 3H); 7.25-7.37 (m, 7H); 8.05-8.07 (d, 1H); 8.07-8.10 (d, 1H); 8.10-8.13 (d, 1H); 8.17-8.20 (d, 1H); 8.20-8.22 (d, 1H); 8.31-8.34 (d, 1H); 8.72-8.84 (m, 3H)

Photoluminescence (2% in a PMMA film): $\lambda_{max}$=477 nm, CIE: (0.16; 0.28); QY=92%.

II Device Examples

All data are obtained at 300 nits.
A Devices with Complex (1) as Emitter

213

Device 1:

HIL Plexcore AJ20-1000—10 nm Ir(DPBIC)₃:MoO₃ (50:50)—10 nm Ir(DPBIC)₃—40 nm complex (1)/SH-2/Ir(DPBIC)₃ (10:80:10)—5 nm SH-2—25 nm ETM-2:Liq (50:50)—4 nm KF—100 nm Al

| Example | Emitter | Voltage [V] | currEff [cd/A] | LumEff [lm/W] | EQE [%] | $CIE_{x,y}$ |
|---|---|---|---|---|---|---|
| | Complex (1) | 4.3 | 23.8 | 17.4 | 11.9 | 0.17; 0.30 |

Device 2:

HIL Plexcore AJ20-1000—10 nm Ir(DPBIC)₃:MoO₃ (50:50)—10 nm Ir(DPBIC)₃—40 nm/complex (1)/SH-1/Ir(DPBIC)₃ (10:80:10)—5 nm SH-1—25 nm ETM-2:Liq (50:50)—4 nm KF—100 nm Al

| Example | Emitter | Voltage [V] | currEff [cd/A] | LumEff [lm/W] | EQE [%] | $CIE_{x,y}$ |
|---|---|---|---|---|---|---|
| | Complex (1) | 5.4 | 24.8 | 14.4 | 12.4 | 0.17; 0.31 |

SH-2

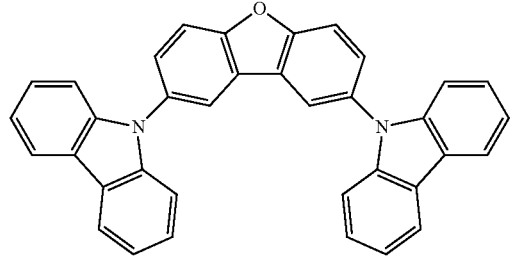

SH-1

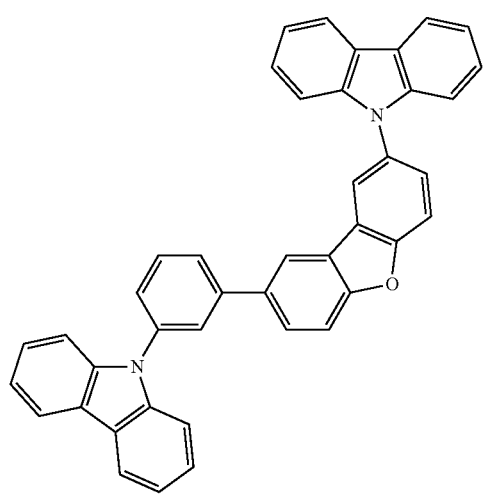

214

-continued

Complex (1)

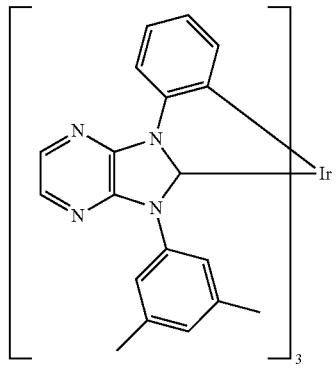

ETM-2

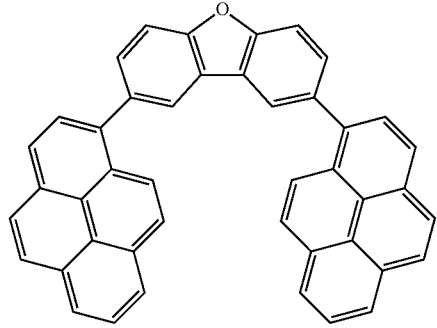

B Devices with Complex (4) as Blocker and Co-Host

HIL Plexcore AJ20-1000—10 nm Ir(DPBIC)₃:MoO₃ (50:50)—10 nm complex (4)—40 nm Ir(DPDABIC)₃/SH-2/complex (4) (10:80:10)—5 nm SH-2—25 nm ETM-2-1:Liq (50:50)—4 nm KF—100 nm Al

| Example | Blocker | Voltage [V] | currEff [cd/A] | LumEff [lm/W] | EQE [%] | CIE x, y |
|---|---|---|---|---|---|---|
| | Complex (4) | 5.5 | 20.9 | 12.7 | 11.8 | 0.17; 0.28 |

SH-2

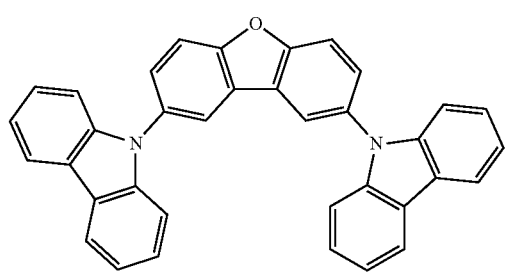

SH-1

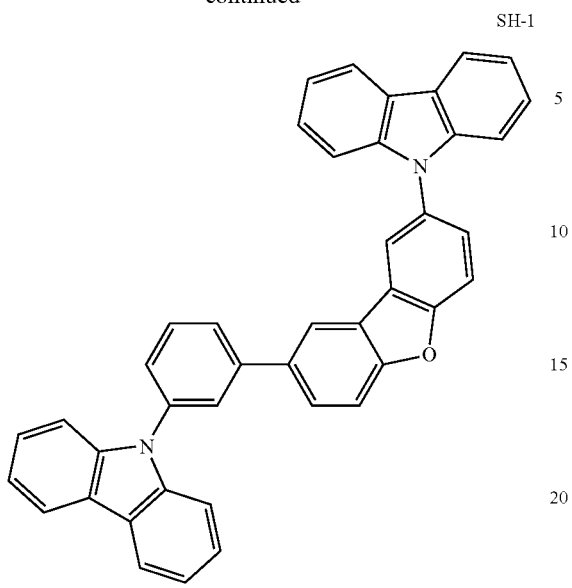

Complex (4)

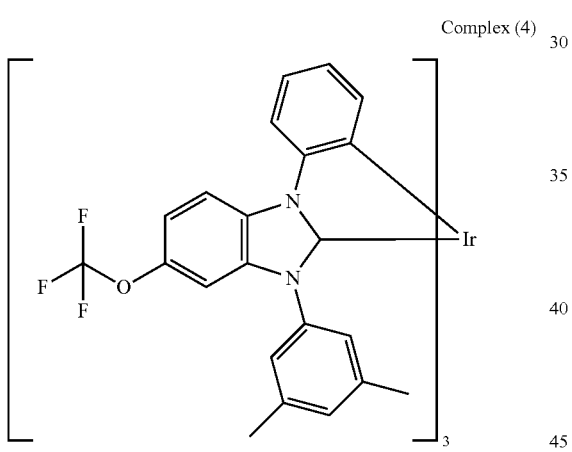

ETM-2

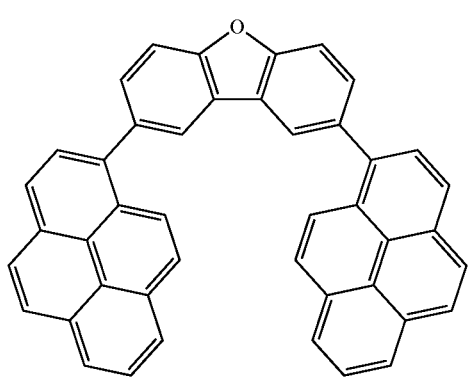

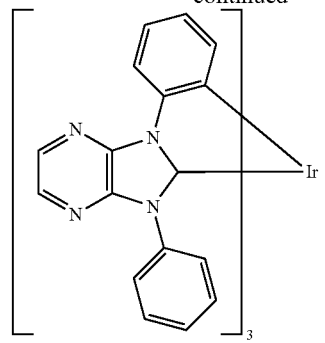

Ir(DPDABIC)₃ desribed in WO2011/073149, Beispiel 1)

The invention claimed is:
1. A cyclometallated Ir complex comprising one, two or three ligands of formula (I) or (I')

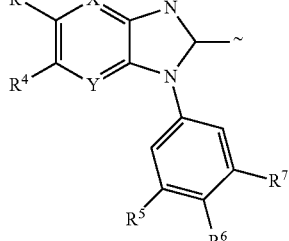

(I)

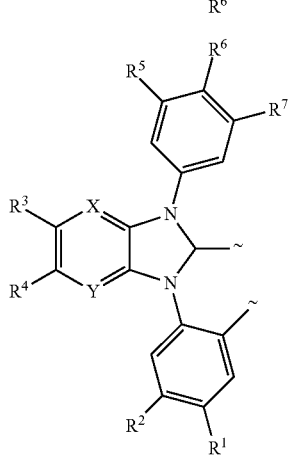

(I')

wherein
$R^1$, $R^2$, $R^3$, $R^4$ and $R^6$
are each independently hydrogen; deuterium; a linear or branched, substituted or unsubstituted alkyl radical having 1 to 20 carbon atoms, optionally interrupted by at least one heteroatom selected from the group consisting of O, S and N; a substituted or unsubstituted cycloalkyl radical having a total of from 3 to 30 carbon atom; a substituted or unsubstituted heterocycle alkyl radical, interrupted by at least one heteroatom selected from the group consisting of O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms selected from the group consisting of O, S and N; or a group with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^{10}R^{11}R^{12}$, halogen radicals, halogenated $C_1$-$C_{20}$-alkyl radicals, carbonyl (—CO($R^{32}$)), carbonylthio (—C=O($SR^{32}$)), carbonyloxy (—C=O($OR^{32}$)), oxycarbonyl (—OC=O($R^{32}$)), thiocarbonyl (—SC=O($R^{32}$)), amino (—$NR^{32}R^{33}$), OH, pseudohalogen radicals, amido (—C=O($NR^{32}R^{33}$)), —$NR^{32}$C=O($R^{33}$), phosphonate (—P(O) ($OR^{32}$)$_2$, phosphate (—OP(O) ($OR^{32}$)$_2$), phosphine (—$PR^{32}R^{33}$), phosphine oxide (—P(O)$R^{32}{}_2$), sulfate (—OS(O)$_2$$OR^{32}$), sulfoxide (—S(O)$R^{32}$), sulfonate (—S(O)$_2$$OR^{32}$), sulfonyl (—S(O)$_2$$R^{32}$), sulfonamide (—S(O)$_2$$NR^{32}R^{33}$), $NO_2$, boronic esters (—OB($OR^{32}$)$_2$), imino (—C=$NR^{32}R^{33}$)), borane radicals, stannate radicals, hydrazine radicals, hydrazone radicals, oxime radicals, nitroso groups, diazo groups, vinyl groups, sulfoximines, alanes, germanes, boroxines and borazines;

$R^{10}$, $R^{11}$, $R^{12}$ are each independently a linear or branched alkyl radical, having from 1 to 6 carbon atoms; a substituted or unsubstituted aryl radical, having from 6 to 18 carbon atoms; a substituted or unsubstituted heteroaryl radical, having a total of from 5 to 18 carbon atoms and/or heteroatoms; a substituted or unsubstituted cycloalkyl radical having a total of from 3 to 18 carbon atoms;

$R^{32}$ and $R^{33}$ are each independently hydrogen, a substituted or unsubstituted $C_1$-$C_{20}$-alkyl, a substituted or unsubstituted $C_6$-$C_{30}$-aryl, or a substituted or unsubstituted heteroaryl having 5 to 30 ring atoms;

or $R^1$ and $R^2$ or $R^3$ and $R^4$ may form, independently of each other, together with the carbon atoms to which they are bonded, a saturated or unsaturated or aromatic, optionally substituted ring, which is optionally interrupted by at least one heteroatom selected from the group consisting of O, S and N, has a total of from 5 to 21 carbon atoms and/or heteroatoms, and may optionally be fused to at least one further optionally substituted saturated or unsaturated or aromatic ring, optionally interrupted by at least one heteroatom selected from the group consisting of O, S and N, and having a total of from 5 to 21 carbon atoms and/or heteroatoms;

$R^5$ and $R^7$ are each independently a linear or branched, substituted or unsubstituted alkyl radical having 1 to 20 carbon atoms, optionally interrupted by at least one heteroatom selected from the group consisting of O, S and N; a substituted or unsubstituted aryl radical, having a total of from 6 to 30 carbon atoms; or a substituted or an unsubstituted heteroaryl radical, having a total of from 5 to 30 carbon atoms and/or heteroatoms selected from the group consisting of O, S and N;

a cycloalkyl radical having a total of from 3 to 30 carbon atoms, optionally substituted by a linear or branched, substituted or unsubstituted alkyl radical, optionally interrupted by at least one heteroatom selected from the group consisting of O, S and N, and/or at least one of the groups mentioned above concerning the linear or branched alkyl radical; or a heterocyclo alkyl radical, interrupted by at least one heteroatom selected from the group consisting of O, S and N, and having a total of from 3 to 30 carbon atoms and/or heteroatoms, optionally substituted by a linear or branched, substituted or unsubstituted alkyl radical, optionally interrupted by at least one heteroatom selected from the group consisting of O, S and N, and/or at least one of the groups mentioned above concerning the linear or branched alkyl radical;

or $R^5$ and $R^6$ or $R^6$ and $R^7$ may form, independently of each other, together with the carbon atoms to which they are bonded, a saturated or unsaturated or aromatic, optionally substituted ring, which is optionally interrupted by at least one heteroatom selected from the group consisting of O, S and N, has a total of from 5 to 21 carbon atoms and/or heteroatoms, and may optionally be fused to at least one further optionally substituted saturated or unsaturated or aromatic ring, optionally interrupted by at least one heteroatom selected from the group consisting of O, S and N, and having a total of from 5 to 21 carbon atoms and/or heteroatoms;

X is $CR^8$ or N;

Y is $CR^9$ or N;

$R^8$ and $R^9$ are each independently hydrogen; deuterium; a linear or branched, substituted or unsubstituted alkyl radical having 1 to 20 carbon atoms, optionally interrupted by at least one heteroatom selected from the group consisting of O, S and N; a substituted or unsubstituted cycloalkyl radical having a total of from 3 to 30 carbon atom; a substituted or unsubstituted heterocyclealkyl radical, interrupted by at least one heteroatom selected from the group consisting of O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms selected from the group consisting of O, S and N; or a group with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^{10}R^{11}R^{12}$, halogen radicals, halogenated $C_1$-$C_{20}$-alkyl radicals, carbonyl (—CO($R^{32}$)), carbonylthio (—C=O($SR^{32}$)), carbonyloxy (—C═O(OR³²)), oxycarbonyl (—OC═O(R³²)), thiocarbonyl (—SC═O(R³²)), amino (—NR³²R³³), OH, pseudohalogen radicals, amido (—C═O(NR³²R³³)), —NR³²C═O(R³³), phosphonate (—P(O) (OR³²)₂, phosphate (—OP(O) (OR³²)₂), phosphine (—PR³²R³³), phosphine oxide (—P(O)R³²₂), sulfate (—OS(O)₂OR³²), sulfoxide (—S(O)R³²), sulfonate (—S(O)₂OR³²), sulfonyl (—S(O)₂R³²), sulfonamide (—S(O)₂NR³²R³³), NO₂, boronic esters (—OB (OR³²)₂), imino (—C═NR³²R³³)), borane radicals, stannate radicals, hydrazine radicals, hydrazone radicals, oxime radicals, nitroso groups, diazo groups, vinyl groups, sulfoximines, alanes, germanes, boroxines and borazines;

R³² and R³³ are each independently hydrogen, a substituted or unsubstituted C₁-C₂₀-alkyl, a substituted or unsubstituted C₆-C₃₀-aryl, or a substituted or unsubstituted heteroaryl having 5 to 30 ring atoms; and ~ is the bonding site to the metal.

2. The cyclometallated Ir complex according to claim 1, wherein

R¹, R², R³, R⁴ and R⁶ are each independently selected from the group consisting of hydrogen, deuterium, methyl, ethyl, n-propyl, isopropyl, n-butyl, tert-butyl, sec-butyl, iso-butyl, OCH₃, Otertbutyl, OCF₃, OPh, OTolyl, OXylyl, CF₃, —CN, phenyl, tolyl, xylyl, diisopropylphenyl, triisopropylphenyl, tertbutylphenyl, dimethoxyphenyl, dicyanophenyl, trifluoromethylphenyl, ditrifluoromethylphenyl, pyridyl, methylpyridyl, dimethylpyridyl, diisopropylpyridyl, tertbutylpyridyl, pyrimidyl, pyrazinyl, carbazolyl, dibenzofuranyl, diisopropyldibenzofuranyl, dibenzothiophenyl, diisopropyldibenzothiophenyl, fluorenyl, dimethylfluorenyl, indolyl, methylindolyl, benzofuranyl and benzothiophenyl;

R⁵ and R⁷ are each independently a linear or branched, substituted or unsubstituted alkyl radical having 1 to 6 carbon atoms, optionally interrupted by at least one heteroatom selected from the group consisting of O, S and N;

a substituted or unsubstituted aryl radical, having a total of from 6 to 18 carbon atoms; or a substituted or an unsubstituted heteroaryl radical, having a total of from 5 to 13 carbon atoms and/or heteroatoms selected from the group consisting of O, S and N;

a cycloalkyl radical having a total of from 3 to 13 carbon atoms, optionally substituted by a linear or branched, substituted or unsubstituted alkyl radical, optionally interrupted by at least one heteroatom selected from the group consisting of O, S and N, and/or at least one of the groups mentioned above concerning the linear or branched alkyl radical; or a heterocycle alkyl radical, interrupted by at least one heteroatom selected from the group consisting of O, S and N, and having a total of from 3 to 13 carbon atoms and/or heteroatoms, optionally substituted by a linear or branched, substituted or unsubstituted alkyl radical, optionally interrupted by at least one heteroatom selected from the group consisting of O, S and N, and/or at least one of the groups mentioned above concerning the linear or branched alkyl radical;

or

R⁵ and R⁶ or R⁶ and R⁷ may form, independently of each other, together with the carbon atoms to which they are bonded, a saturated or unsaturated or aromatic, optionally substituted ring, which is optionally interrupted by at least one heteroatom selected from the group consisting of O, S and N, has a total of from 5 to 21 carbon atoms and/or heteroatoms, and may optionally be fused to at least one further optionally substituted saturated or unsaturated or aromatic ring, optionally interrupted by at least one heteroatom selected from the group consisting of O, S and N, and having a total of from 5 to 21 carbon atoms and/or heteroatoms.

3. The cyclometallated Ir complex according to claim 1, wherein

X, Y are each CH or N.

4. The cyclometallated Ir complex according to claim 1, wherein the cyclometallated Ir complex has one of the following formulae (II), (II') or (II")

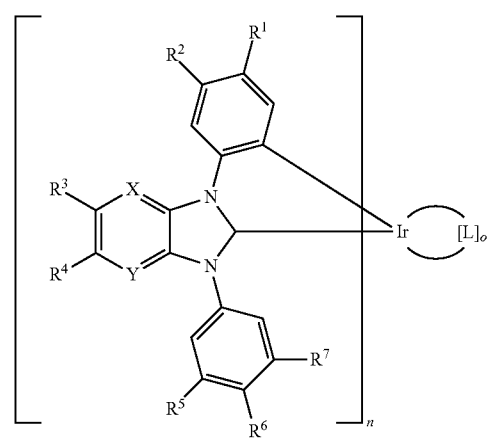

(II)

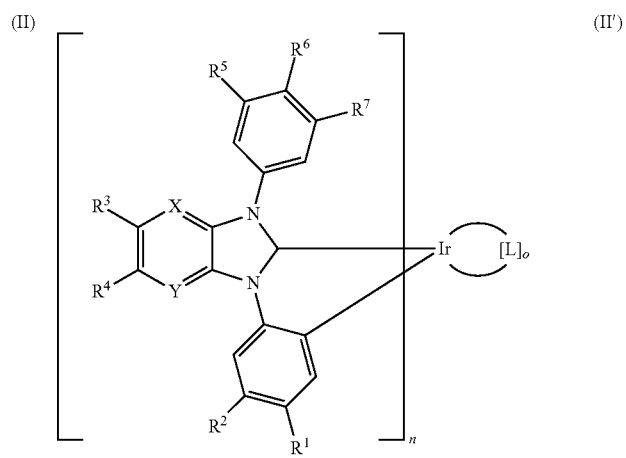

(II')

-continued

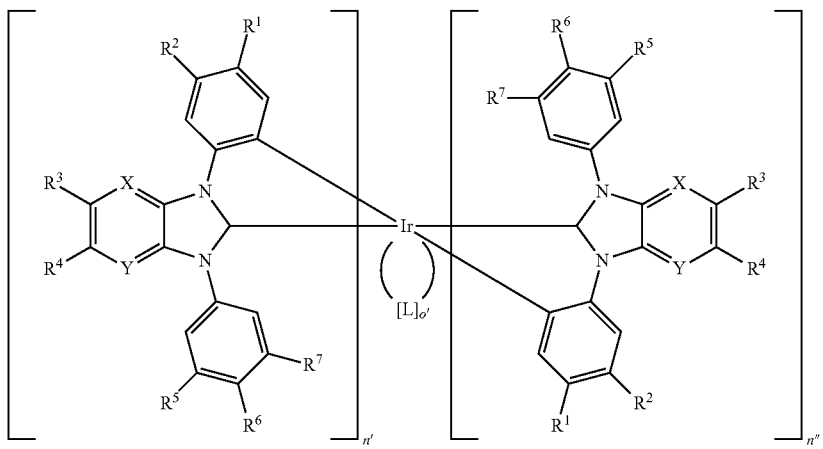

(II″)

wherein $R^1$, $R^2$, $R^3$, $R^4$ and $R^6$ are each independently hydrogen; deuterium; a linear or branched, substituted or unsubstituted alkyl radical having 1 to 20 carbon atoms, optionally interrupted by at least one heteroatom, selected from the group consisting of O, S and N; a substituted or unsubstituted cycloalkyl radical having a total of from 3 to 30 carbon atom; a substituted or unsubstituted heterocycle alkyl radical, interrupted by at least one heteroatom selected from the group consisting of O, S and N and having a total of from 3 to 30 carbon atoms and/or heteroatoms; a substituted or unsubstituted aryl radical having a total of from 6 to 30 carbon atoms; a substituted or unsubstituted heteroaryl radical having a total of from 5 to 30 carbon atoms and/or heteroatoms selected from the group consisting of O, S and N; or a group with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^{10}R^{11}R^{12}$, halogen radicals, halogenated $C_1$-$C_{20}$-alkyl radicals, carbonyl (—CO($R^{32}$)), carbonylthio (—C=O($SR^{32}$)), carbonyloxy (—C=O ($OR^{32}$)), oxycarbonyl (—OC=O($R^{32}$)), thiocarbonyl (—SC=O($R^{32}$)), amino (—$NR^{32}R^{33}$), OH, pseudohalogen radicals, amido (—C=O($NR^{32}R^{33}$)), —$NR^{32}$C=O($R^{33}$), phosphonate (—P(O) ($OR^{32}$)$_2$, phosphate (—OP(O) ($OR^{32}$)$_2$), phosphine (—$PR^{32}R^{33}$), phosphine oxide (—P(O)$R^{32}_2$), sulfate (—OS(O)$_2$O$R^{32}$), sulfoxide (—S(O)$R^{32}$), sulfonate (—S(O)$_2$O$R^{32}$), sulfonyl (—S(O)$_2$$R^{32}$), sulfonamide (—S(O)$_2$$NR^{32}R^{33}$), $NO_2$, boronic esters (—OB ($OR^{32}$)$_2$), imino (—C=$NR^{32}R^{33}$), borane radicals, stannate radicals, hydrazine radicals, hydrazone radicals, oxime radicals, nitroso groups, diazo groups, vinyl groups, sulfoximines, alanes, germanes, boroxines and borazines;

$R^{32}$ and $R^{33}$ are each independently hydrogen, a substituted or unsubstituted $C_1$-$C_{20}$-alkyl, a substituted or unsubstituted $C_6$-$C_{30}$-aryl, or a substituted or unsubstituted heteroaryl having 5 to 30 ring atoms;

$R^{10}$, $R^{11}$, $R^{12}$ are each independently a linear or branched alkyl radical, having from 1 to 6 carbon atoms; a substituted or unsubstituted aryl radical, having from 6 to 18 carbon atoms; a substituted or unsubstituted heteroaryl radical having a total of from 5 to 18 carbon atoms and/or heteroatoms; a substituted or unsubstituted cycloalkyl radical having a total of from 3 to 18 carbon atoms;

or $R^1$ and $R^2$ or $R^3$ and $R^4$ may form, independently of each other, together with the carbon atoms to which they are bonded, a saturated or unsaturated or aromatic, optionally substituted ring, which is optionally interrupted by at least one heteroatom selected from the group consisting of O, S and N, has a total of from 5 to 21 carbon atoms and/or heteroatoms, and may optionally be fused to at least one further optionally substituted saturated or unsaturated or aromatic ring, optionally interrupted by at least one heteroatom selected from the group consisting of O, S and N, and having a total of from 5 to 21 carbon atoms and/or heteroatoms $R^5$ and $R^7$ are each independently a linear or branched, substituted or unsubstituted alkyl radical having 1 to 20 carbon atoms, optionally interrupted by at least one heteroatom selected from the group consisting of O, S and N;

a substituted or unsubstituted aryl radical, having a total of from 6 to 30 carbon atoms; or a substituted or an unsubstituted heteroaryl radical, having a total of from 5 to 30 carbon atoms and/or heteroatoms selected from the group consisting of O, S and N;

a cycloalkyl radical having a total of from 3 to 30 carbon atoms, optionally substituted by a linear or branched, substituted or unsubstituted alkyl radical, optionally interrupted by at least one heteroatom selected from the group consisting of O, S and N, and/or at least one of the groups mentioned above concerning the linear or branched alkyl radical; or a heterocycle alkyl radical, interrupted by at least one heteroatom selected from the group consisting of O, S and N, and having a total of from 3 to 30 carbon atoms and/or heteroatoms, optionally substituted by a linear or branched, substituted or unsubstituted alkyl radical, optionally interrupted by at least one heteroatom, selected from the group consisting of O, S and N, and/or at least one of the groups mentioned above concerning the linear or branched alkyl radical;

or $R^5$ and $R^6$ or $R^6$ and $R^7$ may form, independently of each other, together with the carbon atoms to which they are bonded, a saturated or unsaturated or aromatic, optionally substituted ring, which is optionally interrupted by at least one heteroatom, selected from the group consisting of O, S and N, has a total of from 5 to 18 carbon atoms and/or heteroatoms, and may optionally be fused to at least one further optionally substituted saturated or unsaturated or aromatic ring, optionally interrupted by at least one heteroatom, selected from the group consisting of O, S and N, and having a total of from 5 to 18 carbon atoms and/or heteroatoms;

X is $CR^8$ or N;
Y is $CR^9$ or N;
$R^8$ and $R^9$
are each independently hydrogen; deuterium; a linear or branched, substituted or unsubstituted alkyl radical having 1 to 20 carbon atoms, optionally interrupted by at least one heteroatom, selected from the group consisting of O, S and N; a substituted or unsubstituted cycloalkyl radical having a total of from 3 to 30 carbon atom; a substituted or unsubstituted heterocycle alkyl radical, interrupted by at least one heteroatom selected from the group consisting of O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from the group consisting of O, S and N; or a group with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^{10}R^{11}R^{12}$, halogen radicals, halogenated $C_1$-$C_{20}$-alkyl radicals, carbonyl (—CO($R^{32}$)), carbonylthio (—C=O($SR^{32}$)), carbonyloxy (—C=O($OR^{32}$)), oxycarbonyl (—OC=O($R^{32}$)), thiocarbonyl (—SC=O($R^{32}$)), amino (—$NR^{32}R^{33}$), OH, pseudohalogen radicals, amido (—C=O($NR^{32}R^{33}$)), —$NR^{32}$C=O($R^{33}$), phosphonate (—P(O) ($OR^{32}$)$_2$, phosphate (—OP(O) ($OR^{32}$)$_2$), phosphine (—$PR^{32}R^{33}$), phosphine oxide (—P(O)$R^{32}_2$), sulfate (—OS(O)$_2OR^{32}$), sulfoxide (—S(O)$R^{32}$), sulfonate (—S(O)$_2OR^{32}$), sulfonyl (—S(O)$_2R^{32}$), sulfonamide (—S(O)$_2NR^{32}R^{33}$), $NO_2$, boronic esters (—OB($OR^{32}$)$_2$), imino (—C=$NR^{32}R^{33}$), borane radicals, stannate radicals, hydrazine radicals, hydrazone radicals, oxime radicals, nitroso groups, diazo groups, vinyl groups, sulfoximines, alanes, germanes, boroxines and borazines;

$R^{32}$ and $R^{33}$
are each independently hydrogen, a substituted or unsubstituted $C_1$-$C_{20}$-alkyl, a substituted or unsubstituted $C_6$-$C_{30}$-aryl, or a substituted or unsubstituted heteroaryl having 5 to 30 ring atoms;
n is 1, 2 or 3;
L is a monoanionic bidentate ligand
o is 0, 1 or 2, where, when o=2, the L ligands may be the same or different;
n' is 1 or 2;
n" is 1 or 2;
wherein the sum of n'+n" is 2 or 3;
o' is 0 or 1;
wherein the sum of n+o in formulae (II) and (II') and the sum of n'+n"+o' in formula (II") is 3, with the proviso that n in formula (II) and (II') is at least 1 and n', as well as n" in formula (II") are at least 1.

5. The cyclometallated Ir complex according to claim 1, wherein
$R^1$, $R^2$, $R^3$, $R^4$ and $R^6$
are each independently hydrogen, deuterium, methyl, ethyl, n-propyl, iso-propyl, n-butyl, tert-butyl, sec-butyl, iso-butyl, trifluoromethyl, $OCF_3$, OMe, Ot-Bu, OPh, OTolyl, OXylyl, phenyl, tolyl, xylyl, diisopropylphenyl, triisopropylphenyl, tertbutylphenyl, dimethoxyphenyl, dicyanophenyl, trifluoromethylphenyl, ditrifluoromethylphenyl, pyridyl, methylpyridyl, dimethylpyridyl, diisopropylpyridyl, tertbutylpyridyl, pyrimidyl, pyrazinyl, dibenzofuranyl, diisopropyldibenzofuranylphenyl, carbazolyl, dibenzothiophenyl, diisopropyldibenzothiophenyl, fluorenyl, dimethylfluorenyl, indolyl, methylindolyl, benzofuranyl and benzothiophenyl;

$R^5$ and $R^7$
are each independently methyl, ethyl, n-propyl, iso-propyl, n-butyl, tert-butyl, sec-butyl or iso-butyl;
or
$R^5$ and $R^6$ or $R^6$ and $R^7$ may form, independently of each other, together with the phenyl ring to which they are bonded, a dibenzofuranyl residue;
X, Y are each CH or N.

6. The cyclometallated Ir complex according to claim 1, having one of the following formulae

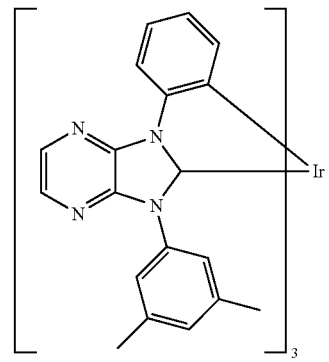

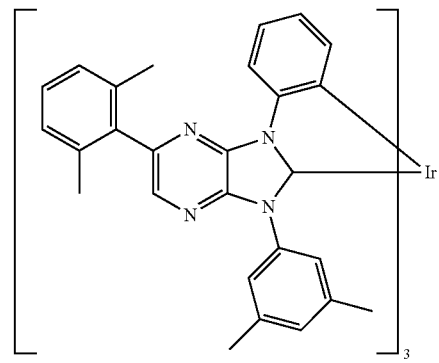

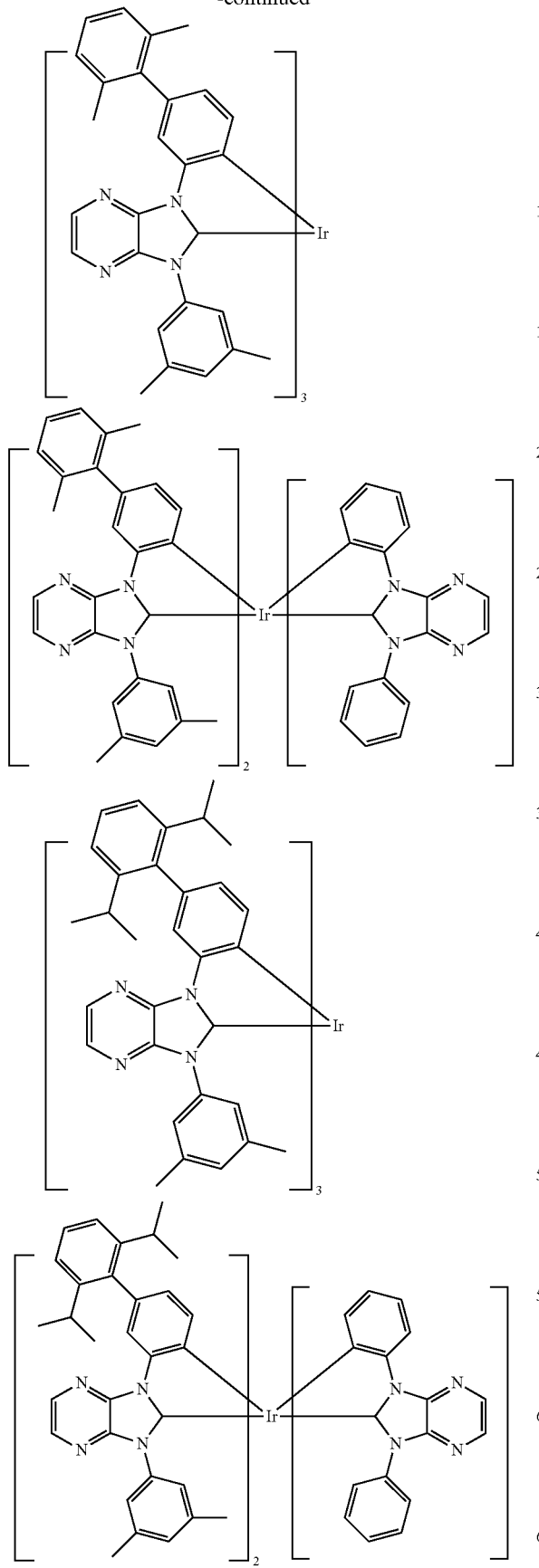
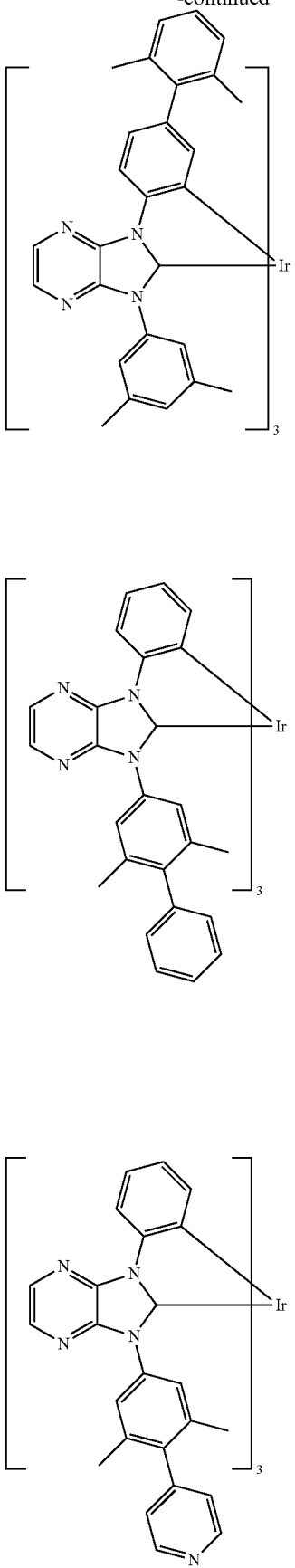

-continued

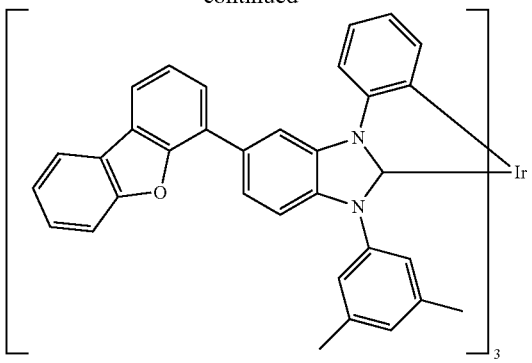

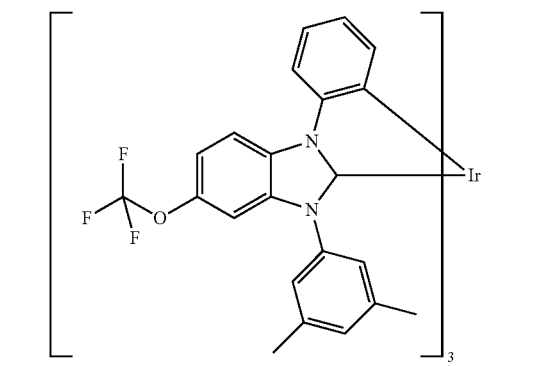

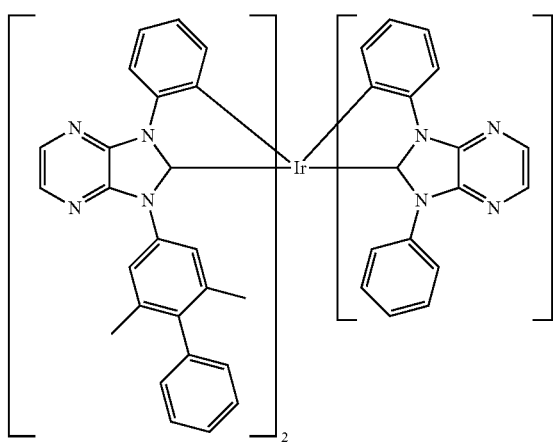

7. An organic electronic device comprising at least one cyclometallated Ir complex according to claim 1.

8. The organic electronic device according to claim 7, wherein the organic electronic device is selected from the group consisting of organic light-emitting diodes (OLED), light-emitting electrochemical cells (LEEC), organic photovoltaic cells (OPV) and organic field-effect transistors (OFET).

9. The organic electronic device according to claim 7, wherein the cyclometallated Ir complex comprising one, two or three bidentate ligands of formula (I) and/or (I') is employed in OLEDs or LEECs or in OPVs.

10. The organic electronic device according to claim 9, wherein the OLED comprises (a) an anode, (b) a cathode, (c) a light-emitting layer between the anode and the cathode, (d) optionally a hole transport layer between the light-emitting layer and the anode, wherein the cyclometallated Ir complex comprising one, two or three bidentate ligands of formula (I) and/or (I') is present in the light-emitting layer and/or—if present—in the hole transport layer of the OLED.

11. The organic electronic device according to claim 7, wherein the cyclometallated Ir complex comprising one, two or three bidentate ligands of formula (I) and/or (I') is employed in combination with at least one host material.

12. A light-emitting layer comprising at least one cyclometallated Ir complex comprising one, two or three bidentate ligands of formula (I) and/or (I') as defined in claim 1 as emitter material.

13. An OLED comprising at least one cyclometallated Ir complex comprising one, two or three bidentate ligands of formula (I) and/or (I') as defined in claim 1.

14. An apparatus selected from the group consisting of stationary visual display units, mobile visual display units, illumination units, units in items of clothing, units in handbags, units in accessories, units in furniture and units in wallpaper, wherein the apparatus comprises the organic electronic device according to claim 7.

15. A process for preparing the cyclometallated Ir complex according to claim 1, comprising one, two or three bidentate ligands of formula (I) and/or (I'), by contacting suitable compounds comprising Ir with appropriate ligands or ligand precursors.

16. A process for preparing metal-carbene complexes of formula (II), (II') or (II")

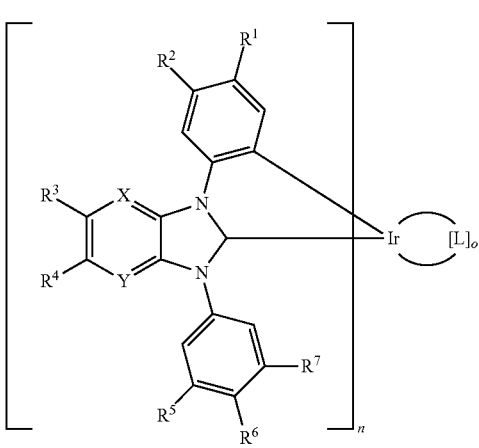

(II)

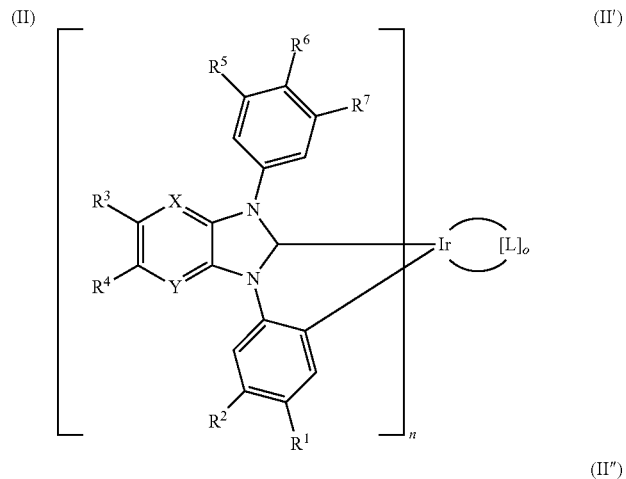

(II')

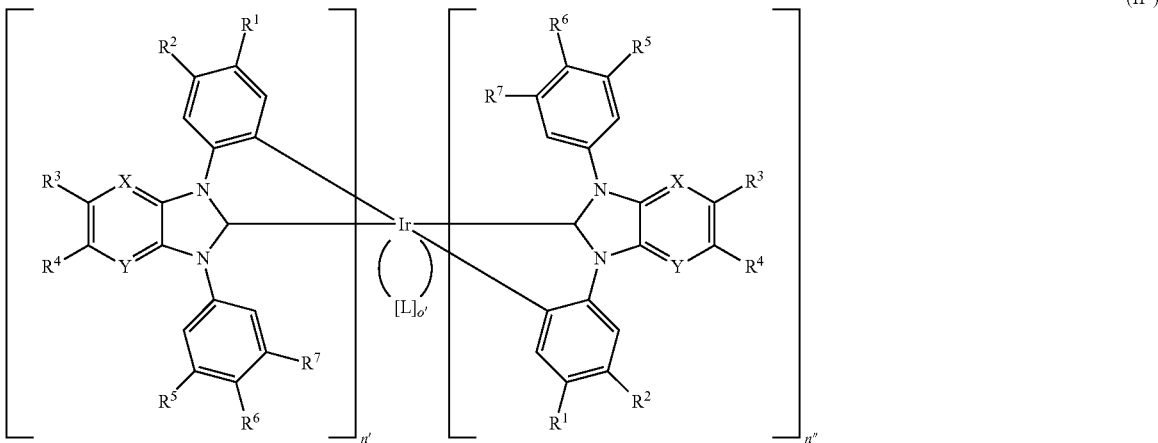

(II")

according to claim 4,
wherein one or more of the residues $R^1$, $R^2$, $R^3$, $R^4$ and $R^6$ are substituted or unsubstituted aryl, comprising reacting a compound of formula (II), (II') or (II"), wherein the respective residue $R^1$, $R^2$, $R^3$, $R^4$ and/or $R^6$ in formula (II), (II') or (II") is replaced by $X^1$, with a substituted or unsubstituted aromatic compound corresponding to the respective substituted or unsubstituted aryl residue of the formula:

(substituted or unsubstituted)aryl-Y, wherein
$X^1$ is $C_1$, Br, or I;
in formula (substituted or unsubstituted)aryl-Y, Y is
—B(OH)$_2$, —B(OY$^1$)$_2$,

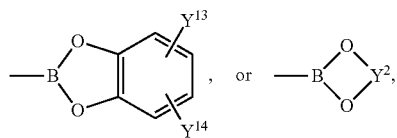

, or wherein $Y^1$ is a $C_1$-$C_{10}$alkyl group and $Y^2$ is independently in each occurrence a $C_2$-$C_{10}$alkylene group, or a $C_1$-$C_{10}$alkyl group, and $Y^{13}$ and $Y^{14}$ are independently of each other hydrogen, or a $C_1$-$C_{10}$alkyl group; —SnR$^{307}$R$^{308}$R$^{309}$, wherein R$^{307}$, R$^{308}$ and R$^{309}$ are identical or different and are H or $C_1$-$C_6$alkyl, wherein two radicals optionally form a common ring and these radicals are optionally branched or unbranched;
ZnR$^{310}$R$^{311}$ wherein R$^{310}$ is halogen and R$^{311}$ is a $C_1$-$C_{10}$alkyl group, a $C_6$-$C_{12}$aryl group, or $C_1$-$C_{10}$alkenyl group; or
SiR$^{312}$R$^{313}$R$^{314}$, wherein R$^{312}$, R$^{313}$ and R$^{314}$ are identical or different and are halogen, or $C_1$-$C_6$alkyl.

17. An apparatus selected from the group consisting of stationary visual display units, mobile visual display units, illumination units, units in items of clothing, units in handbags, units in accessories, units in furniture and units in wallpaper, wherein the apparatus comprises the light-emitting layer according to claim 12.

18. The cyclometallated Ir complex according to claim 1, wherein
X is N and Y is N.

* * * * *